US012577258B2

(12) United States Patent
Ito et al.

(10) Patent No.: US 12,577,258 B2
(45) Date of Patent: Mar. 17, 2026

(54) MACROCYCLIC COMPOUND

(71) Applicants: Asahi Kasei Pharma Corporation, Tokyo (JP); Vernalis (R&D) Limited, Great Abington (GB)

(72) Inventors: Takahiko Ito, Tokyo (JP); Misato Takashima, Tokyo (JP); Masakazu Atobe, Tokyo (JP); Koichiro Arai, Tokyo (JP); Tomohisa Toyama, Tokyo (JP); Yu Yoshii, Tokyo (JP); Andrew John Potter, Great Abington (GB); Daniel Paul Maddox, Great Abington (GB); Stuart Ray, Great Abington (GB); Nicolas Foloppe, Great Abington (GB)

(73) Assignees: VERNALIS (R&D) LIMITED, Great Abington (GB); ASAHI KASEI PHARMA CORPORATION, Tokyo (JP)

( * ) Notice: Subject to any disclaimer, the term of this patent is extended or adjusted under 35 U.S.C. 154(b) by 447 days.

(21) Appl. No.: 18/028,578

(22) PCT Filed: Sep. 30, 2020

(86) PCT No.: PCT/JP2020/037046

§ 371 (c)(1),
(2) Date: Mar. 27, 2023

(87) PCT Pub. No.: WO2022/070287

PCT Pub. Date: Apr. 7, 2022

(65) Prior Publication Data

US 2023/0357271 A1 Nov. 9, 2023

(51) Int. Cl.
*C07D 471/18* (2006.01)
*C07D 498/18* (2006.01)

(52) U.S. Cl.
CPC .................................. *C07D 498/18* (2013.01)

(58) Field of Classification Search
CPC ............................ C07D 471/18; C07D 498/18
See application file for complete search history.

(56) References Cited

U.S. PATENT DOCUMENTS

| | | | |
|---|---|---|---|
| 2011/0294801 | A1 | 12/2011 | Yu et al. |
| 2016/0002265 | A1 | 1/2016 | Jenkins et al. |
| 2017/0204116 | A1 | 7/2017 | Gray et al. |
| 2018/0244646 | A1 | 8/2018 | Lee et al. |
| 2019/0092750 | A1 | 3/2019 | Lee et al. |

FOREIGN PATENT DOCUMENTS

| | | | |
|---|---|---|---|
| CN | 102143750 | A | 8/2011 |
| CN | 107428765 | A | 12/2017 |
| CN | 107849055 | A | 3/2018 |
| CN | 107949559 | A | 4/2018 |
| EA | 032541 | B1 | 6/2019 |
| JP | 2012-502043 | A | 1/2012 |
| JP | 2018-528203 | A | 9/2018 |
| RU | 2 708 066 | C2 | 12/2019 |
| WO | WO 2010/028118 | A1 | 3/2010 |
| WO | WO 2012/068546 | A1 | 5/2012 |
| WO | WO 2013/042137 | A1 | 3/2013 |
| WO | WO 2015/048281 | A1 | 4/2015 |
| WO | WO 2015/150995 | A1 | 10/2015 |
| WO | WO 2015/155197 | A1 | 10/2015 |
| WO | WO 2016/053771 | A1 | 4/2016 |
| WO | WO 2016/127024 | A1 | 8/2016 |
| WO | WO 2016/127025 | A1 | 8/2016 |
| WO | WO 2016/144846 | A1 | 9/2016 |
| WO | WO 2017/033093 | A1 | 3/2017 |
| WO | WO 2019/184955 | A1 | 10/2019 |

OTHER PUBLICATIONS

Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," Journal of Medicinal Chemistry, vol. 58, No. 1, 2015, pp. 96-110.

Flannery et al., "The interleukin-1 receptor-associated kinases: Critical regulators of innate immune signalling," Biochemical Pharmacology, vol. 80, 2010, pp. 1981-1991.

(Continued)

*Primary Examiner* — Brenda L Coleman

(74) *Attorney, Agent, or Firm* — Birch, Stewart, Kolasch & Birch, LLP

(57) ABSTRACT

A compound represented by the general formula (1) or a salt thereof, which has a superior IRAK-4 inhibitory activity, and is useful as active ingredients of medicaments for prophylactic treatment and/or therapeutic treatment of diseases relating to IRAK-4 inhibition.

(1)

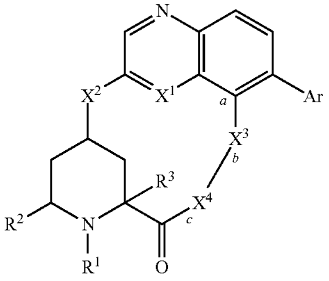

19 Claims, No Drawings

(56) References Cited

OTHER PUBLICATIONS

International Preliminary Report on Patentability and English translation of the Written Opinion of the International Searching Authority for International Application No. PCT/JP2020/037046, dated Mar. 28, 2023.
International Search Report and Written Opinion of the International Searching Authority for International Application No. PCT/JP2020/037046, dated Dec. 1, 2020.
Jain et al., "IL-1 receptor-associated kinase signaling and its role in inflammation, cancer progression, and therapy resistance," Frontiers in Immunology, Nov. 17, 2014, vol. 5, Article 553, pp. 1-8.
Koziczak-Holbro et al., "The Critical Role of Kinase Activity of Interleukin-1 Receptor-Associated Kinase 4 in Animal Models of Joint Inflammation," Arthritis & Rheumatism, vol. 60, No. 6, Jun. 2009, pp. 1661-1671.
McElroy, "Interleukin-1 receptor-associated kinase 4 (IRAK4) inhibitors: an updated patent review (2016-2018)," Expert Opinion on Therapeutic Patents, vol. 29, No. 4, 2019, pp. 243-259.
Picard et al., "Pyogenic Bacterial Infections in Humans with IRAK-4 Deficiency," Science, vol. 299, Mar. 28, 2003, pp. 2076-2079 (5 pages total).
Suzuki et al., "Severe impairment of Interleukin-1 and Toll-like receptor signalling in mice lacking IRAK-4," Nature, vol. 416, Apr. 18, 2002, pp. 750-754.
Wan et al., "Interleukin-1 Receptor-associated Kinase 2 Is Critical for Lipopolysaccharide-mediated Post-transcriptional Control," The Journal of Biological Chemistry, vol. 284, No. 16, Apr. 17, 2009, pp. 10367-10375.
Russian Office Action and Search Report for corresponding Russian Application No. 2023107545, dated Oct. 24, 2023, with English translation.
Bai et al., "The recent advance of Interleukin-1 receptor associated kinase 4 inhibitors for the treatment of inflammation and related diseases," European Journal of Medicinal Chemistry, vol. 258, 2023, pp. 1-21.
Chen et al., "Research progress of small molecule IRAK-4 inhibitors," Central South Pharmacy, vol. 13, No. 10, 2015, pp. 1017-1024, with an English abstract.
Chinese Office Action and Search Report for Chinese Application No. 202080105435.6, dated May 20, 2024.
Extended European Search Report for European Application No. 20956215.6, dated May 21, 2024.
Canadian Office Action for Canadian Application No. 3,194,090, dated Jun. 4, 2024.
Saudi Arabian Office Action for Saudi Arabian Application No. 523440073, dated Jan. 27, 2025, with an English translation.

MACROCYCLIC COMPOUND

TECHNICAL FIELD

The present invention relates to a novel macrocyclic compound, and a medicament containing it as an active ingredient.

BACKGROUND ART

Interleukin 1 receptor-associated kinase 4 (IRAK-4) is a protein-phosphorylating enzyme that plays an important role in downstream signaling of Toll-like receptors (TLRs), interleukin 1 receptor (IL-1R), IL-18R, and IL-33R (Non-patent document 1). Since the TLR/IL-1 receptor family has an important function for inflammation and biophylaxis, it is thought that the downstream signaling plays major roles in many diseases including inflammatory diseases and autoimmune diseases.

TLRs use pathogen-associated molecular patterns (PAMPs) derived from infectious microorganisms such as bacteria, fungi, parasites, and viruses as lig ands. They also recognize damage-associated molecular patterns (DAMPs) released from damaged cells or apoptosizing cells, and are activated. If a lig and binds with TLRs or IL-1 receptor family members, an adaptor molecule, MyD88, is recruited in a common intracellular region called TIR (Toll/IL-1 receptor) region. It is thought that IRAK-4 is recruited to the receptors through the interaction with MyD88, and the downstream signaling is started (Non-patent document 2). IRAK-4 activates IRAK-1 and IRAK-2, and further controls the production of inflammatory mediators such as cytokines and chemokines via activation of signaling molecules in the downstream such as NF—KB and MAPK.

It has been reported that a human IRAK-4 gene-deficient cell does not react to agonists for TLRs other than $TLR^3$, IL-1β and IL-18 (Non-patent document 3). An IRAK-4 gene-deficient mouse also does not react to agonists for TLRs other than $TLR^3$, IL-1β and IL-18 (Non-patent document 4). On the other hand, in IRAK-1 gene-deficient mice and IRAK-2 gene-deficient mice, only a partial suppression of these signals is observed (Non-patent document 5). For this reason, it is thought that, among the IRAK family members, IRAK-4 bears the most important role in these signal transductions. It has been reported that, in kinase activity-deficient IRAK-4 knock-in mice, severities of arthritis, experimental autoallergic encephalomyelitis, and arteriosclerosis model are suppressed compared with those in wild-type mice (Non-patent document 6). Therefore, the kinase activity of IRAK-4 is indispensable for the signal transductions responsible for pathology, and IRAK-4 inhibitors may exhibit superior effectiveness for therapeutic treatment of autoimmune diseases such as acute and chronic inflammations, rheumatoid arthritis, and systemic erythematodes, metabolic disorders such as gout and diabetes, and such diseases as tumors.

As compounds having an IRAK-4 inhibitory activity, there are known, for example, the compounds described in Patent documents 1 to 6.

PRIOR ART REFERENCES

Patent Documents

Patent document 1: International Patent Publication WO2016/144846

Patent document 2: International Patent Publication WO2016/053771

Patent document 3: International Patent Publication WO2015/048281

Patent document 4: International Patent Publication WO2013/042137

Patent document 5: International Patent Publication WO2012/068546

Patent document 6: International Patent Publication WO2015/150995

Non-Patent Documents

Non-patent document 1: Flannery S. & Bowie A. G., Biochemical Pharmacology, 80 (2010) 1981-1991

Non-patent document 2: Jain A. et al., Froniters in Immunology, 5 (2014) Article 553

Non-patent document 3: Picad C. et al., Science, 299 (2003) 2076-2079

Non-patent document 4: Suzuki N. et al., Nature, 416 (2002) 750-754

Non-patent-document 5: Wan Y. et al., J. Biol. Chem., 284 (2009) 10367-10375

Non-patent-document 6: Koziczak-Holbro M. et al., Arthritis & Rheumatism, 60 (2009) 1661-1671

SUMMARY OF THE INVENTION

Object to be Achieved by the Invention

An object of the present invention is to provide a novel compound that has an IRAK-4 inhibitory activity. Another object of the present invention is to provide a novel compound useful as an active ingredient of a medicament for prophylactic and/or therapeutic treatment of a disease relating to IRAK-4 inhibition. Yet another object of the present invention is to provide a medicament containing the compound.

Means for Achieving the Objects

The inventors of the present invention conducted various researches in order to achieve the aforementioned objects. As a result, they found that the compounds of the present invention represented by the following formula (1) have a superior IRAK-4 inhibitory activity, and these compounds are useful for prophylactic and/or therapeutic treatment of a disease relating to IRAK-4 inhibition, and accomplished the present invention.

The present invention is thus embodied, for example, as follows.

[1] A compound represented by the following general formula (1):

[Formula 1]

(1)

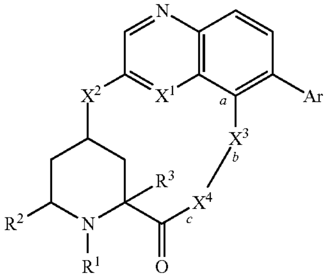

[in the formula (1), $R^1$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —C(O)$R^{12}$, —S($O_2$)$R^{12}$, —C(O)N$R^{11}R^{12}$, —C(O) O$R^{12}$, or a 3- to 7-membered saturated ring group, $R^1$ may be substituted with the same or different 1 to 3 substituents selected from the group $G^1$;

the group $G^1$ is a group consisting of —F, hydroxy, cyano, halogeno-$C_{1-6}$ alkyl, $C_{1-4}$ alkoxy, phenyl, 5- or 6-membered heteroaryl, and a 3- to 7-membered saturated ring group, the phenyl and 5- or 6-membered heteroaryl included in the group $G^1$ may be substituted with the same or different 1 to 3 substituents selected from the group $G^{Ar}$;

the group $G^{Ar}$ is a group consisting of —F, —Cl, hydroxy, cyano, $C_{1-6}$ alkyl, halogeno-$C_{1-6}$ alkyl, and —$NH_2$;

$R^{11}$ is —H, $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, or a 3- to 7-membered saturated ring group;

$R^{12}$ is $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, a 3- to 7-membered saturated ring group, phenyl, or 5- or 6-membered heteroaryl, the phenyl and 5- or 6-membered heteroaryl as $R^{12}$ may be substituted with the same or different 1 to 3 substituents selected from the group $G^{Ar}$;

$R^2$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, or a 3- to 7-membered saturated ring group;

$R^3$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, or a 3- to 7-membered saturated ring group;

Ar is 6- to 10-membered aryl or 5- to 10-membered heteroaryl, Ar may be substituted with the same or different 1 to 3 substituents selected from the group $G^2$;

the group $G^2$ is a group consisting of —F, —Cl, hydroxy, cyano, $C_{1-6}$ alkyl, halogeno-$C_{1-6}$ alkyl, hydroxy-$C_{1-6}$ alkyl, $R^{Ar1}$—O—$C_{1-3}$ alkyl, $R^{Ar1}$—N$R^{13}$—$C_{1-3}$ alkyl, —N$R^{13}$C(O)$R^{14}$, —C(O)N$R^{13}R^{14}$, —C(O)$NH_2$, —N$R^{13}$S($O_2$)$R^{14}$, —S($O_2$) N$R^{13}R^{14}$, —$NH_2$, —S($O_2$) $NH_2$, —N$R^{13}R^{14}$, and —NHC(O)NH$R^{15}$;

$R^{Ar1}$ is —H, $C_{1-6}$ alkyl, halogeno-$C_{1-6}$ alkyl, or a 3- to 7-membered saturated ring group, $R^{Ar1}$ may be substituted with the same or different 1 to 3 substituents selected from the group $G^3$;

the group $G^3$ is a group consisting of —F, hydroxy, $C_{1-3}$ alkyl, halogeno-$C_{1-3}$ alkyl, oxo, $C_{1-3}$ alkoxy, halogeno-$C_{1-3}$ alkoxy, and a 3- to 7-membered saturated ring group;

$R^{13}$ is —H, $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_{1-3}$ alkyl, or a 3- to 7-membered saturated ring group;

$R^{14}$ is $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_{1-3}$ alkyl, or a 3- to 7-membered saturated ring group;

$R^{15}$ is —H, phenyl, or 5- or 6-membered heteroaryl, $R^{15}$ may be substituted with the same or different 1 to 3 substituents selected from the group $G^4$;

the group $G^4$ is a group consisting of halogen, cyano, $C_{1-3}$ alkyl, and halogeno-$C_{1-3}$ alkyl;

$X^1$ is N or CH;

$X^2$ is NH or O;

$X^3$ is a group represented by the following general formula (1-1):

[Formula 2]

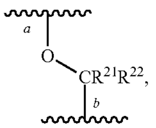

(1-1)

the following general formula (1-2):

[Formula 3]

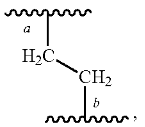

(1-2)

the following general formula (1-3):

[Formula 4]

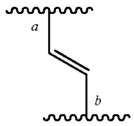

(1-3)

(a and b represent direction of bonding), $R^{21}$ and $R^{22}$ are independently —H, $C_{1-3}$ alkyl, or halogeno-$C_{1-3}$ alkyl;

$X^4$ is a group represented by the following general formula (2-1):

[Formula 5]

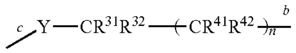

(2-1)

(b and c represent direction of bonding);

in the formula (2-1), n is an integer of 1 to 3;

Y is N$R^{51}$ or O;

$R^{31}$ and $R^{32}$ are independently —H, $C_{1-3}$ alkyl, or halogeno-$C_{1-3}$ alkyl; or $R^{31}$ and $R^{32}$ may combine to form a 3- to 6-membered saturated ring;

$R^{41}$ and $R^{42}$ are independently —H, —F, hydroxy, $C_{1-3}$ alkyl, halogeno-$C_{1-3}$ alkyl, $C_{1-3}$ alkoxy, or halogeno-$C_{1-3}$ alkoxy; or $R^{41}$ and $R^{42}$ may combine to form a 3- to 6-membered saturated ring;

$R^{51}$ is —H, $C_{1-3}$ alkyl, or halogeno-$C_{1-3}$ alkyl; or $R^{51}$ and $R^{31}$ may combine to form a 4- to 6-membered saturated ring;

$X^4$ may be substituted with the same or different 1 to 3 substituents selected from the group $G^5$; and the group $G^5$ is a group consisting of —F, hydroxy, $C_{1-3}$ alkyl, halogeno-$C_{1-3}$ alkyl, $C_{1-3}$ alkoxy, and halogeno-$C_{1-3}$ alkoxy], or a salt thereof.

[2] The compound or a salt thereof according to [1], wherein Ar is 5- or 6-membered heteroaryl.

[2-2] The compound or a salt thereof according to [1] mentioned above, wherein Ar is thienyl, thiazolyl, isothiazolyl, pyrrolyl, pyrazolyl, imidazolyl, pyridyl, pyrimidinyl, or pyrazinyl.

[2-3] The compound or a salt thereof according to [1] mentioned above, wherein Ar is thiazolyl, isothiazolyl, pyrazolyl, imidazolyl, pyridyl, pyrimidinyl, or pyrazinyl.

[2-4] The compound or a salt thereof according to [1] mentioned above, wherein Ar is thiazolyl, isothiazolyl, pyridyl, or pyrimidinyl.

[2-5] The compound or a salt thereof according to [1] mentioned above, wherein Ar is thiazolyl, or pyrimidinyl.

[3] The compound or a salt thereof according to [1] or [2] mentioned above, wherein $R^1$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, or a 3-to 7-membered saturated ring group, and $R^1$ may be substituted with the same or different 1 to 3 substituents selected from the group $G^1$ (the group $G^1$ has the same meaning as that defined above).

[3-2] The compound or a salt thereof according to [1] or [2] mentioned above, wherein $R^1$ is —H, $C_{1-6}$ alkyl, halogeno-$C_{1-6}$ alkyl, $C_{1-6}$ alkoxy-$C_{1-6}$ alkyl, or a 3- to 7-membered saturated ring group, and $R^1$ may be substituted with the same or different 1 to 3 substituents selected from the group $G^1$ (the group $G^1$ has the same meaning as that defined above).

[3-3] The compound or a salt thereof according to [1] or [2] mentioned above, wherein $R^1$ is —H, $C_{1-6}$ alkyl, or a 3- to 7-membered saturated ring group, and $R^1$ may be substituted with the same or different 1 to 3 substituents selected from the group $G^1$ (the group $G^1$ has the same meaning as that defined above).

[4] The compound or a salt thereof according to any one of [1] to [3-3] mentioned above, wherein $X^2$ is NH.

When the cited item numbers are indicated with a range such as “[1] to [3-3]mentioned above”, and an item having a subnumber such as [3-2] is included in such a range, it is meant that the item assigned with the subnumber such as [3-2] is also cited.

The same shall apply to the following descriptions.

[5] The compound or a salt thereof according to any one of [1] to [4] mentioned above, wherein $X^3$ is a group represented by the following general formula (1-1):

[Formula 6]

(1-1)

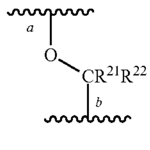

($R^{21}$ and $R^{22}$ have the same meanings as those defined above).

[6] The compound or a salt thereof according to any one of [1] to [5] mentioned above, wherein $X^3$ is a group represented by the following general formula (1-1-1):

[Formula 7]

(1-1-1)

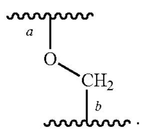

[7] The compound or a salt thereof according to any one of [1] to [6] mentioned above, wherein, in the general formula (2-1) for $X^4$, n is 1.

[8] The compound or a salt thereof according to any one of [1] to [8] mentioned above, wherein Ar is a group represented by the following general formula (3-1):

[Formula 8]

(3-1)

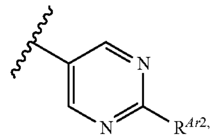

in the formula (3-1), $R^{Ar2}$ is —H, —F, —Cl, hydroxy, cyano, $C_{1-6}$ alkyl, halogeno-$C_{1-6}$ alkyl, hydroxy-$C_1$-alkyl, $R^{Ar1}$—O—$C_{1-3}$ alkyl, or—$NR^{13}R^{14}$ ($R^{Ar1}$, $R^{13}$, and $R^{14}$ have the same meanings as those defined above).

[8-2] The compound or a salt thereof according to any one of [1] to [7] mentioned above, wherein Ar is a group represented by the general formula (3-1), and, in the formula (3-1), $R^{Ar2}$ is —H, $C_{1-6}$ alkyl, hydroxy-$C_{1-6}$ alkyl, or $R^{Ar1}$—O—$C_{1-3}$ alkyl ($R^{Ar1}$ has the same meaning as that defined above).

[8-3] The compound or a salt thereof according to any one of [1] to [8] mentioned above, wherein Ar is a group represented by the general formula (3-1), and, in the formula (3-1), $R^{Ar2}$ is $R^{Ar1}$—O—$C_{1-3}$ alkyl ($R^{Ar1}$ has the same meaning as that defined above).

[8-4] The compound or a salt thereof according to any one of [1] to [8] mentioned above, wherein Ar is a group represented by the general formula (3-1), in the formula (3-1), $R^{Ar2}$ is $R^{Ar1}$—O—$C_{1-3}$ alkyl ($R^{Ar1}$ has the same meaning as that defined above), $R^{Ar1}$ is $C_{1-6}$ alkyl or a 3- to 7-membered saturated ring group, and $R^{Ar1}$ may be substituted with the same or different 1 to 3 substituents selected from the group $G^3$ (the group $G^3$ has the same meaning as that defined above).

[8-5] The compound or a salt thereof according to any one of [1] to [8] mentioned above, wherein Ar is a group represented by the general formula (3-1), in the formula (3-1), $R^{Ar2}$ is $R^{Ar1}$—O—$C_{1-3}$ alkyl ($R^{Ar1}$ has the same meaning as that defined above), $R^{Ar1}$ is $C_{1-6}$ alkyl, and $R^{Ar1}$ may be substituted with the same or different 1 to 3 substituents selected from the group $G^3$ (the group $G^3$ has the same meaning as that defined above). [8-6] The compound or a salt thereof according to any one of [1] to [8] mentioned above, wherein Ar is a group represented by the general formula (3-1), in the formula (3-1), $R^{Ar2}$ is $R^{Ar1}$—O—$C_{1-3}$ alkyl ($R^{Ar1}$ has the same meaning as that defined above), $R^{Ar1}$ is a 3-to 7-membered saturated ring group, and $R^{Ar1}$ may be substituted with the same or different 1 to 3 substituents selected from the group $G^3$ (the group $G^3$ has the same meaning as that defined above).

[8-7] The compound or a salt thereof according to any one of [1] to [7] mentioned above, wherein Ar is a group represented by the general formula (3-1), in the formula (3-1), $R^{Ar2}$ is $R^{Ar1}$—O—$C_{1-3}$ alkyl ($R^{Ar1}$ has the same meaning as that defined above), $R^{Ar1}$ is $C_{3-7}$ cycloalkyl, and $R^{Ar1}$ may be substituted with the same or different 1 to 3 substituents selected from the group $G^3$ (the group $G^3$ has the same meaning as that defined above).

[9] The compound or a salt thereof according to any one of [1] to [8-7] mentioned above, wherein Ar is a group represented by the general formula (3-1); and in the formula (3-1), $R^{Ar2}$ is —H, methyl, hydroxymethyl, —$CH_2$—O—$R^{Ar1}$ ($R^{Ar1}$ has the same meaning as that defined above).

[9-2] The compound or a salt thereof according to any one of [1] to [8-7] mentioned above, wherein Ar is a group represented by the general formula (3-1), in the formula (3-1), $R^{Ar2}$ is $R^{Ar1}$—O—$CH_2$—($R^{Ar1}$ has the same meaning as that defined above), $R^{Ar1}$ is $C_{1-6}$ alkyl or a 3- to 7-membered saturated ring group, and $R^{Ar1}$ may be substituted with the same or different 1 to 3 substituents selected from the group $G^3$ (the group $G^3$ has the same meaning as that defined above).

[9-3] The compound or a salt thereof according to any one of [1] to [8-7] mentioned above, wherein Ar is a group represented by the general formula (3-1), in the formula (3-1), $R^{Ar2}$ is $R^{Ar1}$—O—$CH_2$—($R^{Ar1}$ has the same meaning as that defined above), $R^{Ar1}$ is $C_{1-6}$ alkyl, and $R^{Ar1}$ may be substituted with the same or different 1 to 3 substituents selected from the group $G^3$ (the group $G^3$ has the same meaning as that defined above).

[9-4] The compound or a salt thereof according to any one of [1] to [8-7] mentioned above, wherein Ar is a group represented by the general formula (3-1), in the formula (3-1), $R^{Ar2}$ is $R^{Ar1}$—O—$CH_2$—($R^{Ar1}$ has the same meaning as that defined above), $R^{Ar1}$ is a 3- to 7-membered saturated ring group, and $R^{Ar1}$ may be substituted with the same or different 1 to 3 substituents selected from the group $G^3$ (the group $G^3$ has the same meaning as that defined above).

[9-5] The compound or a salt thereof according to any one of [1] to [8-7] mentioned above, wherein Ar is a group represented by the general formula (3-1), in the formula (3-1), $R^{Ar2}$ is $R^{Ar1}$—O—$CH_2$—($R^{Ar1}$ has the same meaning as that defined above), $R^{Ar1}$ is $C_{3-7}$ cycloalkyl, and $R^{Ar1}$ may be substituted with the same or different 1 to 3 substituents selected from the group $G^3$ (the group $G^3$ has the same meaning as that defined above).

[9-6] The compound or a salt thereof according to any one of [1] to [8-7] mentioned above, wherein Ar is a group represented by the general formula (3-1), and in the formula (3-1), $R^{Ar2}$ is methyl or hydroxymethyl.

[9-7] The compound or a salt thereof according to any one of [1] to [8-7] mentioned above, wherein Ar is a group represented by the general formula (3-1), and in the formula (3-1), $R^{Ar2}$ is methyl.

[9-8] The compound or a salt thereof according to any one of [1] to [8-7] mentioned above, wherein Ar is a group represented by the general formula (3-1), and in the formula (3-1), $R^{Ar2}$ is hydroxymethyl.

The compound or a salt thereof according to any one of [1] to [9-8] mentioned above, wherein $R^3$ is —H.

The compound or a salt thereof according to any one of [1] to mentioned above, wherein $R^2$ is —H or methyl.

The compound or a salt thereof according to any one of [1] to mentioned above, wherein $R^1$ is —H or $C_{1-3}$ alkyl.

[12-2] The compound or a salt thereof according to any one of [1] to mentioned above, wherein $R^1$ is —H.

[12-3] The compound or a salt thereof according to any one of [1] to mentioned above, wherein $R^1$ is $C_{1-3}$ alkyl.

[12-4] The compound or a salt thereof according to any one of [1] to mentioned above, wherein $R^1$ is methyl or ethyl.

[12-5] The compound or a salt thereof according to any one of [1] to mentioned above, wherein $R^1$ is methyl.

[12-6] The compound or a salt thereof according to any one of [1] to mentioned above, wherein $R^1$ is ethyl.

[13] A compound represented by the following formula:

[Formula 9]

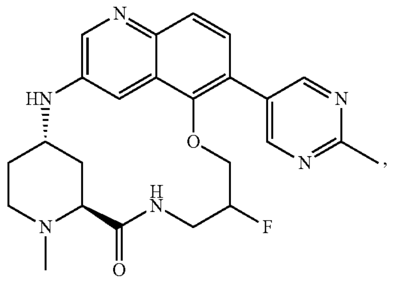

or a salt thereof.

[14] A compound represented by the following formula:

[Formula 10]

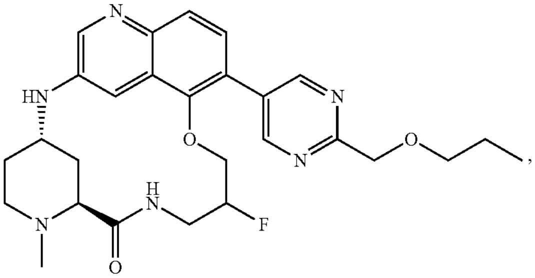

or a salt thereof.

[15] A compound represented by the following formula:

[Formula 11]

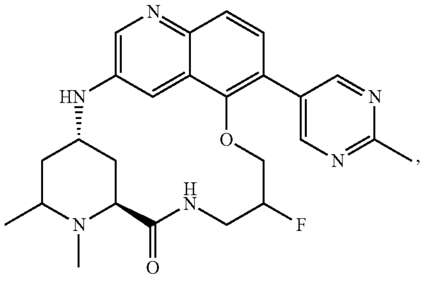

or a salt thereof.

A compound represented by the following formula:

[Formula 12]

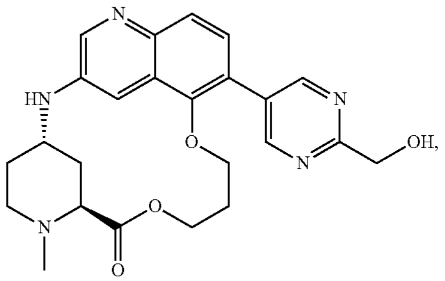

or a salt thereof.

A compound represented by the following formula:

Formula 13

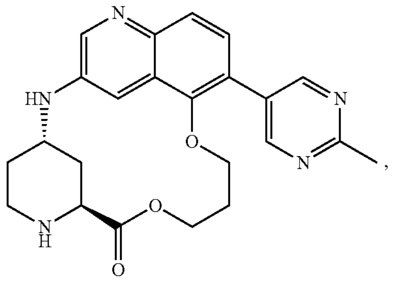

or a salt thereof.

A compound represented by the following formula:

[Formula 14]

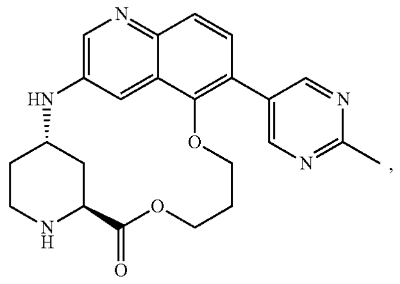

or a salt thereof.

A compound represented by the following formula:

[Formula 15]

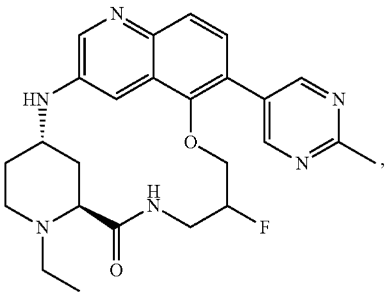

or a salt thereof.

[20] A medicament containing the compound according to any one of [1] to mentioned above, or a pharmaceutically acceptable salt thereof as an active ingredient.

[21] The medicament according to mentioned above, which is for prophylactic and/or therapeutic treatment of a disease relating to inhibition of IRAK4.

[22] The medicament according to mentioned above, which is for prophylactic and/or therapeutic treatment of rheumatism.

[23] An IRAK4 inhibitor containing the compound according to any one of [1] to mentioned above, or a pharmaceutically acceptable salt thereof as an active ingredient.

[24] A pharmaceutical composition for prophylactic and/or therapeutic treatment of rheumatism, which contains the compound according to any one of [1] to mentioned above, or a pharmaceutically acceptable salt thereof, and a pharmaceutically acceptable carrier.

[25] The compound according to any one of [1] to mentioned above, or a pharmaceutically acceptable salt thereof, which is used for prophylactic and/or therapeutic treatment of rheumatism.

[26] A method for prophylactic and/or therapeutic treatment of rheumatism in a mammal, which comprises the step of administrating an effective amount of the compound according to any one of [1] to mentioned above, or a pharmaceutically acceptable salt thereof to the mammal.

Effect of the Invention

The "compounds represented by the formula (1) or a salt thereof" (henceforth also simply referred to as the "compounds of the present invention" have a superior IRAK-4 inhibitory activity. The compounds of the present invention according to a certain embodiment exhibit strong selectivity for other kinases, especially FLT3. Moreover, the compounds of the present invention according to a certain embodiment show low genetic toxicity. Furthermore, the compounds of the present invention according to a certain embodiment can be used as an active ingredient of a medicament for prophylactic and/or therapeutic treatment of a disease relating to IRAK-4 inhibition, for example, prophylactic and/or therapeutic treatment of an autoimmune disease. The compounds of the present invention according to a certain embodiment can also be used as a reagent having an IRAK-4 inhibitory activity.

MODES FOR CARRYING OUT THE INVENTION

Hereafter, the present invention will be specifically explained.

In the present specification, unless especially indicated, carbon atom may be simply represented as "C", hydrogen atom as H", oxygen atom as "O", sulfur atom as "S", and nitrogen atom as N". Further, carbonyl group may be simply represented as "—C(O)—", carboxyl group as "—COO—", sulfinyl group as "—S(O)—", sulfonyl group as "—$S(O)_2$—", ether bond as "—O—", and thioether bond as "—S—" (each "-" in these groups indicates a bond).

In this specification, alkyl may be a linear, branched, or cyclic saturated hydrocarbon group, or a combination of such groups, unless it is particularly indicated. Examples include, for example, methyl, ethyl, propyl, butyl, an isomer thereof [normal (n), iso, secondary (sec), tertiary (t) and the like], and cycloalkyl such as cyclopropyl and cyclobutyl. Examples of alkyl include alkyl having 1 to 6 carbon atoms. According to another embodiment, examples include alkyl having 1 to 3 carbon atoms. Alkyl having 1 to 6 carbon atoms may be indicated as $C_{1-6}$ alkyl.

"Alkoxy" may be linear, branched, or cyclic saturated alkyloxy, or a combination of such groups, unless it is especially indicated. Examples include, for example, methoxy, ethoxy, propoxy, butoxy, an isomer thereof [normal (n), iso, secondary (sec), tertiary (t) and the like], and cycloalkyloxy such as cyclopropoxy and cyclobutoxy. Examples of alkoxy include alkoxy having 1 to 6 carbon atoms. In another embodiment, examples include alkoxy having 1 to 3 carbon atoms. Alkoxy having 1 to 6 carbon atoms may be indicated as $C_{1-6}$ alkoxy.

"Alkylene" may be linear or branched alkylene. Examples include, for example, methylene, ethylene, propylene, butylene, methylmethylene, ethylmethylene, methylethylene, 1,2-dimethylethylene, 1,1,2,2-tetramethylethylene, and 1-methylbutylene. Examples of alkylene include alkylene having 1 to 6 carbon atoms. According to another embodiment, examples thereof include alkylene having 1 to 3 carbon atoms. Alkylene having 1 to 6 carbon atoms may be referred to as $C_{1-6}$ alkylene.

"Halogen" is fluoro (—F), chloro (—Cl), bromo (—Br), or iodo (—I). According to another embodiment, examples thereof include —F and —Cl. According to further another embodiment, examples thereof include —F. The term "halogeno-" means substitution with the same or different 1 to 7 halogens. According to another embodiment, it means substitution with the same or different 1 to 5 halogens. According to further another embodiment, it means substitution with 1 to 3 halogens. According to further another embodiment, it means substitution with 1 of halogen. Examples include substitution with—F.

The "aromatic ring" is not particularly limited so long as it is a ring having aromaticity, and examples include a monocyclic to tricyclic aromatic ring. Examples of the aromatic ring include an aromatic hydrocarbon ring and an aromatic heterocyclic ring. Specific examples thereof include benzene, naphthalene, phenanthrene, thiophene, furan, thiazole, isothiazole, oxazole, isoxazole, oxadiazole, pyrrole, pyrazole, imidazole, pyridine, pyrimidine, pyrazine, pyridazine, pyridone, pyrimidinone, indole, isoindole, indazole, quinoline, isoquinoline, benzimidazole, benzotriazole, benzothiophene, benzofuran, benzothiazole, phthalazine, quinoxaline, pyrrolopyridine, and carbazole.

Examples of the "aromatic ring group" include a monovalent group formed by eliminating one arbitrary hydrogen atom from an aromatic ring. The aromatic ring group may be a monocyclic to tricyclic aromatic ring group. Examples thereof include, for example, aryl and heteroaryl.

"Aryl" may be a monocyclic to tricyclic aromatic hydrocarbon ring group. The aryl may also be an aromatic hydrocarbon ring group condensed with a saturated hydrocarbon ring described later. Examples thereof include 6- to 14-membered aryl. According to another embodiment, examples thereof include 6- to 10-membered aryl. According to further another embodiment, examples thereof include 6-membered aryl. Specific examples thereof include phenyl, naphthyl, anthranyl, phenanthrenyl, fluorenyl, indanyl, and 1,2,3,4-tetrahydronaphthalenyl. According to another embodiment, examples thereof include phenyl, and according to still another embodiment, examples thereof include naphthyl. Indanyl and 1,2,3,4-tetrahydronaphthalenyl fall within the scope of 6- to 10-membered aryl.

"Heteroaryl" may be a monocyclic to tricyclic aromatic heterocyclic ring group containing 1 to 4 heteroatoms as ring-constituting atoms. Examples of heteroatom include O, S, and N. Examples thereof include 5- to 14-membered heteroaryl. According to another embodiment, examples thereof include 5- to 10-membered heteroaryl. According to further another embodiment, examples thereof include 5- or 6-membered heteroaryl. Specific examples thereof include thienyl, furanyl, thiazolyl, isothiazolyl, oxazolyl, isoxazolyl, oxadiazolyl, pyrrolyl, pyrazolyl, imidazolyl, pyridyl, pyrimidinyl, pyrazinyl, pyridazinyl, pyridon-yl, pyrimidinon-yl, indolyl, isoindolyl, indazolyl, quinolyl, isoquinolyl, benzimidazolyl, benzotriazolyl, benzothienyl, benzofuranyl, benzothiazolyl, phthalazinyl, quinoxalinyl, pyrrolopyridyl, and carbazolyl.

Examples of "saturated ring" include a saturated hydrocarbon ring and saturated heterocyclic ring. The saturated ring may have a crosslink, or condense with the aforementioned aromatic ring.

The "saturated hydrocarbon ring" may be a monocyclic to tricyclic saturated hydrocarbon ring. Examples thereof include a 3- to 10-membered saturated hydrocarbon ring. According to another embodiment, examples thereof include a 3- to 7-membered saturated hydrocarbon ring. According to further another embodiment, examples thereof include a 5 or 6-membered saturated hydrocarbon ring. The saturated hydrocarbon ring may contain a crosslink, and may condense with the aforementioned aromatic ring. Specific examples thereof include cyclopropane, cyclobutane, cyclopentane, cyclohexane, and adamantane.

The "saturated heterocyclic ring" may be a monocyclic to tricyclic saturated heterocyclic ring containing 1 to 4 heteroatoms as ring-constituting atoms. Examples of heteroatom include O, S, and N. Examples thereof include a 3- to 10-membered saturated heterocyclic ring. According to another embodiment, examples thereof include a 3- to 7-membered saturated heterocyclic ring. According to further another embodiment, examples thereof include a 5- or 6-membered saturated heterocyclic ring. This saturated heterocyclic ring may contain a crosslink, and may condense with the aforementioned aromatic ring. Specific examples thereof include tetrahydropyran, tetrahydrofuran, piperidine, pyrrolidine, azetidine, oxetane, aziridine, oxirane, tetrahydrothiopyran, tetrahydrothiophene, morpholine, oxazepane, and piperazine.

Examples of the "condensed ring" include a cyclic compound consisting of two or more rings bonding together so that the rings share two or more atoms, where the two or more rings are independently a 3- to 7-membered saturated ring. The condensed ring may contain 1 to 3 heteroatoms selected from O, S, and N. Examples of the condensed ring include a cyclic compound where two rings share two adjacent atoms.

Examples of the "spiro ring" include a cyclic compound consisting of two rings sharing one carbon atom, wherein the two rings are independently a 3- to 7-membered saturated ring. The spiro ring may contain 1 to 3 heteroatoms selected from O, S, and N. When the spiro ring is constituted by 7 to 11 atoms, this spiro ring may be referred to as 7- to 11-membered spiro ring. Examples of the spiro ring include a 7- to 13-membered spiro ring. According to another embodiment, examples thereof include a 7- to 11-membered spiro ring. According to further another embodiment, examples thereof include a 7- to 9-membered spiro ring.

Examples of the "saturated ring group" include a monovalent group formed by eliminating one arbitrary hydrogen atom from a saturated ring, and a divalent group formed by eliminating one each of hydrogen atom from two different ring-constituting atoms of a saturated ring. Examples thereof include a saturated hydrocarbon ring group and a saturated heterocyclic ring group. Examples thereof include a 3- to 10-membered saturated ring group. According to another embodiment, examples thereof include a 3- to 7-membered saturated ring group. According to further another embodiment, examples thereof include a 5- or 6-membered saturated ring group.

Examples of the "saturated hydrocarbon ring group" include a monovalent group formed by eliminating one arbitrary hydrogen atom from a saturated hydrocarbon ring, and a divalent group formed by eliminating one each of hydrogen atom from two different ring-constituting atoms of a saturated hydrocarbon ring. The saturated hydrocarbon ring group may be a monocyclic to tricyclic saturated hydrocarbon ring group. The saturated hydrocarbon ring group may contain a crosslink, and may condense with the aforementioned aromatic ring. Examples thereof include a 3- to 10-membered saturated hydrocarbon ring group. According to another embodiment, examples thereof include a 3- to 7-membered saturated hydrocarbon ring group. According to further another embodiment, examples thereof include a 5- or 6-membered saturated hydrocarbon ring group. Specific examples of the monovalent group include cyclopropyl, cyclobutyl, cyclopentyl, cyclohexyl, and adamantyl. Specific examples of the divalent group include a divalent group formed from any of the aforementioned specific examples of the monovalent group by further eliminating hydrogen atom from a ring-constituting atom other than the ring-constituting atom from which hydrogen atom has been eliminated when the monovalent group has been formed.

Examples of the "saturated heterocyclic ring group" include a monovalent group formed by eliminating one arbitrary hydrogen atom from a saturated heterocyclic ring, and a divalent group formed by eliminating one each of hydrogen atom from two different ring-constituting atoms of a saturated heterocyclic ring. The saturated heterocyclic ring group may be a monocyclic to tricyclic saturated heterocyclic ring group containing 1 to 4 heteroatoms as ring-constituting atoms. This saturated heterocyclic ring group may contain a crosslink, and may condense with the aforementioned aromatic ring. Examples of heteroatom include O, S, and N. Examples thereof include a 3- to 10-membered heterocyclic ring group. According to another embodiment, examples thereof include a 3- to 7-membered saturated heterocyclic ring group. According to further another embodiment, examples thereof include a 5- or 6-membered saturated heterocyclic ring group. Specific examples of the monovalent group include tetrahydropyranyl, tetrahydrofuranyl, piperidinyl, pyrrolidinyl, azetidinyl, oxetanyl, tetrahydrothiopyranyl, tetrahydrothienyl, morpholinyl, and piperazinyl.

The "partially unsaturated ring group" may be a saturated ring group a part of which is unsaturated, and examples include a partially unsaturated hydrocarbon ring group, and a partially unsaturated heterocyclic ring group. Examples include a 3- to 10-membered partially unsaturated ring group. According to another embodiment, examples thereof include a 3- to 7-membered partially unsaturated ring group. According to further another embodiment, examples thereof include a 5- or 6-membered partially unsaturated ring group.

The "partially unsaturated hydrocarbon ring group" may be a saturated hydrocarbon ring group a part of which is unsaturated. Specific examples thereof include cyclopentenyl, cyclopentadienyl, cyclohexenyl, cyclohexadienyl, and bicyclooctatrienyl.

The "partially unsaturated heterocyclic ring group" may be a saturated heterocyclic ring group a part of which is unsaturated. Specific examples thereof include dihydropyranyl, dihydrofuranyl, dihydrothiopyranyl, dihydrothienyl, 1,2-dihydroquinolyl, and 1,2,3,4-tetrahydroquinolyl.

In the present invention, all isomers are included, unless specifically indicated. For example, alkyl, alkenyl, alkynyl, alkoxy, alkylthio, alkylene, alkenylene, and alkynylene include linear and branched groups. Further, any of isomers based on a double bond, ring, or condensed ring (E- or Z-isomer, or cis - or trans-isomer), isomers based on the presence of an asymmetric carbon, or the like (R- or S-isomer, isomers based on α- or β-configuration, enantiomers, diastereomers, and the like), optically active substances having optical rotation (D- or L-isomer, or d- or 1-isomer), isomers based on polarity observed in chromatographic separation (high polarity isomer or low polarity isomer), equilibrated compounds, rotational isomers, mixtures of these isomers at arbitrary ratios, and racemates fall within the scope of the present invention.

In the present specification, as apparent for those skilled in the art, the symbol:

[Formula 16]

indicates that the bond is on the back of the plane (i.e., α-configuration), the symbol:

[Formula 17]

indicates that the bond is in front of the plane (i.e., β-configuration), and the symbol:

[Formula 18]

means α-configuration or β-configuration, or a mixture thereof, unless especially indicated.

Hereafter, the compounds represented by the formula (1) and a salt thereof will be explained in detail.

[Formula 19]

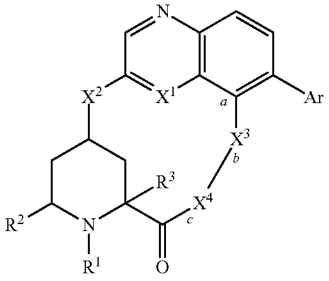

(1)

In this specification, the expression "may be substituted" means that the corresponding group has no substituent or the same or different 1 to 5 substituents, unless especially indicated. According to another embodiment, the expression means that the corresponding group has no substituent or the same or different 1 to 3 substituents. According to further another embodiment, the expression means that the corresponding group has no substituent or 1 substituent. According to further another embodiment, the expression means that the corresponding group has no substituent.

Examples of $R^1$ include —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —C(O)$R^{12}$, —S($O_2$)$R^{12}$, —C(O)$NR^{11}R^{12}$, —C(O) $OR^{12}$, and a 3- to 7-membered saturated ring group. According to another embodiment, examples thereof include —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, and a 3- to 7-membered saturated ring group. According to further another embodiment, examples thereof include —H, $C_{1-6}$ alkyl, and a 3- to 7-membered saturated ring group. According to further another embodiment, examples thereof include —H, methyl, and ethyl. According to further another embodiment, examples thereof include methyl.

$R^1$ may be substituted with the same or different 1 to 3 substituents selected from the group $G^1$.

Examples of the group $G^1$ include a group consisting of —F, hydroxy, cyano, halogeno-$C_{1-6}$ alkyl, $C_{1-4}$ alkoxy, phenyl, 5- or 6-membered heteroaryl, and a 3- to 7-membered saturated ring group. According to another embodiment, examples thereof include the group $G^{11}$ consisting of —F, hydroxy, halogeno-$C_{1-6}$ alkyl, $C_{1-4}$ alkoxy, and a 3- to 7-membered saturated ring group. According to further another embodiment, examples thereof include the group $G^{12}$ consisting of —F, hydroxy, $C_{1-4}$ alkoxy, and a 3-to 7-membered saturated ring group.

The phenyl and 5- or 6-membered heteroaryl included in the group $G^1$ may be substituted with the same or different 1 to 3 substituents selected from the group $G^{Ar}$.

Examples of the group $G^{Ar}$ include a group consisting of —F, —Cl, hydroxy, cyano, $C_{1-6}$ alkyl, halogeno-$C_{1-6}$ alkyl, and —$NH_2$. According to another embodiment, examples thereof include the group $G^{Ar1}$ consisting of —F, —Cl, cyano, $C_{1-6}$ alkyl, and halogeno-$C_{1-6}$ alkyl.

Examples of $R^{11}$ include —H, $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, and a 3- to 7-membered saturated ring group. According to another embodiment, examples thereof include $C_{1-6}$ alkyl, $C_{1-6}$ alkoxy-$C_{1-6}$ alkyl, and a 3- to 7-membered saturated ring group.

Examples of $R^{12}$ include $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, a 3- to 7-membered saturated ring group, phenyl, and 5- or 6-membered heteroaryl. According to another embodiment, examples thereof include $C_{1-6}$ alkyl, a 3- to 7-membered saturated ring group, phenyl, and 5- or 6-membered heteroaryl. According to further another embodiment, examples thereof include $C_{1-6}$ alkyl, and a 3- to 7-membered saturated ring group.

The phenyl and 5- or 6-membered heteroaryl as $R^{12}$ may be substituted with the same or different 1 to 3 substituents selected from the group $G^{Ar}$.

There is also exemplified another embodiment wherein the group $G^{Ar}$ is the group $G^{Ar1}$, in addition to the embodiment using the group $G^{Ar}$ mentioned above.

Examples of $R^2$ include —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, and a 3- to 7-membered saturated ring group. According to another embodiment, examples thereof include —H, $C_{1-6}$ alkyl, and a 3- to 7-membered saturated ring group. According to further another embodiment, examples thereof include —H, $C_{1-3}$ alkyl, and cyclopropyl. According to further another embodiment, examples thereof include —H, and methyl. According to further another embodiment, examples thereof include —H.

Examples of $R^3$ include —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, and a 3- to 7-membered saturated ring group. According to another embodiment, examples thereof include —H, $C_{1-6}$ alkyl, and a 3- to 7-membered saturated ring group. According to further another embodiment, examples thereof include —H, $C_{1-3}$ alkyl, and cyclopropyl. According to further another embodiment, examples thereof include —H and methyl. According to further another embodiment, examples thereof include —H.

Examples of Ar include 6- to 10-membered aryl and 5- to 10-membered heteroaryl. According to another embodiment, examples thereof include phenyl and 5- or 6-membered heteroaryl. According to further another embodiment, examples thereof include 5- or 6-membered heteroaryl.

Examples of the 6- to 10-membered aryl as Ar include phenyl, naphthyl, and indanyl. According to further another embodiment, examples thereof include phenyl.

Examples of the 5- to 10-membered heteroaryl as Ar include thienyl, furanyl, thiazolyl, isothiazolyl, oxazolyl, isoxazolyl, oxadiazolyl, pyrrolyl, pyrazolyl, imidazolyl, pyridyl, pyrimidinyl, pyrazinyl, pyridazinyl, pyridon-yl, pyrimidinon-yl, indolyl, isoindolyl, indazolyl, quinolyl, isoquinolyl, benzimidazolyl, benzotriazolyl, benzothienyl, benzofuranyl, benzothiazolyl, phthalazinyl, quinoxalinyl, and pyrrolopyridyl. According to another embodiment, examples thereof include thienyl, furanyl, thiazolyl, isothiazolyl, oxazolyl, isoxazolyl, oxadiazolyl, pyrrolyl, pyrazolyl, imidazolyl, pyridyl, pyrimidinyl, pyrazinyl, pyridazinyl, pyridon-yl, and pyrimidinon-yl. According to further another embodiment, examples thereof include thienyl, thiazolyl, isothiazolyl, pyrrolyl, pyrazolyl, imidazolyl, pyridyl, pyrimidinyl, and pyrazinyl. According to further another embodiment, examples thereof include thienyl, thiazolyl, isothiazolyl, pyrrolyl, imidazolyl, pyridyl, and pyrimidinyl. According to further another embodiment, examples thereof include thiazolyl, isothiazolyl, pyridyl, and pyrimidinyl. According to further another embodiment, examples thereof include thiazolyl and pyrimidinyl. According to further another embodiment, examples thereof include pyrimidinyl.

Ar may be substituted with the same or different 1 to 3 substituents selected from the group $G^2$.

Examples of the group $G^2$ include a group consisting of —F, —Cl, hydroxy, cyano, $C_{1-6}$ alkyl, halogeno-$C_{1-6}$ alkyl, hydroxy-$C_{1-6}$ alkyl, $R^{Ar1}$—O—$C_{1-3}$ alkyl, $R^{Ar1}$—$NR^{13}$—$C_{1-3}$ alkyl, —$NR^{13}C(O)R^{14}$, —$C(O)NR^{13}R^{14}$, —$C(O)NH_2$, —$NR^{13}S(O_2)R^{14}$, —$S(O_2)$ $NR^{13}R^{14}$, —$NH_2$, —$S(O_2)NH_2$, —$NR^{13}R^{14}$, and —$NHC(O)NHR^{15}$. According to another embodiment, examples thereof include the group $G^{21}$ consisting of $C_{1-6}$ alkyl, halogeno-$C_{1-6}$ alkyl, hydroxy-$C_{1-6}$ alkyl, and $R^{Ar1}$—O—$C_{1-3}$ alkyl. According to further another embodiment, examples thereof include the group $G^{22}$ consisting of $C_{1-6}$ alkyl, hydroxy-$C_{1-6}$ alkyl, and $R^{Ar1}$—O—$C_{1-3}$ alkyl. According to further another embodiment, examples thereof include the group $G^{22}$ consisting of $C_{1-6}$ alkyl, hydroxy-$C_{1-6}$ alkyl, and $R^{Ar1}$—O—$C_{1-3}$ alkyl. According to further another embodiment, examples thereof include $R^{Ar1}$—O—$C_{1-3}$ alkyl. According to further another embodiment, examples thereof include $R^{Ar1}$—O-methyl. According to further another embodiment, examples thereof include methyl.

Examples of $R^{Ar1}$ include —H, $C_{1-6}$ alkyl, halogeno-$C_{1-6}$ alkyl, and a 3- to 7-membered saturated ring group. According to another embodiment, examples thereof include $C_{1-6}$ alkyl, and a 3- to 7-membered saturated ring group. According to further another embodiment, examples thereof include $C_{1-6}$ alkyl. According to further another embodiment, examples thereof include normal propyl. According to further another embodiment, examples thereof include cyclobutyl and cyclopentyl. According to further another embodiment, examples thereof include cyclopentyl. According to further another embodiment, examples thereof include a 3- to 7-membered saturated ring group. Examples of the 3- to 7-membered saturated ring group include $C_{3-7}$ cycloalkyl and a 3- to 7-membered saturated heterocyclic ring group. Examples of the 3- to 7-membered saturated heterocyclic ring group include oxetanyl, azetidinyl, tetrahydrofuranyl, pyrrolidinyl, tetrahydrothienyl, tetrahydropyranyl, piperidinyl, tetrahydrothiopyranyl, morpholinyl, and piperazinyl. According to another embodiment, examples thereof include tetrahydrofuranyl.

$R^{Ar1}$ may be substituted with the same or different 1 to 3 substituents selected from the group $G^3$.

Examples of the group $G^3$ include a group consisting of —F, hydroxy, $C_{1-3}$ alkyl, halogeno-$C_{1-3}$ alkyl, oxo, $C_{1-3}$ alkoxy, halogeno-$C_{1-3}$ alkoxy, and a 3- to 7-membered saturated ring group. According to another embodiment, examples thereof include the group $G^{31}$ consisting of —F, hydroxy, and a 3- to 7-membered saturated ring group. According to further another embodiment, examples thereof include the group $G^{32}$ consisting of —F, hydroxy, $C_{1-3}$ alkyl, halogeno-$C_{1-3}$ alkyl, oxo, $C_{1-3}$ alkoxy, and a 3- to 7-membered saturated ring group. According to further another embodiment, examples thereof include the group $G^{33}$ consisting of —F, hydroxy, and $C_{3-7}$ cycloalkyl. According to further another embodiment, examples thereof include the group $G^{34}$ consisting of —F, hydroxy, and cyclopropyl.

Examples of $R^{13}$ include —H, $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_{1-3}$ alkyl, and a 3- to 7-membered saturated ring group. According to another embodiment, examples thereof include —H, $C_{1-3}$ alkyl, halogeno-$C_{1-3}$ alkyl, $C_{1-3}$ alkoxy-$C_{1-3}$ alkyl, and halogeno-$C_{1-3}$ alkyl. According to further another embodiment, examples thereof include a 3- to 7-membered saturated ring group.

Examples of $R^{14}$ include $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_{1-3}$ alkyl, and a 3- to 7-membered saturated ring group. According to another embodiment, examples thereof include $C_{1-3}$ alkyl, halogeno-$C_{1-3}$ alkyl, $C_{1-3}$ alkoxy-$C_{1-3}$ alkyl, and halogeno-$C_{1-3}$ alkyl. According to further another embodiment, examples thereof include a 3- to 7-membered saturated ring group. Examples of the 3- to 7-membered saturated ring group as $R^{13}$ and $R^{14}$ include $C_{3-7}$ cycloalkyl and a 3- to 7-membered saturated heterocyclic ring group. According to another embodiment, examples thereof include cyclopropyl, cyclobutyl, and oxetanyl. Examples of $R^{15}$ include —H, phenyl, and 5- or 6-membered heteroaryl.

Examples of 5- or 6-membered heteroaryl include thienyl, furanyl, thiazolyl, isothiazolyl, oxazolyl, isoxazolyl, oxadiazolyl, pyrrolyl, pyrazolyl, imidazolyl, pyridyl, pyrimidinyl, pyrazinyl, and pyridazinyl. According to another embodiment, examples of $R^{13}$ include phenyl and trifluoromethylphenyl.

$R^{15}$ may be substituted with the same or different 1 to 3 substituents selected from the group $G^4$.

Examples of the group $G^4$ include a group consisting of halogen, cyano, $C_{1-3}$ alkyl, and halogeno-$C_{1-3}$ alkyl. According to another embodiment, examples thereof include the group $G^{41}$ consisting of —F, cyano, methyl, and trifluoromethyl.

As another embodiment of Ar, there is exemplified a group represented by the formula (3-1).

[Formula 20]

(3-1)

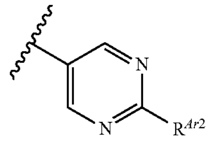

Examples of $R^{Ar2}$ include —H, —F, —Cl, hydroxy, cyano, $C_{1-6}$ alkyl, halogeno-$C_{1-6}$ alkyl, hydroxy-$C_{1-6}$ alkyl, $R^{Ar1}$—O—$C_{1-3}$ alkyl, and —$NR^{13}R^{14}$ ($R^{Ar1}$, $R^{13}$, and $R^{14}$ have the same meanings as those defined above). According to another embodiment, examples thereof include $R^{Ar1}$—O—$C_{1-3}$ alkyl. According to further another embodiment, examples thereof include —$CH_2$—O—$R^{Ar1}$ ($R^{Ar1}$ has the same meaning as that defined above). According to further another embodiment, examples thereof include methyl, and hydroxymethyl. According to further another embodiment, examples thereof include methyl. According to further another embodiment, examples thereof include hydroxymethyl.

Specific examples of $R^{Ar1}$—O—$C_{1-3}$ alkyl include the groups represented by the following formulas.

[Formula 21]

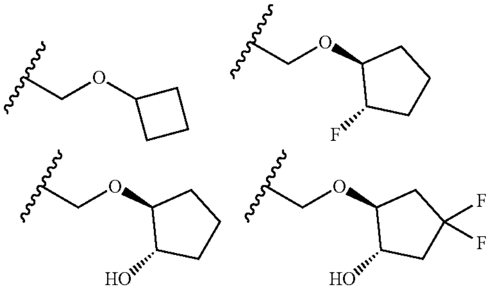

-continued

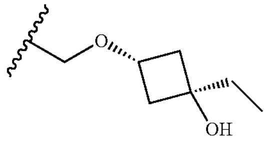

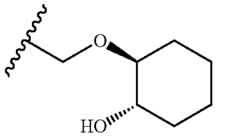

According to another embodiment, specific examples of $R^{Ar1}$—O—$C_{1-3}$ alkyl include the groups represented by the following formulas.

[Formula 22]

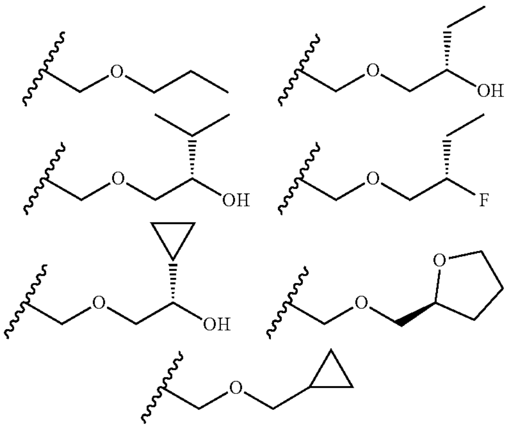

Examples of $X^1$ include N and CH. According to another embodiment, examples thereof include N. According to further another embodiment, examples thereof include CH.

Examples of $X^2$ include NH and O. According to another embodiment, examples thereof include NH.

Examples of $X^3$ include groups represented by the following general formula (1-1) to (1-3) (a and b represent direction of bonding).

[Formula 23]

(1-1)

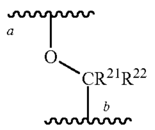

(1-2)

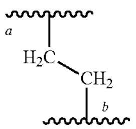

(1-3)

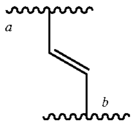

According to another embodiment, examples thereof include a group represented by the general formula (1-1). According to further another embodiment, examples thereof include a group represented by the following general formula (1-1-1).

[Formula 24]

(1-1-1)

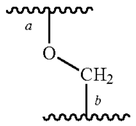

Examples of $R^{21}$ and $R^{22}$ independently include —H, $C_{1-3}$ alkyl, and halogeno-$C_{1-3}$ alkyl. According to another embodiment, examples thereof include —H and methyl. According to further another embodiment, examples thereof include —H.

Examples of $X^4$ include a group represented by the following general formula (2-1) (b and c represent direction of bonding).

[Formula 25]

(2-1)

$$_{c}\diagup Y—CR^{31}R^{32}—(CR^{41}R^{42})_n—^{b}$$

Examples of n include integers of 1 to 3. According to another embodiment, examples thereof include an integer of 1.

Examples of Y include $NR^{51}$ and O. According to another embodiment, examples thereof include $NR^{51}$. According to further another embodiment, examples thereof include O.

Examples of $R^{31}$ and $R^{32}$ independently include —H, $C_{1-3}$ alkyl, and halogeno-$C_{1-3}$ alkyl. According to another embodiment, examples thereof include —H and methyl. According to further another embodiment, examples thereof include —H.

$R^{31}$ and $R^{32}$ also can combine to form a 3- to 6-membered saturated ring. Examples of the 3- to 6-membered saturated ring include cyclopropyl, cyclobutyl, oxetanyl, cyclopentyl, cyclohexyl, tetrahydrofuranyl, and tetrahydropyranyl. According to another embodiment, examples thereof include cyclopropyl, cyclobutyl, and oxetanyl. According to further another embodiment, examples thereof include cyclopropyl and cyclobutyl.

Examples of $R^{41}$ and $R^{42}$ independently include —H, —F, hydroxy, $C_{1-3}$ alkyl, halogeno-$C_{1-3}$ alkyl, $C_{1-3}$ alkoxy, and halogeno-$C_{1-3}$ alkoxy. According to another embodiment, examples thereof include —H, —F, $C_{1-3}$ alkyl, halogeno-$C_{1-3}$ alkyl, $C_{1-3}$ alkoxy, and halogeno-$C_{1-3}$ alkoxy. According to further another embodiment, examples thereof include —H, —F, and $C_{1-3}$ alkyl. According to further another embodiment, examples thereof include —H, —F, and methyl. According to further another embodiment, examples thereof include —H and —F.

$R^{41}$ and $R^{42}$ also can combine to form a 3- to 6-membered saturated ring. Examples of the 3- to 6-membered saturated ring include cyclopropyl, cyclobutyl, oxetanyl, cyclopentyl, cyclohexyl, tetrahydrofuranyl, and tetrahydropyranyl. According to another embodiment, examples thereof include cyclopropyl, cyclobutyl, and oxetanyl. According to further another embodiment, examples thereof include cyclopropyl and cyclobutyl. According to further another embodiment, examples thereof include cyclopropyl.

Examples of $R^{51}$ include —H, $C_{1-3}$ alkyl, and halogeno-$C_{1-3}$ alkyl. According to another embodiment, examples thereof include —H and methyl. According to further another embodiment, examples thereof include —H.

$R^{51}$ and $R^{31}$ also can combine to form a 4- to 6-membered saturated ring. Examples of the 4- to 6-membered saturated ring include azetidinyl, pyrrolidinyl, and piperazinyl. According to further another embodiment, examples thereof include pyrrolidinyl.

$X^4$ may be substituted with the same or different 1 to 3 substituents selected from the group $G^5$.

Examples of the group $G^5$ include a group consisting of —F, hydroxy, $C_{1-3}$ alkyl, halogeno-$C_{1-3}$ alkyl, $C_{1-3}$ alkoxy, and halogeno-$C_{1-3}$ alkoxy. According to another embodiment, examples thereof include the group $G^{51}$ consisting of —F, hydroxy, and $C_{1-3}$ alkyl. According to further another embodiment, examples thereof include the group $G^{52}$ consisting of —F and hydroxy.

Specific examples of $X^4$ include, for example, the groups represented by the following formulas.

[Formula 26]

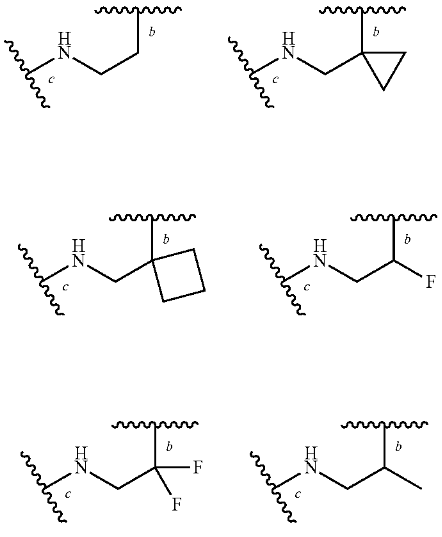

According to another embodiment, specific examples of $X^4$ include the groups represented by the following formulas.

[Formula 27]

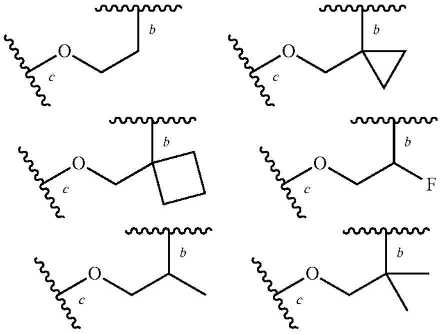

Specific examples of the compounds falling within the scope of the present invention include the following compounds. However, the scope of the present invention is not limited to these.

TABLE 1

| | |
|---|---|
| 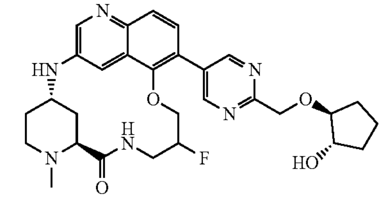 [SMILES: CN1CC[C@H]2C[C@H]1C(=O)NCC(F)COc1c(-c3cnc(CO[C@H]4CCC[C@@H]4O)nc3)ccc3ncc(cc13)N2] | Ref. 001 |
| 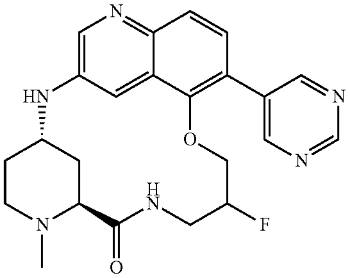 [SMILES: CN1CC[C@H]2C[C@H]1C(=O)NCC(F)COc1c(-c3cncnc3)ccc3ncc(cc13)N2] | Ref. 002 |
| 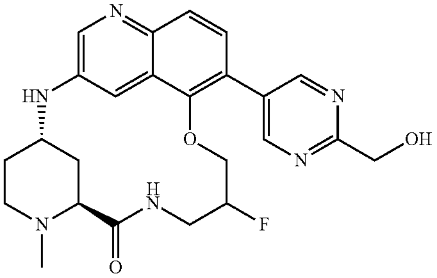 [SMILES: CN1CC[C@H]2C[C@H]1C(=O)NCC(F)COc1c(-c3cnc(CO)nc3)ccc3ncc(cc13)N2] | Ref. 003 |
| 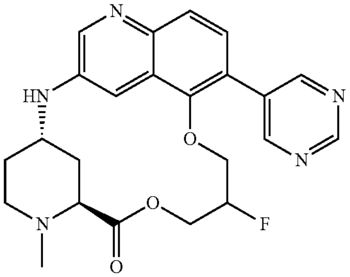 [SMILES: CN1CC[C@H]2C[C@H]1C(=O)OCC(F)COc1c(-c3cncnc3)ccc3ncc(cc13)N2] | Ref. 004 |
| 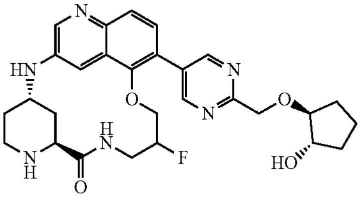 | Ref. 005 |
| 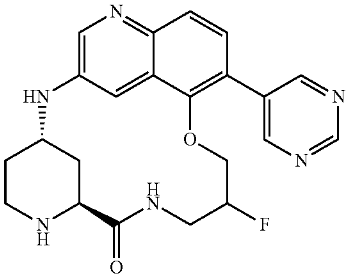 [SMILES: O=C1NCC(F)COc2c(-c3cncnc3)ccc3ncc(cc23)N[C@H]2CCN[C@H]1C2] | Ref. 006 |

TABLE 1-continued

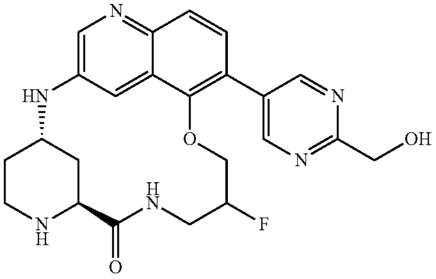 [SMILES: O=C1NCC(F)COc2c(-c3cnc(CO)nc3)ccc3ncc(cc23)N[C@H]2CCN[C@H]1C2]

Ref. 007

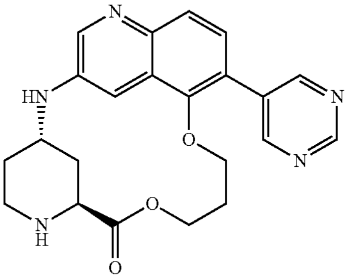 [SMILES: O=C1OCCCOc2c(-c3cncnc3)ccc3ncc(cc23)N[C@H]2CCN[C@H]1C2]

Ref. 008

In this specification, the "compounds represented by the formula (1)" are generally understood as the compounds represented by the formula (1) in the free form. Examples of the salt thereof include the following salts.

The type of the salt of the compounds represented by the formula (1) is not particularly limited, and it may be an acid addition salt, or a base addition salt, and may be in the form of an intramolecular counter ion. In particular, when the salt is used as an active ingredient of a medicament, the salt is preferably a pharmaceutically acceptable salt. When disclosure is made for use as a medicament in this specification, the salt of the compounds represented by the formula (1) is usually understood to be a pharmaceutically acceptable salt. Acid addition salts include, for example, acid addition salts with an inorganic acid such as hydrochloric acid, hydrobromic acid, hydroiodic acid, sulfuric acid, nitric acid, and phosphoric acid, and acid addition salts with an organic acid such as formic acid, acetic acid, propionic acid, oxalic acid, malonic acid, succinic acid, methanesulfonic acid, ethanesulfonic acid, benzenesulfonic acid, citric acid, malic acid, tartaric acid, dibenzoyltartaric acid, mandelic acid, maleic acid, fumaric acid, aspartic acid, and glutamic acid. As base addition salts, for example, base addition salts with an inorganic base such as sodium, potassium, magnesium, calcium, and aluminum, base addition salts with an organic base such as methylamine, 2-aminoethanol, arginine, lysine, and ornithine, and the like can be exemplified. However, the type of the salt is not limited to these, and it can of course be appropriately selected by those skilled in the art.

The compounds of the present invention may be in the form of hydrate. The compounds of the present invention may also be in the form of anhydride.

The compounds of the present invention may be in the form of solvate. The compounds of the present invention may also be in the form of non-solvate.

The compounds of the present invention may be in the form of crystal. The compounds of the present invention may also be in an amorphous form.

The compounds of the present invention may be labeled with any of various radioactive or non-radioactive isotopes.

More specifically, the compounds of the present invention include anhydrides and non-solvates of the "compounds represented by the formula (1)", hydrates and/or solvates thereof, and crystals thereof.

The compounds of the present invention also include anhydrides and non-solvates of "salts of the compounds represented by the formula (1)", hydrates and/or solvates of the salts, and crystals thereof.

The compounds of the present invention may also be a pharmaceutically acceptable prodrug of the "compounds represented by the formula (1)". The pharmaceutically acceptable prodrug is a compound having a group that can be changed into amino group, hydroxyl group, carboxyl group, or the like by solvolysis or under physiological conditions. For example, as a group that forms a prodrug for hydroxy group, or amino group, for example, an acyl group and an alkoxycarbonyl group are exemplified. As a group that forms a prodrug for carboxyl group, for example, methyl group, ethyl group, n-propyl group, isopropyl group, n-butyl group, isobutyl group, s-butyl group, t-butyl group, amino group, methylamino group, ethylamino group, dimethylamino group, and diethylamino group are exemplified.

Such a prodrug can be prepared by, for example, appropriately introducing a group that forms a prodrug into any of the compounds of the present invention at one or more arbitrary groups selected from hydroxyl group and amino group using a prodrug-forming reagent such as a corresponding halide in a conventional manner, then, if desired, appropriately isolating and purifying the compound in a conventional manner. A group that forms a prodrug can also be appropriately introduced into the compounds of the present invention at carboxyl group by using such a prodrug-forming reagent as a corresponding alcohol or amine in a conventional manner.

<General Preparation Methods>

The compounds represented by the formula (1) can be prepared according to known methods such as the methods described below, methods similar to these, or the methods described in the examples. The compounds used in the following preparation methods as starting materials are commercially available, or can be prepared by using known methods described in, for example, "Compendium of Organic Synthesis Methods, Vols. I to XII, Wiley Inter-Science".

Some of the intermediates can be used after introduction of protective groups or deprotection according to known methods, for example, the methods described in Peter G. M., Wuts, Greene's Protective Groups in Organic Chemistry, John Wiley & Sons, 2014".

A mixture of stereoisomers can be resolved by a known method, for example, the methods described in "E. L. Eloel, S. H. Wilen, Stereochemistry of Organic Compounds, John Wiley & Sons, 1994", methods similar to these, and the method described in the examples. Conglomerates can also be resolved by such methods as mentioned above.

The reactions for synthesizing the compounds of the present invention are performed in appropriate solvents selected according to known methods. The appropriate solvents do not substantially react with starting materials, intermediates, or products at the temperatures at which the reactions are performed (for example, temperatures in the range of from the melting point to the boiling point of the solvent). The reactions can be performed in a single kind of solvent or a mixed solvent. A solvent suitable for each reaction is used.

The reactions can be monitored by an appropriate method according to a known method. For example, a product can be monitored by a spectroscopic method using, for example, nuclear magnetic resonance (NMR) apparatus using $^1H$, $^{13}C$, or the like, infrared spectrophotometer (IR), mass spectrometer (MS), high speed liquid chromatography (HPLC), thin layer chromatography (TLC), or the like.

The compounds of the present invention may be prepared by any methods other than the methods described in this description by appropriately utilizing the methods described in this description and common general technical knowledge of this technical field. The reaction formulas and the examples are mentioned for the purpose of exemplification, and do not limit the scope of the present invention.

The abbreviations used in the schemes mentioned below are the abbreviations generally used in this technical field. The meanings of the abbreviations for chemical terms used in this specification including examples are defines as follows: DMF, N,N-dimethylformamide; DMSO, dimethyl sulfoxide; THF, tetrahydrofuran; DME, 1,2-dimethoxyethane; TFA, trifluoroacetic acid; h, hour; rt, room temperature; RT, retention time; LG, leaving group.

The compounds of the present invention represented by the formula (1) can be prepared in accordance with, for example, the following reaction schemes. In the following schemes, "STEP" means a process step, for example, "STEP 1" means step 1.

The macrocyclic compounds represented by the formula (1) consist of four parts, i.e., the nitrogen-containing bicyclic heterocyclic ring mother nucleus, substituted piperidine, linker connecting the a and c moieties, and aromatic ring directly bonded to the nitrogen-containing bicyclic heterocyclic ring mother nucleus.

The scheme 1 shows the first synthesis method of the macrocyclic compounds. This method is a method comprising first bonding the substituted piperidine and the linker connecting the a and c moieties, allowing the resultant to react with the nitrogen-containing bicyclic heterocyclic ring mother nucleus to form the $X^2$ bond, then forming the $X^3$ bond to form the macrocycle, and finally introducing the aromatic ring directly bonding to the nitrogen-containing bicyclic heterocyclic ring mother nucleus.

various types of coupling using ZnI, MgBr, boronic acid, boronic acid ester, or the like, LG1 and LG2 represent a leaving group such as —Cl, —B—Br, —I, —OTf, —OMs, —OMs, and —Ots, Q1 and Q2 represent, for example, hydroxyl group, a leaving group such as —Cl, —Br, —I, —OTf, —OMs, and —OTs, or a substituent capable of forming C—O or C—C bond such as an alkenyl group and borane derivative, and Q3 represents a substituent capable of forming C—O or C—N bond by a reaction with the LG2 group such as hydroxyl group and amino group). The compounds represented by the formulas (2) to (6) are commercially available, or can be produced according to known methods, for example, the methods shown below, or methods similar to these.

Step 1

The compounds represented by the formula (1) can be prepared by a coupling reaction with a compound represented by the formula (2) using a metal catalyst. More specifically, the compounds can be prepared by, for example, the Suzuki-Miyaura coupling of a compound represented by the formula (2) and a reagent represented by the formula (6). As the reaction catalyst, for example, $Pd(dppf)Cl_2$, PdAmphos, $Pd(PPh_3)_4$, or the like can be used. As the base, cesium carbonate, cesium fluoride, sodium carbonate, or the like can be used. As the reaction solvent, THE, 1,4-dioxane, DMF, acetonitrile, or the like can be used. The reaction temperature is usually from room temperature to 180° C.

As the reagent represented by the formula (6), commercially available boronic acid, pinacol esters, and catechol esters can be used. It can also be prepared from commercially available aryl bromide, aryl chloride, and aryl iodide compounds by a metal-catalyzed coupling reaction or halogen-metal exchange reaction. More specifically, it can be prepared by, for example, the Suzuki-Miyaura coupling with bis(pinacolato)diboron, or the like As the reaction catalyst, for example, $Pd(dppf)Cl_2$, or the like can be used. As the

SCHEME 1

[Formula 28]

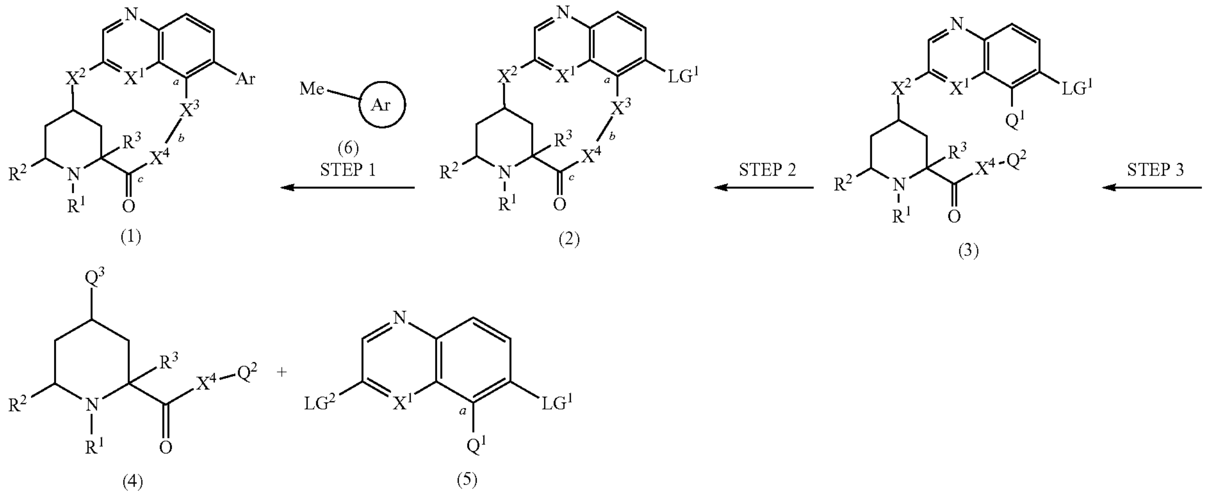

(1) (2) (3) (4) (5)

The compounds represented by the formula (1) can be prepared by, for example, the method described in the reaction scheme 1 (in the formulas of the compounds, M represents, for example, a substituent that can react through base, potassium acetate or the like can be used. As the reaction solvent, 1,4-dioxane or the like can be used. The reaction temperature can usually be 40 to 150° C. In addition to the above two kinds of methods, the reagent represented by the formula (6) can be prepared by a C—H activation type boronation reaction using an iridium catalyst, electron-donating bidentate ligand, and boron source such as bis (pinacolato)diboron without using aryl halides.

addition, the compound represented by the formula (3) can also be synthesized with a combination of reagents usually used in the Buchwald-Hartwig cross-coupling reaction in this field, and C—O or C—N bond can be thereby formed.

SCHEME 2

[Formula 29]

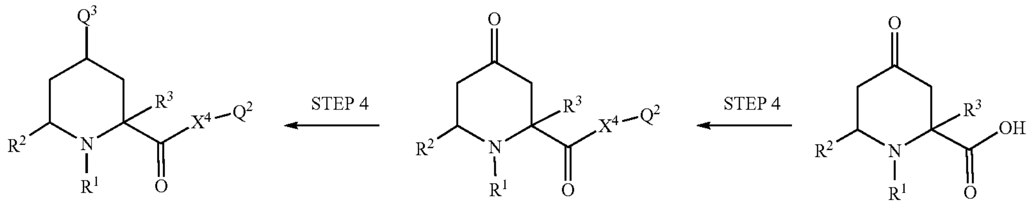

(4) (6) (7)

Step 2

The compound represented by the formula (2) can be prepared from a compound represented by the formula (3) by a C—O bond formation reaction such as alkylation and Mitsunobu reaction, or a C—C bond formation reaction such as metal coupling. In the Mitsunobu reaction, OH groups are prepared at the Q1 and Q2 moieties included in the formula (3), and the reaction is performed by adding diethyl azodicarboxylate, diisopropyl azodicarboxylate, or di-tert-butyl azodicarboxylate in the presence of triphenylphosphine. As the reaction solvent, THE, toluene, or the like can be used. To allow the intramolecular cyclization reaction to proceed in preference to the intermolecular reaction, the reaction is performed under a highly diluted condition of 0.1 to 0.001 mol/L. The reaction temperature can usually be room temperature to 80° C. The alkylation reaction can be carried out by preparing hydroxyl group at the Q' moiety and a leaving group such as —Cl, —Br, —I, —OTf, —OMs, or—OTs at the Q2 moiety, and allowing the reaction under a highly diluted condition in the presence of a base such as sodium hydride, potassium carbonate, cesium carbonate, or diisopropylethylamine. As the reaction solvent, THF, DMF, acetonitrile, or the like can be used. The reaction temperature can usually be from room temperature to 100° C.

Step 3

The compound represented by the formula (3) is synthesized by an alkylation reaction or metal coupling reaction of a substituted piperidine represented by the formula (4) and a compound represented by the formula (5). Specifically, the alkylation reaction can be carried out in the presence of a base such as sodium hydride, potassium carbonate, cesium carbonate, or diisopropylethylamine by using THE, DMF, acetonitrile, DMF, acetonitrile, or the like as the reaction solvent at room temperature to 100° C. to form C—O or C—N bond.

Specifically, in the metal coupling reaction, a mixture of [(2-di-tert-butylphosphino-3,6-dimethoxy-2',4',6'-triisopropyl-1,1'-biphenyl)-2-(2'-amino-1,1'-biphenyl)]palladium (II) methanesulfonate, or tris(dibenzylideneacetone) dipalladium (0) as the catalyst and dicyclohexylphosphino-2',4',6'-triisopropyl-1,1'-biphenyl as the ligand is added, and phosphazene base $P_2$-Et or sodium phenoxide is used as the base. As the reaction solvent, THF, 1,4-dioxane, DMF, acetonitrile, or the like can be used. The reaction temperature can be usually from room temperature to 180° C. In The compound represented by the formula (4) can be prepared by, for example, the method described in the reaction scheme 2 (in the formulas of the compounds, Q2 represents, for example, hydroxyl group, a leaving group such as —Cl, —Br, —I, —OTf, —OMs, and —OTs, or a substituent capable of forming C—O bond or C—C bond such as an alkenyl group and borane derivative, and Q3 represents a substituent capable of forming C—O bond or C—N bond by a reaction with the LG2 group such as hydroxyl group and amino group). The compounds represented by the formulas (6) and (7) are commercially available, or can be prepared according to known methods, e.g., the methods shown below, or methods similar to these.

Step 4

The compound represented by formula (4) is synthesized by reducing the ketone moiety of the compound represented by the formula (6). As the reducing agent, sodium borohydride, L-Selectolide, or the like that can reduce only the ketone moiety in the presence of an ester and amide can be used. The reaction is carried out by using methanol, THF, or the like as the solvent, and usually proceeds at −78° C. to room temperature. When the Q3 group is amino group, the hydroxyl group generated by the reduction is converted into a leaving group such as —Cl, —Br, —I, —OTf, —OMs, and —OTs, then converted into azido group, and finally converted into $NH_2$. For example, secondary hydroxyl group can be converted into a leaving group with methanesulfonyl chloride, p-toluenesulfonyl chloride or the like in the presence of a base such as triethylamine in dichloromethane solvent. The reaction usually proceeds at 0 to 40° C. By reacting the resultant with sodium azide in DMF, a $Q^3$ moiety-azidated compound can be obtained. The azido group can be reduced into primary amino group by hydrogenation using palladium-carbon or palladium hydroxide, or the Staudinger reaction using triphenylphosphine.

Step 5

The compound represented by the formula (6) is synthesized by amidation, esterification, or acylation of a compound represented by the formula (7). Specifically, a hydroxyl group-protected $C_{2-5}$ amino alcohol or a monohydroxyl group-protected $C_{2-5}$ diol is amide- or ester-bonded to the 4-oxopiperidine-2-carboxylic acid derivative represented by the formula (7). As the condensing agent for the amidation or esterification, 1-propanophosphonic anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be from 0 to 150° C. In the acylation reaction, the carboxylic acid moiety of the 4-oxopiperidine-2-carboxylic acid derivative can be activated by using oxalyl dichloride, isobutyl chloroformate, or the like, and then reacted with a hydroxyl group-protected $C_{2-5}$ amino alcohol or mono-hydroxyl group-protected $C_{2-5}$ diol to form an amide or ester bond.

The scheme 3 shows the second synthesis method of the macrocyclic compounds, which is a method as described below. First, the nitrogen-containing bicyclic heterocyclic ring mother nucleus is reacted with the substituted piperidine to form the $X^2$ bond, and the resultant is bonded with a linker connecting the a and c moieties. Then, as in the scheme 1, the final product is obtained through the formation of the macrocyclic ring and the introduction of the aromatic ring into the nitrogen-containing bicyclic heterocyclic ring mother nucleus.

The metal-catalyzed coupling reaction between the compound represented by the formula (2) and the reagent represented by the formula (6) (STEP 1) and the macrocycle formation reaction (STEP 2) using the compound represented by the formula (3) as the starting material are common to the methods of the schemes 1 and 3,.

Step 6

The compound represented by the formula (3) can be synthesized by amide- or ester-bonding a hydroxyl group-protected $C_{2-5}$ amino alcohol or mono-hydroxyl group-protected $C_{2-5}$ diol to a carboxylic acid represented by the formula (8). The reaction used is amidation reaction, esterification reaction, acylation reaction, or the like. As the condensing agent for the amidation or esterification, 1-propanephosphonic anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be from 0 to 150° C. In the acylation reaction, the carboxylic acid moiety can be activated by using oxalyl dichloride, isobutyl chloroformate, or the like, and reacted with a hydroxyl group-protected $C_{2-5}$ amino alcohol or mono-hydroxyl group-protected $C_{2-5}$ diol to form an amide or ester bond.

Step 7

The compound represented by the formula (8) is synthesized by alkylation or metal coupling reaction of a substituted piperidine represented by the formula (9) with a compound represented by the formula (5), and the following

SCHEME 3

[Formula 30]

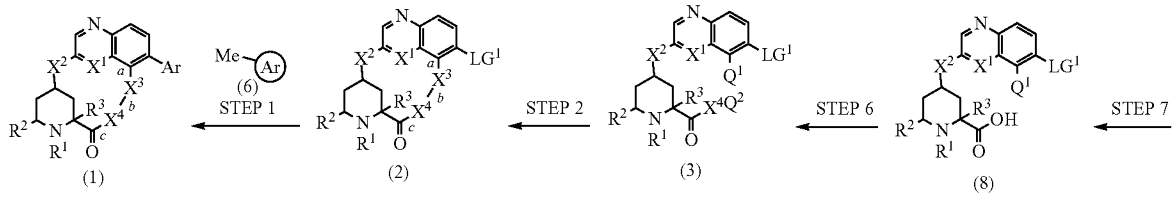

(1) (6) (2) (3) (8)

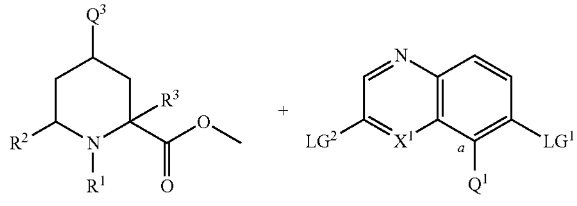

(9) + (5)

The compounds represented by the formula (1) can be prepared by, for example, the method described in the reaction scheme 3 (in the formulas of the compounds, M represents, for example, a substituent that can react through various types of coupling using ZnI, MgBr, boronic acid, boronic acid ester, or the like, LG1 and LG2 represent a leaving group such as —Cl, —Br, —I, —OTf, —OMs, and —Ots, $Q^1$ and $Q^2$ represent, for example, hydroxyl group, a leaving group such as —CI, —Br, —I, —OTf, —OMs, and —OTs, or a substituent capable of forming C—O or C—C bond such as an alkenyl group and borane derivative, and $Q^3$ represents a substituent capable of forming C—O or C—N bond by a reaction with the LG2 group such as hydroxyl group and amino group). The compounds represented by the formulas (2), (3), (5), (6), (8), and (9) are commercially available, or can be produced according to known methods, for example, the methods shown below, or methods similar to these.

solvolysis of the ester. The reaction conditions used for the alkylation and metal coupling reactions are similar to those used in the scheme 1, STEP 3. For the hydrolysis of the ester, a base such as sodium hydroxide, potassium hydroxide, and lithium hydroxide is used, and the reaction proceeds at 40 to 80° C. in a solvent such as methanol or ethanol. It is recommended to carry out the reaction at 40° C. in order to prevent isomerization of the chiral point at the 2-position of the piperidine. The compound represented by the formula (9) can be synthesized in the same manner as that of STEP 5 of the schemes 1 and 2. That is, it is synthesized from a 4-oxopiperidine-2-carboxylic acid derivative represented by the formula (7) used as the starting material by methyl esterification with trimethylsilyldiazomethane, or esterification using 1-propanephosphonic anhydride, 1-(3-dimethylaminopropyl)-3-ethylcarbodiidine, HATU or the like as the condensing agent.

The scheme 4 shows the third synthesis method of the macrocyclic compounds. In this method, the linker connecting the substituted piperidine and the a and c moieties is linked first, and then the resultant is reacted with the nitrogen-containing bicyclic heterocyclic mother nucleus to form the $X^3$ bond. Subsequently, the $X^2$ bond is formed to form the macrocycle, and finally, the aromatic ring to be directly bonded to the nitrogen-containing bicyclic heterocyclic mother nucleus is introduced.

of the scheme 1, but the reaction can be carried out under such a condition that the substrate concentration is, for example, 1.0 to 0.1 mol/L.

The preparation methods of the compounds of the present invention are not limited to the methods described herein. For example, the compounds of the present invention can be prepared by modifying or converting substituents of com-

SCHEME 4

[Formula 31]

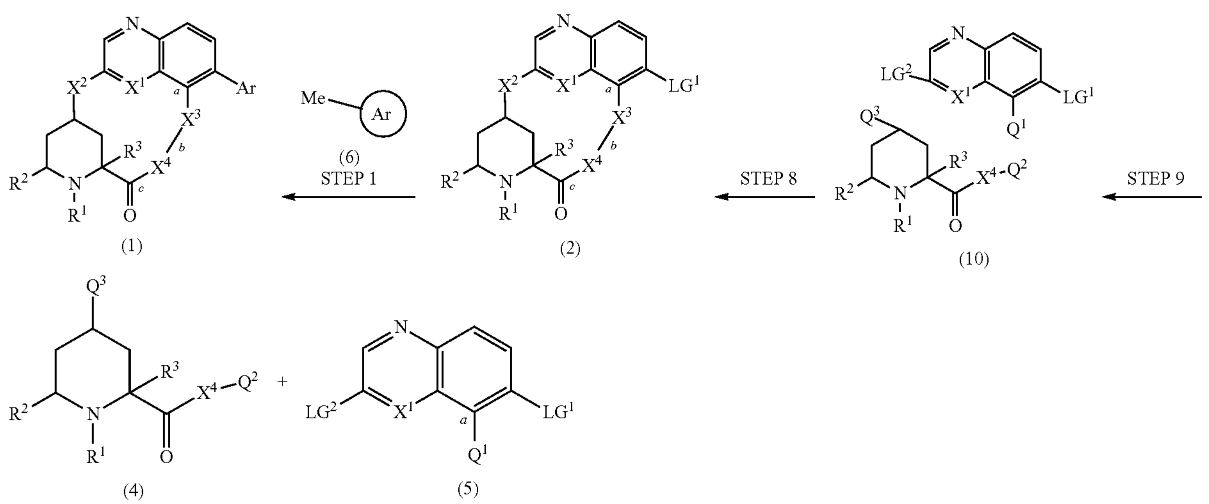

(1) (2) (10) (4) (5)

The compounds represented by the formula (1) can be prepared by, for example, the method described in the reaction scheme 4 (in the formulas of the compounds, M represents a substituent that can react through various types of coupling using ZnI, MgBr, boronic acid, boronic acid ester, or the like, LG1 and LG2 represent a leaving group such as —Cl, —Br, —I, —OTf, —OMs, and —Ots, $Q^1$ and $Q^2$ represent, for example, hydroxyl group, a leaving group such as —Cl, —Br, —I, —OTf, —OMs, and —OTs, or a substituent capable of forming C—O or C—C bond such as an alkenyl group and borane derivative, and $Q^3$ represents a substituent capable of forming C—O or C—N bond by a reaction with the LG2 group such as hydroxyl group and amino group). The compounds represented by the formulas (2), (4) to (6), and (10) are commercially available, or can be produced according to known methods, for example, the methods shown below, or methods similar to these.

Step 8

A compound represented by the formula (11) is synthesized by, for example, a method similar to the method of STEP 10 of the scheme 3, through intramolecular alkylation or metal coupling reaction of a compound represented by the formula (10). In this case, by conducting the reaction under such a highly diluted condition that the substrate concentration is, for example, 0.1 to 0.001 mol/L in order to preferentially allow the intramolecular reaction over the intermolecular reaction, the compound represented by the formula (11) can be synthesized.

Step 9

A compound represented by the formula (14) is synthesized by intermolecular Mitsunobu reaction or intermolecular alkylation reaction of the compound represented by the formula (4) and the compound represented by the formula (5). The reaction conditions are similar to those of STEP 2 pounds as precursors of the compounds of the present invention using one or a combination of two or more of reactions described in ordinary chemical articles, and the like.

Examples of the preparation method for the compounds of the present invention which contain an asymmetric carbon include a preparation method based on asymmetric reduction, a method of using a commercially available starting material (or starting material that can be prepared by a known method or a method similar to a known method) of which moiety corresponding to the asymmetric carbon is originally optically active, a method of performing optical resolution, or preparing an optically active compound using an enzyme, and the like. A method is also available in which a compound of the present invention or a precursor thereof is separated as an optically active isomer by a conventional method. Examples of such a method include, for example, a method utilizing high performance liquid chromatography (HPLC) using a chiral column, or supercritical fluid chromatography (SFC), the classical fractional crystallization for separation of optically active substances comprising formation of a salt with an optically active regent, separation by fractional crystallization or the like, and conversion of the salt into a compound of free form, a method comprising condensation with an optically active regent to form a diastereomer, followed by separation, purification, and decomposition of the prepared diastereomer, and the like. When a precursor is separated to obtain an optically active substance, an optically active compound of the present invention can then be prepared by performing the aforementioned preparation methods with the optically active substance.

When a compound of the present invention contains an acidic functional group such as carboxyl group, phenolic hydroxyl group, or tetrazole ring, the compound can be converted into a pharmaceutically acceptable salt (e.g., inorganic salts with sodium, and the like, or organic salts with triethylamine and the like) by a known means. For example, when an inorganic salt is to be obtained, it is preferable to dissolve the compound of the present invention in water containing hydroxide, carbonate, bicarbonate or the like corresponding to the desired inorganic salt. For the reaction, a water-miscible inactive organic solvent such as methanol, ethanol, acetone, and dioxane may be mixed. For example, by using sodium hydroxide, sodium carbonate, or sodium hydrogencarbonate, a solution of sodium salt can be obtained.

When a compound of the present invention contains amino group, another basic functional group, or an aromatic ring which itself has a basicity (e.g., pyridine ring and the like), the compound can also be converted into a pharmaceutically acceptable salt (e.g., salt with an inorganic acid such as hydrochloric acid, or salt with an organic acid such as acetic acid) by a known means. For example, when a salt with an inorganic acid is to be obtained, it is preferable to dissolve the compound of the present invention in an aqueous solution containing a desired inorganic acid. For the reaction, a water-miscible inactive organic solvent such as methanol, ethanol, acetone, and dioxane may be mixed. For example, by using hydrochloric acid, a solution of hydrochloride can be obtained.

If a solid salt is desired, the solution may be evaporated, or a water-miscible organic solvent having polarity to some extent, such as n-butanol or ethyl methyl ketone, can be added to the solution to obtain a solid salt.

The various compounds disclosed by the present invention can be purified by known methods such as variety of chromatography techniques (column chromatography, flash column chromatography, thin layer chromatography, high performance liquid chromatography, supercritical fluid chromatography, and the like).

The compounds of the present invention according to a certain embodiment have an IRAK-4 inhibitory activity, and can be used as an IRAK-4 inhibitor. That is, the compounds of the present invention according to a certain embodiment can be used as a medicament for prophylactic and/or therapeutic treatment of a disease relating to IRAK-4 inhibition. More precisely, the disease relating to IRAK-4 inhibition is a disease for which IRAK-4 inhibition is effective, and more specifically, the disease relating to IRAK-4 inhibition is not particularly limited so long as it is a disease that can be prevented and/or treated by suppressing production of inflammatory mediators such as TNFα, and IL-6 through inhibition of TLRs or IL-1 family signal transduction system.

The IRAK-4 inhibitory activity can be measured by, for example, the method described in Test Examples 1 or 2 mentioned later.

The disease relating to IRAK-4 inhibition is not particularly limited so long as it is a disease for which IRAK-4 inhibition is effective, and specific examples include, for example, acute or chronic inflammation, autoimmune diseases (rheumatoid arthritis, systemic erythematodes, lupus nephritis, and the like), autoinflammatory diseases (TNF receptor-associated periodic syndrome (TRAPS), familial mediterranean fever, cryopyrin-associated periodic syndrome, high IgD syndrome, and the like), metabolic disorders (gout and the like), and the like.

According to a certain embodiment, the compounds of the present invention have a TLR/IL-1β signaling-suppressing action, and are useful as an active ingredient of a medicament as shown in the test examples mentioned later. In particular, it is preferred that the compounds of the present invention according to a certain embodiment are used for prophylactic and/or therapeutic treatment of a disease in which IRAK-4 signaling is involved.

The compounds of the present invention according to a certain embodiment show strong selectivity for other kinases. Examples of the other kinases include FLT3, ITK, CK2, IKKb, JAK1, Syk, PKC0, and p38. According to another embodiment, examples include, especially, FLT3.

Usefulness of the medicament of present invention according to a certain embodiment for prophylactic and/or therapeutic treatment of a disease in which IRAK-4 signaling is involved can be confirmed by, for example, a cytokine production inhibition test using immunocytes, or by using a collagen-induced arthritis model. Specifically, the method described in Test Example 3 mentioned later can be exemplified.

The medicament of the present invention according to a certain embodiment can be prepared as a medicament containing a compound represented by the formula (1) or a pharmaceutically acceptable salt thereof as an active ingredient, and for example, a medicament containing a compound or pharmaceutically acceptable salt thereof that is metabolized in a living body to produce a compound represented by the formula (1) or a pharmaceutically acceptable salt thereof when it is administered as a prodrug also falls within the scope of the medicament of the present invention.

Although administration route of the medicament of the present invention according to a certain embodiment is not particularly limited, the administration scheme can be appropriately selected from, for example, oral administration, subcutaneous administration, intracutaneous administration, intramuscular injection, intravenous administration, pernasal administration, intravaginal administration, intrarectal administration, local administration to an affected part, and the like.

As the medicament of the present invention, a compound represented by the formula (1) or a pharmaceutically acceptable salt thereof, per se, may be used. However, it is preferable to add one or more kinds of pharmaceutically acceptable carriers to a compound represented by the formula (1) or a pharmaceutically acceptable salt thereof to prepare a pharmaceutical composition and administer the composition. Further, as the active ingredient of the medicament of the present invention, a hydrate or solvate of a compound represented by the general formula (1) or a pharmaceutically acceptable salt thereof may be used.

Examples of dosage form used for preparing the aforementioned pharmaceutical composition include tablet, powder, granule, syrup, suspension, capsule, inhalant, injection, and the like. For the manufacture of them, various carriers suitable for these preparations are used. For example, examples of the carrier for oral preparations include excipients, binders, lubricants, fluid accelerators, and colorants. Examples of the method for using the composition as an inhalant include a method of inhaling powder of the pharmaceutical composition or a liquid dosage form prepared by dissolving or suspending the pharmaceutical composition in a solvent as it is, a method of inhaling mist thereof by using a sprayer called atomizer or nebulizer, and the like. When the composition is formulated as an injection, distilled water for injection, physiological saline, aqueous glucose solution, vegetable oil for injection, propylene glycol, polyethylene glycol, and the like can generally be used as a diluent. Disinfectants, antiseptics, stabilizers, isotonic agents, soothing agents, and the like may be further added, as required.

A clathrate compound in which a compound of the present invention is clathrated in cyclodextrin may also be prepared, and used as the medicament of the present invention.

When the medicament of the present invention according to a certain embodiment is administered, an appropriate dosage form can be suitably chosen and administered via an appropriate route. For example, it can be orally administered in the form of tablet, powder, granule, syrup, suspension, capsule, or the like. The medicament can also be administered via the respiratory tract in the form of an inhalant. In addition, the medicament can be subcutaneously, intracutaneously, intravascularly, intramuscularly, or intraperitoneally administered in the form of an injection including drip infusion. Furthermore, the medicament can be transmucosally administered in the form of sublingual tablet, suppository, or the like, and can be percutaneously administered in the form of gel, lotion, ointment, cream, spray, or the like. In addition, the medicament can also be administered as a prolonged action dru g, for example, a sustained-release injection, or an embedding preparation (e.g., film preparation, and the like).

The administration period of the medicament of the present invention according to a certain embodiment is not particularly limited. In principle, the medicament is administered during a period where it is judged that clinical symptoms of a disease are expressed, and it is common to continue the administration for several weeks to one year. However, it is also possible to extend the administration period depending on pathological conditions, or continue the administration even after recovery from the clinical symptoms. The medicament may also be prophylactically administered by a decision of a clinician even if any clinical symptom is not expressed. The dose of the medicament of the present invention according to a certain embodiment is not particularly limited. For example, when the medicament of the present invention is orally administered, 0.01 to 1000 mg of the active ingredient can be administered to an adult per each time of administration. As for administration frequency in the above case, the administration can be performed at a frequency of every 6 months to every day, preferably once a day.

The daily dose and/or dose per one time, administration period, and administration frequency may be suitably increased or decreased depending on various conditions such as age, weight, degree of physical healthiness of a patient, type and severity of a disease to be treated, administration route, and dosage form (sustained release property of carrier for active ingredient, and the like).

When the medicament of the present invention according to a certain embodiment is used for prophylactic treatment and/or therapeutic treatment of the aforementioned diseases, the medicament of the present invention according to a certain embodiment can be used together with one or more kinds of medicaments selected from the drugs mentioned below at the same time or different times. Further, the medicament of the present invention according to a certain embodiment can also be prepared as a so-called combined drug together with the drugs exemplified above, and then administered. Such a combined drug may be in a dosage form of a complete mixture of the active ingredients similar to typical compositions of such type, as well as a dosage form, kit, or package including a non-mixed combination of ingredients separately administered from two or more containers each of which contains each active ingredient.

Examples of the drugs that can be used together with the medicament of the present invention according to a certain embodiment include, for example, immunosuppressants (tacrolimus, cyclosporin, rapamycin, mofetil mycophenolate, interferon preparations, cyclophosphamide, azathioprine, methotrexate, and the like), antiphlogistics (steroids (prednisolone, dexamethasone, betamethasone, cortisone, and the like) and non-steroidal anti-inflammatory drugs (NSAIDs, ibuprofen, celecoxib, and the like), disease-modifying antirheumatic drugs (gold preparations, methotrexate, leflunomide, sulfasalazine, penicillamine, iguratimod, chloroquine, tofacitinib, etc), antimalarials (hydroxychloroquine, and the like), therapeutic agents for multiple sclerosis (interferon, anti-α4 integrin preparations, fingolimod, mitoxantrone, and the like), and anti-cytokine drugs (anti-TNFα preparations, anti-IL-6 preparations, anti-IL-12/23 preparations, and the like). Examples further include biological preparations used as therapeutic agents for autoimmune diseases (anti-CD20 preparations, CTLA-4-Ig, and the like), drugs for disturbances in uric acid metabolism (colchicine, probenecid, bucolome, benzbromarone, allopurinol, and the like), hypoglycemic agents (alogliptin, nateglinide, acarbose, metformin, pioglitazone, insulin preparations, and the like), hypotensive drugs (imidapril, valsartan, candesartan, and the like), choleretics (ursodeoxycholic acid, and the like), bronchodilators (salmeterol and salbutamol, which are adrenalin β2 agonists, ipratropium and tiotropium, which are anticholinergic drugs, and the like), therapeutic drugs for allergic diseases (theophylline and the like), antiallergic drugs (fexoquinadine, epinastine, olopatadine, loratadine, cetirizine, bepotastine, ketotifen, sodium cromoglycate, pemirolast, chlorpheniramine, and the like) leukotriene antagonists (zafirlukast, montelukast, pranlukast, and the like), antihyperlipidemic drugs (atorvastatin, simvastatin, clinofibrate, bezafibrate, probucol, elastase, ethyl icosapentate, and the like), neurotransmitter controlling agents (donepezil, galanthamine, memantine, and the like), antioxidants (vitamin E, acetylcysteine, carnitine, betaine, pentoxifylline, and the like), and antibiotics (various antibiotics of β lactam type, macrolide type, tetracycline type, aminoglycoside type, quinolone type, and the like, chloramphenicol and the like). The medicament of the present invention can also be used together with various kinds of drugs to be created in the future. These combined drugs are no way limited so long as the combinations are clinically meaningful.

The compounds of the present invention according to a certain embodiment include compounds showing superior safety (concerning various toxicities and safety pharmacology), pharmacokinetic performance, and the like, and usefulness thereof as an active ingredient of a medicament can be confirmed by, for example, the methods shown below.

Examples of tests concerning safety include, for example, those listed below. However, they are not limited to these examples. Examples include cytotoxic tests (tests using HL60 cells, hepatocytes, and the like), genotoxicity tests (Ames test, mouse lymphoma TK test, chromosomal aberration test, micronucleus test, and the like), skin sensitization tests (Buehler method, GPMT method, APT method, LLNA test, and the like), skin photosensitization tests (adjuvant and strip method, and the like), eye irritation tests (single instillation, short-term continuous instillation, repetitive instillation, and the like), safety pharmacology tests for the cardiovascular system (telemetry method, APD method, hERG inhibition assay, and the like), safety pharmacology tests for the central nervous system (FOB method, modified Irwin method, and the like), safety pharmacology tests for the respiratory system (measurement method utilizing a respiratory function measuring apparatus, measurement method utilizing a blood gas analyzer, and the like), general toxicity tests, reproductive and developmental toxicity tests, and the like.

Examples of tests concerning pharmacokinetic performance include, for example, those listed below. However, they are not limited to these examples. Examples include cytochrome P450 enzyme inhibition or induction tests, cell permeability tests (tests using CaCO-2 cells, MDCK cells, and the like), drug transporter ATPase assay, oral absorption tests, blood concentration transition measurement tests, metabolism tests (stability test, metabolite molecular species test, reactivity test, and the like), solubility tests (solubility test based on turbidity method, and the like), and the like.

Usefulness of the compounds of the present invention according to a certain embodiment as an active ingredient of a medicament can be confirmed by performing, for example, a cytotoxic test. Examples of the cytotoxic test include methods utilizing various cultured cells, for example, HL-60 cells, which are human preleukemia cells, primary isolated cultured cells of hepatocytes, a neutrophil fraction prepared from human peripheral blood, and the like. Although the test can be carried out by the method described below, the method is not limited only to the following description. Cells are prepared as a suspension of 105 to $10^7$ cells/ml, and the suspension is added to microtubes or microplate in a volume of 0.01 to 1 mL. To the suspension, a solution dissolving a compound is added in a volume of 1/100 to 1 fold volume of the cell suspension, and the cells were cultured in a cell culture medium having a final concentration of the compound of 0.001 to 1000 UM for 30 minutes to several days at 37° C. under 5% $CO_2$. After terminating the culture, survival rate of the cells is evaluated by using the MTT method, WST-1 method (Ishiyama, M., et al., In Vitro Toxicology, 8, p. 187, 1995), or the like. By measuring cytotoxicity of a compound to cells, usefulness of the compound as an active ingredient of a medicament can be confirmed.

Usefulness of the compounds of the present invention according to a certain embodiment as an active ingredient of a medicament can be confirmed by performing, for example, a genotoxicity test. Examples of the genotoxicity test include, the Ames test, mouse lymphoma TK test, chromosomal aberration test, micronucleus test, and the like. The Ames test is a method of determining reverse mutation by culturing *Salmonella* or *Escherichia* bacteria of designated species on a culture dish or the like to which a compound is added (refer to IYAKUSHIN (Notification by the chief of Evaluation and Licensing Division, Pharmaceutical and Medical Safety Bureau, Ministry of Health, Labor and Welfare, Japan), No. 1604, 1999, "Guideline for Genotoxicity Test", II-1. Genotoxicity Test, and the like). The mouse lymphoma TK test is a genetic mutation ability detection test targeting the thymidine kinase gene of the mouse lymphoma L5178Y cell (refer to IYAKUSHIN No. 1604, 1999, "Guideline for Genotoxicity Test", II-3. Mouse Lymphoma TK Test; Clive, D. et al., Mutat. Res., 31, pp. 17-29, 1975; Cole, J., et al., Mutat. Res., 111, pp. 371-386, 1983, and the like). The chromosomal aberration test is a method for determining activity of causing chromosomal aberration by culturing mammalian cultured cells in the presence of a compound, then after fixation of the cells, staining and observing chromosomes of the cells (refer to IYAKUSHIN No. 1604, 1999, "Guideline for Genotoxicity Test", II-2. Chromosomal Aberration Test Utilizing Mammalian Cultured Cells, and the like). The micronucleus test is a method of evaluating micronucleus-forming ability caused by chromosomal aberration, and a method of using a rodent (in vivo test) (IYAKUSHIN No. 1604, 1999, "Guideline for Genotoxicity Test", II-4. Micronucleus Test Using Rodent; Hayashi M. et al., Mutat. Res., 312, pp. 293-304, 1994; Hayashi, M. et al., Environ. Mol. Mutagen., 35, pp. 234-252, 2000), a method of using cultured cells (in vitro test) (Fenech M., et al., Mutat. Res., 147, pp. 29-36, 1985; Miller, B., et al., Mutat. Res., 392, pp. 45-59, 1997), and the like are available. By elucidating genotoxicity of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a skin sensitization test. Skin sensitization tests include, as the skin sensitization tests using guinea pi g, the Buehler method (Buehler, E. V., Arch. Dermatol., 91, pp. 171-177, 1965), GPMT method (maximization method, Magnusson B., et al., J. Invest. Dermatol., 52, pp. 268-276, 1969), APT method (adjuvant and patching test method (Sato, Y. et al., Contact Dermatitis, 7, pp. 225-237, 1981)), and the like. Further, as the skin sensitization test using mouse, the LLNA (local lymph node assay) method (OECD Guideline for the testing of chemicals 429, Skin sensitization 2002; Takeyoshi, M. et al., Toxicol. Lett., 119 (3), pp. 203-8, 2001; Takeyoshi, M. et al., J. Appl. Toxicol., 25 (2), pp. 129-34, 2005), and the like are available. By elucidating skin sensitization property of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a skin photosensitization test. Examples of the skin photosensitization test include a skin photosensitization test using guinea pig (refer to "Drug Nonclinical Test Guideline Commentary 2002", Yakuji Nippo, published on 2002, 1-9: Skin Photosensitization Test, and the like), and the like, and examples of the method include the adjuvant and strip method (Ichikawa, H. et al., J. Invest. Dermatol., 76, pp. 498-501, 1981), Harber method (Harber, L. C., Arch. Dermatol., 96, pp. 646-653, 1967), Horio method (Horio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and Man", Tokyo Univ. Press, Tokyo, pp. 529-557, 1974), Vinson method (Vinson, L. J., J. Soc. Cosm. Chem., 17, pp. 123-130, 1966), and the like. By elucidating skin photosensitization property of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, an eye irritation test. Examples of the eye irritation test include the single instillation test method (instillation of one time), short term continuous instillation test method (instillation of multiple times in a short period of time with equal intervals), repetitive instillation test method (repetitive intermittent instillation over several days to several 10 days) using rabbit eyes, monkey eyes, and the like, and the like, and a method of evaluating eye irritation symptoms at a certain time point after the instillation according to the improved Draize scores (Fukui, N. et al., Gendai no Rinsho, 4 (7), pp. 277-289, 1970), and the like is available. By elucidating eye irritation of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the cardiovascular system. Examples of the safety pharmacology test for the cardiovascular system include the telemetry method (method for measuring influence of administration of a compound under no anesthetization on electrocardiogram, heart rate, blood pressure, blood stream, and the like (Electrocardiogram, Echocardiography, Blood Pressure and Pathological Tests of Animals for Fundamental and Clinical Medicine, edited by Sugano S., Tsubone H., Nakada Y., published on 2003, Maruzen), APD method (method for measuring cardiac muscle cell action potential retention time (Muraki, K. et al., AM. J. Physiol., 269, H524-532, 1995; Ducic, I. et al., J. Cardiovasc. Pharmacol., 30 (1), pp. 42-54, 1997)), hERG inhibition evaluation method (patch clamping method (Chachin, M. et al., Nippon Yakurigaku Zasshi, 119, pp. 345-351, 2002), binding assay method (Gilbert, J. D. et al., J. Pharm. Tox. Methods, 50, pp. 187-199, 2004), $Rb^+$efflex assay method (Cheng, C. S. et al., Drug Develop. Indust. Pharm., 28, pp. 177-191, 2002), membrane potential assay method (Dorn, A. et al., J. Biomol. Screen., 10, pp. 339-347, 2005), and the like. By elucidating influence on the cardiovascular system of a compound using on one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the central nervous system. Examples of the safety pharmacology test for the central nervous system include the FOB method (Functional Observational Battery, Mattson, J. L. et al., J. American College of Technology, 15 (3), pp. 239-254, 1996)), modified Irwin method (method for evaluating observation of general symptoms and behavior (Irwin, S., Comprehensive Observational Assessment (Berl.) 13, pp. 222-257, 1968)), and the like. By elucidating action on the central nervous system of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the respiratory system. Examples of the safety pharmacology test for the respiratory system include the measurement method using a respiratory function measuring apparatus (method of measuring respiration rate, single ventilation volume, minute ventilation, and the like, Drorbaugh, J. E. et al., Pediatrics, 16, pp. 81-87, 1955; Epstein, M. A. et al., Respir. Physiol., 32, pp. 105-120, 1978), measurement method of using a blood gas analyzer (method of measuring blood gas, hemoglobin oxygen saturation, and the like, Matsuo, S., Medicina, 40, pp. 188-, 2003), and the like. By elucidating action on the respiratory system of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a general toxicity test. The general toxicity test is a method of orally or intravenously administering a compound dissolved or suspended in an appropriate solvent once or repetitively (over several days) to a rodent such as rat and mouse or non-rodent such as monkey and do g, and evaluating observation of general conditions, clinicochemical changes, pathohistological changes, and the like of the administered animal. By elucidating general toxicity of a compound using these methods, usefulness of the compound as an active ingredient of a medicament can be confirmed.

Usefulness of the compounds of the present invention according to a certain embodiment as an active ingredient of a medicament can be confirmed by performing, for example, a reproductive and developmental toxicity test. The reproductive and developmental toxicity test is a test for examining induction of harmful effect caused by a compound on the reproductive and developmental processes by using a rodent such as rat and mouse, or non-rodent such as monkey and dog (refer to "Drug Nonclinical Test Guideline Commentary 2002", Yakuji Nippo, published on 2002, 1-6: Reproductive and Developmental Toxicity Test, and the like). Examples of the reproductive and developmental toxicity test include tests concerning fertility and early embryogenesis up to nidation, tests concerning development and maternal functions before and after birth, tests concerning embryogenesis and fetal development (refer to IYAKUSHIN No. 1834, 2000, Appendix, "Guideline for Drug Toxicity Test", [3] Reproductive and Developmental Toxicity Test, and the like), and the like. By elucidating reproductive and developmental toxicity of a compound using these methods, usefulness of the compound as an active ingredient of medicament can be confirmed.

Usefulness of the compounds of the present invention according to a certain embodiment as an active ingredient of a medicament can be confirmed by performing, for example, a cytochrome P450 enzyme inhibition or induction test (Gomez-Lechon, M. J. et al., Curr. Drug Metab., 5 (5), pp. 443-462, 2004). Examples of the cytochrome P450 enzyme inhibition or induction test include, for example, the method of determining in vitro whether a compound inhibits activity of a cytochrome P450 enzyme by using a cytochrome P450 enzyme of each molecular species purified from cells or prepared by using a genetic recombinant, or a human P450 expression system microsome (Miller, V. P. et al., Ann. N.Y. Acad. Sci., 919, pp. 26-32, 2000), method of measuring changes of expression of cytochrome P450 enzyme of each molecular species or enzyme activity thereof by using human liver microsomes or disrupted cell suspension (Hengstler, J. G. et al., Drug Metab. Rev., 32, pp. 81-118, 2000), method of extracting RNA from human hepatocytes exposed to a compound, and comparing mRNA expression amount with that of a control to investigate enzyme induction ability of the compound (Kato, M. et al., Drug Metab. Pharmacokinet., 20 (4), pp. 236-243, 2005), and the like. By elucidating action of a compound on inhibition or induction of cytochrome P450 enzyme using one or more of these methods, usefulness of the compound as an active ingredient of a medicament can be confirmed.

Usefulness of the compounds of the present invention according to a certain embodiment as an active ingredient of a medicament can be confirmed by performing, for example, a reactive metabolite production-confirming test. Examples of the reactive metabolite production-confirming test include, for example, the method of incubating human liver microsomes in the presence of NADPH and glutathione labeled with fluorescence using dansyl group (dGSH), trapping the reactive metabolites as dGSH-adducts, and comprehensively detecting peaks of the reactive metabolites from the production amounts of the dGSH-adducts on the basis of fluorescence intensity used as an index (Junping Gan, et al., Chem. Res. Toxicol., 2005, 18, 896-903), method of incubating a 14C-labeled compound with human liver microsomes in the presence of NADPH, and measuring radioactivity of the carbon atom covalently bonded to proteins (Baillie T. A., Drug Metabolizing Enzymes. Cytochrome P450 and Other Enzymes in Drug Discovery and Development, pp. 147-154, 2003), and the like. By elucidating risk of a compound for generation of idiosyncratic drug toxicity, which is generated through production of reactive metabolite of a compound, using one or two or more of these methods, usefulness of the compound as an active ingredient of a medicament can be confirmed.

Usefulness of the compounds of the present invention according to a certain embodiment as an active ingredient of a medicament can be confirmed by performing, for example, a cell permeability test. Examples of the cell permeability test include, for example, the method of measuring cell membrane permeability of a compound in an in vitro cell culture system using CaCO-2 cells (Delie, F. et al., Crit. Rev. Ther. Drug Carrier Syst., 14, pp. 221-286, 1997; Yamashita, S. et al., Eur. J. Pham. Sci., 10, pp. 195-204, 2000; Ingels, F. M. et al., J. Pham. Sci., 92, pp. 1545-1558, 2003), method of measuring cell membrane permeability of a compound in an in vitro cell culture system using MDCK cells (Irvine, J. D. et al., J. Pham. Sci., 88, pp. 28-33, 1999), and the like. By elucidating cell permeability of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a drug transporter ATPase assay for ATP-binding cassette (ABC) transporter. Examples of the drug transporter ATPase assay include the method of examining whether a compound is a substrate of P-glycoprotein (P-gp) by using a P-gp baculovirus expression system (Germann, U. A., Methods Enzymol., 292, pp. 427-41, 1998), and the like Furthermore, the usefulness can also be confirmed by performing, for example, a transport test using oocytes collected from African clawed frog (*Xenopus laevis*) for a solute carrier (SLC) transporter. Transport tests include a method of examining whether a test compound is a substrate of OATP2 using OATP2-expressing oocytes (Tamai I. et al., Pharm. Res., 2001 September; 18 (9), 1262-1269), and the like. By elucidating action of a compound on the ABC transporter or SLC transporter using these methods, usefulness of the compound as an active ingredient of a medicament can be confirmed.

Usefulness of the compounds of the present invention according to a certain embodiment as an active ingredient of a medicament can be confirmed by performing, for example, an oral absorption test. Examples of the oral absorption test include a method of orally administering a compound of a certain amount dissolved or suspended in an appropriate solvent to a rodent, monkey, dog or the like, and measuring blood level of the compound after the oral administration over time using the LC-MS/MS method ("Newest Mass Spectrometry for Life Science", Kodansha Scientific, 2002, edited by Harada K. et al, and the like) to evaluate blood transition of the compound by oral administration, and the like. By elucidating oral absorption of a compound using these methods, usefulness of the compound as an active ingredient of a medicament can be confirmed.

Usefulness of the compounds of the present invention according to a certain embodiment as an active ingredient of a medicament can be confirmed by performing, for example, a blood concentration transition measurement test. Examples of the blood concentration transition measurement test include a method of administering a compound orally or parenterally (e.g., intravenously, intramuscularly, intraperitoneally, subcutaneously, transdermally, by instillation, transnasally, and the like) to a rodent, monkey, dog or the like, and measuring change of the blood level of the compound over time after the administration using the LC-MS/MS method ("Newest Mass Spectrometry for Life Science", Kodansha Scientific, 2002, edited by Harada K. et al, and the like), and the like. By elucidating blood concentration transition of a compound using these methods, usefulness of the compound as an active ingredient of a medicament can be confirmed.

Usefulness of the compounds of the present invention according to a certain embodiment as an active ingredient of a medicament can be confirmed by performing, for example, a metabolic test. Examples of the metabolic test include the blood stability test method (method of predicting metabolic clearance in vivo on the basis of metabolic rate of a compound in hepatic microsomes of human or other animal species (refer to Shou, W. Z. et al., J. Mass Spectrom., 40 (10) pp. 1347-1356, 2005; Li, C. et al., Drug Metab. Dispos., 34 (6), 901-905, 2006, and the like), metabolite molecular species test method, reactive metabolite test method, and the like. By elucidating metabolic profile of a compound by using one or more of these methods, usefulness of the compound as an active ingredient of a medicament can be confirmed.

Usefulness of the compounds of the present invention according to a certain embodiment as an active ingredient of a medicament can be confirmed by performing, for example, a solubility test. As the method for evaluating solubility in water, the methods of confirming the solubility under acidic conditions, neutral conditions, or basic conditions are exemplified, and confirming change of solubility depending on the presence or absence of bile acid is also included. Examples of the solubility test include the solubility test based on the turbidity method (Lipinski, C. A. et al., Adv. Drug Deliv. Rev., 23, pp. 3-26, 1997; Bevan, C. D. et al., Anal. Chem., 72, pp. 1781-1787, 2000), and the like. By elucidating solubility of a compound using these methods, usefulness of the compound as an active ingredient of a medicament can be confirmed.

Usefulness of the compounds of the present invention according to a certain embodiment as an active ingredient of a medicament can be confirmed by examining, for example, upper gastrointestinal injury, renal dysfunction, and the like. As a pharmacological test for the upper gastrointestinal tract, actions on gastric mucosa can be investigated by using a starved rat gastric mucosa injury model. Examples of pharmacological test for kidney functions include renal blood flow and glomerular filtration rate measuring method [Physiology, 18th edition, Bunkodo, 1986, Chapter 17], and the like. By elucidating actions of a compound on the upper gastrointestinal tract and renal functions using one or more of these methods, usefulness of the compound as an active ingredient of a medicament can be confirmed.

Examples

Hereafter, the present invention will be further specifically explained with reference to examples, and test examples (these may be henceforth collectively referred to as "examples and the like"). However, the scope of the present invention is not limited to the following examples and the like.

All the purchased reagents were used without further purification. The purchased anhydrous solvents were used without further drying. For the column chromatography, the medium pressure preparative purification system prepared by YAMAZEN, SmartFlash, or the medium pressure preparative purification system prepared by BIOTAGE, Isolera ONE, to which BIOTAGE Dalton was connected as an MS detector, was used. As the column, SNAP Ultra prepared by BIOTAGE, or DispoPack AT prepared by YMC was used. In some cases, purification was performed by using BondElute SCX prepared by Agilent as an ion exchange resin. BondElute SCX may be henceforth referred to simply as SCX. An exemplary method for using SCX is a method of washing the cartridge with methanol and dichloromethane, then allowing adsorption of a crude product dissolved in a minimum volume of solvent (for example, a mixed solvent of dichloromethane and methanol, or the like), then flushing impurities with methanol with pressurization, and eluting the product with 2.0 M ammonia in methanol. For the thin layer chromatography (TLC), Precoated Silica Gel 60 F254 (produced by Merck, product number 5715-1 M)) was used. After development with chloroform:methanol (1:0 to 1:1), or ethyl acetate: hexane (1:0 to 0:1), confirmation was performed by UV irradiation (254 nm or 365 nm), or coloration with iodine solution, aqueous potassium permanganate, phosphomolybdic acid (ethanol solution), or the like. Preparative thin layer chromatography (henceforth also referred to as "PTLC") was performed by using one or several plates of PLC Plate Silica Gel 60 F254 (20×20 cm, layer thickness 2 mm, including concentration zone (4 cm), prepared by Merck, product number 13793-1 M) were used depending on the amount of sample. For drying organic solvents, anhydrous magnesium sulfate or anhydrous sodium sulfate was used.

NMR

For 1H (400 MHx) nuclear magnetic resonance (henceforth also abbreviated as NMR) analysis, AVANCE III HD-400 MHz prepared by Bruker, or AVANCE III HD-600 MHz prepared by Bruker was used.

As the internal standard, known values of used solvents or additives were used. As the 1H NMR data, chemical shifts, parts per million (henceforth abbreviated as ppm), integral values (described as, for example, 1H), and multiplets (s means singlet, d means doublet, t means triplet, q means quartet, qui means quintet, m means multiplet, br means broad, dd means double doublet, and the like) are mentioned.

For LCMS, mass spectrum was measured by liquid chromatography-mass spectrometry (LC-MS). Unless especially indicated, a single quadrupole mass spectrometer, SQD System (prepared by Waters) was used as the mass spectrometer, and the measurement was performed by the electrospray ionization (ESI) method. As the liquid chromatography apparatus, Acquity Ultra Performance LC System prepared by Waters was used. As the separation column, ACQUITY UPLC BEH C18 (2.1×50 mm, 1.7 um, prepared by Waters) was used.

When the LC conditions are especially mentioned in the examples and reference examples, it means that the measurement was performed with the following solvent conditions. m/z means mass spectrum data ($MH^+$, or $MH^-$ is also indicated).

(LC-1) The measurement was performed under the conditions that the elution was performed at a flow rate of 0.6 ml/minute using a linear gradient of 5 to 90% (v/v) of Solution B (acetonitrile) in Solution A (10 mM aqueous ammonium acetate) from 0 minute to 2.0 minutes, and then a linear gradient of 90 to 98% (v/v) of Solution B in Solution A from 2.0 to 2.5 minutes.

(LC-6) The measurement was performed under the conditions that the elution was performed at a flow rate of 0.6 ml/minute using a linear gradient of 70 to 90% (v/v) of Solution B (acetonitrile) in Solution A (10 mM aqueous ammonium acetate) from 0 minute to 2.0 minutes, and then a linear gradient of 90 to 98% (v/v) of Solution B in Solution A from 2.0 to 2.5 minutes.

For the HPLC purification, the preparative purification system prepared by Waters Japan, and Triart C18 ExRS (prepared by YMC), or the like as the column were used, and 10 mM aqueous ammonium acetate/acetonitrile solution was used as the eluent.

The abbreviation, quant., mentioned in the descriptions of the following examples and synthesis methods of intermediates means that the objective substance was quantitatively obtained.

Method A-1

[Formula 32]

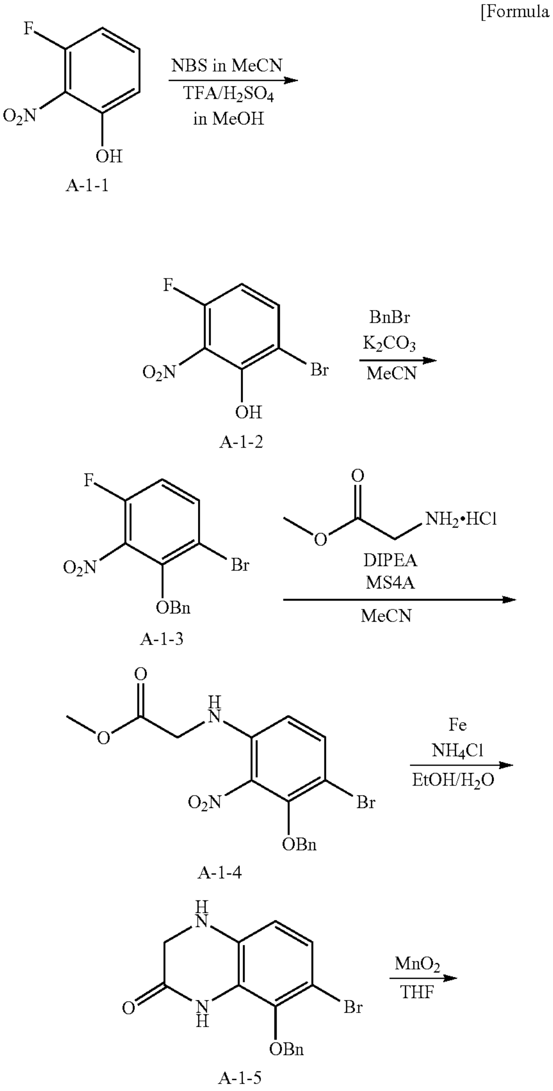

A-1-1

A-1-2

A-1-3

A-1-4

A-1-5

-continued

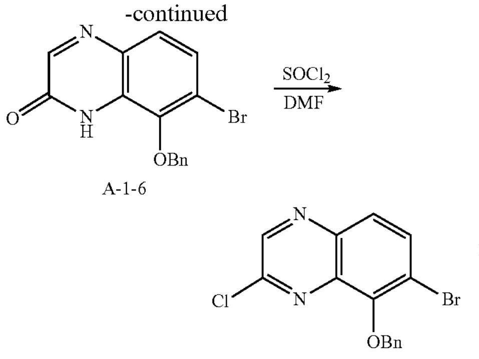

A-1-6

A-1-7

Intermediate A-1-2:6-Bromo-3-fluoro-2-nitrophenol

[Formula 33]

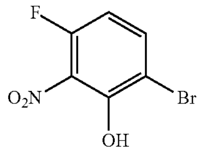

3-Fluoro-2-nitrophenol (Intermediate A-1-1, 30.9 g, 196 mmol) was dissolved in acetonitrile (20 mL), and concentrated sulfuric acid (44 mL) was added to the solution while the reaction temperature was maintained at 30° C. or lower. Subsequently, a solution of N-bromosuccinimide (35.4 g, 198 mmol) in acetonitrile (281 mL) was added dropwise to the reaction mixture over 1 hour and 30 minutes under ice cooling. Then, the reaction mixture was stirred for 12 hours, while the temperature thereof was allowed to naturally increase from 0° C. to room temperature. After completion of the reaction, ice water (300 mL) was added to the reaction mixture, the resulting mixture was extracted with ethyl acetate, and then the organic layer was washed with water and saturated brine. The organic layer was dried over anhydrous magnesium sulfate, filtered, and then concentrated under reduced pressure. The resulting crude product (62.1 g) was a mixture of the objective compound and the positional isomers for the bromine, but the resulting crude product was used as it was for the next step without performing separation and purification in this step.

LCMS (LC-1): RT=1.03, m/z 234 $[M-H]^+$

Intermediate A-1-3:2-(Benzyloxy)-1-bromo-4-fluoro-3-nitrobenzene

[Formula 34]

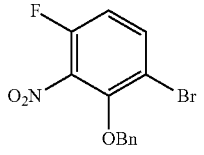

6-Bromo-3-fluoro-2-nitrophenol (Intermediate A-1-2, 62.1 g, the mixture with positional isomers for bromine mentioned above) was dissolved in acetonitrile (1000 mL), benzyl bromide (24.6 mL, 206 mmol), and potassium carbonate (95.0 g, 689 mmol) were added to the solution, and the resulting mixture was stirred at 90° C. for 1 hour. Then, water (300 mL) was added to the reaction mixture at room temperature, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=100:0 to 40:60) to obtain 2-(benzyloxy)-1-bromo-4-fluoro-3-nitrobenzene (17.5 g, yield for 2 steps 27%).

LCMS (LC-1): RT=1.95 (detected only with UV)

1H-NMR ($CDCl_3$): δ (ppm) 7.71 (1H, dd, J=9.2, 5.6 Hz), 7.51-7.44 (2H, m), 7.43-7.34 (3H, m), 6.99 (1H, t, 8.7 Hz), 5.19 (2H, s)

Intermediate A-1-4: Methyl (3-(benzyloxy)-4-bromo-2-nitrophenyl)glycinate

[Formula 35]

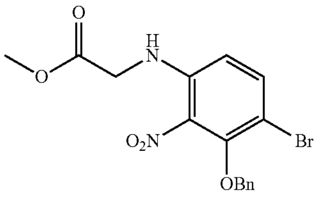

2-(Benzyloxy)-1-bromo-4-fluoro-3-nitrobenzene (Intermediate A-1-3, 30.5 g, 93.5 mmol), and methylglycine hydrochloride (41.1 g, 327 mmol) were dissolved in acetonitrile (467 mL), N,N-diisopropylethylamine (95.0 mL, 542 mmol), and Molecular sieve 4A (30.5 g) were added to the solution, and the resulting mixture was stirred at 50° C. for 72 hours. Then, the reaction mixture was filtered through a Celite layer, the filtrate was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=100:0 to 50:50) to obtain a roughly purified product (43.1 g). This product was used for the following reaction without further purification.

LCMS (LC-1): RT=1.88, m/z 395 $[M+H]^+$1H-NMR ($CDCl_3$): δ (ppm) 7.56-7.49 (3H, m), 7.43-7.32 (3H, m), 6.39-6.30 (2H, m), 5.18 (2H, s), 3.98 (2H, d, J=5.3 Hz), 3.81 (3H, s)

Intermediate A-1-5:8-(Benzyloxy)-7-bromo-3,4-dihydroquinoxalin-2 (1H)-one

[Formula 36]

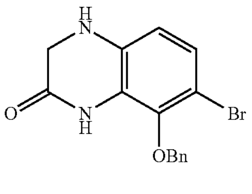

Ethanol (550 mL) and water (550 mL) were added to methyl (3-(benzyloxy)-4-bromo-2-nitrophenyl)glycinate (Intermediate A-1-4, 43.1 g, the roughly purified product mentioned above), iron (97.5 g, 1744 mmol), and ammonium chloride (58.3 g, 1090 mmol) to suspend them, and the resulting suspension was stirred at 80° C. for 4 hours. After completion of the reaction, ethanol (100 mL), and chloroform (100 mL) were added to the reaction mixture at room temperature, and the resulting mixture was filtered through a Celite layer. The filtrate was concentrated under reduced pressure to obtain a crude product (29.6 g). This product was used for the following reaction without purification.

LCMS (LC-1): RT=1.51, m/z 331 [M−H]$^+$

1H-NMR (DMSO-d$_6$): δ (ppm) 9.84 (1H, s), 7.58 (2H, d, J=6.9 Hz), 7.43-7.30 (3H, m), 6.99 (1H, d, J=8.6 Hz), 6.45 (1H, d, J=8.6 Hz), 6.22 (1H, s), 4.93 (2H, s), 3.68 (2H, s)

Intermediate A-1-6:8-(Benzyloxy)-7-bromoquinoxalin-2 (1H)-one

[Formula 37]

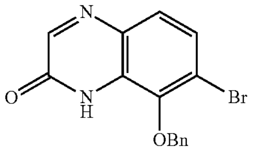

8-(Benzyloxy)-7-bromo-3,4-dihydroquinoxalin-2 (1H)-one (Intermediate A-1-5, 29.6 g, the crude product mentioned above) was dissolved in tetrahydrofuran (592 mL), manganese dioxide (27.0 g, 311 mmol) was added to the solution, and the resulting mixture was stirred at 70° C. for 12 hours. After completion of the reaction, tetrahydrofuran (300 mL) was added to the reaction mixture at room temperature, and the resulting mixture was filtered through a Celite layer. The filtrate was concentrated under reduced pressure, then tetrahydrofuran (40 mL), ethyl acetate (250 mL), and hexane (250 mL) were added to the resulting solid, and the resulting mixture was stirred at room temperature for 30 minutes. Then, the suspension was filtered, and the solid obtained by the filtration was dried under reduced pressure to obtain 8-(benzyloxy)-7-bromoquinoxalin-2 (1H)-one (19.9 g, yield for 3 steps 64%).

LCMS (LC-1): RT=1.49, m/z 331 [M+H]$^+$

1H-NMR (CDCl$_3$): δ (ppm) 9.05 (1H, brs), 8.18 (1H, s), 7.55-7.48 (2H, m), 7.47-7.36 (5H, m), 5.18 (2H, s)

Intermediate A-1-7:8-(Benzyloxy)-7-bromo-2-chloroquinoxaline

[Formula 38]

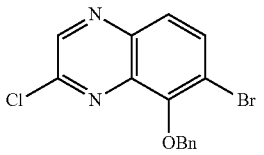

8-(Benzyloxy)-7-bromoquinoxalin-2 (1H)-one (Intermediate A-1-6, 1.0 g, 3.02 mmol) was dissolved in thionyl chloride (10 mL), N,N-dimethylformamide (0.234 mL, 3.02 mmol) was added to the solution, and the resulting mixture was stirred at 80° C. for 1 hour. After completion of the reaction, water (30 mL) was added to the reaction mixture at room temperature, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=100:0 to 60:40) to obtain 8-(benzyloxy)-7-bromo-2-chloroquinoxaline (644 mg, yield 61%).

LCMS (LC-1): RT=2.06, m/z 349 [M+H]$^+$

1H-NMR (CDCl$_3$): δ (ppm) 8.77 (1H, s), 7.91 (1H, d, J=9.1 Hz), 7.75 (1H, d, J=9.1 Hz), 7.63 (2H, d, J=7.4 Hz), 7.42-7.31 (3H, m), 5.48 (2H, s)

Method A-2

[Formula 39]

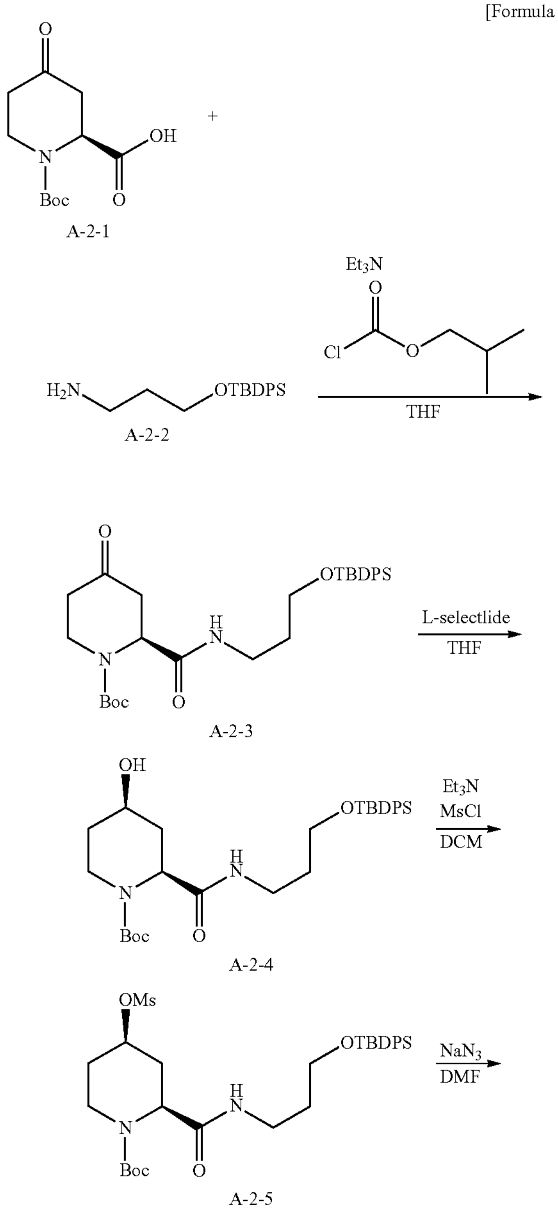

-continued

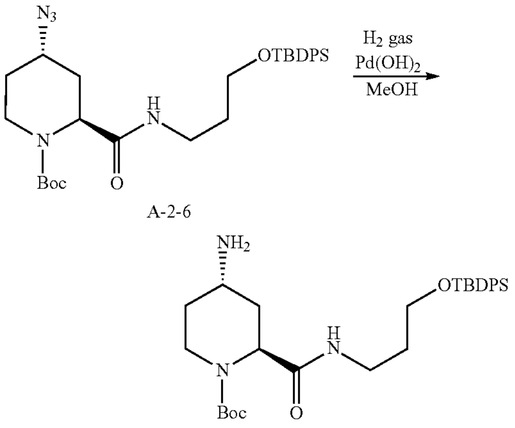

A-2-6

A-2-7

Intermediate A-2-3: tert-Butyl(S)-2-((3-((tert-butyldiphenylsilyl)oxy)propyl)carbamoyl)-4-oxopiperidine-1-carboxylate

[Formula 40]

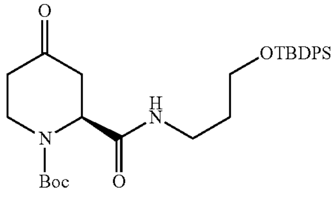

(S)-1-(tert-Butoxycarbonyl)-4-oxopiperidine-2-carboxylic acid (Intermediate A-2-1, 1.57 g, 6.46 mmol) was dissolved in tetrahydrofuran (33 mL), triethylamine (1.32 mL, 9.69 mmol), and isobutyl carbonochloridate (1.02 mL, 7.75 mmol) were added to the solution under ice cooling, and the resulting mixture was stirred for 30 minutes. Then, 3-((tert-butyldiphenylsilyl)oxy)propan-1-amine (Intermediate A-2-2, 2.43 g, 7.76 mmol) was added to the reaction mixture, and the resulting mixture was stirred at room temperature for 1 hour. After completion of the reaction, water (50 mL) was added to theb reaction mixture, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=100:0 to 70:30) to obtain tert-butyl(S)-2-((3-((tert-butyldiphenylsilyl)oxy)propyl)carbamoyl)-4-oxopiperidine-1-carboxylate (2.15 g, yield 62%).

LCMS (LC-1): RT=2.26, m/z 539 $[M+H]^+$

1H-NMR ($CDCl_3$): δ (ppm) 7.64 (4H, dd, J=7.8, 1.6 Hz), 7.46-7.35 (6H, m), 6.58 (1H, brs), 4.82 (1H, m), 3.96-3.80 (1H, m), 3.69 (2H, t, J=5.4 Hz), 3.55 (1H, ddd, J=13.3, 8.3, 5.0 Hz), 3.39 (2H, m), 2.82 (1H, dd, J=16.5, 2.8 Hz), 2.64-2.46 (2H, m), 2.45-2.35 (1H, m), 1.72 (1H, q, J=6.3 Hz), 1.59-1.52 (1H, m), 1.47 (9H, s), 1.05 (9H, s)

Intermediate A-2-4: tert-Butyl (2S,4R)-2-((3-((tert-butyldiphenylsilyl)oxy)propyl)carbamoyl)-4-hydroxypiperidine-1-carboxylate

[Formula 41]

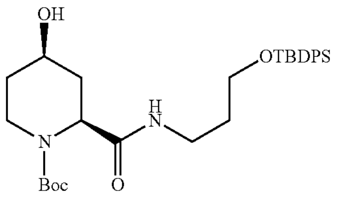

tert-Butyl(S)-2-((3-((tert-butyldiphenylsilyl)oxy)propyl)carbamoyl)-4-oxopiperidine-1-carboxylate (Intermediate A-2-3, 2.15 g, 4.00 mmol) was dissolved in tetrahydrofuran (8 mL), a 1 M solution of L-Selectride in tetrahydrofuran (6.0 mL, 6.00 mmol) was added to the solution at −78° C., and the resulting mixture was stirred for 1 hour. After completion of the reaction, saturated aqueous ammonium chloride (20 mL) was added to the reaction mixture, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=100:0 to 0:100) to obtain tert-butyl (2S,4R)-2-((3-((tert-butyldiphenylsilyl)oxy)propyl)carbamoyl)-4-hydroxypiperidine-1-carboxylate (1.72 g, yield 80%).

LCMS (LC-1): RT=2.25, m/z 541 $[M+H]^+$

1H-NMR ($CDCl_3$): δ (ppm) 7.65 (4H, dd, J=7.8, 1.4 Hz), 7.46-7.35 (6H, m), 6.82 (1H, brs), 5.75 (1H, brs), 4.81-4.70 (1H, m), 4.08-4.00 (1H, br), 3.87-3.74 (1H, m), 3.73-3.53 (2H, m), 3.50-3.39 (1H, m), 3.38-3.28 (1H, m), 3.14 (1H, td, J=13.3, 2.6 Hz), 2.30-2.16 (1H, m), 1.89-1.80 (1H, m), 1.79-1.67 (3H, m), 1.64-1.53 (1H, m), 1.46 (9H, m), 1.05 (9H, s)

Intermediate A-2-5: tert-Butyl (2S,4R)-2-((3-((tert-butyldiphenylsilyl)oxy)propyl)carbamoyl)-4-((methylsulfonyl)oxy)piperidine-1-carboxylate

[Formula 42]

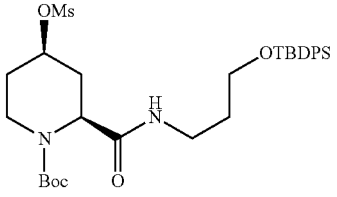

tert-Butyl (2S,4R)-2-((3-((tert-butyldiphenylsilyl)oxy)propyl)carbamoyl)-4-hydroxypiperidine-1-carboxylate (Intermediate A-2-4, 1.72 g, 3.19 mmol) was dissolved in dichloromethane (6.4 mL), triethylamine (0.80 mL, 5.74 mmol), and methanesulfonyl chloride (0.345 mL, 4.47 mmol) were added to the solution under ice cooling, and the resulting mixture was stirred at 0° C. for 2 hours. Then, water (20 mL) was added to the reaction mixture at room temperature, the resulting mixture was extracted with ethyl acetate, and then the organic layer was washed with water and saturated brine. The organic layer was dried over anhydrous magnesium sulfate, filtered, and then concentrated under reduced pressure. The resulting crude product (2.46 g) was used for the following reaction without purification.

LCMS (LC-1): RT=2.25, m/z 619 [M+H]$^+$

Intermediate A-2-6: tert-Butyl (2S,4S)-4-azido-2-((3-((tert-butyldiphenylsilyl)oxy)propyl)carbamoyl)piperidine-1-carboxylate

[Formula 42]

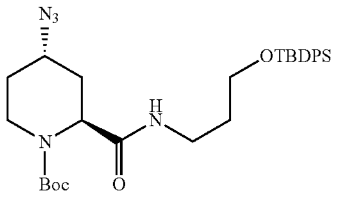

tert-Butyl (2S,4R)-2-((3-((tert-butyldiphenylsilyl)oxy)propyl)carbamoyl)-4-((methylsulfonyl)oxy)piperidine-1-carboxylate (Intermediate A-2-5, 2.46 g, the crude product mentioned above) was dissolved in N,N-dimethylformamide (40 mL), sodium azide (388 mg, 5.79 mmol) was added to the solution, and the resulting mixture was stirred at 90° C. for 6 hours. After completion of the reaction, water (80 mL) was added to the reaction mixture at room temperature, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=100:0 to 80:20) to obtain tert-butyl (2S,4S)-4-azido-2-((3-((tert-butyldiphenylsilyl)oxy)propyl)carbamoyl)piperidine-1-carboxylate (362 mg, yield for 2 steps 20%).

LCMS (LC-1): RT=2.47, m/z 566 [M+H]$^+$

1H-NMR ($CDCl_3$): δ (ppm) 7.64 (4H, dd, J=6.5, 4.0 Hz), 7.46-7.35 (6H, m), 6.46-5.85 (1H, m), 4.92-4.62 (1H, m), 4.07-3.93 (0.5H, m), 3.91-3.75 (0.5H, m), 2.89-2.68 (1H, m), 2.58-2.35 (1H, m), 3.69 (2H, t, J=6.0 Hz), 3.49-3.29 (2H, m), 1.91-1.83 (1H, m), 1.73 (1H, quint, J=6.4 Hz), 1.49-1.23 (12H, m), 1.05 (9H, s), 0.91-0.84 (1H, m)

Intermediate A-2-7: tert-Butyl (2S,4S)-4-amino-2-((3-((tert-butyldiphenylsilyl)oxy)propyl)carbamoyl)piperidine-1-carboxylate

[Formula 44]

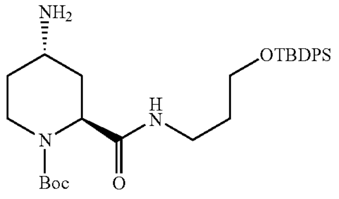

tert-Butyl (2S,4S)-4-azido-2-((3-((tert-butyldiphenylsilyl)oxy)propyl)carbamoyl)piperidine-1-carboxylate (Intermediate A-2-6, 362 mg, 0.64 mmol) was dissolved in methanol (6.4 mL), palladium hydroxide (181 mg, 50 wt %) was added to the solution, and the resulting mixture was stirred at room temperature for 2 hours under hydrogen atmosphere. The atmosphere inside the reaction system was substituted to nitrogen, and then the reaction mixture was filtered through a Celite layer. The filtrate was concentrated under reduced pressure to obtain tert-butyl (2S,4S)-4-amino-2-((3-((tert-butyldiphenylsilyl)oxy)propyl)carbamoyl)piperidine-1-carboxylate (345 mg, yield 97%).

LCMS (LC-1): RT=1.93, m/z 540 [M+H]$^+$

1H-NMR ($CDCl_3$): δ (ppm) 7.64 (4H, dd, J=6.4, 4.0 Hz), 7.46-7.34 (6H, m), 6.34-5.96 (1H, m), 4.90-4.63 (1H, m), 4.24-3.89 (1H, m), 3.75-3.64 (2H, m), 3.45-3.28 (3H, m), 3.15-2.98 (0.5H, m), 2.92-2.64 (1.5H, m), 2.55-2.30 (111, m), 1.79-1.68 (3.511, m), 1.46 (9H, m), 1.32-1.13 (2.5H, m), 1.05 (9H, m)

Method A-3

[Formula 45]

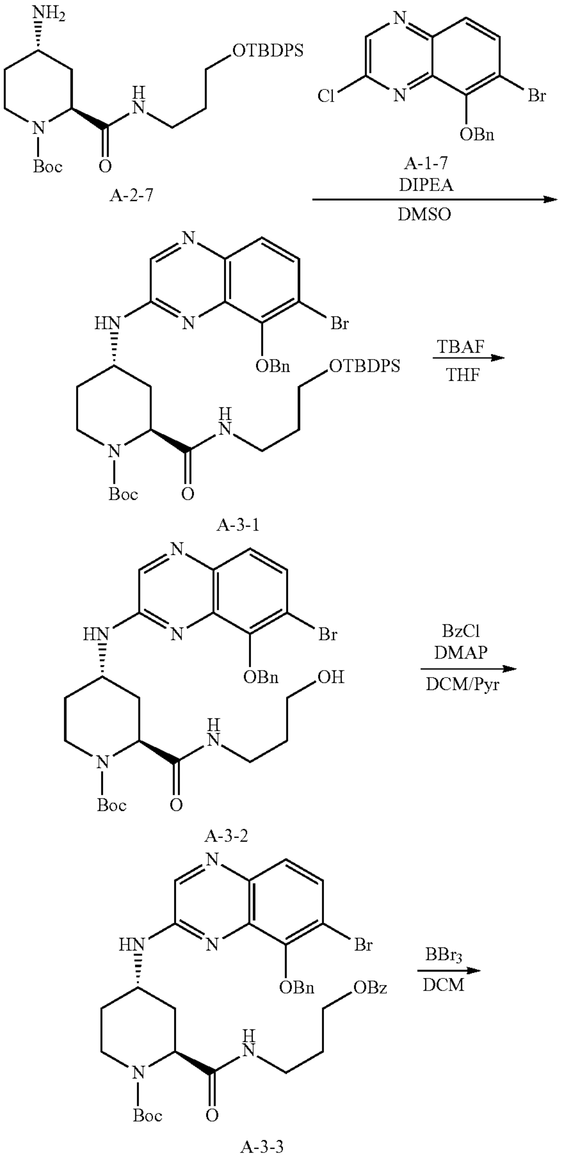

-continued

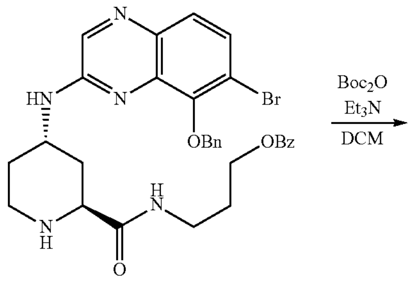

A-3-4

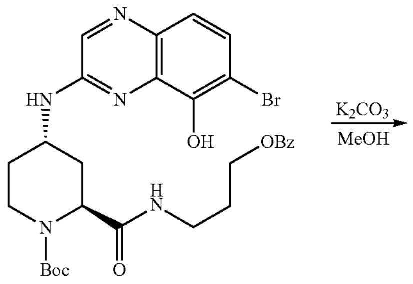

A-3-5

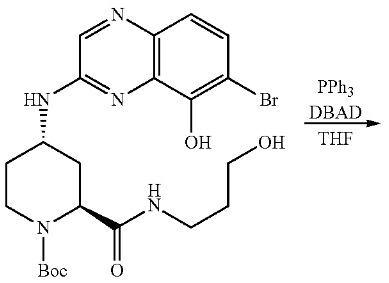

A-3-6

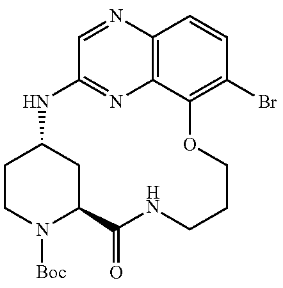

A-3-7

Intermediate A-3-1: tert-Butyl (2S,4S)-4-((8-(benzyloxy)-7-bromoquinoxalin-2-yl)amino)-2-((3-((tert-butyldiphenylsilyl)oxy)propyl)carbamoyl)piperidine-1-carboxylate

[Formula 46]

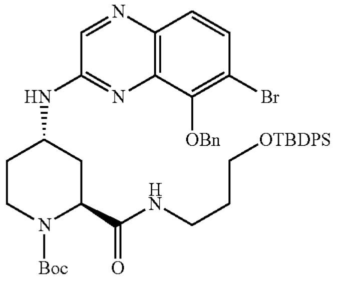

tert-Butyl (2S,4S)-4-amino-2-((3-((tert-butyldiphenylsilyl)oxy)propyl)carbamoyl)piperidine-1-carboxylate (Intermediate A-2-7, 345 mg, 0.64 mmol) was dissolved in dimethyl sulfoxide (5.8 mL), 8-(benzyloxy)-7-bromo-2-chloroquinoxaline (Intermediate A-1-7, 202 mg, 0.582 mmol), and N,N-diisopropylethylamine (0.152 mL, 0.87 mmol) were added to the solution, and the resulting mixture was stirred at 120° C. for 12 hours. After completion of the reaction, water (30 mL) was added to the reaction mixture, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, chloroform: methanol=100:0 to 90:10) to obtain tert-butyl (2S,4S)-4-((8-(benzyloxy)-7-bromoquinoxalin-2-yl)amino)-2-((3-((tert-butyldiphenylsilyl)oxy)propyl)carbamoyl)piperidine-1-carboxylate (147 mg, yield 27%).

LCMS (LC-1): RT=2.31, m/z 852 $[M+H]^+$

1H-NMR ($CDCl_3$): δ (ppm) 8.24-8.18 (1H, m), 7.68-7.57 (6H, m), 7.55-7.48 (2H, m), 7.45-7.29 (9H, m), 6.34 (1H, brs), 5.44 (1H, d, J=10.8 Hz), 5.29 (1H, d, J=10.8 Hz), 4.79 (1H, d, J=8.0 Hz), 4.48-3.86 (1H, m), 3.67 (2H, t, J=8.0 Hz), 3.48-3.26 (2H, m), 2.89-2.74 (1H, m), 2.72-2.57 (1H, m), 2.29 (1H, d, J=12.0 Hz), 1.75-1.65 (2H, m), 1.54-1.42 (10H, m), 1.34-1.18 (2H, m), 1.09-1.01 (10H, m)

Intermediate A-3-2: tert-Butyl (2S,4S)-4-((8-(benzyloxy)-7-bromoquinoxalin-2-yl)amino)-2-((3-hydroxypropyl)carbamoyl)piperidine-1-carboxylate

[Formula 47]

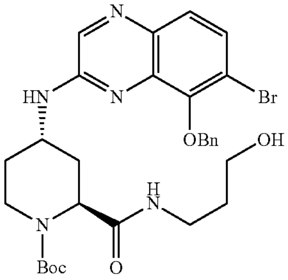

tert-Butyl (2S,4S)-4-((8-(benzyloxy)-7-bromoquinoxalin-2-yl)amino)-2-((3-((tert-butyldiphenylsilyl)oxy)propyl)carbamoyl)piperidine-1-carboxylate (Intermediate A-3-1, 147 mg, 0.172 mmol) was dissolved in tetrahydrofuran (0.86 mL), a 1 M solution of tetrabutylammonium fluoride in tetrahydrofuran (0.863 mL, 0.863 mmol) was added to the solution, and the resulting mixture was stirred at room temperature for 2 hours. After completion of the reaction, the reaction mixture was directly purified by using automatic silica gel column chromatography (eluent, chloroform: methanol=100:0 to 80:20) to obtain tert-butyl (2S,4S)-4-((8-(benzyloxy)-7-bromoquinoxalin-2-yl)amino)-2-((3-hydroxypropyl)carbamoyl)piperidine-1-carboxylate (104 mg, yield 98%).

LCMS (LC-1): RT=1.77, m/z 614 $[M+H]^+$

1H-NMR ($CDCl_3$): δ (ppm) 8.24-8.18 (1H, m), 7.61 (2H, d, J=7.3 Hz), 7.55-7.48 (2H, m), 7.42-7.30 (3H, m), 6.51 (1H, brs), 5.43 (1H, d, J=10.8 Hz), 5.30 (1H, d, J=10.8 Hz), 5.02-4.82 (2H, m), 4.45-3.95 (1H, m), 3.60-3.51 (2H, m), 3.06-2.94 (2H, m), 2.93-2.64 (2H, m), 2.39-2.28 (1H, m), 1.86-1.73 (2H, m), 1.50 (9H, s), 1.44-1.21 (4H, m)

Intermediate A-3-3: tert-Butyl (2S,4S)-2-((3-(benzoyloxy)propyl)carbamoyl)-4-((8-(benzyloxy)-7-bromoquinoxalin-2-yl)amino)piperidine-1-carboxylate

[Formula 48]

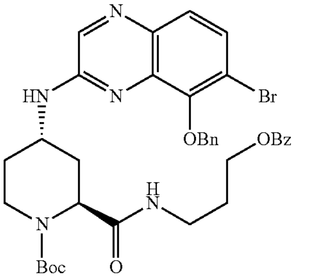

tert-Butyl (2S,4S)-4-((8-(benzyloxy)-7-bromoquinoxalin-2-yl)amino)-2-((3-hydroxypropyl)carbamoyl)piperidine-1-carboxylate (Intermediate A-3-2, 104 mg, 0.170 mmol) was dissolved in a mixed solvent of dichloromethane (0.85 mL) and pyridine (0.85 mL), benzoyl chloride (0.024 mL, 0.20 mmol), and N,N-dimethylaminopyridine (2 mg, 0.017 mmol) were added to the solution under ice cooling at 0° C., the resulting mixture was stirred at room temperature for 1 hour. After completion of the reaction, the reaction mixture was directly purified by using automatic silica gel column chromatography (eluent, chloroform:methanol=100:0 to 90:10) to obtain tert-butyl (2S,4S)-2-((3-(benzoyloxy)propyl)carbamoyl)-4-((8-(benzyloxy)-7-bromoquinoxalin-2-yl)amino)piperidine-1-carboxylate (109 mg, yield 89%).

LCMS (LC-1): RT=2.18, m/z 718 $[M+H]^+$

1H-NMR ($CDCl_3$): δ (ppm) 8.22 (1H, s), 8.02 (2H, d, J=7.4 Hz), 7.61 (2H, d, J=8.0 Hz), 7.59-7.53 (1H, m), 7.51 (2H, d, J=3.2 Hz), 7.44 (2H, t, J=8.0 Hz), 7.33 (2H, t, J=7.1 Hz), 6.66-6.32 (1H, m), 5.45 (1H, d, J=10.8 Hz), 5.29 (1H, d, J=10.8 Hz), 5.12-4.88 (1H, m), 4.84 (1H, d, J=6.8 Hz), 4.39-4.25 (3H, m), 3.46-3.35 (1H, m), 3.34-3.22 (1H, m), 2.95-2.66 (2H, m), 2.37-2.26 (1H, m), 1.97-1.88 (2H, m), 1.56-1.44 (11H, m), 1.37-1.27 (2H, m)

Intermediate A-3-4:3-((2S,4S)-4-((7-Bromo-8-hydroxyquinoxalin-2-yl)amino)piperidine-2-carboxamido)propyl benzoate

[Formula 49]

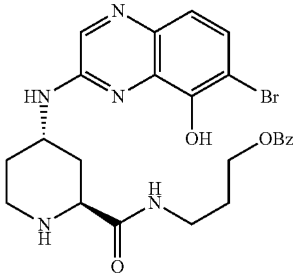

tert-Butyl (2S,4S)-2-((3-(benzoyloxy)propyl)carbamoyl)-4-((8-(benzyloxy)-7-bromoquinoxalin-2-yl)amino)piperidine-1-carboxylate (Intermediate A-3-3, 108 mg, 0.12 mmol) was dissolved in dichloromethane (2.5 mL), a 1 M solution of boron tribromide in dichloromethane (0.742 mL, 0.74 mmol) was added to the solution under ice cooling, and then the resulting mixture was stirred for 30 minutes. After the starting materials disappeared, methanol (2.5 mL) was added dropwise to the reaction mixture at 0° C. to terminate the reaction. The resulting reaction mixture was directly purified with SCX to obtain 3-((2S,4S)-4-((7-bromo-8-hydroxyquinoxalin-2-yl)amino)piperidine-2-carboxamido) propyl benzoate (77 mg, yield 97%). LCMS (LC-1): RT=1.52, m/z 528 $[M+H]^+$1H-NMR ($CDCl_3$): δ (ppm) 8.87 (1H, brs), 8.18 (1H, s), 8.09-8.03 (2H, m), 7.66-7.59 (1H, m), 7.57-7.51 (1H, m), 7.48-7.40 (3H, m), 7.29 (1H, d, J=8.4 Hz), 4.91 (1H, d, J=5.6 Hz), 5.81 (2H, t, J=5.6 Hz), 5.06-4.95 (1H, m), 3.69 (1H, t, J=3.9 Hz), 3.62-3.51 (2H, m), 3.21 (1H, d, J=12.8 Hz), 3.08 (1H, dt, J=4.4, 3.7 Hz), 2.92-2.80 (1H, m), 2.06 (2H, quint, J=6.5 Hz), 1.94-1.88 (1H, m), 1.54-1.45 (2H, m), 1.27 (1H, ddd, J=12.6, 10.0, 4.7 Hz)

Intermediate A-3-5: tert-Butyl (2S,4S)-2-((3-(benzoyloxy)propyl)carbamoyl)-4-((7-bromo-8-hydroxyquinoxalin-2-yl)amino)piperidine-1-carboxylate

[Formula 50]

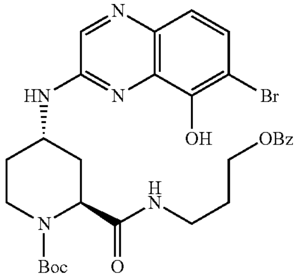

3-((2S,4S)-4-((7-Bromo-8-hydroxyquinoxalin-2-yl)amino)piperidine-2-carboxamido)propyl benzoate (Intermediate A-3-4, 77 mg, 0.146 mmol) was dissolved in dichloromethane (7.4 mL), triethylamine (0.204 mL, 1.46 mmol), and di-tert-butyl dicarbonate (240 mg, 1.10 mmol) were added to the solution, and the resulting mixture was stirred at room temperature for 1 hour. Then, the reaction mixture was directly purified by using automatic silica gel column chromatography (eluent, chloroform:methanol=100:0 to 80:20) to obtain tert-butyl (2S,4S)-2-((3-(benzoyloxy)propyl)carbamoyl)-4-((7-bromo-8-hydroxyquinoxalin-2-yl)amino)piperidine-1-carboxylate (77 mg, yield 84%).

LCMS (LC-1): RT=1.98, m/z 628 $[M+H]^+$

1H-NMR ($CDCl_3$): δ (ppm) 9.28-8.76 (1H, m), 8.48-7.90 (3H, m), 7.78-7.16 (4H, m), 6.92-5.92 (1H, m), 4.96-4.85 (1H, m), 4.49-4.01 (4H, m), 3.52-3.33 (2H, m), 2.98 (1H, d, J=6.7 Hz), 2.10-1.88 (2H, m), 1.56-1.45 (11H, m), 1.37-1.18 (4H, m)

Intermediate A-3-6: tert-Butyl (2S,4S)-4-((7-bromo-8-hydroxyquinoxalin-2-yl)amino)-2-((3-hydroxypropyl)carbamoyl)piperidine-1-carboxylate

[Formula 51]

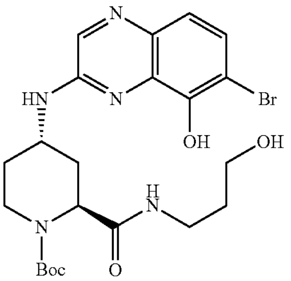

tert-Butyl (2S,4S)-2-((3-(benzoyloxy)propyl)carbamoyl)-4-((7-bromo-8-hydroxyquinoxalin-2-yl)amino)piperidine-1-carboxylate (Intermediate A-3-5, 77 mg, 0.12 mmol) was dissolved in methanol (2.5 mL), potassium carbonate (170 mg, 1.23 mmol) was added to the solution, and the resulting mixture was stirred at room temperature for 15 minutes. Then, the reaction mixture was directly purified by using automatic silica gel column chromatography (eluent, chloroform:methanol=100:0 to 60:40) to obtain tert-butyl (2S,4S)-4-((7-bromo-8-hydroxyquinoxalin-2-yl)amino)-2-((3-hydroxypropyl)carbamoyl)piperidine-1-carboxylate (45 mg, yield 70%).

LCMS (LC-1): RT=1.47, m/z 524 $[M+H]^+$

1H-NMR ($CDCl_3$): δ (ppm) 8.88 (1H, brs), 8.26-8.17 (1H, m), 7.70-7.44 (1H, m), 7.33-7.28 (1H, m), 6.68 (1H, brs), 5.04-4.83 (2H, m), 4.45-4.00 (2H, m), 3.71-3.43 (5H, m), 3.40-2.86 (2H, m), 1.96 (1H, d, J=12.0 Hz), 1.82-1.67 (2H, m), 1.66-1.45 (9H, m), 1.42-1.17 (2H, m)

Intermediate A-3-7: tert-Butyl ($3^2S,3^4S$)-17-bromo-4-oxo-9-oxa-2,5-diaza-1 (2,8)-quinoxaline-3 (4,2)-piperidinacyclononaphane-$3^1$-carboxylate

[Formula 52]

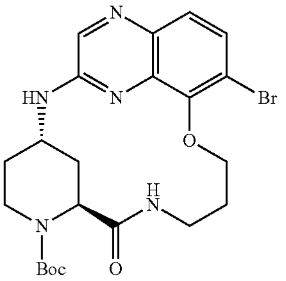

tert-Butyl (2S,4S)-4-((7-bromo-8-hydroxyquinoxalin-2-yl)amino)-2-((3-hydroxypropyl)carbamoyl)piperidine-1-carboxylate (Intermediate A-3-6, 45 mg, 0.086 mmol) was dissolved in tetrahydrofuran (17.2 mL), triphenylphosphine (56 mg, 0.22 mmol), and a 20% solution of di-tert-butyl azodicarboxylate in toluene (0.30 mL) were added to the solution, and the resulting mixture was stirred at room temperature for 12 hours. Then, the reaction mixture was concentrated under reduced pressure. The resulting crude product was purified by using automatic silica gel column chromatography (eluent, chloroform:methanol=100:0 to 90:10) to obtain tert-butyl ($3^2S,3^4S$)-17-bromo-4-oxo-9-oxa-2,5-diaza-1 (2,8)-quinoxaline-3 (4,2)-piperidinacyclononaphane-$3^1$-carboxylate (26.3 mg, yield 61%).

LCMS (LC-1): RT=1.56, m/z 506 $[M+H]^+$

1H-NMR ($CDCl_3$): δ (ppm) 8.22 (1H, d, J=5.4 Hz), 7.60-7.52 (2H, m), 5.16-5.04 (1.5H, m), 4.91-4.85 (0.5H, m), 4.47-4.38 (1H, m), 4.35-4.26 (1.5H, m), 4.19-4.01 (1.5H, m), 3.86-3.71 (1.5H, m), 3.70-3.59 (0.5H, m), 3.13 (0.5H, dt, J=16.0, 4.0 Hz), 2.95 (1.5H, dt, J=16.0, 4.0 Hz), 2.24-2.03 (2H, m), 1.99-1.86 (1H, m), 1.75-1.62 (1H, m), 1.53-1.45 (9.5H, m), 1.39-1.18 (1.5H, m)

Method B-1

[Formula 53]

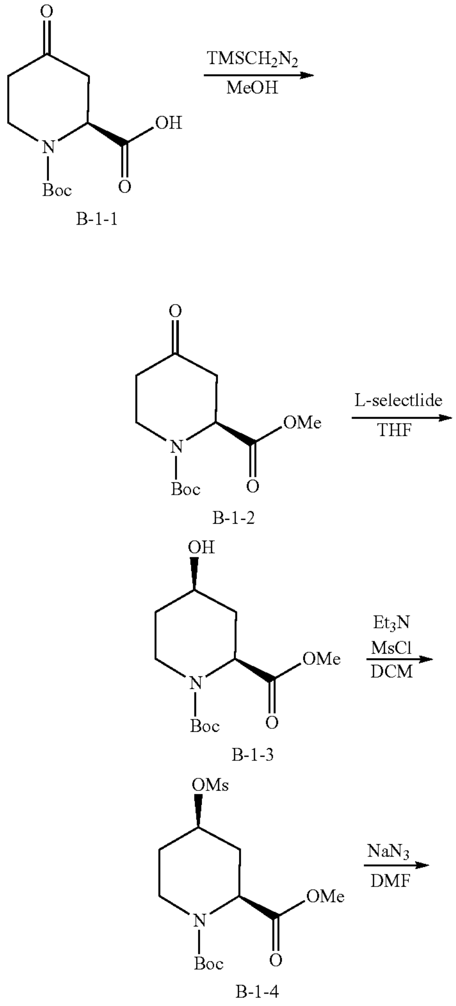

-continued

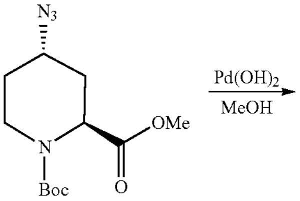

B-1-5

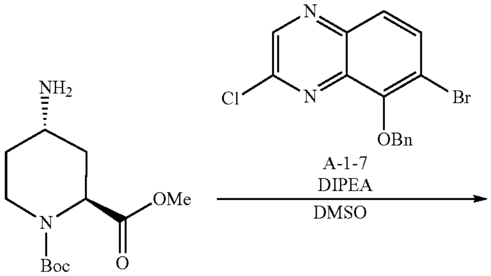

B-1-6

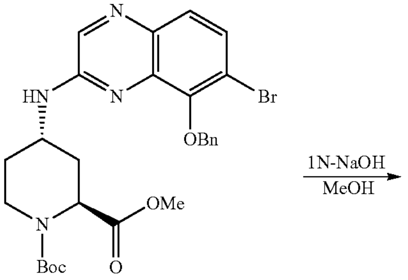

B-1-7

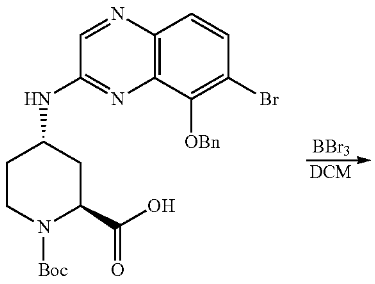

B-1-8

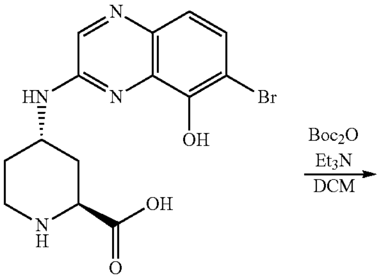

B-1-9

-continued

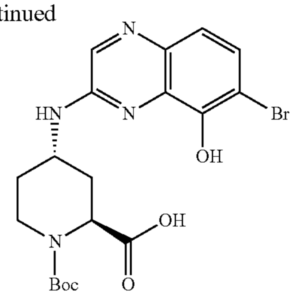

B-1-10

Intermediate B-1-2:1-(tert-Butyl) 2-methyl(S)-4-oxopiperidine-1,2-dicarboxylate

[Formula 54]

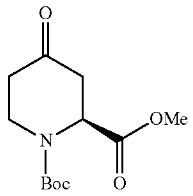

(S)-1-(tert-Butoxycarbonyl)-4-oxopiperidine-2-carboxylic acid (Intermediate B-1-1, 38.9 g, 160 mmol) was dissolved in a mixed solvent of toluene (800 mL) and methanol (266 mL), a 2 M solution of trimethylsilyldiazomethane in diethyl ether (100 mL, 200 mmol) was added dropwise to the solution under ice cooling, and the resulting mixture was stirred at room temperature for 3 hours. After completion of the reaction, acetic acid (100 mL) was added to the reaction mixture under ice cooling, and the resulting mixture was concentrated under reduced pressure. Then, water (200 mL) was added to the concentrated mixture, the resulting mixture was extracted with ethyl acetate, and then the organic layer was washed with water and saturated brine. The organic layer was dried over anhydrous magnesium sulfate, filtered, and then concentrated under reduced pressure to obtain a crude product (41.1 g). This product was used for the following reaction without purification.

LCMS (LC-1): RT=1.12, m/z 258 $[M+H]^+$

1H-NMR ($CDCl_3$): δ (ppm) 5.18-5.08 (0.5H, m), 4.91-4.82 (0.5H, m), 4.16-4.02 (1H, m), 3.75 (3H, s), 3.72-3.56 (1H, m), 2.78 (2H, d, J=6.2 Hz), 2.55-2.46 (2H, m), 1.48 (9H, s)

Intermediate B-1-3:1-(tert-Butyl) 2-methyl (2S,4R)-4-hydroxypiperidine-1,2-dicarboxylate

[Formula 55]

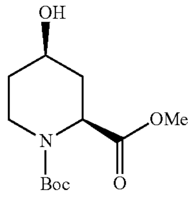

1-(tert-Butyl) 2-methyl(S)-4-oxopiperidine-1,2-dicarboxylate (Intermediate B-1-2, 11.1 g, 43.1 mmol) was dissolved in tetrahydrofuran (86 mL), a 1 M solution of L-Selectride in tetrahydrofuran (65 mL, 64.7 mmol) was added to the solution at −78° C., and the resulting mixture was stirred for 2 hours. After completion of the reaction, saturated aqueous ammonium chloride (200 mL) was added to the reaction mixture, the resulting mixture was extracted with ethyl acetate, and then the organic layer was washed with water and saturated brine. The organic layer was dried over anhydrous sodium sulfate, filtered, and then concentrated under reduced pressure. The resulting crude product was purified by using silica gel column chromatography (eluent, hexane:ethyl acetate=100:0 to 0:100) to obtain 1-(tert-butyl) 2-methyl (2S,4R)-4-hydroxypiperidine-1,2-dicarboxylate (8.69 g, yield 78%).

LCMS (LC-1): RT=0.77, m/z 260 [M+H]+

1H-NMR ($CDCl_3$): δ (ppm) 5.07-4.57 (1H, m), 4.19-4.08 (1H, m), 3.96-3.60 (4H, m), 3.47-3.21 (1H, m), 2.42 (1H, d, J=14.2 Hz), 1.92 (1H, ddd, J=14.2, 6.8, 2.4 Hz), 1.79-1.62 (3H, m), 1.47 (9H, s)

Intermediate B-1-4:1-(tert-Butyl) 2-methyl (2S,4R)-4-((methylsulfonyl)oxy)piperidine-1,2-dicarboxylate

[Formula 56]

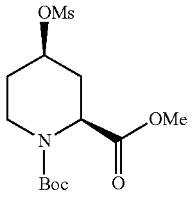

1-(tert-Butyl) 2-methyl (2S,4R)-4-hydroxypiperidine-1,2-dicarboxylate (Intermediate B-1-3, 16.5 g, 63.6 mmol) was dissolved in dichloromethane (127 mL), triethylamine (36 mL, 255 mmol), and methanesulfonyl chloride (9.85 mL, 127 mmol) were added to the solution under ice cooling, and the resulting mixture was stirred at room temperature for 1 hour. Then, the reaction mixture was extracted with ethyl acetate, and the organic layer was washed with water and saturated brine. The organic layer was dried over anhydrous magnesium sulfate, filtered, and then concentrated under reduced pressure. The resulting crude product (21.5 g) was used for the following reaction without purification.

LCMS (LC-1): RT=1.32, m/z 338 [M+H]+

Intermediate B-1-5:1-(tert-Butyl) 2-methyl (2S,4S)-4-azidopiperidine-1,2-dicarboxylate

[Formula 57]

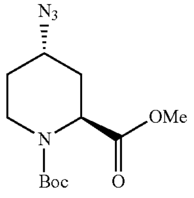

1-(tert-Butyl) 2-methyl (2S,4R)-4-((methylsulfonyl)oxy)piperidine-1,2-dicarboxylate (Intermediate B-1-4, 21.5 g, the crude product mentioned above) was dissolved in N,N-dimethylformamide (319 mL), sodium azide (8.29 g, 127 mmol) was added to the solution, and the resulting mixture was stirred at 80° C. for 11 hours. After completion of the reaction, the reaction mixture was extracted with ethyl acetate, and then the organic layer was washed with water and saturated brine. The organic layer was dried over anhydrous sodium sulfate, filtered, and then concentrated under reduced pressure. The resulting crude product (18.1 g) was used for the following reaction without purification.

LCMS (LC-1): RT=1.53, m/z 285 [M+H]+

1H-NMR ($CDCl_3$): δ (ppm) 5.12-4.60 (1H, m), 4.24-4.13 (0.5H, m), 4.10-4.02 (0.5H, m), 3.81-3.72 (3H, m), 3.43-3.32 (1H, m), 3.11-2.89 (1H, m), 2.56-2.38 (1H, m), 2.04-1.85 (1H, m), 1.75-1.60 (2H, m), 1.52-1.39 (9H, m)

Intermediate B-1-6:1-(tert-Butyl) 2-methyl (2S,4S)-4-aminopiperidine-1,2-dicarboxylate

[Formula 58]

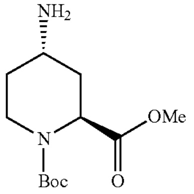

1-(tert-Butyl) 2-methyl (2S,4S)-4-azidopiperidine-1,2-dicarboxylate (Intermediate B-1-5, 18.1 g, 63.7 mmol) was dissolved in methanol (318 mL), palladium hydroxide (3.8 g, 20 wt %) was added to the solution, and the resulting mixture was stirred at room temperature for 21 hours under hydrogen atmosphere. The atmosphere inside the reaction system was substituted to nitrogen, and then the reaction mixture was filtered through a Celite layer. The filtrate was concentrated under reduced pressure to obtain 1-(tert-butyl) 2-methyl (2S,4S)-4-aminopiperidine-1,2-dicarboxylate (15.0 g, yield for 3 steps 91%).

LCMS (LC-1): RT=0.81, m/z 259 [M+H]+

1H-NMR ($CDCl_3$): δ (ppm) 4.99 (0.5H, d, J=4.8 Hz), 4.80 (0.5H, d, J=4.8 Hz), 4.18-4.14 (0.5H, m), 4.12-3.94 (1H, m), 3.76-3.69 (4H, m), 3.37-3.30 (0.5H, t, J=4.0 Hz), 2.71 (1H, t, J=11.3 Hz), 2.47-2.28 (1H, m), 2.26-2.14 (0.5H, m), 1.91 (0.5H, ddd, J=14.4, 6.8, 2.6 Hz), 1.85-1.64 (2H, m), 1.56-1.40 (9H, m), 1.33-1.16 (1H, m)

Intermediate B-1-7:1-(tert-Butyl) 2-methyl (2S,4S)-4-((8-(benzyloxy)-7-bromoquinoxalin-2-yl)amino)piperidine-1,2-dicarboxylate

[Formula 59]

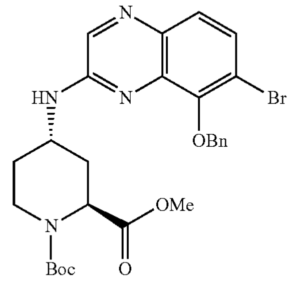

1-(tert-Butyl) 2-methyl (2S,4S)-4-aminopiperidine-1,2-dicarboxylate (Intermediate B-1-6, 11.2 g, 43.2 mmol) was dissolved in dimethyl sulfoxide (79 mL), 8-(benzyloxy)-7-bromo-2-chloroquinoxaline (Intermediate A-1-7, 13.7 g, 39.3 mmol), and N,N-diisopropylethylamine (27.4 mL, 157 mmol) were added to the solution, and the resulting mixture was stirred at 100° C. for 18 hours. Then, water (300 mL) was added to the reaction mixture, the resulting mixture was extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, chloroform:methanol=100:0 to 90:10) to obtain 1-(tert-butyl) 2-methyl (2S,4S)-4-((8-(benzyloxy)-7-bromoquinoxalin-2-yl)amino)piperidine-1,2-dicarboxylate (11.7 g, yield 39%).

LCMS (LC-1): RT=2.12, m/z 571 $[M+H]^+$

1H-NMR ($CDCl_3$): δ (ppm) 8.19-8.13 (1H, m), 7.63-7.50 (4H, m), 7.44-7.28 (3H, m), 5.34 (2H, q, J=10.6 Hz), 5.16-4.87 (1H, m), 4.79 (1H, d, J=7.2 Hz), 4.23-4.12 (2H, m), 3.65 (3H, s), 3.09 (1H, brs), 2.64 (1H, d, J=12.6 Hz), 2.38-2.30 (1H, m), 1.72 (1H, dt, J=12.6, 6.2 Hz), 1.54-1.27 (10H, m)

Intermediate B-1-8: (2S,4S)-4-((8-(Benzyloxy)-7-bromoquinoxalin-2-yl)amino)-1-(tert-butoxycarbonyl)piperidine-2-carboxylic acid

[Formula 60]

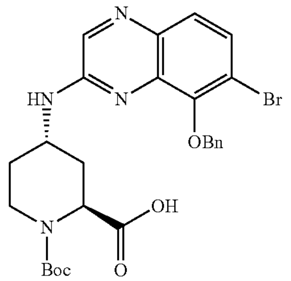

1-(tert-Butyl) 2-methyl (2S,4S)-4-((8-(benzyloxy)-7-bromoquinoxalin-2-yl)amino)piperidine-1,2-dicarboxylate (Intermediate B-1-7, 11.7 g, 20.6 mmol) was dissolved in methanol (680 mL), 1 M aqueous sodium hydroxide (206 mL) was added to the solution, and the resulting mixture was stirred at 40° C. for 1 hour. After completion of the reaction, 2 M aqueous hydrochloric acid (103 mL) was added to the reaction mixture, the resulting mixture was extracted with chloroform, and then the organic layer was washed with water and saturated brine. The organic layer was dried over anhydrous magnesium sulfate, filtered, and then concentrated under reduced pressure. The resulting crude product was purified by using silica gel column chromatography (eluent, chloroform:methanol=100:0 to 80:20) to obtain (2S,4S)-4-((8-(benzyloxy)-7-bromoquinoxalin-2-yl)amino)-1-(tert-butoxycarbonyl)piperidine-2-carboxylic acid (8.97 g, yield 78%).

LCMS (LC-1): RT=1.41, m/z 555 $[M-H]^+$

1H-NMR ($CDCl_3$): δ (ppm) 8.17 (1H, brs), 7.62-7.41 (5H, m), 7.40-7.27 (4H, m), 5.35-5.15 (3H, m), 5.12-4.84 (2H, m), 4.12-4.00 (1H, m), 3.20-3.12 (1H, m), 2.69 (2H, s), 1.47 (9H, s), 1.02-0.95 (1H, m)

Intermediate B-1-9: (2S,4S)-4-((7-Bromo-8-hydroxyquinoxalin-2-yl)amino)piperidine-2-carboxylic acid

[Formula 61]

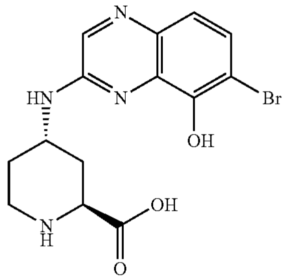

(2S,4S)-4-((8-(Benzyloxy)-7-bromoquinoxalin-2-yl)amino)-1-(tert-butoxycarbonyl)piperidine-2-carboxylic acid (Intermediate B-1-8, 8.97 g, 16.1 mmol) was dissolved in dichloromethane (161 mL), a 1 M solution of boron tribromide in dichloromethane (96.7 mL, 96.7 mmol) was added to the solution under ice cooling at 0° C., and then the resulting mixture was stirred for 2 hours. After the starting materials disappeared, tert-butanol (160 mL) was added dropwise to the reaction mixture at 0° C. to terminate the reaction. The resulting reaction mixture was directly purified with SCX to obtain (2S,4S)-4-((7-bromo-8-hydroxyquinoxalin-2-yl)amino)piperidine-2-carboxylic acid (6.13 g, yield 100%).

LCMS (LC-1): RT=0.89, m/z 367 $[M+H]^+$

1H-NMR ($CD_3OD$): δ (ppm) 8.00 (1H, d, J=6.6 Hz), 7.46-7.34 (2H, m), 7.26-7.09 (2H, m), 4.32-4.24 (1H, m), 3.65-3.46 (2H, m), 3.24-3.07 (2H, m), 2.48-2.29 (1H, m), 2.15-1.94 (2H, m), 1.94-1.82 (1H, m), 1.81-1.68 (1H, m)

Intermediate B-1-10: (2S,4S)-4-((7-Bromo-8-hydroxyquinoxalin-2-yl)amino)-1-(tert-butoxycarbonyl)piperidine-2-carboxylic acid

[Formula 62]

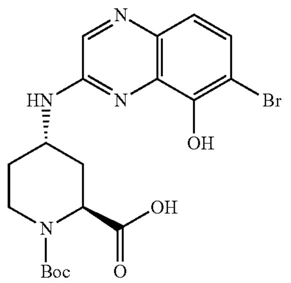

(2S,4S)-4-((7-Bromo-8-hydroxyquinoxalin-2-yl)amino)piperidine-2-carboxylic acid (Intermediate B-1-9, 5.31 g, 14.5 mmol) was dissolved in N,N-dimethylformamide (725 mL), triethylamine (6.05 mL, 43.5 mmol), and di-tert-butyl dicarbonate (4.75 g, 21.8 mmol) were added to the solution, and the resulting mixture was stirred at room temperature for 1 hour. Then, 1 M aqueous hydrochloric acid was added to the reaction mixture, the resulting mixture was extracted with ethyl acetate, and then the organic layer was washed with water and saturated brine. The organic layer was dried over anhydrous magnesium sulfate, filtered, and then concentrated under reduced pressure. The resulting crude product was used for the following reaction without purification.

LCMS (LC-1): RT=1.08, m/z 467 $[M+H]^+$

Method B-2

[Formula 63]

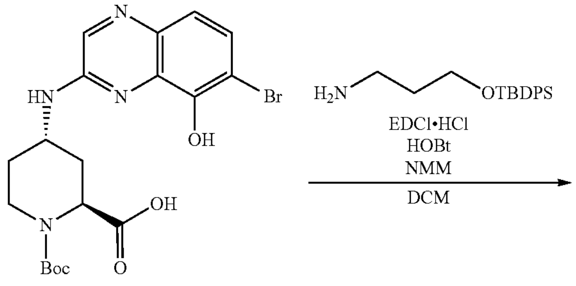

B-1-10

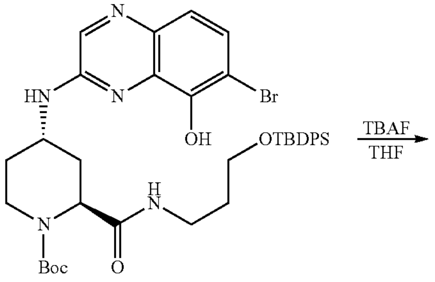

B-2-1

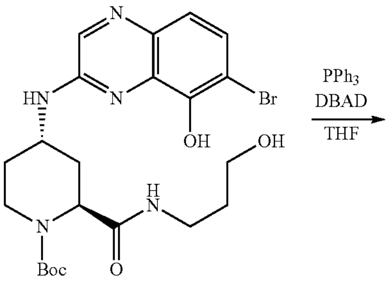

A-3-6

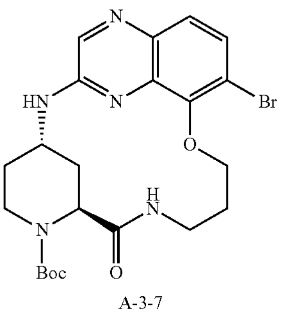

A-3-7

Intermediate B-2-1: tert-Butyl (2S,4S)-4-((7-bromo-8-hydroxyquinoxalin-2-yl)amino)-2-((3-((tert-butyldiphenylsilyl)oxy)propyl)carbamoyl)piperidine-1-carboxylate

[Formula 64]

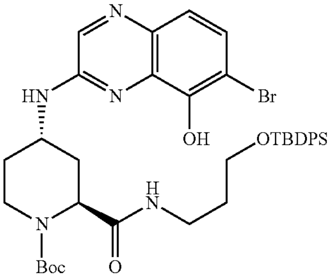

(2S,4S)-4-((7-Bromo-8-hydroxyquinoxalin-2-yl)amino)-1-(tert-butoxycarbonyl)piperidine-2-carboxylic acid (Intermediate B-1-10, 4.23 g, 9.07 mmol), and 3-((tert-butyldiphenylsilyl)oxy)propan-1-amine (4.26 g, 13.6 mmol) were dissolved in dichloromethane (45 mL), N-methylmorpholine (2.49 mL, 22.7 mmol), 1-ethyl-3-(3-dimethylaminopropyl)carbodiimide hydrochloride (5.64 g, 36.3 mmol), and 1-hydroxybenzotriazol (2.69 g, 19.9 mmol) were added to the solution, and the resulting mixture was stirred at room temperature for 2 hours. After completion of the reaction, the reaction mixture was extracted with dichloromethane, and then the organic layer was washed with water and saturated brine. The organic layer was dried over anhydrous magnesium sulfate, filtered, and then concentrated under reduced pressure. The resulting crude product was used for the following reaction without purification.

LCMS (LC-1): RT=2.56, m/z 764 $[M+H]^+$

Intermediate A-3-6: tert-Butyl (2S,4S)-4-((7-bromo-8-hydroxyquinoxalin-2-yl)amino)-2-((3-hydroxypropyl)carbamoyl)piperidine-1-carboxylate

[Formula 65]

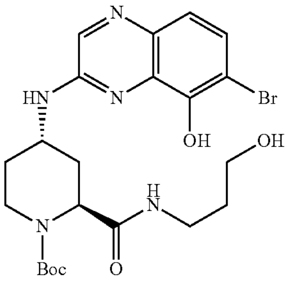

tert-Butyl (2S,4S)-4-((7-bromo-8-hydroxyquinoxalin-2-yl)amino)-2-((3-((tert-butyldiphenylsilyl)oxy)propyl)carbamoyl)piperidine-1-carboxylate (Intermediate B-2-1, 4.64 g, 6.10 mmol) was dissolved in tetrahydrofuran (30 mL), a 1 M solution of tetrabutylammonium fluoride in tetrahydrofuran (30 mL, 30 mmol) was added to the solution, and the resulting mixture was stirred at room temperature for 1 hour. After completion of the reaction, the reaction mixture was directly purified by using automatic silica gel column chromatography (eluent, chloroform:methanol=100:0 to 60:40) to obtain tert-butyl (2S,4S)-4-((7-bromo-8-hydroxyquinoxalin-2-yl)amino)-2-((3-hydroxypropyl)carbamoyl)piperidine-1-carboxylate (2.90 g, yield 91%).

LCMS (LC-1): RT=1.47, m/z 524 [M+H]$^+$

1H-NMR ($CDCl_3$): δ (ppm) 8.88 (1H, brs), 8.26-8.17 (1H, m), 7.70-7.44 (1H, m), 7.33-7.28 (1H, m), 6.68 (1H, brs), 5.04-4.83 (2H, m), 4.45-4.00 (2H, m), 3.71-3.43 (5H, m), 3.40-2.86 (2H, m), 1.96 (1H, d, J=12.0 Hz), 1.82-1.67 (2H, m), 1.66-1.53 (8H, m), 1.50-1.45 (1H, m), 1.42-1.17 (2H, m)

Intermediate A-3-7: tert-Butyl ($3^2$S,$3^4$S)-17-bromo-4-oxo-9-oxa-2,5-diaza-1 (2,8)-quinoxalina-3 (4,2)-piperidinacyclononaphane-$3^1$-carboxylate

[Formula 66]

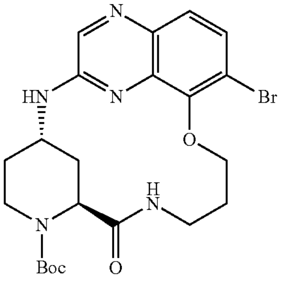

tert-Butyl (2S,4S)-4-((7-bromo-8-hydroxyquinoxalin-2-yl)amino)-2-((3-hydroxypropyl)carbamoyl)piperidine-1-carboxylate (Intermediate B-3-6, 2.90 g, 5.55 mmol) was dissolved in THF (1109 mL), triphenylphosphine (3.64 mg, 13.8 mmol), and a 20% solution of di-tert-butyl azodicarboxylate in toluene (19.2 mL) were added to the solution, and the resulting mixture was stirred at room temperature for 2 hours. Then, the reaction mixture was concentrated under reduced pressure. The resulting crude product was purified by using automatic silica gel column chromatography (eluent, chloroform:methanol=100:0 to 90:10) to obtain tert-butyl ($3^2$S,$3^4$S)-17-bromo-4-oxo-9-oxa-2,5-diaza-1 (2,8)-quinoxalina-3 (4,2)-piperidinacyclononaphane-$3^1$-carboxylate (1.96 g, yield 70%).

LCMS (LC-1): RT=1.56, m/z 506 [M+H]$^+$

1H-NMR ($CDCl_3$): δ (ppm) 8.22 (1H, d, J=5.4 Hz), 7.60-7.52 (2H, m), 5.16-5.04 (1.5H, m), 4.91-4.85 (0.5H, m), 4.47-4.38 (1H, m), 4.35-4.26 (1.5H, m), 4.19-4.01 (1.5H, m), 3.86-3.71 (1.5H, m), 3.70-3.59 (0.5H, m), 3.13 (0.5H, dt, J=16.0, 4.0 Hz), 2.95 (1.5H, dt, J=16.0, 4.0 Hz), 2.24-2.03 (2H, m), 1.99-1.86 (1H, m), 1.75-1.62 (1H, m), 1.53-1.45 (9.5H, m), 1.39-1.18 (1.5H, m)

Method C-1

[Formula 67]

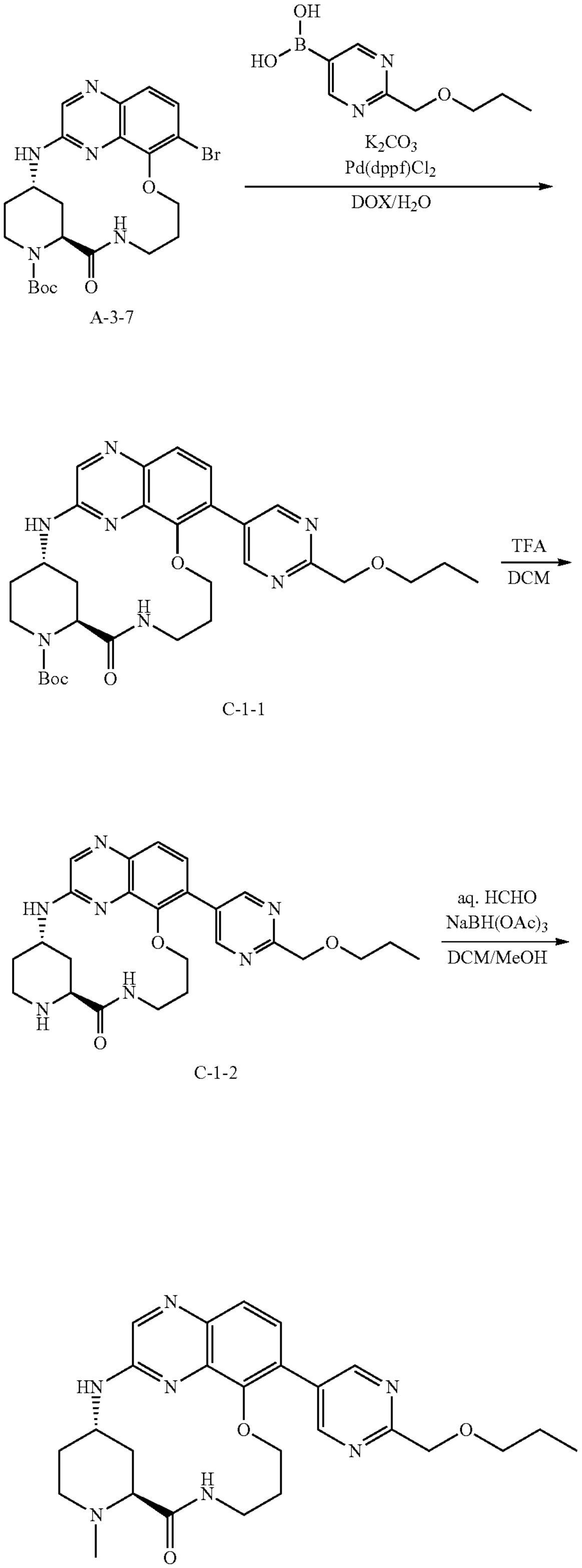

A-3-7

C-1-1

C-1-2

C-1-3

Intermediate C-1-1: tert-Butyl (3$^2$S,3$^4$S)-4-oxo-17-(2-(propoxymethyl)pyrimidin-5-yl)-9-oxa-2,5-diaza-1 (2,8)-quinoxalina-3 (4,2)-piperidinacyclononaphane-3$^1$-carboxylate

[Formula 68]

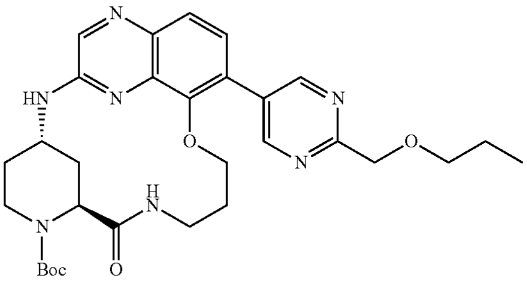

tert-Butyl (3$^2$S,3$^4$S)-17-bromo-4-oxo-9-oxa-2,5-diaza-1 (2,8)-quinoxalina-3 (4,2)-piperidinacyclononaphane-3$^1$-carboxylate (Intermediate A-3-7, 51 mg, 0.099 mmol), and (2-(propoxymethyl)pyrimidin-5-yl)boronic acid (165 mg, 45 wt %, 0.25 mmol) were dissolved in a mixed solvent of 1,4-dioxane (2.0 mL) and water (0.50 mL), potassium carbonate (40 mg, 0.30 mmol), and [1,1'-bis(diphenylphosphino) ferrocene]palladium (II) dichloride dichloromethane complex (20.2 mg, 0.020 mmol) were added to the solution, and the resulting mixture was stirred at 100° C. for 4 hours under microwave irradiation. Then, the reaction mixture was filtered through a Celite layer, and the filtrate was concentrated under reduced pressure. The crude product was purified by using automatic amine silica gel column chromatography (eluent, chloroform: ethyl acetate=50:50) to obtain a roughly purified product (313 mg). This product was used for the following reaction without further purification.

LCMS (LC-1): RT=1.44, m/z 578 [M+H]$^+$

Intermediate C-1-2: (3$^2$S,3$^4$S)-17-(2-(Propoxymethyl)pyrimidin-5-yl)-9-oxa-2,5-diaza-1 (2,8)-quinoxalina-3 (4,2)-piperidinacyclononaphan-4-one

[Formula 69]

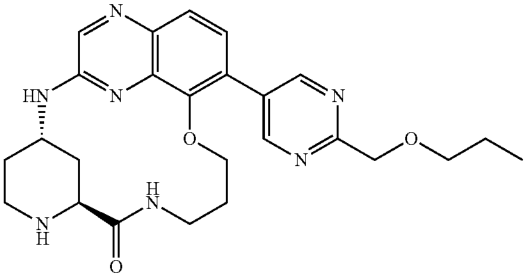

tert-Butyl (3$^2$S,3$^4$S)-4-oxo-17-(2-(propoxymethyl)pyrimidin-5-yl)-9-oxa-2,5-diaza-1 (2,8)-quinoxalina-3 (4,2)-piperidinacyclononaphane-3$^1$-carboxylate (Intermediate C-1-1, 313 mg, 0.54 mmol, the roughly purified product) was dissolved in dichloromethane (1 mL), trifluoroacetic acid (0.25 mL) was added to the solution, and the resulting mixture was stirred at room temperature for 14 hours. The obtained reaction mixture was roughly purified directly with SCX. Then, the resultant was purified by using automatic amine silica gel column chromatography (eluent, chloroform:methanol=100:0 to 90:10) to obtain (3$^2$S,3$^4$S)-17-(2-(propoxymethyl)pyrimidin-5-yl)-9-oxa-2,5-diaza-1 (2,8)-quinoxalina-3 (4,2)-piperidinacyclononaphan-4-one (29.9 mg, yield for 2 steps 63%).

LCMS (LC-1): RT=1.02, m/z 478 [M+H]$^+$

Example α-01-07 (End product C-1-3): (3$^2$S,3$^4$S)-3'-Methyl-17-(2-(propoxymethyl)pyrimidin-5-yl)-9-oxa-2,5-diaza-1 (2,8)-quinoxalina-3 (4,2)-piperidinacyclononaphan-4-one

[Formula 70]

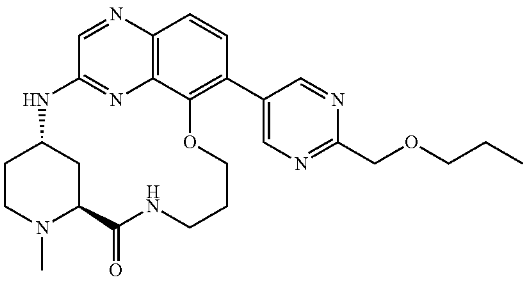

(3$^2$S,3$^4$S)-17-(2-(Propoxymethyl)pyrimidin-5-yl)-9-oxa-2,5-diaza-1 (2,8)-quinoxalina-3 (4,2)-piperidinacyclononaphan-4-one (Intermediate C-1-2, 29.9 mg, 0.063 mmol) was dissolved in a mixed solvent of dichloromethane (0.32 mL) and methanol (0.32 mL), 37% aqueous formaldehyde (0.014 mL, 0.19 mmol), and sodium triacetoxyborohydride (20 mg, 0.094 mmol) were added to the solution, and the resulting mixture was stirred at room temperature for 1 hour. The resulting reaction mixture was roughly purified directly with SCX, and then purified by using reverse phase liquid column chromatography to obtain (3$^2$S,3$^4$S)-31-methyl-17-(2-(propoxymethyl)pyrimidin-5-yl)-9-oxa-2,5-diaza-1 (2,8)-quinoxalina-3 (4,2)-piperidinacyclononaphan-4-one (4.8 mg, yield 15%).

LCMS (LC-1): RT=1.07, m/z 492 [M+H]$^+$

1H-NMR ($CD_3OD$): δ (ppm) 9.05 (2H, s), 8.20 (1H, s), 7.66 (1H, d, J=8.4 Hz), 7.41 (1H, d, J=8.4 Hz), 4.78-4.65 (3H, m), 4.20-4.10 (1H, m), 3.88-3.74 (3H, m), 3.62 (2H, t, J=6.8 Hz), 3.57-3.48 (1H, m), 3.36-3.33 (2H, m), 2.93-2.73 (2H, m), 2.57 (4H, s), 2.26 (1H, d, J=7.8 Hz), 2.01-1.93 (1H, m), 1.90-1.61 (5H, m), 0.98 (3H, t, J=7.8 Hz)

The following compounds mentioned in the following tables were synthesized by similar methods. In the following tables, the preparation methods that should be referred to are mentioned in the columns of "Reference Methods".

TABLE 2
| Example | Structure | Reference Methods | LCMS Data |
|---|---|---|---|
| a-01-01 | 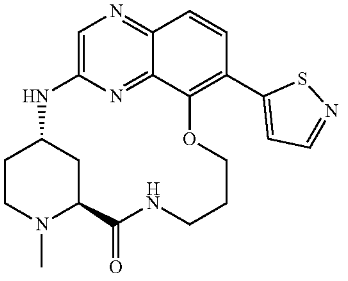 [SMILES: CN1CC[C@H]2C[C@H]1C(=O)NCCCOc1c(-c3ccns3)ccc3ncc(nc13)N2] | Methods A-2, A-3, and C-1 | (LC-1): RT = 1.04, m/z 425 [M + H]+ |
| a-01-02 | 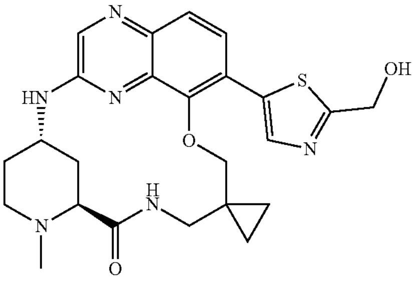 [SMILES: CN1CC[C@H]2C[C@H]1C(=O)NCC1(CC1)COc1c(-c3cnc(CO)s3)ccc3ncc(nc13)N2] | Methods A-2, A-3, and C-1 | (LC-1): RT = 0.90, m/z 481 [M + H]+ |
| a-01-03 | 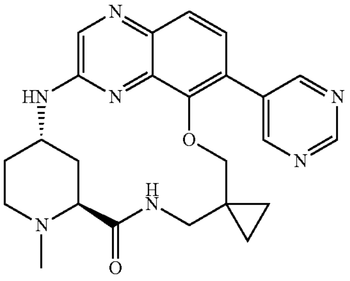 [SMILES: CN1CC[C@H]2C[C@H]1C(=O)NCC1(CC1)COc1c(-c3cncnc3)ccc3ncc(nc13)N2] | Methods A-2, A-3, and C-1 | (LC-1): RT = 0.89, m/z 446 [M + H]+ |
| a-01-04 | 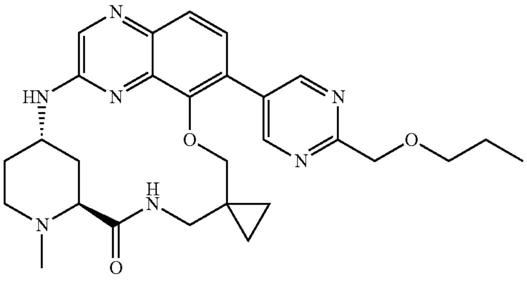 [SMILES: CCCOCc1ncc(-c2ccc3ncc4nc3c2OCC2(CC2)CNC(=O)[C@@H]2C[C@H](CCN2C)N4)cn1] | Methods A-2, A-3, and C-1 | (LC-1): RT = 1.13, m/z 518 [M + H]+ |
| a-01-05 | 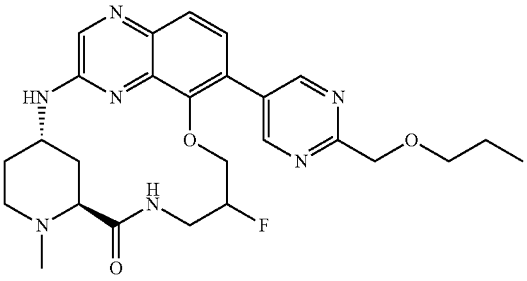 [SMILES: CCCOCc1ncc(-c2ccc3ncc4nc3c2OCC(F)CNC(=O)[C@@H]2C[C@H](CCN2C)N4)cn1] | Methods B-1, B-2, and C-1 | (LC-1): RT = 1.11, m/z 510 [M + H]+ |

TABLE 2-continued
| Example | Structure | Reference Methods | LCMS Data |
|---|---|---|---|
| a-01-06 | 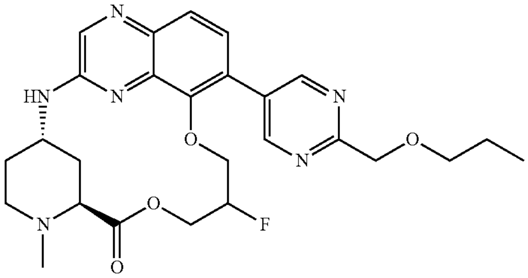 | Methods B-1, B-2, and C-1 | (LC-1): RT = 1.39, m/z 511 $[M + H]^+$ |
| a-01-07 | 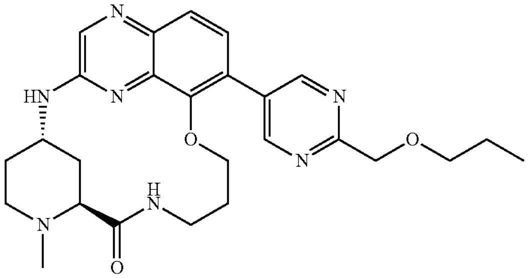 | Methods A-2, A-3, and C-1 | (LC-1): RT = 1.08, m/z 492 $[M + H]^+$ |
| a-01-08 | 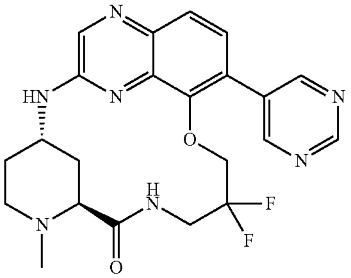 | Methods A-2, A-3, and C-1 | (LC-1): RT = 0.96, m/z 456 $[M + H]^+$ |
| a-01-09 | 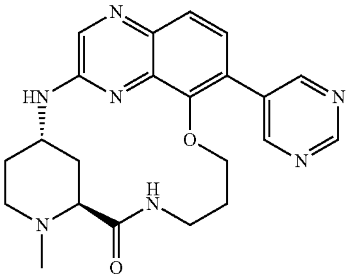 [SMILES: CN1CC[C@H]2C[C@H]1C(=O)NCCCOc1c(-c3cncnc3)ccc3ncc(nc13)N2] | Methods A-2, A-3, and C-1 | (LC-1): RT = 0.83, m/z 420 $[M + H]^+$ |
| a-01-10 | 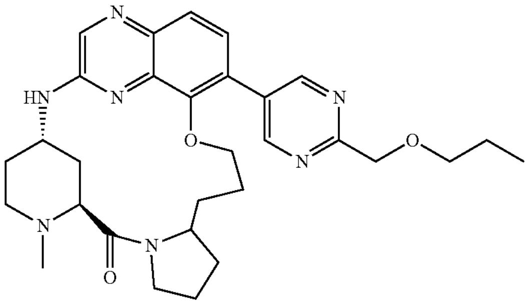 [SMILES: CCCOCc1ncc(-c2ccc3ncc4nc3c2OCCCC2CCCN2C(=O)[C@@H]2C[C@H](CCN2C)N4)cn1] | Methods B-1, B-2, and C-1 | (LC-1): RT = 1.16, m/z 546 $[M + H]^+$ |

TABLE 2-continued
| Example | Structure | Reference Methods | LCMS Data |
|---|---|---|---|
| a-01-11 | 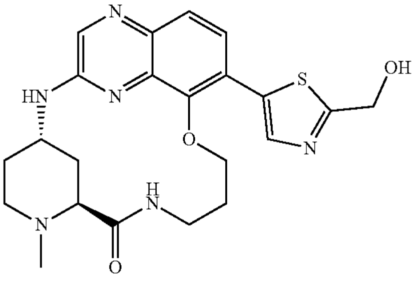 [SMILES: CN1CC[C@H]2C[C@H]1C(=O)NCCCOc1c(-c3cnc(CO)s3)ccc3ncc(nc13)N2] | Methods A-2, A-3, and C-1 | (LC-1): RT = 0.83, m/z 455 $[M + H]^+$ |
| a-01-12 | 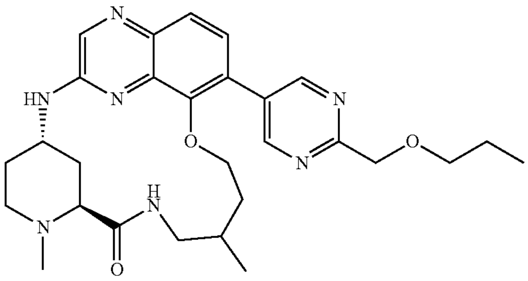 [SMILES: CCCOCc1ncc(-c2ccc3ncc4nc3c2OCCC(C)CNC(=O)[C@@H]2C[C@H](CCN2C)N4)cn1] | Methods B-1, B-2, and C-1 | (LC-1): RT = 1.20, m/z 520 $[M + H]^+$ |
| a-01-13 | 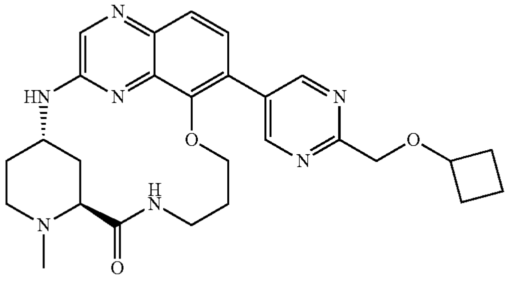 [SMILES: CN1CC[C@H]2C[C@H]1C(=O)NCCCOc1c(-c3cnc(COC4CCC4)nc3)ccc3ncc(nc13)N2] | Methods A-2, A-3, and C-1 | (LC-1): RT = 1.10, m/z 504 $[M + H]^+$ |
| a-01-14 | 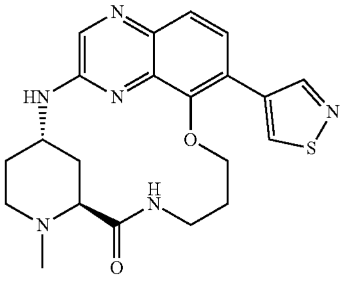 [SMILES: CN1CC[C@H]2C[C@H]1C(=O)NCCCOc1c(-c3cnsc3)ccc3ncc(nc13)N2] | Methods A-2, A-3, and C-1 | (LC-1): RT = 1.03, m/z 425 $[M + H]^+$ |
| a-01-15 | 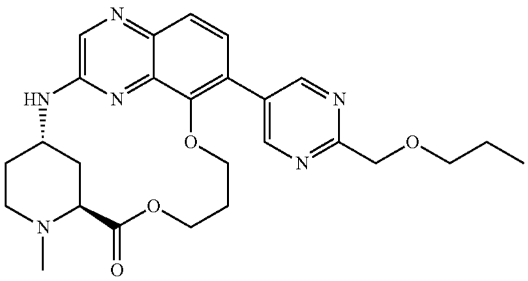 | Methods B-1, B-2, and C-1 | (LC-1): RT = 1.38, m/z 493 $[M + H]^+$ |

TABLE 2-continued
| Example | Structure | Reference Methods | LCMS Data |
| --- | --- | --- | --- |
| a-01-16 | 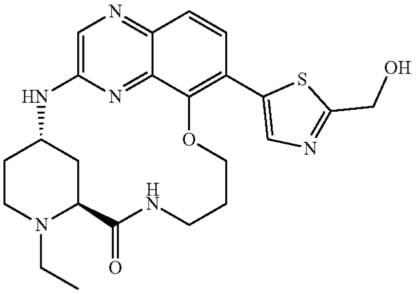 [SMILES: CCN1CC[C@H]2C[C@H]1C(=O)NCCCOc1c(-c3cnc(CO)s3)ccc3ncc(nc13)N2] | Methods A-2, A-3, and C-1 | (LC-1): RT = 0.86, m/z 469 $[M + H]^+$ |
| a-01-17 | 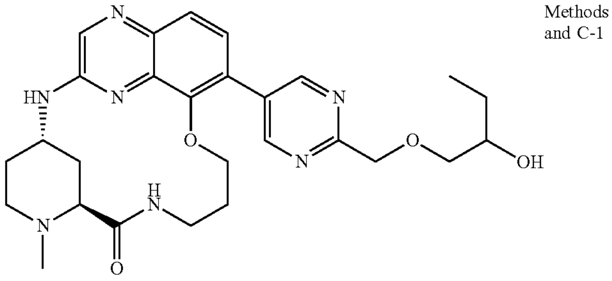 | Methods A-2, A-3, and C-1 | (LC-1): RT = 0.94, m/z 522 $[M + H]^+$ |
| a-01-18 | 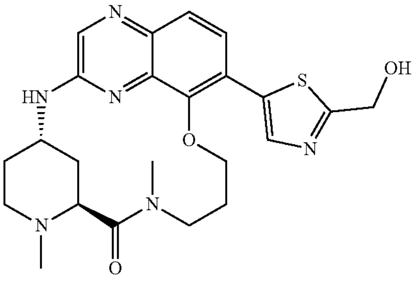 [SMILES: CN1CCCOc2c(-c3cnc(CO)s3)ccc3ncc(nc23)N[C@H]2CCN(C)[C@@H](C2)C1=O] | Methods A-2, A-3, and C-1 | (LC-1): RT = 0.85, m/z 469 $[M + H]^+$ |
| a-01-19 | 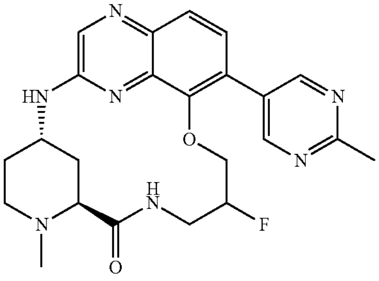 [SMILES: Cc1ncc(-c2ccc3ncc4nc3c2OCC(F)CNC(=O)[C@@H]2C[C@H](CCN2C)N4)cn1] | Methods B-1, B-2, and C-1 | (LC-1): RT = 0.90, m/z 452 $[M + H]^+$ |
| a-01-20 | 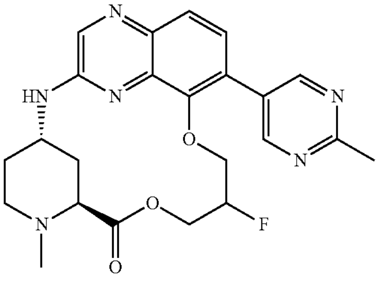 [SMILES: Cc1ncc(-c2ccc3ncc4nc3c2OCC(F)COC(=O)[C@@H]2C[C@H](CCN2C)N4)cn1] | Methods B-1, B-2, and C-1 | (LC-1): RT = 1.14, m/z 453 $[M + H]^+$ |

TABLE 2-continued
| Example | Structure | Reference Methods | LCMS Data |
|---|---|---|---|
| a-01-21 | 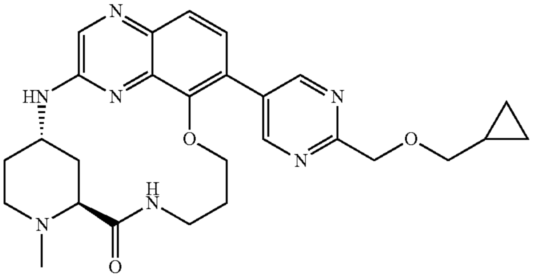 [SMILES: CN1CC[C@H]2C[C@H]1C(=O)NCCCOc1c(-c3cnc(COCC4CC4)nc3)ccc3ncc(nc13)N2] | Methods A-2, A-3, and C-1 | (LC-1): RT = 1.08, m/z 504 [M + H]$^+$ |
| a-01-22 | 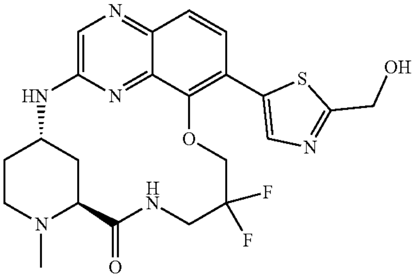 [SMILES: CN1CC[C@H]2C[C@H]1C(=O)NCC(F)(F)COc1c(-c3cnc(CO)s3)ccc3ncc(nc13)N2] | Methods A-2, A-3, and C-1 | (LC-1): RT = 0.93, m/z 491 [M + H]$^+$ |
| a-01-23 | 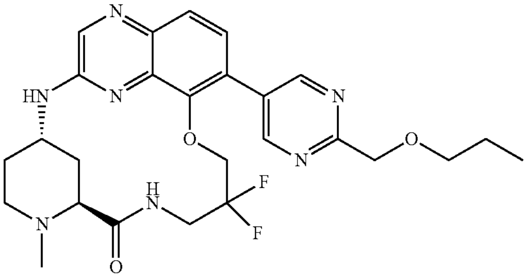 [SMILES: CCCOCc1ncc(-c2ccc3ncc4nc3c2OCC(F)(F)CNC(=O)[C@@H]2C[C@H](CCN2C)N4)cn1] | Methods A-2, A-3, and C-1 | (LC-1): RT = 1.20, m/z 528 [M + H]$^+$ |
| a-01-24 | 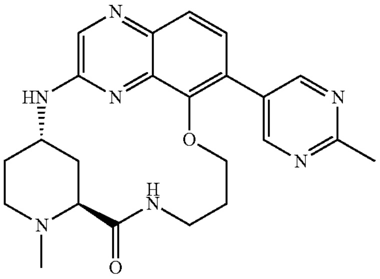 [SMILES: Cc1ncc(-c2ccc3ncc4nc3c2OCCCNC(=O)[C@@H]2C[C@H](CCN2C)N4)cn1] | Methods A-2, A-3, and C-1 | (LC-1): RT = 0.87, m/z 434 [M + H]$^+$ |
| a-01-25 | 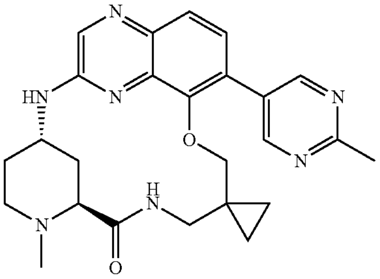 [SMILES: Cc1ncc(-c2ccc3ncc4nc3c2OCC2(CC2)CNC(=O)[C@@H]2C[C@H](CCN2C)N4)cn1] | Methods A-2, A-3, and C-1 | (LC-1): RT = 0.93, m/z 460 [M + H]$^+$ |

TABLE 2-continued
| Example | Structure | Reference Methods | LCMS Data |
|---|---|---|---|
| a-01-26 | 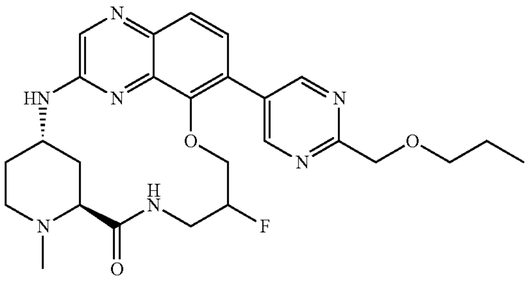 [SMILES: CCCOCc1ncc(-c2ccc3ncc4nc3c2OCC(F)CNC(=O)[C@@H]2C[C@H](CCN2C)N4)cn1] | Methods B-1, B-2, and C-1 | (LC-1): RT = 1.16, m/z 510 $[M + H]^+$ |
| a-01-27 | 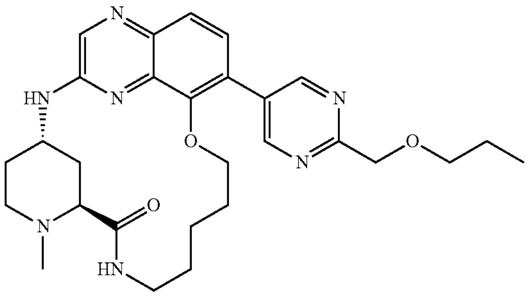 [SMILES: CCCOCc1ncc(-c2ccc3ncc4nc3c2OCCCCCNC(=O)[C@@H]2C[C@H](CCN2C)N4)cn1] | Methods A-2, A-3, and C-1 | (LC-1): RT = 1.25, m/z 520 $[M + H]^+$ |
| a-01-28 | 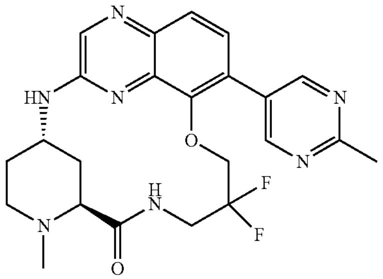 [SMILES: Cc1ncc(-c2ccc3ncc4nc3c2OCC(F)(F)CNC(=O)[C@@H]2C[C@H](CCN2C)N4)cn1] | Methods A-2, A-3, and C-1 | (LC-1): RT = 0.98, m/z 470 $[M + H]^+$ |
| a-01-29 | 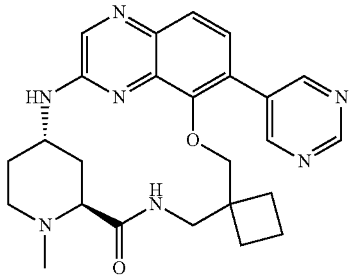 [SMILES: CN1CC[C@H]2C[C@H]1C(=O)NCC1(CCC1)COc1c(-c3cncnc3)ccc3ncc(nc13)N2] | Methods A-2, A-3, and C-1 | (LC-1): RT = 1.01, m/z 460 $[M + H]^+$ |
| a-01-30 | 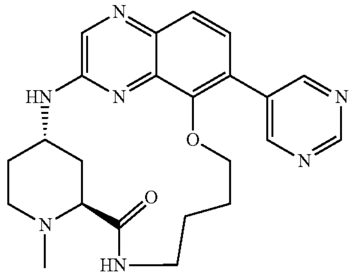 [SMILES: CN1CC[C@H]2C[C@H]1C(=O)NCCCCOc1c(-c3cncnc3)ccc3ncc(nc13)N2] | Methods A-2, A-3, and C-1 | (LC-1): RT = 0.88, m/z 434 $[M + H]^+$ |

TABLE 2-continued
| Example | Structure | Reference Methods | LCMS Data |
|---|---|---|---|
| a-01-31 | 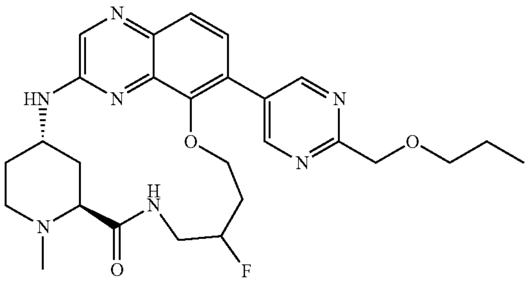 [SMILES: CCCOCc1ncc(-c2ccc3ncc4nc3c2OCCC(F)CNC(=O)[C@@H]2C[C@H](CCN2C)N4)cn1] | Methods B-1, B-2, and C-1 | (LC-1): RT = 1.16, m/z 524 $[M + H]^+$ |
| a-01-32 | 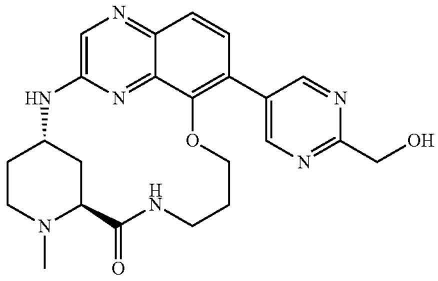 [SMILES: CN1CC[C@H]2C[C@H]1C(=O)NCCCOc1c(-c3cnc(CO)nc3)ccc3ncc(nc13)N2] | Methods A-2, A-3, and C-1 | (LC-1): RT = 0.74, m/z 450 $[M + H]^+$ |
| a-01-33 | 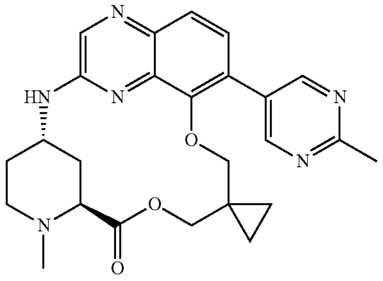 [SMILES: Cc1ncc(-c2ccc3ncc4nc3c2OCC2(CC2)COC(=O)[C@@H]2C[C@H](CCN2C)N4)cn1] | Methods A-2, A-3, and C-1 | (LC-1): RT = 1.23, m/z 461 $[M + H]^+$ |
| a-01-34 | 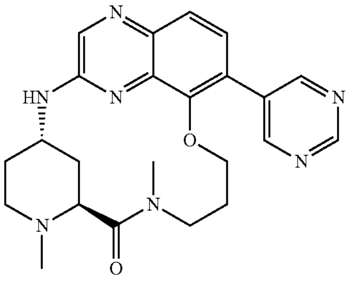 | Methods A-2, A-3, and C-1 | (LC-1): RT = 0.88, m/z 434 $[M + H]^+$ |
| a-01-35 | 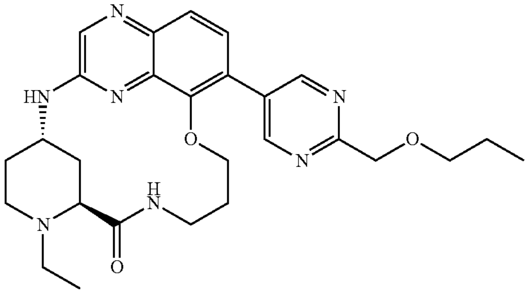 [SMILES: CCCOCc1ncc(-c2ccc3ncc4nc3c2OCCCNC(=O)[C@@H]2C[C@H](CCN2CC)N4)cn1] | Methods A-2, A-3, and C-1 | (LC-1): RT = 1.11, m/z 506 $[M + H]^+$ |

TABLE 2-continued
| Example | Structure | Reference Methods | LCMS Data |
|---|---|---|---|
| a-01-36 | 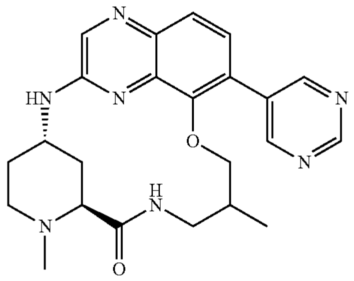 | Methods A-2, A-3, and C-1 | (LC-1): RT = 0.88, m/z 434 $[M + H]^+$ |
| a-01-37 | 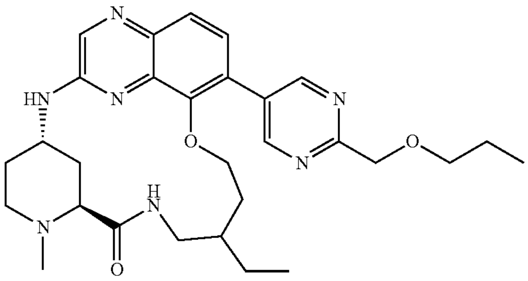 [SMILES: CCCOCc1ncc(-c2ccc3ncc4nc3c2OCCC(CC)CNC(=O)[C@@H]2C[C@H](CCN2C)N4)cn1] | Methods B-1, B-2, and C-1 | (LC-1): RT = 1.29, m/z 534 $[M + H]^+$ |
| a-01-38 | 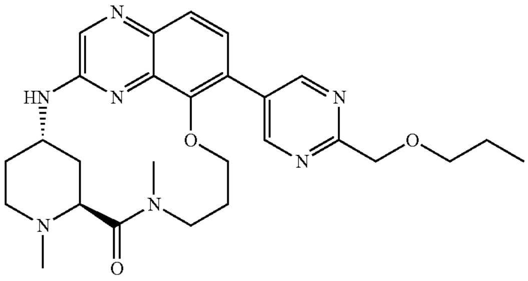 | Methods A-2, A-3, and C-1 | (LC-1): RT = 1.12, m/z 506 $[M + H]^+$ |
| a-01-39 | 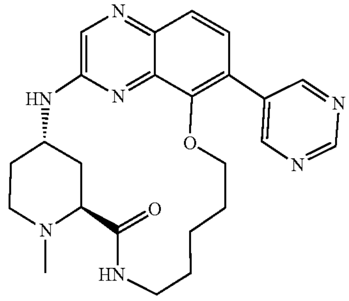 [SMILES: CN1CC[C@H]2C[C@H]1C(=O)NCCCCCOc1c(-c3cncnc3)ccc3ncc(nc13)N2] | Methods A-2, A-3, and C-1 | (LC-1): RT = 0.99, m/z 448 $[M + H]^+$ |
| a-01-40 | 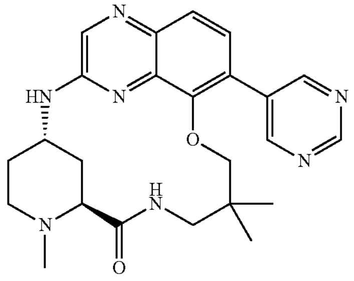 [SMILES: CN1CC[C@H]2C[C@H]1C(=O)NCC(C)(C)COc1c(-c3cncnc3)ccc3ncc(nc13)N2] | Methods A-2, A-3, and C-1 | (LC-1): RT = 1.00, m/z 448 $[M + H]^+$ |

TABLE 2-continued
| Example | Structure | Reference Methods | LCMS Data |
|---|---|---|---|
| a-01-41 | 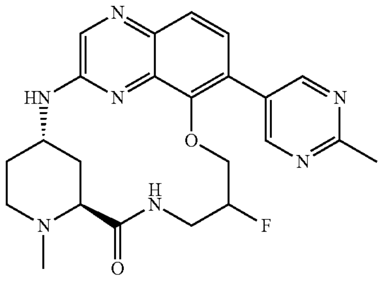 [SMILES: Cc1ncc(-c2ccc3ncc4nc3c2OCC(F)CNC(=O)[C@@H]2C[C@H](CCN2C)N4)cn1] | Methods B-1, B-2, and C-1 | (LC-1): RT = 0.94, m/z 452 $[M + H]^+$ |
| a-01-42 | 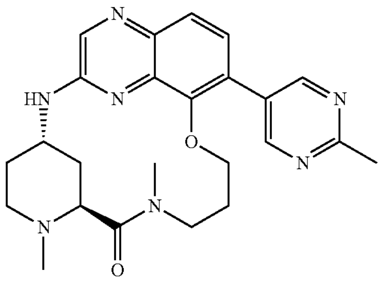 [SMILES: Cc1ncc(-c2ccc3ncc4nc3c2OCCCN(C)C(=O)[C@@H]2C[C@H](CCN2C)N4)cn1] | Methods A-2, A-3, and C-1 | (LC-1): RT = 0.92, m/z 448 $[M + H]^+$ |
| a-01-43 | 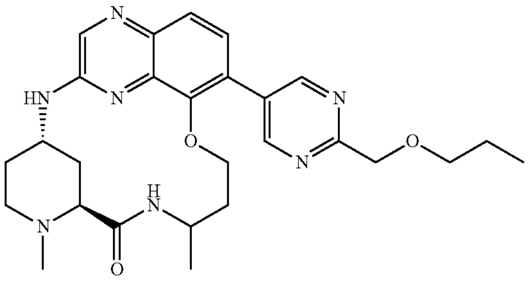 [SMILES: CCCOCc1ncc(-c2ccc3ncc4nc3c2OCCC(C)NC(=O)[C@@H]2C[C@H](CCN2C)N4)cn1] | Methods A-2, A-3, and C-1 | (LC-1): RT = 1.24, m/z 506 $[M + H]^+$ |
| a-01-44 | 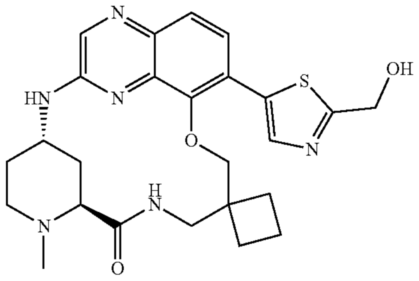 [SMILES: CN1CC[C@H]2C[C@H]1C(=O)NCC1(CCC1)COc1c(-c3cnc(CO)s3)ccc3ncc(nc13)N2] | Methods A-2, A-3, and C-1 | (LC-1): RT = 1.01, m/z 495 $[M + H]^+$ |
| a-01-45 | 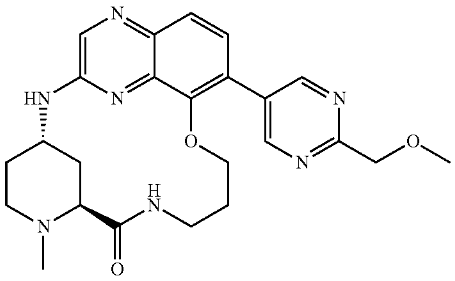 [SMILES: COCc1ncc(-c2ccc3ncc4nc3c2OCCCNC(=O)[C@@H]2C[C@H](CCN2C)N4)cn1] | Methods A-2, A-3, and C-1 | (LC-1): RT = 0.85, m/z 464 $[M + H]^+$ |

Method D-1

[Formula 71]

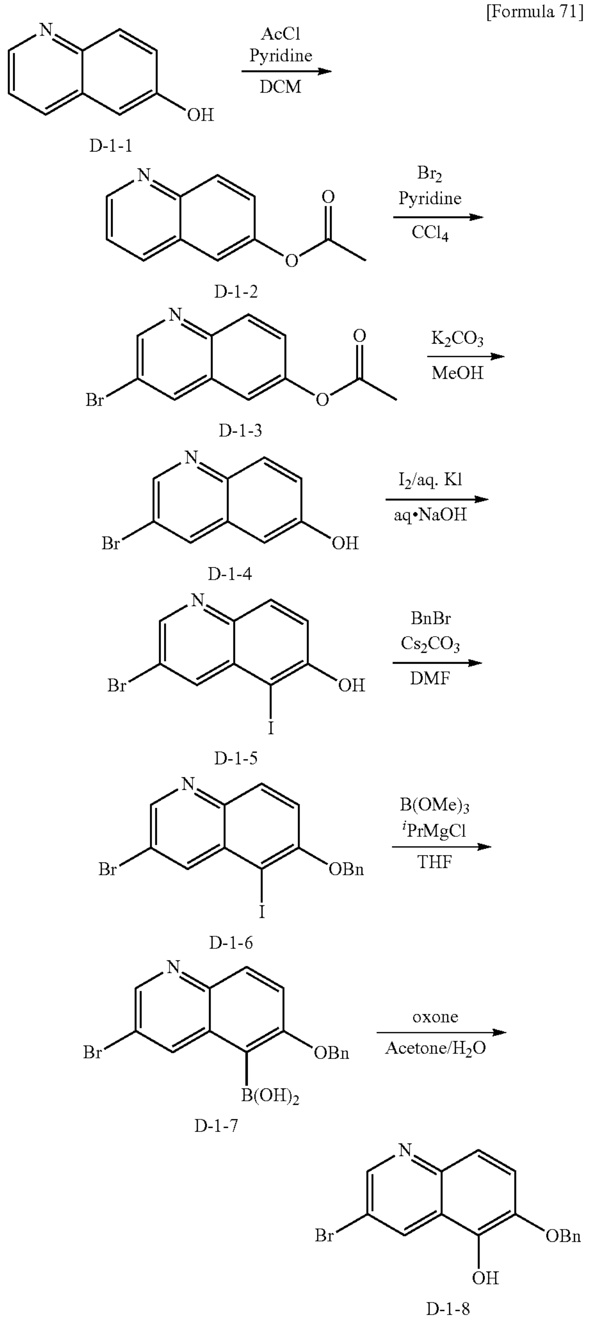

Intermediate D-1-2: Quinolin-6-yl acetate

[Formula 72]

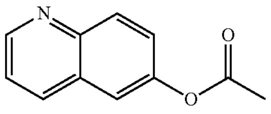

Quinolin-6-ol (Intermediate D-1-1, 20.0 g, 138 mmol) was dissolved in dichloromethane (222 mL), pyridine (13.3 mL, 165 mmol), and acetyl chloride (11.7 mL, 164 mmol) were added to the solution under ice cooling, and the resulting mixture was stirred at room temperature for 1 hour. After completion of the reaction, saturated aqueous sodium hydrogencarbonate (300 mL) was added to the reaction mixture, and the resulting mixture was stirred at room temperature for 45 minutes until foaming ceased. The reaction mixture was extracted with chloroform, and then the organic layer was washed with water and saturated brine. The organic layer was dried over anhydrous magnesium sulfate, filtered, and then concentrated under reduced pressure. The resulting crude product (26.1 g) was used for the following reaction without purification.

LCMS (LC-1): RT=1.05, m/z 188 $[M+H]^+$

1H-NMR ($CDCl_3$): δ (ppm) 8.91 (1H, dd, J=4.2, 1.7 Hz), 8.13 (2H, d, J=1.7 Hz), 7.57 (1H, d, J=2.6 Hz), 7.47 (1H, dd, J=8.3, 2.6 Hz), 7.42 (1H, dd, J=8.3, 4.2 Hz), 2.37 (3H, s)

Intermediate D-1-3:3-Bromoquinolin-6-yl acetate

[Formula 73]

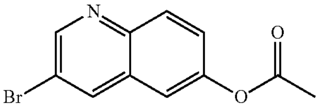

Quinolin-6-yl acetate (Intermediate D-1-2, 26.1 g, the crude product mentioned above) was dissolved in carbon tetrachloride (500 mL), pyridine (28 mL, 343 mmol), and bromine (50 g, 313 mmol) were independently added to the solution using a dropping funnel under ice cooling. Then, the resulting mixture was stirred at 90° C. for 3 hours. After completion of the reaction, dichloromethane (300 mL), and saturated aqueous sodium hydrogencarbonate (250 mL) were added to the reaction mixture, and the resulting mixture was stirred at room temperature for 15 minutes. The organic layer was dried over anhydrous magnesium sulfate, filtered, and then concentrated under reduced pressure. The crude product was purified by using automatic silica gel column chromatography (eluent, chloroform:methanol=100:0 to 90:10) to obtain 3-bromoquinolin-6-yl acetate (25.9 g, yield 71%).

LCMS (LC-1): RT=1.46, m/z 266 $[M+H]^+$

1H-NMR ($CDCl_3$): δ (ppm) 8.89 (1H, d, J=2.1 Hz), 8.28 (1H, d, J=2.1 Hz), 8.10 (1H, d, J=8.9 Hz), 7.52-7.45 (2H, m), 2.37 (3H, s)

Intermediate D-1-4:3-Bromoquinolin-6-ol

[Formula 74]

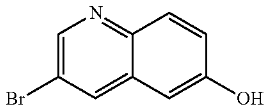

3-Bromoquinolin-6-yl acetate (Intermediate D-1-3, 25.9 g, 97.6 mmol) was dissolved in methanol (130 mL), water (78 mL), and potassium carbonate (27.0 g, 195 mmol) were added to the solution, and the resulting mixture was stirred at room temperature for 1 hour and 30 minutes. After completion of the reaction, methanol was evaporated under reduced pressure. The crude product was washed 3 times with water (20 mL), and then dried at 40° C. for 4 hours under reduced pressure to obtain 3-bromoquinolin-6-ol (21.0 g, yield 96%).

LCMS (LC-1): RT=1.19, m/z 224 $[M+H]^+$

1H-NMR ($CDCl_3$): δ (ppm) 8.75 (1H, d, J=2.2 Hz), 8.16 (1H, d, J=2.2 Hz), 7.99 (1H, d, J=9.3 Hz), 7.32 (1H, dd, J=9.3, 2.6 Hz), 7.03 (1H, d, J=2.6 Hz), 5.24 (1H, brs)

Intermediate D-1-5:3-Bromo-5-iodoquinolin-6-ol

[Formula 75]

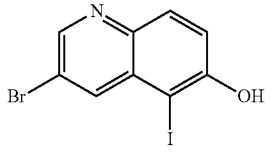

3-Bromoquinolin-6-ol (Intermediate D-1-4, 21.0 g, 93.8 mmol) was suspended in 2 M aqueous sodium hydroxide (204 mL), a solution containing iodine (28.6 g, 112 mmol) dissolved in 20% aqueous potassium iodide (potassium iodide 54 g/water 270 mL) was added dropwise to the solution over 45 minutes, and the resulting mixture was stirred at room temperature for 1 hour. After completion of the reaction, acetic acid (27 mL) was added to the reaction mixture, and then the resulting mixture was stirred at room temperature for 1 hour, and then filtered. The crude product was washed 3 times with water (100 mL), and dried at 40° C. for 12 hours under reduced pressure to obtain 3-bromo-5-iodoquinolin-6-ol (33.6 g).

LCMS (LC-1): RT=1.54, m/z 349 $[M+H]^+$

1H-NMR ($CDCl_3$): δ (ppm) 8.73 (1H, d, J=2.1 Hz), 8.42 (1H, dd, J=2.1, 0.6 Hz), 7.98 (1H, d, J=9.2 Hz), 7.49 (1H, d, J=9.2 Hz), 5.98 (1H, brs)

Intermediate D-1-6:6-(Benzyloxy)-3-bromo-5-iodoquinoline

[Formula 76]

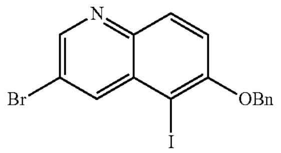

3-Bromo-5-iodoquinolin-6-ol (Intermediate D-1-5, 33.6 g, 93.8 mmol) was dissolved in N,N-dimethylformamide (313 mL), cesium carbonate (36.6 g, 112 mmol), and benzyl bromide (12.3 mL, 103 mmol) were added to the solution, and the resulting mixture was stirred at room temperature for 2 hours. After completion of the reaction, water (300 mL) was added to the reaction mixture, and the resulting mixture was stirred at room temperature for 45 minutes, and then filtered. The crude product was dried under reduced pressure to obtain 6-(benzyloxy)-3-bromo-5-iodoquinoline (39.9 g, yield 96%).

LCMS (LC-1): RT=2.32, m/z 440 $[M+H]^+$

1H-NMR ($CDCl_3$): δ (ppm) 8.73 (1H, d, J=2.1 Hz), 8.64 (1H, d, J=2.1 Hz), 8.02 (1H, d, J=9.2 Hz), 7.53 (2H, d, J=7.6 Hz), 7.47-7.39 (3H, m), 7.38-7.31 (1H, m), 5.35 (2H, s)

Intermediate D-1-7: (6-(Benzyloxy)-3-bromoquinolin-5-yl)boronic acid

[Formula 77]

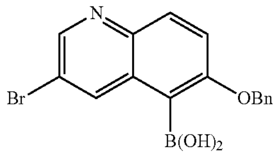

6-(Benzyloxy)-3-bromo-5-iodoquinoline (Intermediate D-1-6, 17.6 g, 40.0 mmol) was dissolved in tetrahydrofuran (400 mL), and trimethyl borate (9.8 mL, 87.9 mmol) was added to the solution at room temperature. The reaction mixture was cooled to −78° C., and a 2 M solution of isopropylmagnesium chloride in tetrahydrofuran (50 mL, 100 mmol) was added dropwise to the reaction mixture over 15 minutes over. Then, the resulting mixture was stirred for 2 hours with warming to room temperature. After completion of the reaction, acetic acid (200 mL), and water (200 mL) were added to the reaction mixture, and the resulting mixture was stirred at room temperature for 30 minutes. Then, the reaction mixture was extracted with ethyl acetate, and the organic layer was washed with water and saturated brine. The organic layer was dried over anhydrous sodium sulfate, filtered, and then concentrated under reduced pressure. The resulting crude product (11.7 g) was used for the following reaction without purification.

LCMS (LC-1): RT=1.45, m/z 358 $[M+H]^+$

Intermediate D-1-8:6-(Benzyloxy)-3-bromoquinolin-5-ol

[Formula 78]

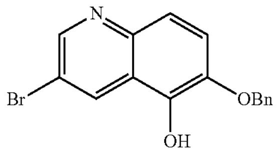

(6-(Benzyloxy)-3-bromoquinolin-5-yl)boronic acid (Intermediate D-1-7, 11.5 g, the crude product mentioned above) was dissolved in acetone (400 mL), water (200 mL), and Oxone (40.2 g, 65.6 mmol) were added to the solution, and the resulting mixture was stirred at room temperature for 1 hour. After completion of the reaction, saturated aqueous sodium thiosulfate (200 mL) was added to the reaction mixture, the resulting mixture was extracted with chloroform, and then the organic layer was washed with water and saturated brine. The organic layer was dried over anhydrous magnesium sulfate, filtered, and then concentrated under reduced pressure. The resulting crude product (10.6 g) was used for the following reaction without purification.

LCMS (LC-1): RT=1.69, m/z 330 $[M+H]^+$

1H-NMR ($CDCl_3$): δ (ppm) 8.76 (1H, d, J=2.2 Hz), 8.65-8.60 (1H, m), 7.63 (1H, d, J=9.3 Hz), 7.50 (1H, d, J=9.3 Hz), 7.48-7.35 (5H, m), 6.09 (1H, s), 5.25 (2H, s)

Method D-2

[Formula 79]

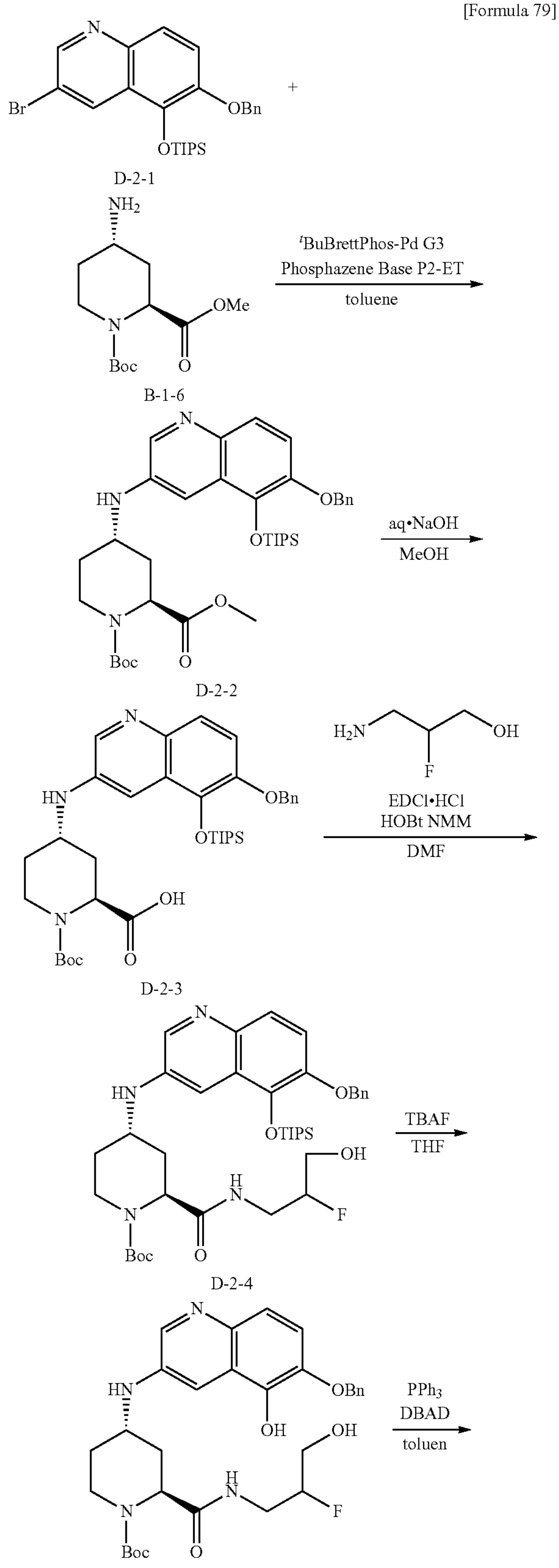

D-2-1

B-1-6

D-2-2

D-2-3

D-2-4

D-2-5

-continued

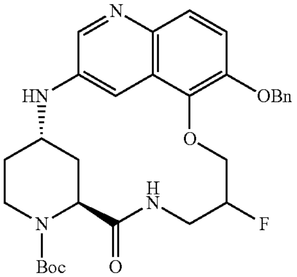

D-2-6

Intermediate D-2-2:1-(tert-Butyl) 2-methyl (2S,4S)-4-((6-(benzyloxy)-5-((triisopropylsilyl)oxy)quinolin-3-yl)amino)piperidine-1,2-dicarboxylate

[Formula 80]

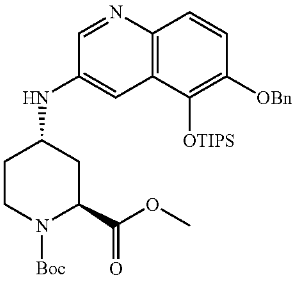

6-(Benzyloxy)-3-bromo-5-((triisopropylsilyl)oxy)quinoline (Intermediate D-2-1, 3.60 g, 7.41 mmol), and 1-(tert-butyl) 2-methyl (2S,4S)-4-aminopiperidine-1,2-dicarboxylate (Intermediate B-1-6, 3.20 g, 12.4 mmol) were dissolved in toluene (22 mL), [(2-di-tert-butylphosphino-3,6-dimethoxy-2',4',6'-triisopropyl-1,1'-biphenyl)-2-(2'-amino-1,1'-biphenyl)]palladium (II) methanesulfonate (320 mg, 0.37 mmol), and phosphazene base P2-Et (5 mL, 15 mmol) were added to the solution, and the resulting mixture was stirred at room temperature for 30 minutes. After completion of the reaction, the reaction mixture was directly purified by using automatic silica gel column chromatography (eluent, chloroform:methanol=100:0 to 80:20) to obtain 1-(tert-butyl) 2-methyl (2S,4S)-4-((6-(benzyloxy)-5-((triisopropylsilyl)oxy)quinolin-3-yl)amino)piperidine-1,2-dicarboxylate (2.10 g, yield 43%).

LCMS (LC-6): RT=2.10, m/z 664 $[M+H]^+$

1H-NMR ($CDCl_3$): δ (ppm) 8.24 (1H, d, J=2.8 Hz), 7.52-7.28 (9H, m), 7.15 (1H, d, J=9.2 Hz), 5.25-5.08 (0.5H, m), 4.93 (0.5H, brs), 4.18 (0.5H, d, J=14.2 Hz), 4.05 (0.5H, d, J=14.2 Hz), 3.80-3.71 (3H, m), 3.47-3.30 (1H, m), 3.22-2.95 (1H, m), 2.58 (1H, brs), 2.41-2.16 (1H, m), 2.15-1.89 (1H, m), 1.80-1.61 (1H, m), 1.53-1.42 (9H, m), 1.36-1.17 (4H, m), 1.03 (18H, d, J=7.3 Hz)

Intermediate D-2-3: (2S,4S)-4-((6-(Benzyloxy)-5-((triisopropylsilyl)oxy)quinolin-3-yl)amino)-1-(tert-butoxycarbonyl)piperidine-2-carboxylic acid

[Formula 81]

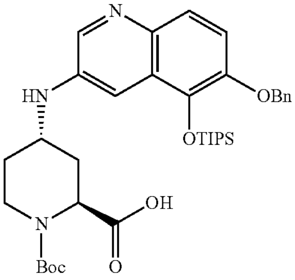

1-(tert-Butyl) 2-methyl (2S,4S)-4-((6-(benzyloxy)-5-((triisopropylsilyl)oxy)quinolin-3-yl)amino)piperidine-1,2-dicarboxylate (Intermediate D-2-2, 2.10 g, 3.16 mmol) was dissolved in methanol (210 mL), 1 M aqueous sodium hydroxide (32 mL) was added to the solution, and the resulting mixture was stirred at 40° C. for 15 hours. After completion of the reaction, 1 M aqueous hydrochloric acid (33 mL) was added to the reaction mixture, the resulting mixture was extracted with chloroform, and then the organic layer was washed with water and saturated brine. The organic layer was dried over anhydrous magnesium sulfate, filtered, and then concentrated under reduced pressure. The resulting crude product (2.15 g) was used for the following reaction without purification.

LCMS (LC-1): RT=1.95, m/z 650 $[M+H]^+$

Intermediate D-2-4: tert-Butyl (2S,4S)-4-((6-(benzyloxy)-5-((triisopropylsilyl)oxy)quinolin-3-yl)amino)-2-((2-fluoro-3-hydroxypropyl)carbamoyl)piperidine-1-carboxylate

[Formula 82]

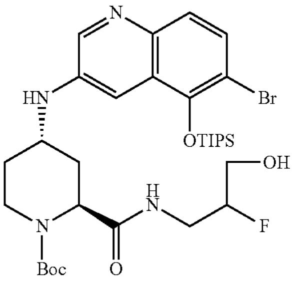

(2S,4S)-4-((6-(Benzyloxy)-5-((triisopropylsilyl)oxy)quinolin-3-yl)amino)-1-(tert-butoxycarbonyl)piperidine-2-carboxylic acid (Intermediate D-2-3, 2.15 g, 3.16 mmol), and 3-amino-2-fluoropropan-1-ol (348 mg, 3.79 mmol) were dissolved in N,N-dimethylformamide (16 mL), N-methylmorpholine (0.87 mL, 7.90 mmol), 1-ethyl-3-(3-dimethylaminopropyl)carbodiimide hydrochloride (2.45 g, 12.6 mmol), and 1-hydroxybenzotriazol (1.01 g, 6.96 mmol) were added to the solution, and the resulting mixture was stirred at room temperature for 30 minutes. After completion of the reaction, the reaction mixture was extracted with ethyl acetate, and the organic layer was washed with water and saturated brine. The organic layer was dried over anhydrous magnesium sulfate, filtered, and then concentrated under reduced pressure. The crude product was purified by using automatic silica gel column chromatography (eluent, ethyl acetate: methanol=100:0 to 98:2) to obtain tert-butyl (2S,4S)-4-((6-(benzyloxy)-5-((triisopropylsilyl)oxy)quinolin-3-yl)amino)-2-((2-fluoro-3-hydroxypropyl)carbamoyl)piperidine-1-carboxylate (886 mg, yield 39%).

LCMS (LC-1): RT=2.35, m/z 725 $[M+H]^+$

1H-NMR ($CDCl_3$): δ (ppm) 8.27-8.23 (1H, m), 7.54-7.46 (1H, m), 7.44-7.28 (6H, m), 7.14 (1H, d, J=9.2 Hz), 5.16 (2H, s), 4.98 (1H, brs), 4.77-4.44 (1H, m), 4.12 (1H, q, J=7.2 Hz), 3.71 (5H, m), 3.28-3.10 (1H, m), 2.96 (1H, brs), 2.75-2.49 (1H, m), 2.29 (1H, d, J=10.8 Hz), 2.05 (1H, s), 1.54-1.47 (1H, m), 1.35-1.17 (9H, m), 1.35-1.17 (5H, m), 1.03 (18H, d, J=7.3 Hz)

Intermediate D-2-5: tert-Butyl (2S,4S)-4-((6-(benzyloxy)-5-hydroxyquinolin-3-yl)amino)-2-((2-fluoro-3-hydroxypropyl)carbamoyl)piperidine-1-carboxylate

[Formula 83]

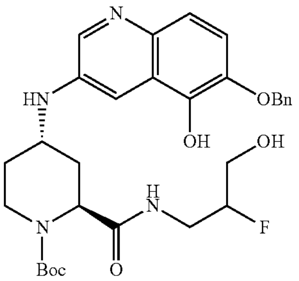

tert-Butyl (2S,4S)-4-((6-(benzyloxy)-5-((triisopropylsilyl)oxy)quinolin-3-yl)amino)-2-((2-fluoro-3-hydroxypropyl)carbamoyl)piperidine-1-carboxylate (Intermediate D-2-4, 886 mg, 1.22 mmol) was dissolved in tetrahydrofuran (6.1 mL), a 1 M solution of tetrabutylammonium fluoride in tetrahydrofuran (2.44 mL, 2.44 mmol) was added to the solution, and the resulting mixture was stirred at room temperature for 30 minutes. After completion of the reaction, the reaction mixture was directly purified by using automatic silica gel column chromatography (eluent, chloroform:methanol=100:0 to 80:20) to obtain tert-butyl (2S,4S)-4-((6-(benzyloxy)-5-hydroxyquinolin-3-yl)amino)-2-((2-fluoro-3-hydroxypropyl)carbamoyl)piperidine-1-carboxylate (660 mg, yield 95%).

LCMS (LC-1): RT=1.46, m/z 569 $[M+H]^+$

1H-NMR ($CDCl_3$): δ (ppm) 8.29 (1H, d, J=2.8 Hz), 7.55-7.28 (6H, m), 7.22-7.12 (2H, m), 6.92-6.37 (1H, m), 6.03 (1H, brs), 4.99 (1H, brs), 4.73 (0.5H, brs), 4.61 (0.5H, brs), 4.46-4.06 (2H, m), 3.93-3.70 (3H, m), 3.66 (2H, brs), 3.10-2.95 (2H, m), 2.93-2.57 (2II, m), 2.10 (2H, d, J=11.8 Hz), 1.53-1.48 (9H, m), 1.47-1.22 (2H, m)

Intermediate D-2-6: tert-Butyl ($3^2$S,$3^4$S)-$1^6$-(benzyloxy)-7-fluoro-4-oxo-9-oxa-2,5-diaza-1 (3,5)-qunolina-3 (4,2)-piperidinacyclononaphane-$3^1$-carboxylate

[Formula 84]

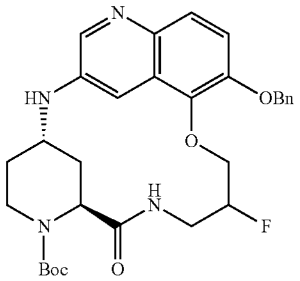

tert-Butyl (2S,4S)-4-((6-(benzyloxy)-5-hydroxyquinolin-3-yl)amino)-2-((2-fluoro-3-hydroxypropyl)carbamoyl)piperidine-1-carboxylate (Intermediate D-2-5, 660 mg, 1.161 mmol) was dissolved in toluene (240 mL), triphenylphosphine (773 mg, 2.90 mmol), and a 20% solution of di-tert-butyl azodicarboxylate in toluene (4.16 mL, 3.48 mmol) were added to the solution, and the resulting mixture was stirred at room temperature for 1 hour. Then, the reaction mixture was concentrated under reduced pressure. The resulting crude product was purified by using automatic silica gel column chromatography (eluent, chloroform: methanol=100:0 to 90:10) to obtain tert-butyl ($3^2$S,$3^4$S)-$1^6$-(benzyloxy)-7-fluoro-4-oxo-9-oxa-2,5-diaza-1 (3,5)-qunolina-3 (4,2)-piperidinacyclononaphane-$3^1$-carboxylate (431 mg, yield 67%).

LCMS (LC-1): RT=1.62, m/z 551 $[M+H]^+$

1H-NMR ($CDCl_3$): δ (ppm) 8.29 (1H, d, J=2.8 Hz), 7.72-7.62 (1H, m), 7.53-7.28 (5H, m), 7.21 (1H, d, J=9.4 Hz), 5.91 (1H, d, J=7.2 Hz), 5.31 (1H, d, J=12.0 Hz), 5.22 (1H, d, J=12.0 Hz), 4.96 (0.5H, brs), 4.91 (0.5H, brs), 4.81 (0.5H, brs), 4.61 (1H, dd, J=8.9, 3.5), 4.48-4.32 (1.5H, m), 4.07-3.99 (1H, m), 3.78-3.71 (2H, m), 3.68-3.57 (1H, m), 3.56-3.37 (2H, m), 2.72 (1H, d, J=11.6 Hz), 1.99-1.92 (1H, m), 1.85 (2H, td, J=6.8, 3.2 Hz), 1.73-1.59 (1H, m), 1.53-1.39 (9H, m)

Method D-3

[Formula 85]

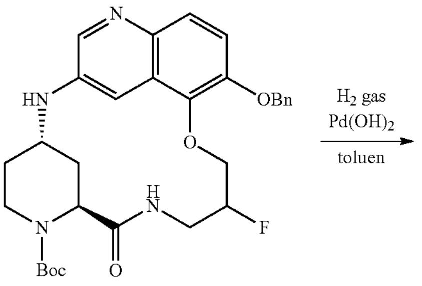

D-2-6

-continued

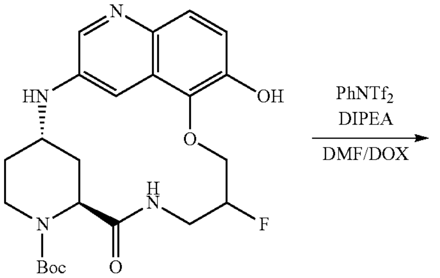

D-3-1

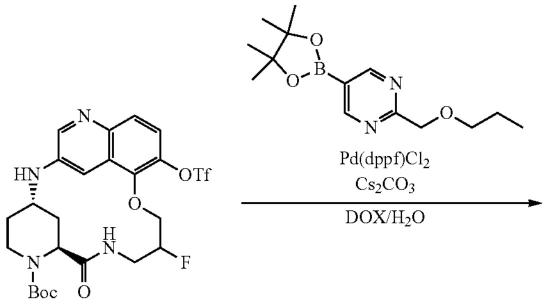

D-3-2

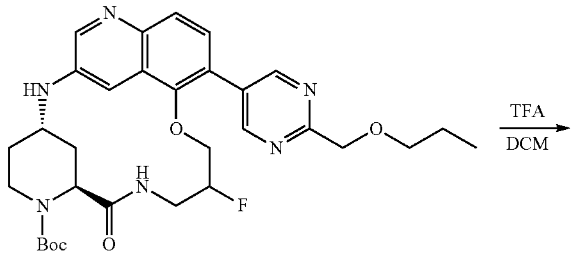

D-3-3

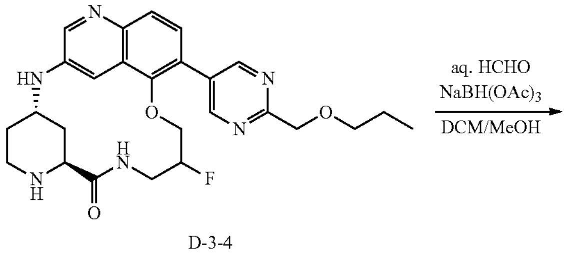

D-3-4

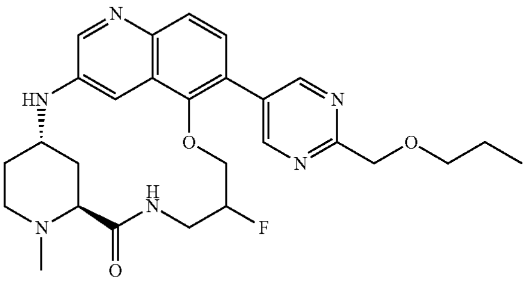

D-3-5

Intermediate D-3-1: tert-Butyl ($3^2$S,$3^4$S)-7-fluoro-$1^6$-hydroxy-4-oxo-9-oxa-2,5-diaza-1 (3,5)-qunolina-3 (4,2)-piperidinacyclononaphene-$3^1$-carboxylate

[Formula 86]

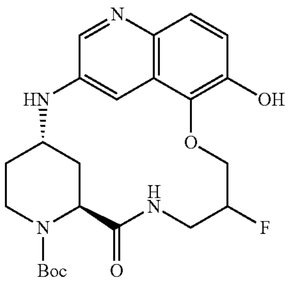

tert-Butyl ($3^2$S,$3^4$S)-$1^6$-(benzyloxy)-7-fluoro-4-oxo-9-oxa-2,5-diaza-1 (3,5)-qunolina-3 (4,2)-piperidinacyclononaphane-$3^1$-carboxylate (Intermediate D-2-6, 325 mg, 0.59 mmol) was dissolved in a mixed solvent of methanol (3 mL) and tetrahydrofuran (3 mL), palladium hydroxide (65 mg, 20 wt %) was added to the solution, and the resulting mixture was stirred at room temperature for 18 hours under hydrogen atmosphere. The atmosphere inside the reaction system was substituted to nitrogen, and then the reaction mixture was filtered through a Celite layer. The filtrate was concentrated under reduced pressure to obtain tert-butyl ($3^2$S,$3^4$S)-7-fluoro-$1^6$-hydroxy-4-oxo-9-oxa-2,5-diaza-1 (3,5)-qunolina-3 (4,2)-piperidinacyclononaphene-$3^1$-carboxylate (330 mg, yield 92%) as a crude product. The crude product was used for the following reaction without purification.

LCMS (LC-1): RT=1.13, m/z 461 $[M+H]^+$

Intermediate D-3-2: tert-Butyl ($3^2$S,$3^4$S)-7-fluoro-4-oxo-$1^6$-(((trifluoromethyl) sulfonyl)oxy)-9-oxa-2,5-diaza-1 (3,5)-qunolina-3 (4,2)-piperidinacyclononaphene-$3^1$-carboxylate

[Formula 87]

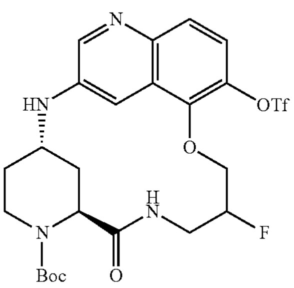

tert-Butyl ($3^2$S,$3^4$S)-7-fluoro-$1^6$-hydroxy-4-oxo-9-oxa-2,5-diaza-1 (3,5)-qunolina-3 (4,2)-piperidinacyclononaphene-$3^1$-carboxylate (Intermediate D-3-1, 330 mg, 0.72 mmol) was dissolved in 1,4-dioxane (7.2 mL), N,N-dimethylformamide (6 drops), N,N-diisopropylethylamine (0.748 mL, 4.30 mmol), and N-phenyl-bis(trifluoromethanesulfonimide) (824 mg, 2.30 mmol) were added to the solution, and the resulting mixture was stirred at room temperature for 7 hours. After completion of the reaction, the reaction mixture was directly purified by using automatic silica gel column chromatography (eluent, chloroform:methanol=100:0 to 90:10) to obtain tert-butyl ($3^2$S,$3^4$S)-7-fluoro-4-oxo-$1^6$-(((trifluoromethyl) sulfonyl)oxy)-9-oxa-2,5-diaza-1 (3,5)-qunolina-3 (4,2)-piperidinacyclononaphene-$3^1$-carboxylate (420 mg, 99%).

LCMS (LC-1): RT=1.65, m/z 593 $[M+H]^+$

1H-NMR (DMSO-$d_6$): δ (ppm) 8.55 (1H, d, J=2.6 Hz), 8.18 (1H, d, J=7.0 Hz), 7.75 (1H, d, J=9.2 Hz), 7.23 (1H, d, J=7.9 Hz), 7.05 (1H, s), 6.93-6.87 (1H, m), 5.14 (0.5H, brs), 5.08-4.93 (0.5H, m), 4.71 (0.5H, d, J=2.4 Hz), 4.65-4.52 (0.5H, m), 4.46-4.22 (2H, m), 4.11 (1H, brs), 3.98 (1H, d, J=9.0 Hz), 3.65-3.48 (3H, m), 3.29-3.11 (2H, m), 1.99-1.87 (1H, m), 1.59 (1H, d, J=13.4 Hz), 1.42-1.23 (9H, m)

Intermediate D-3-3: tert-Butyl ($3^2$S,$3^4$S)-7-fluoro-4-oxo-$1^6$-(2-(propoxymethyl)pyrimidin-5-yl)-9-oxa-2,5-diaza-1 (3,5)-qunolina-3 (4,2)-piperidinacyclononaphane-$3^1$-carboxylate

[Formula 88]

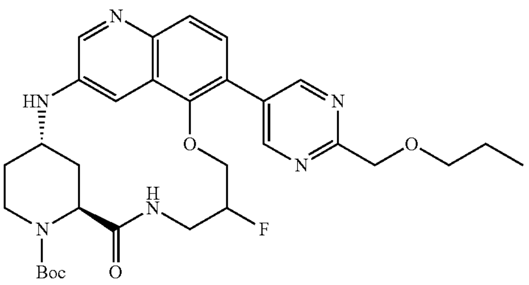

tert-Butyl ($3^2$S,$3^4$S)-7-fluoro-4-oxo-$1^6$-(((trifluoromethyl) sulfonyl)oxy)-9-oxa-2,5-diaza-1 (3,5)-qunolina-3 (4,2)-piperidinacyclononaphene-$3^1$-carboxylate (Intermediate D-3-2, 420 mg, 0.71 mmol), and 2-(propoxymethyl)-5-(4,4,5,5-tetramethyl-1,3,2-dioxaborolan-2-yl)pyrimidine (1.30 g, 31 wt %, 1.77 mmol) were dissolved in a mixed solvent of 1,4-dioxane (2.8 mL) and water (0.28 mL), cesium carbonate (705 mg, 2.12 mmol), and [1,1'-bis(diphenylphosphino) ferrocene]palladium (II) dichloride dichloromethane complex (117 mg, 0.14 mmol) were added to the solution, and the resulting mixture was stirred at 100° C. for 2 hours under microwave irradiation. The reaction mixture was filtered through a Celite layer, the filtrate was concentrated under reduced pressure, and then the crude product was purified by using automatic silica gel column chromatography (eluent, chloroform:methanol=100:0 to 90:10) to obtain tert-butyl ($3^2$S,$3^4$S)-7-fluoro-4-oxo-$1^6$-(2-(propoxymethyl)pyrimidin-5-yl)-9-oxa-2,5-diaza-1 (3,5)-qunolina-3 (4,2)-piperidinacyclononaphane-$3^1$-carboxylate (180 mg, yield 43%) as a roughly purified product. The roughly purified product was used for the following reaction without further purification.

LCMS (LC-1): RT=1.44, m/z 595 $[M+H]^+$

Intermediate D-3-4: (3$^{2}$S,3$^{4}$S)-7-Fluoro-1$^{6}$-(2-(propoxymethyl)pyrimidin-5-yl)-9-oxa-2,5-diaza-1 (3,5)-qunolina-3 (4,2)-piperidinacyclononaphan-4-one

[Formula 89]

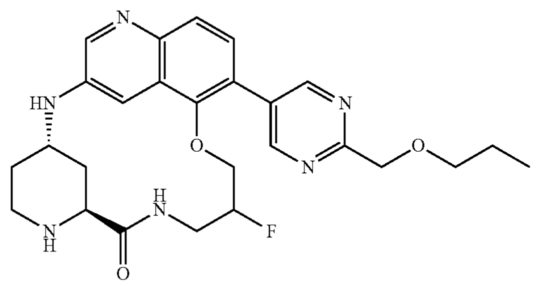

tert-Butyl (3$^{2}$S,3$^{4}$S)-7-fluoro-4-oxo-1$^{6}$-(2-(propoxymethyl)pyrimidin-5-yl)-9-oxa-2,5-diaza-1 (3,5)-qunolina-3 (4,2)-piperidinacyclononaphane-3$^{1}$-carboxylate (Intermediate D-3-3, 180 mg, 0.30 mmol) was dissolved in dichloromethane (3.0 mL), trifluoroacetic acid (0.75 mL) was added to the solution, and the resulting mixture was stirred at room temperature for 30 minutes. The obtained reaction mixture was roughly purified directly with SCX to obtain (3$^{2}$S,3$^{4}$S)-7-fluoro-1$^{6}$-(2-(propoxymethyl)pyrimidin-5-yl)-9-oxa-2,5-diaza-1 (3,5)-qunolina-3 (4,2)-piperidinacyclononaphan-4-one (148 mg, yield 98%). The roughly purified product was used for the following reaction without further purification.

LCMS (LC-1): RT=1.01, m/z 495 [M+H]$^{+}$

Example α-02-02 (End product D-3-5): (3$^{2}$S,3$^{4}$S)-7-Fluoro-31-methyl-16-(2-(propoxymethyl)pyrimidin-5-yl)-9-oxa-2,5-diaza-1 (3,5)-qunolina-3 (4,2)-piperidinacyclononaphan-4-one

[Formula 90]

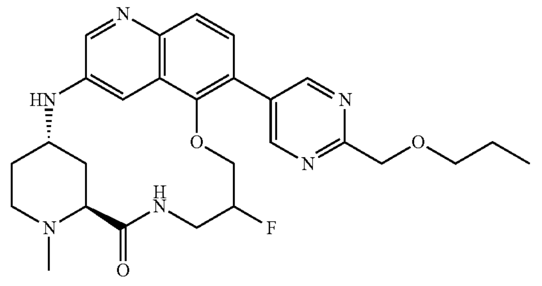

(3$^{2}$S,3$^{4}$S)-7-Fluoro-1$^{6}$-(2-(propoxymethyl)pyrimidin-5-yl)-9-oxa-2,5-diaza-1 (3,5)-qunolina-3 (4,2)-piperidinacyclononaphan-4-one (Intermediate D-3-4, 148 mg, 0.30 mmol) was dissolved in a mixed solvent of dichloromethane (1.5 mL) and methanol (1.5 mL), 37% aqueous formaldehyde (0.068 mL, 0.91 mmol), and sodium triacetoxyborohydride (96 mg, 0.45 mmol) were added to the solution, and the resulting mixture was stirred at room temperature for 1 hour. The obtained reaction mixture was roughly purified directly with SCX, and then purified by using reverse phase liquid column chromatography to obtain (3$^{2}$S,3$^{4}$S)-7-fluoro-31-methyl-16-(2-(propoxymethyl)pyrimidin-5-yl)-9-oxa-2,5-diaza-1 (3,5)-qunolina-3 (4,2)-piperidinacyclononaphan-4-one (106 mg, yield for 2 steps 69%).

LCMS (LC-1): RT=1.11, m/z 509 [M+H]$^{+}$

1H-NMR ($CDCl_3$): δ (ppm) 9.07 (2H, s), 8.43 (1H, d, J=2.7 Hz), 7.87 (1H, d, J=8.7 Hz), 7.46-7.39 (2H, m), 6.64 (1H, brs), 5.20-4.87 (1H, m), 4.83 (2H, s), 4.23-4.10 (1H, m), 3.97-3.78 (3H, m), 3.74-3.62 (3H, m), 3.30-3.20 (2H, m), 2.84-2.76 (1H, m), 2.41 (3H, s), 2.34 (1H, brs), 2.21 (1H, d, J=13.1 Hz), 2.03 (1H, d, J=9.2 Hz), 1.80-1.63 (4H, m), 0.99 (3H, t, J=7.4 Hz)

Method E-1

[Formula 91]

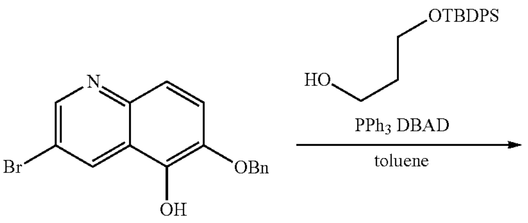

D-1-8

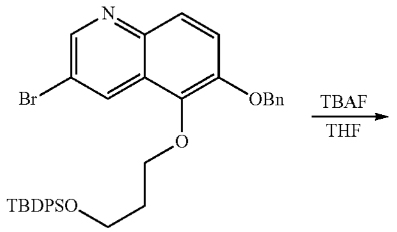

E-1-1

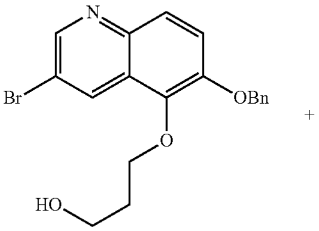

E-1-2

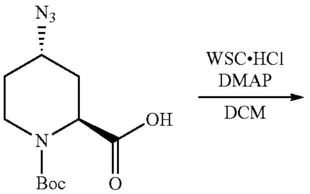

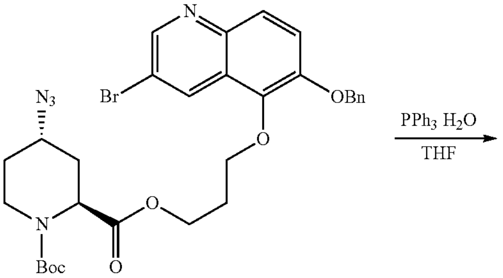

E-1-3

-continued

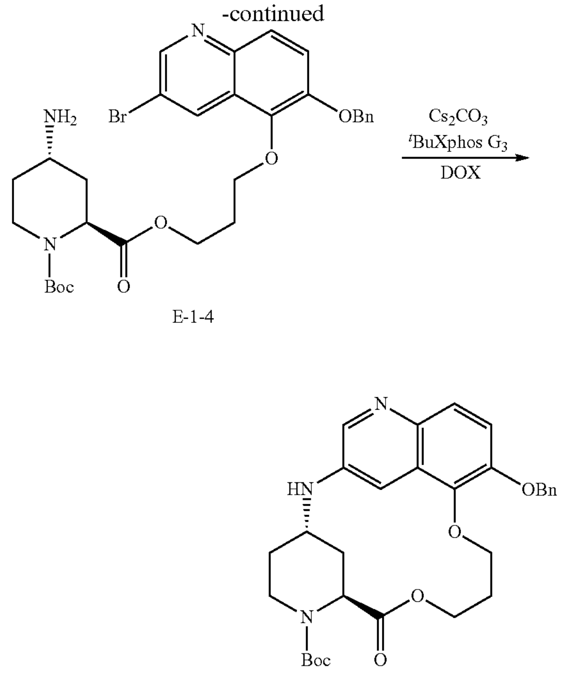

E-1-4

E-1-5

Intermediate E-1-1:6-(Benzyloxy)-3-bromo-5-(3-((tert-butyldiphenylsilyl)oxy)propoxy)quinoline

[Formula 92]

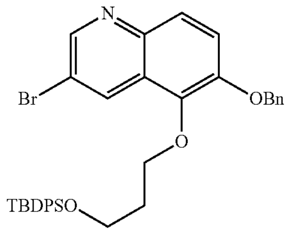

6-(Benzyloxy)-3-bromoquinolin-5-ol (Intermediate D-1-8, 3.00 g, 9.1 mmol) was dissolved in toluene (91 mL), 3-((tert-butyldiphenylsilyl)oxy)propan-1-ol (4.2 g, 18.2 mmol), triphenylphosphine (4.80 g, 18.2 mmol), and di-tert-butyl azodicarboxylate (18.2 mmol) were added to the solution, and the resulting mixture was stirred at room temperature for 1 hour. After completion of the reaction, the solvent was removed under reduced pressure, and then the crude product was roughly purified by using automatic silica gel column chromatography (eluent, hexane:ethyl acetate=100:0 to 70:30) to obtain 6-(benzyloxy)-3-bromo-5-(3-((tert-butyldiphenylsilyl)oxy)propoxy)quinoline (6.49 g) as a roughly purified product. The roughly purified product was used for the following reaction without further purification.

LCMS (LC-6): RT=2.71, m/z 626 $[M+H]^+$

Intermediate E-1-2:3-((6-(Benzyloxy)-3-bromoquinolin-5-yl)oxy)propan-1-ol

[Formula 93]

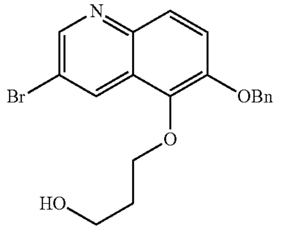

6-(Benzyloxy)-3-bromo-5-(3-((tert-butyldiphenylsilyl)oxy)propoxy)quinoline (Intermediate E-1-1, 6.49 g, 10.36 mmol) was dissolved in tetrahydrofuran (80 mL), tetrabutylammonium fluoride (30 mL, 1 M solution in THF) was added to the solution, and the resulting mixture was stirred at room temperature for 16 hours. After completion of the reaction, the reaction mixture was extracted with ethyl acetate, and the organic layer was washed with water and saturated brine. The organic layer was dried over anhydrous magnesium sulfate, filtered, and then concentrated under reduced pressure. The crude product was purified by using automatic silica gel column chromatography (eluent, chloroform:methanol=100:0 to 50:50) to obtain 3-((6-(benzyloxy)-3-bromoquinolin-5-yl)oxy)propan-1-ol (4.72 g) as a roughly purified product.

LCMS (LC-1): RT=1.66, m/z 388 $[M+H]^+$

1H-NMR ($CDCl_3$): δ (ppm) 8.77 (1H, d, J=2.2 Hz), 8.58 (1H, dd, J=2.2, 0.7 Hz), 7.93-7.75 (1H, m), 7.55-7.29 (6H, m), 5.27 (2H, s), 4.28 (2H, t, J=5.8 Hz), 3.90 (2H, q, J=5.8 Hz), 3.70 (1H, brs), 2.11-2.02 (2H, m)

Intermediate E-1-3:2-(3-((6-(Benzyloxy)-3-bromoquinolin-5-yl)oxy)propyl) 1-(tert-butyl) (2S,4S)-4-azidopiperidine-1,2-dicarboxylate

[Formula 94]

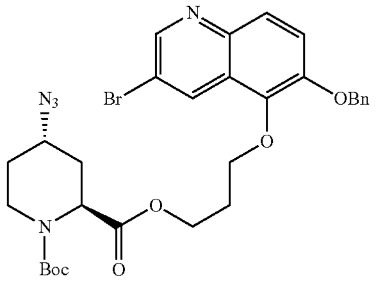

3-((6-(Benzyloxy)-3-bromoquinolin-5-yl)oxy)propan-1-ol (Intermediate E-1-2, 4.02 g, 10.3 mmol), and (2S,4S)-4-azido-1-(tert-butoxycarbonyl)piperidine-2-carboxylic acid (4.81 g, 17.8 mmol) were dissolved in dichloromethane (100 mL), 1-(3-dimethylaminopropyl)-3-ethylcarbodiimide hydrochloride (4.06 g, 21.1 mmol), and N,N-dimethylaminopyridine (2.70 g, 22.1 mmol) were added to the solution, and the resulting mixture was stirred at room temperature for 3 hours. After completion of the reaction, the reaction mixture was extracted with dichloromethane, and the organic layer was washed with water and saturated brine.

The organic layer was dried over anhydrous magnesium sulfate, filtered, and then concentrated under reduced pressure. The crude product was purified by using automatic silica gel column chromatography (eluent, hexane:ethyl acetate=90:10 to 0:100) to obtain 2-(3-((6-(benzyloxy)-3-bromoquinolin-5-yl)oxy)propyl) 1-(tert-butyl) (2S,4S)-4-azidopiperidine-1,2-dicarboxylate (5.69 g) as a roughly purified product. The roughly purified product was used for the following reaction without further purification.

LCMS (LC-1): RT=2.36, m/z 640 [M+H]$^+$

Intermediate E-1-4:2-(3-((6-(Benzyloxy)-3-bromoquinolin-5-yl)oxy)propyl) 1-(tert-butyl) (2S,4S)-4-aminopiperidine-1,2-dicarboxylate

[Formula 95]

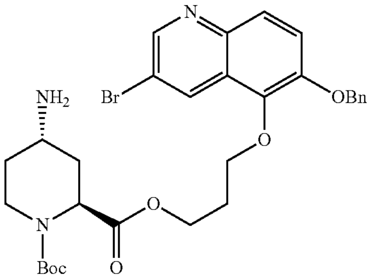

2-(3-((6-(Benzyloxy)-3-bromoquinolin-5-yl)oxy)propyl) 1-(tert-butyl) (2S,4S)-4-azidopiperidine-1,2-dicarboxylate (Intermediate E-1-3, 5.69 g, 8.88 mmol) was dissolved in tetrahydrofuran (100 mL), triphenylphosphine (5.0 g, 19.0 mmol), and water (5.0 mL) were added to the solution, and the resulting mixture was stirred at 70° C. for 15 hours. After completion of the reaction, the solvent was removed under reduced pressure, and the crude product was purified by using automatic silica gel column chromatography (eluent, hexane:ethyl acetate=90:10 to 0:100) to obtain 2-(3-((6-(benzyloxy)-3-bromoquinolin-5-yl)oxy)propyl) 1-(tert-butyl) (2S,4S)-4-aminopiperidine-1,2-dicarboxylate (5.78 g) as a roughly purified product. The roughly purified product was used for the following reaction without further purification.

LCMS (LC-1): RT=1.70, m/z 614 [M+H]$^+$

Intermediate E-1-5: tert-Butyl (3$^2$S,3$^4$S)-1$^6$-(benzyloxy)-4-oxo-5,9-dioxa-2-aza-1 (3,5)-qunolina-3 (4,2)-piperidinacyclononaphane-3$^1$-carboxylate

[Formula 96]

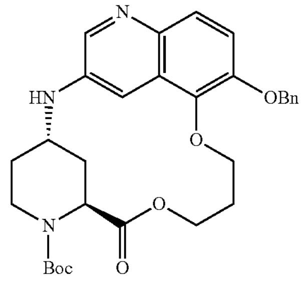

2-(3-((6-(Benzyloxy)-3-bromoquinolin-5-yl)oxy)propyl) 1-(tert-butyl) (2S,4S)-4-aminopiperidine-1,2-dicarboxylate (Intermediate E-1-4, 5.46 g, 8.89 mmol) was dissolved in 1,4-dioxane (90 mL), cesium carbonate (9.00 g, 27.6 mmol), and [(2-di-tert-butylphosphino-2',4',6'-triisopropyl-1,1'-biphenyl)-2-(2'-amino-1,1'-biphenyl)]palladium (II) methanesulfonate (1.10 g, 1.38 mmol) was added to the solution, and the resulting mixture was stirred at 120° C. for 3 days. After the reaction, the reaction mixture was filtered through a Celite layer, and the filtrate was concentrated under reduced pressure. The resulting crude product was purified by using automatic silica gel column chromatography (eluent, hexane:ethyl acetate=90:10 to 0:100) to obtain tert-butyl (3$^2$S, 3$^4$S)-1$^6$-(benzyloxy)-4-oxo-5,9-dioxa-2-aza-1 (3,5)-qunolina-3 (4,2)-piperidinacyclononaphane-3$^1$-carboxylate (360 mg, yield 7%).

LCMS (LC-1): RT=1.98, m/z 534 [M+H]$^+$

1H-NMR ($CDCl_3$): δ (ppm) 8.76 (1H, d, J=2.3 Hz), 8.58-8.53 (1H, m), 7.79 (1H, d, J=9.3 Hz), 7.53-7.30 (6H, m), 5.28-5.21 (0.5H, m), 4.97 (0.5H, d, J=5.3 Hz), 4.46-4.34 (2H, m), 4.25 (2H, t, J=6.2 Hz), 4.15-4.01 (0.5H, m), 3.95 (0.5H, d, J=12.5 Hz), 3.06-2.84 (1H, m), 2.66 (1H, dt, J=11.4, 3.7 Hz), 2.31 (1H, t, J=10.0 Hz), 2.23-2.12 (2H, m), 1.80-1.63 (1H, m), 1.50-1.37 (13H, m), 1.33-1.15 (1H, m)

Method F-1

[Formula 97]

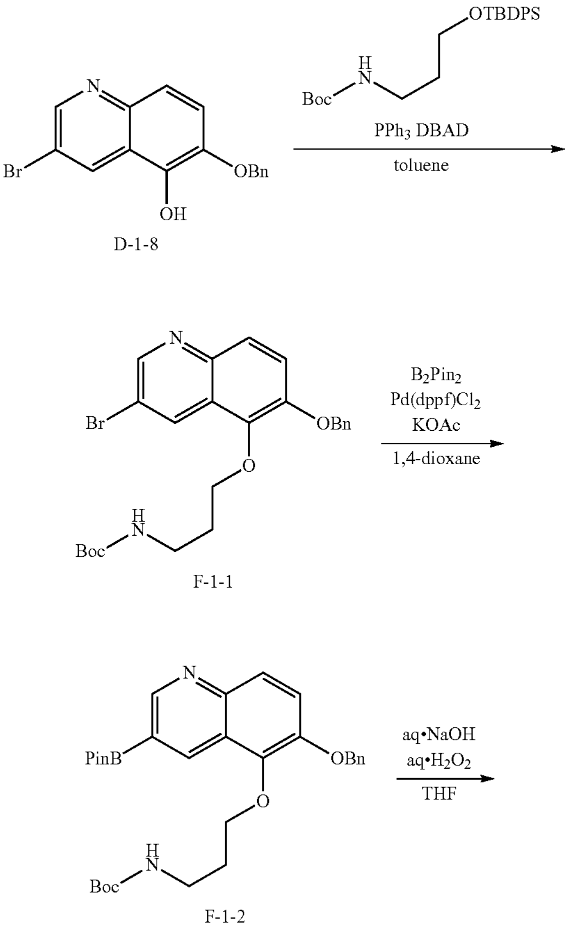

D-1-8

F-1-1

F-1-2

-continued

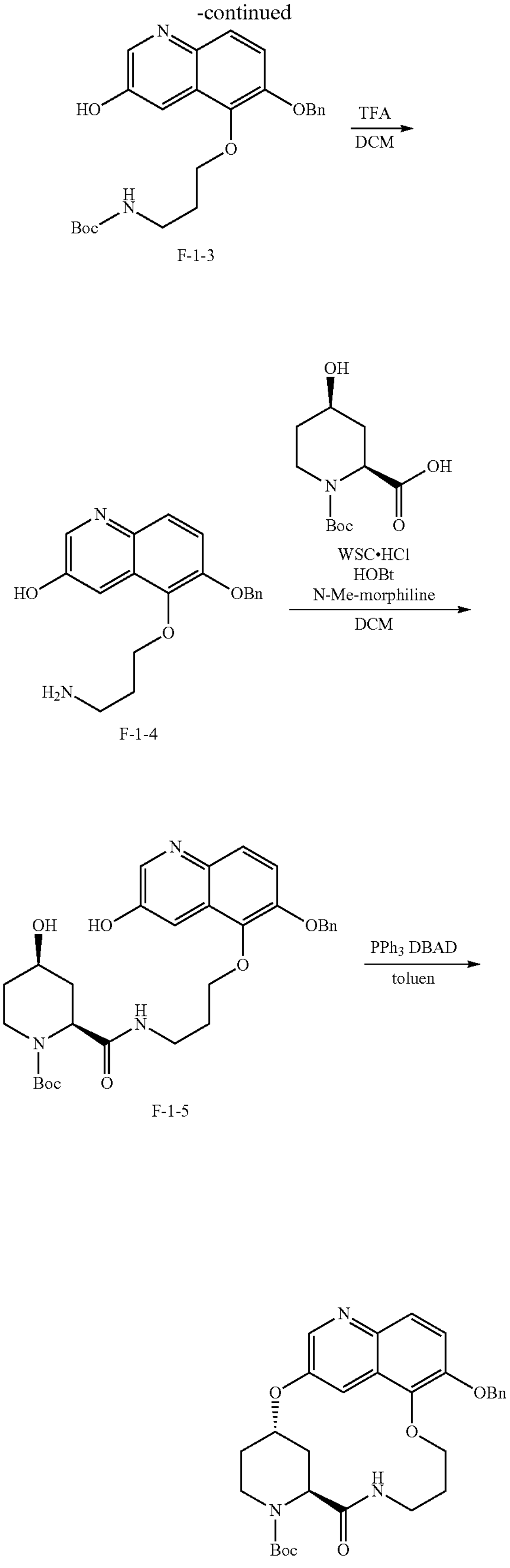

F-1-3

F-1-4

F-1-5

F-1-6

Intermediate F-1-1: tert-Butyl (3-((6-(benzyloxy)-3-bromoquinolin-5-yl)oxy)propyl)carbamate

[Formula 98]

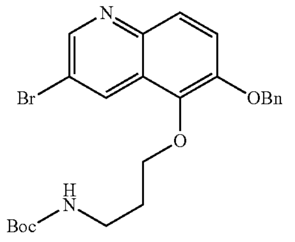

6-(Benzyloxy)-3-bromoquinolin-5-ol (Intermediate D-1-8, 1.0 g, 3.03 mmol) was dissolved in toluene (15 mL), tert-butyl (3-hydroxypropyl)carbamate (1.59 g, 9.09 mmol), and triphenylphosphine (1.99 g, 7.57 mmol) were added to the solution, a 20% solution of di-tert-butyl azodicarboxylate in toluene (10 mL, 9.09 mmol) was finally added to the solution, and the resulting mixture was stirred at room temperature for 1 hour. The solvent of the reaction solution was evaporated, and the residue was purified by using automatic silica gel column chromatography (eluent, hexane:ethyl acetate=1:1) to obtain tert-butyl (3-((6-(benzyloxy)-3-bromoquinolin-5-yl)oxy)propyl)carbamate (3.11 g, yield 99%).

LCMS (LC-1): RT=2.11, m/z 487 $[M+H]^+$

1H-NMR ($CDCl_3$): δ (ppm) 8.76 (1H, d, J=2.0 Hz), 8.56 (1H, d, J=2.0 Hz), 7.80 (1H, d, J=9.0 Hz), 7.53 (1H, s), 7.40 (5H, s), 5.29 (2H, s), 5.11-4.84 (2H, m), 4.26-4.17 (2H, m), 3.44-3.32 (2H, m), 2.04-1.97 (2H, m), 1.44 (9H, s)

Intermediate F-1-2: tert-Butyl (3-((6-(benzyloxy)-3-(4,4,5,5-tetramethyl-1,3,2-dioxaborolan-2-yl)quinolin-5-yl)oxy)propyl)carbamate

[Formula 99]

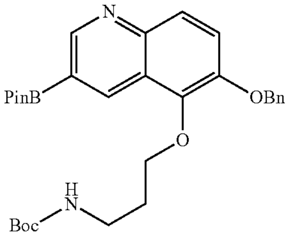

tert-Butyl (3-((6-(benzyloxy)-3-bromoquinolin-5-yl)oxy) propyl)carbamate (Intermediate F-1-1,1.0 g, 3.03 mmol) was dissolved in 1,4-dioxane (15 mL), bis(pinacolato)diboron (451 mg, 1.79 mmol), [1,1'-bis(diphenylphosphino) ferrocene]palladium (II) (175 mg, 0.24 mmol), and potassium acetate (237 mg, 2.38 mmol) were added to the solution, and the resulting mixture was stirred at 100° C. for 14 hours. The reaction solution was cooled to room temperature, the deposited solid was removed by filtration, and then the solvent was evaporated to obtain tert-butyl (3-((6-(benzyloxy)-3-(4,4,5,5-tetramethyl-1,3,2-dioxaborolan-2-yl)quinolin-5-yl)oxy)propyl)carbamate as a crude product.

LCMS (LC-1): RT=2.14, m/z 534 $[M+H]^+$

Intermediate F-1-3: tert-Butyl (3-((6-(benzyloxy)-3-hydroxyquinolin-5-yl)oxy)propyl)carbamate

[Formula 100]

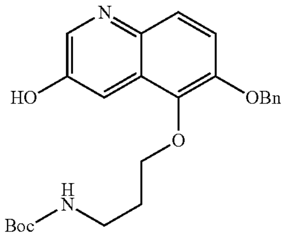

tert-Butyl (3-((6-(benzyloxy)-3-(4,4,5,5-tetramethyl-1,3,2-dioxabororan-2-yl)quinolin-5-yl)oxy)propyl)carbamate (Intermediate F-1-2, 636 mg, 1.19 mmol) was dissolved in tetrahydrofuran (13 mL), 1 M aqueous sodium hydroxide (520 μL), and 20% aqueous hydrogen peroxide (520 μL) were added to the solution under ice cooling, and the resulting mixture was stirred at the same temperature for 2 hours. Saturated aqueous sodium thiosulfate, and 1 M hydrochloric acid were added to the reaction mixture, the resulting mixture was extracted with chloroform, the organic layer was dried over magnesium sulfate, then the solvent was evaporated, and the residue was purified by using automatic silica gel column chromatography (eluent, hexane:ethyl acetate=50:50) to obtain tert-butyl (3-((6-(benzyloxy)-3-hydroxyquinolin-5-yl)oxy)propyl)carbamate (678 mg, yield 99%).

LCMS (LC-1): RT=1.68, m/z 425 $[M+H]^+$

1H-NMR ($CDCl_3$): δ (ppm) 8.65-8.48 (1H, m), 8.37-8.10 (1H, m), 8.04-7.86 (1H, m), 7.85-7.69 (1H, m), 7.52-7.43 (2H, m), 7.43-7.27 (4H, m), 5.25 (2H, s), 4.18-4.13 (2H, m), 3.61-3.50 (2H, m), 1.96-1.86 (2H, m), 1.26 (2H, s), 1.24 (9H, s)

Intermediate F-1-4:5-(3-Aminopropoxy)-6-(benzyloxy)quinolin-3-ol

[Formula 101]

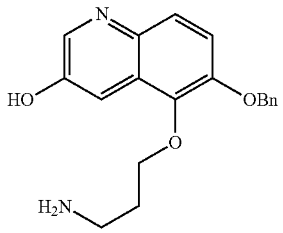

tert-Butyl (3-((6-(benzyloxy)-3-hydroxyquinolin-5-yl)oxy)propyl)carbamate (Intermediate F-1-3, 678 mg, 1.60 mmol) was dissolved in dichloromethane (17 mL), trifluoroacetic acid (4.0 mL) was added to the solution at room temperature, and the resulting mixture was stirred for 20 minutes. The reaction mixture was concentrated, and the concentrated reaction mixture was treated by using SCX cartridge to obtain 5-(3-aminopropoxy)-6-(benzyloxy)quinolin-3-ol (312 mg, yield 60%).

LCMS (LC-1): RT=0.96, m/z 325 $[M+H]^+$

1H-NMR ($CDCl_3$): δ (ppm) 8.64 (1H, d, J=2.5 Hz), 7.83-7.76 (1H, m), 7.76-7.72 (1H, m), 7.49-7.44 (2H, m), 7.43-7.28 (4H, m), 5.25-5.20 (2H, m), 4.25-4.17 (2H, m), 3.09-2.99 (2H, m), 2.03-1.90 (2H, m)

Intermediate F-1-5: tert-Butyl (2S,4R)-2-((3-((6-(benzyloxy)-3-hydroxyquinolin-5-yl)oxy)propyl)carbamoyl)-4-hydroxypiperidine-1-carboxylate

[Formula 102]

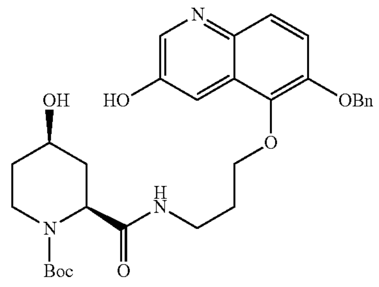

5-(3-Aminopropoxy)-6-(benzyloxy)quinolin-3-ol (Intermediate F-1-4, 312 mg, 0.81 mmol) was dissolved in dichloromethane (4.0 mL), N-methylmorpholine (222 μL, 2.01 mmol), 1-ethyl-3-(3-dimethylaminopropyl)carbodiimide hydrochloride (627 mg, 3.22 mmol), 1-hydroxybenzotriazol (239 mg, 1.77 mmol), and (2S,4R)-1-(tert-butoxycarbonyl)-4-hydroxypiperidine-2-carboxylic acid (376 mg, 1.45 mmol) were added to the solution, and the resulting mixture was stirred at room temperature for 3 hours. Water was added to the reaction mixture, and the resulting mixture was extracted with chloroform, the solvent was evaporated, and the residue was purified by using automatic silica gel column chromatography (eluent, chloroform:methanol=9:1) to obtain tert-butyl (2S,4R)-2-((3-((6-(benzyloxy)-3-hydroxyquinolin-5-yl)oxy)propyl)carbamoyl)-4-hydroxypiperidine-1-carboxylate (122 mg, yield 27%).

LCMS (LC-1): RT=1.43, m/z 552 $[M+H]^+$

Intermediate F-1-6: tert-Butyl ($3^2$S,$3^4$S)-$1^6$-(benzyloxy)-4-oxy-2,9-dioxa-5-aza-1 (3,5)-qunolina-3 (4,2)-piperidinacyclononaphane-$3^1$-carboxylate

[Formula 103]

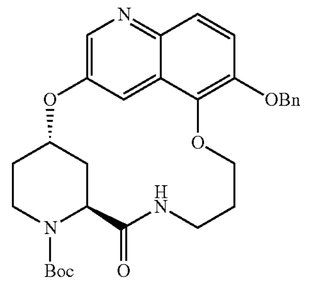

tert-Butyl (2S,4R)-2-((3-((6-(benzyloxy)-3-hydroxyquinolin-5-yl)oxy)propyl)carbamoyl)-4-hydroxypiperidine-1-carboxylate (Intermediate F-1-5, 122 mg, 0.22 mmol) was dissolved in toluene (20 mL), triphenylphosphine (149 mg, 0.54 mmol), and a 20% solution of di-tert-butyl azodicarboxylate in toluene (780 μL, 0.65 mmol) were added to the solution, and the resulting mixture was stirred for 1 hour and 30 minutes. The reaction mixture was concentrated, and the residue was purified by using automatic silica gel column chromatography (eluent, chloroform:methanol=90:10) to obtain tert-butyl ($3^2$S,$3^4$S)-$1^6$-(benzyloxy)-4-oxy-2,9-dioxa-5-aza-1 (3,5)-qunolina-3 (4,2)-piperidinacyclononaphane-$3^1$-carboxylate (84 mg, 72%).

LCMS (LC-1): RT=1.60, m/z 534 $[M+H]^+$

Method F-2

[Formula 104]

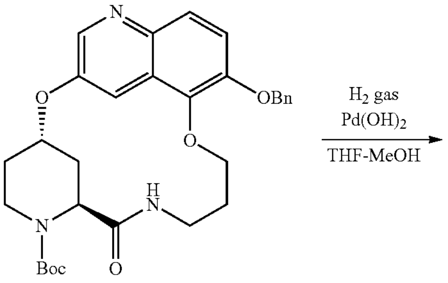

F-1-6

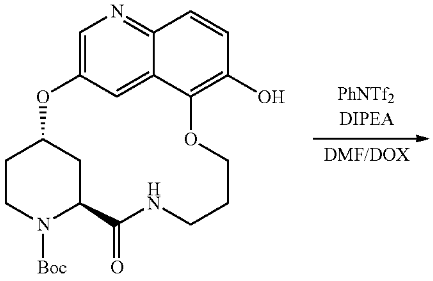

F-2-1

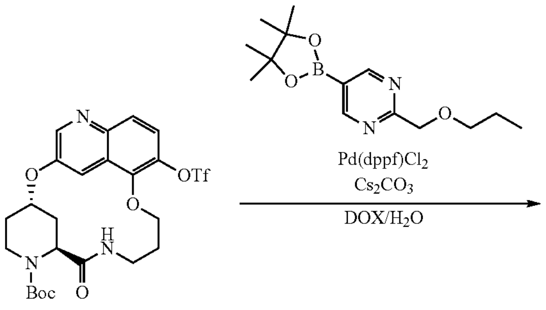

F-2-2

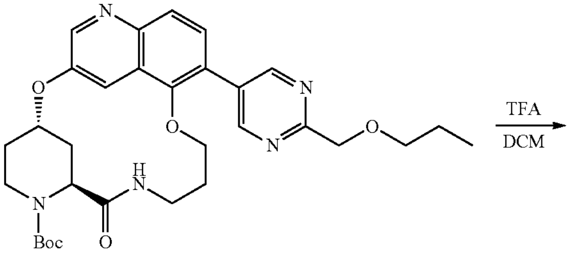

F-2-3

-continued

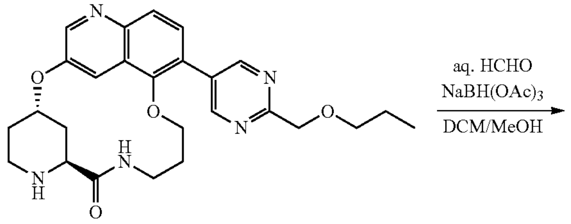

F-2-4

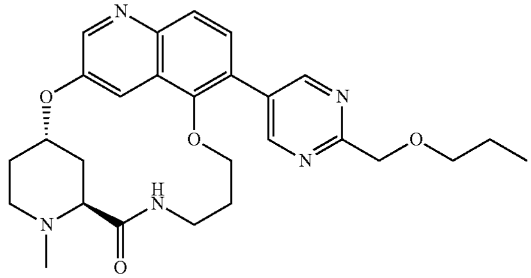

F-2-5

Intermediate F-2-1: tert-Butyl ($3^2$S,$3^4$S)-16-hydroxy-4-oxy-2,9-dioxa-5-aza-1 (3,5)-qunolina-3 (4,2)-piperidinacyclononaphane-$3^1$-carboxylate

[Formula 105]

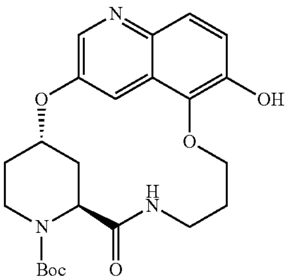

tert-Butyl ($3^2$S,$3^4$S)-$1^6$-(benzyloxy)-4-oxy-2,9-dioxa-5-aza-1 (3,5)-qunolina-3 (4,2)-piperidinacyclononaphane-$3^1$-carboxylate (Intermediate F-1-6, 84 mg, 0.15 mmol) was dissolved in methanol (0.8 mL), and tetrahydrofuran (0.8 mL), palladium hydroxide (16.6 mg) was added to the solution under nitrogen atmosphere, the atmosphere was manually substituted to hydrogen gas, and the mixture was vigorously stirred at room temperature for 14 hours. The insoluble matter contained in the reaction mixture was removed by filtration, then the solvent was evaporated, and the residue was purified by using automatic silica gel column chromatography (eluent, chloroform:methanol=90:10) to obtain tert-butyl ($3^2$S,$3^4$S)-16-hydroxy-4-oxy-2,9-dioxa-5-aza-1 (3,5)-qunolina-3 (4,2)-piperidinacyclononaphane-$3^1$-carboxylate (31.2 mg, yield 46%).

LCMS (LC-1): RT=1.12, m/z 444 $[M+H]^+$

Intermediate F-2-2: tert-Butyl ($3^2$S,$3^4$S)-16-(((trifluoromethyl) sulfonyl)oxy)-4-oxy-2,9-dioxa-5-aza-1 (3,5)-qunolina-3 (4,2)-piperidinacyclononaphane-$3^1$-carboxylate

[Formula 106]

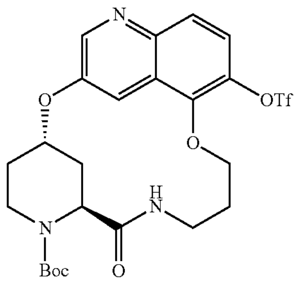

tert-Butyl ($3^2$S,$3^4$S)-16-hydroxy-4-oxy-2,9-dioxa-5-aza-1 (3,5)-qunolina-3 (4,2)-piperidinacyclononaphane-$3^1$-carboxylate (Intermediate F-2-1, 31.2 mg, 70 μmol) was dissolved in 1,4-dioxane (700 μL), N,N-bis(trifluoromethylsulfonyl) aniline (85 mg, 0.22 mmol), diisopropylethylamine (73 μL, 0.42 mmol), and dimethylformamide (2 drops) were added to the solution, and the resulting mixture was stirred at room temperature for 3 hours. The reaction mixture was concentrated, and the residue was purified by using automatic silica gel column chromatography (eluent, chloroform:methanol=90:10) to obtain tert-butyl ($3^2$S,$3^4$S)-16-(((trifluoromethyl) sulfonyl)oxy)-4-oxy-2,9-dioxa-5-aza-1 (3,5)-qunolina-3 (4,2)-piperidinacyclononaphane-$3^1$-carboxylate (44.3 mg, yield 99%).

LCMS (LC-1): RT=1.68, m/z 576 $[M+H]^+$

1H-NMR ($CDCl_3$): δ (ppm) 8.80 (1H, d, J=2.5 Hz), 8.01 (1H, s), 7.93 (1H, d, J=9.5 Hz), 7.84-7.79 (1H, m), 7.53-7.47 (1H, m), 7.43-7.34 (2H, m), 7.30 (3H, s), 5.76-5.59 (1H, m), 4.74-4.64 (1H, m), 4.42-4.22 (3H, m), 4.16-3.86 (4H, m), 3.43-3.26 (1H, m), 2.50-2.40 (1H, m), 2.34-2.27 (1H, m), 2.21-2.13 (1H, m), 1.90-1.75 (4H, m), 1.46 (9H, s)

Intermediate F-2-3: tert-Butyl ($3^2$S,$3^4$S)-16-(2-(propoxymethyl)pyrimidin-5-yl)-4-oxy-2,9-dioxa-5-aza-1 (3,5)-qunolina-3 (4,2)-piperidinacyclononaphane-$3^1$-carboxylate

[Formula 107]

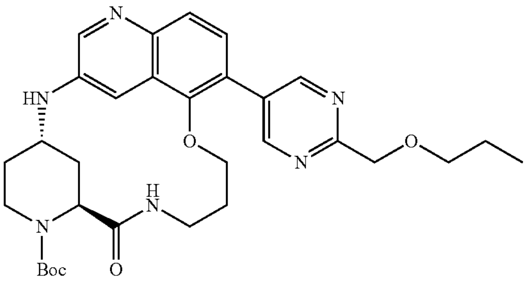

tert-Butyl ($3^2$S,$3^4$S)-16-(((trifluoromethyl) sulfonyl)oxy)-4-oxy-2,9-dioxa-5-aza-1 (3,5)-qunolina-3 (4,2)-piperidinacyclononaphane-$3^1$-carboxylate (Intermediate F-2-2, 44 mg, 76 μmol) was dissolved in 1,4-dioxane (600 μL) and water (60 μL), (2-(propoxymethyl)pyrimidin-5-yl)boronic acid (175 mg, 0.19 mmol), [1,1'-bis(diphenylphosphino) ferrocene]palladium (II) (13 mg, 15 μmol), and cesium carbonate (78 mg, 0.23 mmol) were added to the solution, and the resulting mixture was irradiated with microwaves at 100° C. for 3 hours. The insoluble matter contained in the reaction mixture was removed by filtration through a Celite layer, then the solvent was evaporated, and the residue was purified by using automatic silica gel column chromatography (eluent, chloroform:methanol=90:10) to obtain tert-butyl (328,34S)-16-(2-(propoxymethyl)pyrimidin-5-yl)-4-oxy-2,9-dioxa-5-aza-1 (3,5)-qunolina-3 (4,2)-piperidinacyclononaphane-$3^1$-carboxylate (22.8 mg, yield 52%).

LCMS (LC-1): RT=1.42, m/z 578 $[M+H]^+$

Intermediate F-2-4: ($3^2$S,$3^4$S)-16-(2-(Propoxymethyl)pyrimidin-5-yl)-2,9-dioxa-5-aza-1 (3,5)-qunolina-3 (4,2)-piperidinacyclononaphan-4-one

[Formula 108]

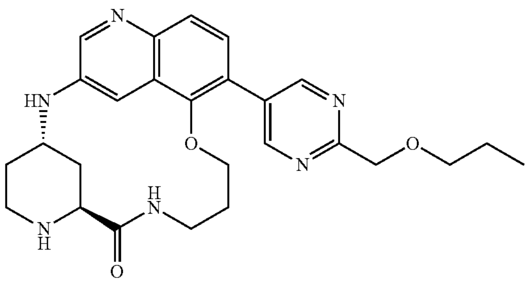

tert-Butyl ($3^2$S,$3^4$S)-16-(2-(propoxymethyl)pyrimidin-5-yl)-4-oxy-2,9-dioxa-5-aza-1 (3,5)-qunolina-3 (4,2)-piperidinacyclononaphane-$3^1$-carboxylate (Intermediate F-2-3, 22.8 mg, 39 μmol) was dissolved in dichloromethane (400 μL), trifluoroacetic acid (100 μL) was added to the solution, and the resulting mixture was stirred at room temperature for 20 minutes. The reaction mixture was treated with SCX to obtain ($3^2$S,$3^4$S)-16-(2-(propoxymethyl)pyrimidin-5-yl)-2,9-dioxa-5-aza-1 (3,5)-qunolina-3 (4,2)-piperidinacyclononaphan-4-one (13.4 mg, yield 99%).

LCMS (LC-1): RT=0.98, m/z 478 $[M+H]^+$

Example α-02-25 (End product F-2-5): ($3^2$S,$3^4$S)-31-Methyl-16-(2-(propoxymethyl)pyrimidin-5-yl)-2,9-dioxa-5-aza-1 (3,5)-qunolina-3 (4,2)-piperidinacyclononaphan-4-one

[Formula 109]

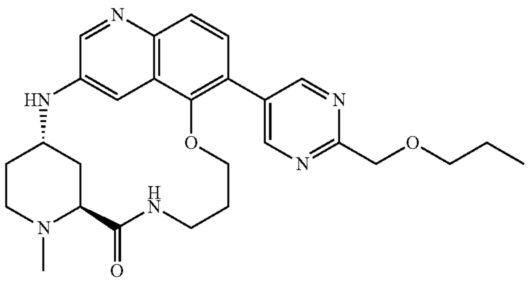

($3^2$S,$3^4$S)-16-(2-(Propoxymethyl)pyrimidin-5-yl)-2,9-dioxa-5-aza-1 (3,5)-qunolina-3 (4,2)-piperidinacyclononaphan-4-one (Intermediate F-2-4, 13.4 mg, 39 μmol) was dissolved in dichloromethane (200 μL) and methanol (200 μL), 37% aqueous formaldehyde (8.7 μL, 0.12 mmol), and sodium triacetoxyborohydride (12.5 mg, 59 μmol) were added to the solution, and the resulting mixture was stirred at room temperature for 10 minutes. The reaction mixture was treated with SCX, and then purified by using preparative thin layer chromatography (eluent, chloroform: 2 M ammonia solution in methanol=97:3) to obtain ($3^2$S,$3^4$S)-31-methyl-16-(2-(propoxymethyl)pyrimidin-5-yl)-2,9-dioxa-5-aza-1 (3,5)-qunolina-3 (4,2)-piperidinacyclononaphan-4-one (6.2 mg, yield 32%).

LCMS (LC-1): RT=1.00, m/z 492 $[M+H]^+$

1H-NMR ($CD_3OD$): δ (ppm) 9.19 (2H, s), 8.82 (1H, d, J=2.5 Hz), 7.97 (1H, d, J=9.0 Hz), 7.90-7.84 (2H, m), 4.78 (2H, s), 4.41 (1H, dd, J=2.5, 2.5 Hz), 4.30-4.22 (1H, m), 4.17-4.04 (1H, m), 3.86-3.69 (1H, m), 3.69-3.55 (4H, m), 3.40 (1H, d, J=6.8 Hz), 3.29-3.11 (1H, m), 2.59 (3H, s), 2.35-2.25 (1H, m), 2.19-2.04 (3H, m), 1.98-1.84 (1H, m), 1.81-1.75 (1H, m), 1.75-1.67 (2H, m), 1.17 (1H, t, J=7.5 Hz), 0.98 (3H, t, J=7.5 Hz)

Method G-1

[Formula 110]

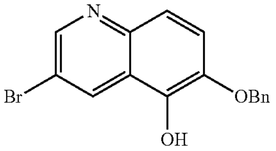

D-1-8

+

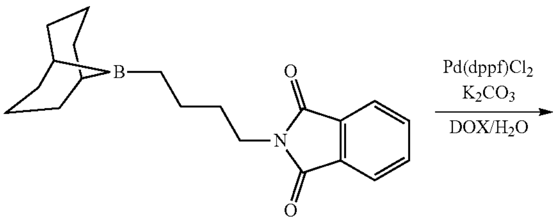

G-1-1

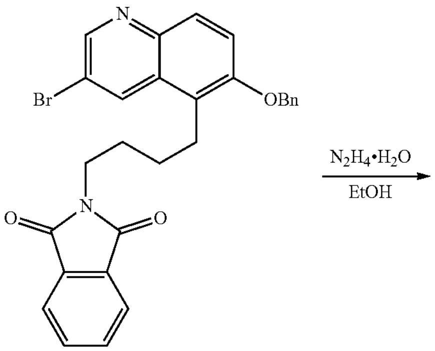

G-1-2

-continued

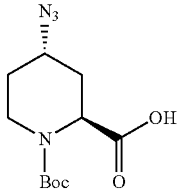

G-1-3′

WSC•HCl
HOBt
N-Me-morphiline
DCM

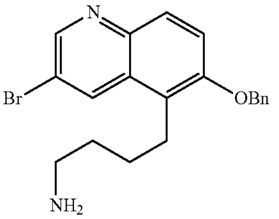

G-1-3

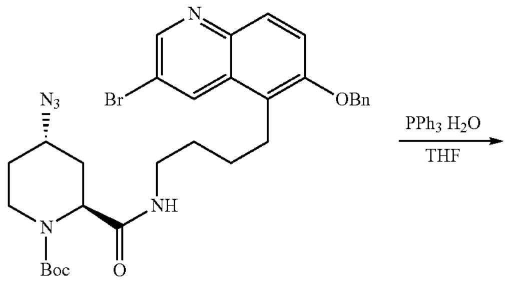

G-1-4

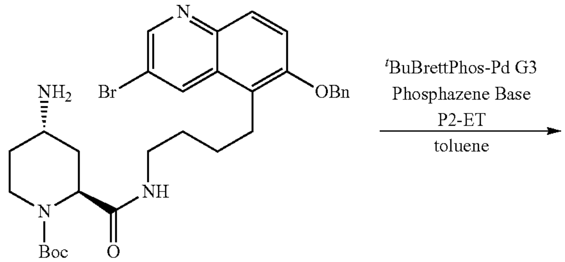

G-1-5

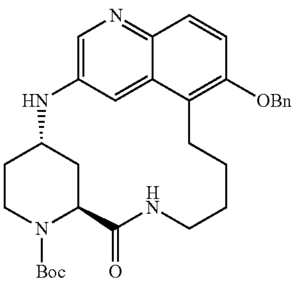

G-1-6

Intermediate G-1-3': (2S,4S)-4-Azido-1-(tert-butoxycarbonyl)piperidine-2-carboxylic acid

[Formula 111]

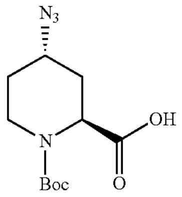

1-(tert-Butyl) 2-methyl (2S,4S)-4-azidopiperidine-1,2-dicarboxylate (5.3 g, 19 mmol) prepared according to the method described in the literature (Eur. J. Org. Chem., 2004, 2928-2935) was dissolved in methanol (220 mL), 1 M aqueous sodium hydroxide (190 mL) was added to the solution, and the resulting mixture was stirred at 40° C. for 1 hour. The reaction mixture was neutralized by addition of 1 M hydrochloric acid, and extracted with ethyl acetate, the organic layer was washed with saturated brine, and dried over sodium sulfate, and the solvent was evaporated to obtain a crude reaction mixture containing (2S,4S)-4-azido-1-(tert-butoxycarbonyl)piperidine-2-carboxylic acid.

LCMS (LC-1): RT=0.89, m/z 269 [M−H]$^+$

1H-NMR ($CDCl_3$): δ (ppm) 5.07 (1H, brs), 4.92 (1H, brs), 4.24-3.97 (1H, m), 3.49-3.36 (1H, m), 3.18-2.92 (1H, m), 2.58-2.41 (1H, m), 2.01-1.88 (1H, m), 1.54-1.41 (9H, s)

Intermediate G-1-1:2-(4-((1s,5s)-9-Borabicyclo[3.3.1]nonan-9-yl)butyl)isoindoline-1,3-dione

[Formula 112]

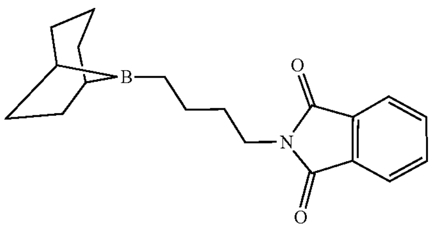

2-(But-3-en-1-yl)isoindoline-1,3-dione (2 g, 10 mmol) was dissolved in a 0.5 M solution of 9-borabicyclo[3.3.1]nonane in tetrahydrofuran (20 mL) under ice cooling, and the resulting mixture was stirred at the same temperature for 1.5 hours. The solvent of the reaction mixture was evaporated to obtain a crude reaction mixture containing 2-(4-((1s,5s)-9-borabicyclo[3.3.1]nonan-9-yl)butyl)isoindoline-1,3-dione.

Intermediate G-1-2:2-(4-(6-(Benzyloxy)-3-bromoquinolin-5-yl)butyl)isoindoline-1,3-dione

[Formula 113]

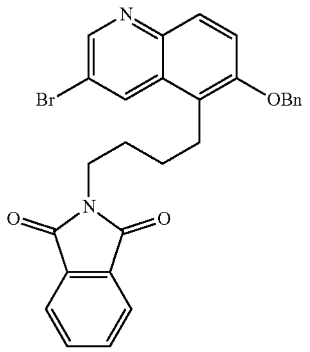

6-(Benzyloxy)-3-bromo-5-iodoquinoline (Intermediate D-1-8, 1.8 g, 4.1 mmol) was dissolved in 1,4-dioxane (8.2 mL) and water (820 μL), 2-(4-((1s,5s)-9-borabicyclo[3.3.1]nonan-9-yl)butyl)isoindoline-1,3-dione (Intermediate G-1-1, 1.3 g, 4.1 mmol), 1,1'-bis(diphenylphosphino) ferrocene] palladium (II) (600 mg, 820 μmol), and potassium carbonate (1.7 g, 12 mmol) were added to the solution, and the resulting mixture was stirred with heating at 100° C. for 14 hours. The insoluble matter contained in the reaction mixture was removed by filtration through a Celite layer, then the solvent was evaporated, and the residue was purified by using automatic silica gel column chromatography (eluent, hexane:ethyl acetate=50:50) to obtain 2-(4-(6-(benzyloxy)-3-bromoquinolin-5-yl)butyl)isoindoline-1,3-dione (340 mg, yield 16%).

LCMS (LC-1): RT=2.29, m/z 440 [M+H]$^+$

Intermediate G-1-3:4-(6-(Benzyloxy)-3-bromoquinolin-5-yl)butan-1-amine

[Formula 114]

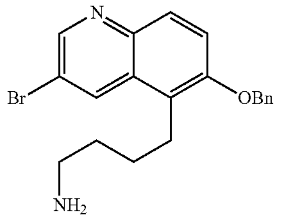

2-(4-(6-(Benzyloxy)-3-bromoquinolin-5-yl)butyl)isoindoline-1,3-dione (Intermediate G-1-2, 553 mg, 1.07 mmol) was dissolved in ethanol (11 mL), hydrazine hydrate (105 μL, 2.15 mmol) was added to the solution, and the resulting mixture was stirred with heating at 85° C. for 9 hours. The resulting crude reaction mixture was concentrated, the insoluble matter was removed by filtration, then the solvent was further evaporated, and the residue was purified by using automatic silica gel column chromatography (eluent, hexane:ethyl acetate=50:50->chloroform:methanol=90:10) to obtain 4-(6-(benzyloxy)-3-bromoquinolin-5-yl)butan-1-amine (264 mg, yield 64%).

LCMS (LC-1): RT=1.30, m/z 385 [M+H]$^+$

Intermediate G-1-4: tert-Butyl (2S,4S)-4-azido-2-((4-(6-(benzyloxy)-3-bromoquinolin-5-yl)butyl)carbamoyl)piperidine-1-carboxylate

[Formula 115]

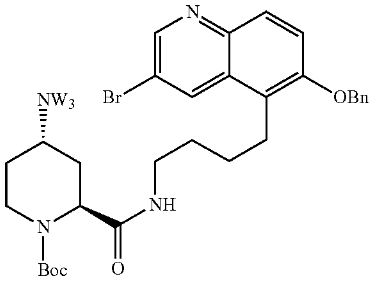

4-(6-(Benzyloxy)-3-bromoquinolin-5-yl)butan-1-amine (Intermediate G-1-3, 214 mg, 0.55 mmol) was dissolved in dimethylformamide (2.8 mL), N-methylmorpholine (150 μL, 1.39 mmol), 1-ethyl-3-(3-dimethylaminopropyl)carbodiimide hydrochloride (638 mg, 3.33 mmol), 1-hydroxybenzotriazol (223 mg, 1.66 mmol), and (2S,4S)-4-azido-1-(tert-butoxycarbonyl)piperidine-2-carboxylic acid (Intermediate G-1-3', 150 mg, 0.55 mmol) were added to the solution, and the resulting mixture was stirred at room temperature for 14 hours. Water was added to the reaction mixture, the resulting mixture was extracted with chloroform, the solvent was evaporated, and the residue was purified by using automatic silica gel column chromatography (eluent, chloroform: methanol=90:10) to obtain tert-butyl (2S,4R)-2-((3-((6-(benzyloxy)-3-hydroxyquinolin-5-yl)oxy)propyl)carbamoyl)-4-hydroxypiperidine-1-carboxylate (220 mg, yield 62%).

LCMS (LC-1): RT=2.23, m/z 637 $[M+H]^+$

1H-NMR ($CDCl_3$): δ (ppm) 8.85-8.72 (1H, m), 8.48-8.36 (1H, m), 7.98-7.89 (1H, m), 7.60-7.30 (6H, m), 6.37-6.11 (1H, m), 5.34-5.20 (2H, m), 4.88-4.72 (1H, m), 4.05-3.90 (1H, m), 3.90-3.70 (1H, m), 3.38-3.00 (3H, m), 2.87-2.39 (3H, m), 1.91-1.76 (1H, m), 1.60 (1H, m), 1.51-1.40 (9H, m)

Intermediate G-1-5: tert-Butyl (2S,4S)-4-amino-2-((4-(6-(benzyloxy)-3-bromoquinolin-5-yl)butyl)carbamoyl)piperidine-1-carboxylate

[Formula 116]

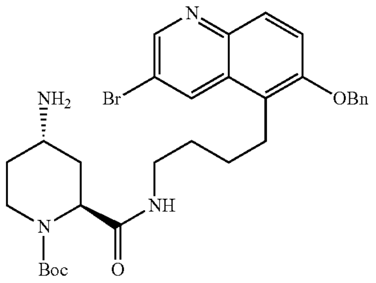

tert-Butyl (2S,4R)-2-((3-((6-(benzyloxy)-3-hydroxyquinolin-5-yl)oxy)propyl)carbamoyl)-4-hydroxypiperidine-1-carboxylate (Intermediate G-1-4, 190 mg, 298 μmol) was dissolved in tetrahydrofuran (1.2 mL), triphenylphosphine (86 mg, 0.33 mmol) was added to the solution, and the resulting mixture was stirred with heating at 50° C. for 5.5 hours. Water was added to the resulting crude reaction mixture, the resulting mixture was extracted with ethyl acetate, the organic layer was washed with saturated brine, and dried over sodium sulfate, the solvent was evaporated, and the residue was purified by using automatic silica gel column chromatography (eluent, chloroform:methanol=95:5) to obtain tert-butyl (2S,4S)-4-amino-2-((4-(6-(benzyloxy)-3-bromoquinolin-5-yl)butyl)carbamoyl)piperidine-1-carboxylate (134 mg, yield 74%).

LCMS (LC-1): RT=1.62, m/z 611 $[M+H]^+$

Intermediate G-1-6: tert-Butyl ($3^2$S,$3^4$S)-$1^6$-(benzyloxy)-4-oxo-2,5-diaza-1 (3,5)-qunolina-3 (4,2)-piperidinacyclononaphane-$3^1$-carboxylate

[Formula 117]

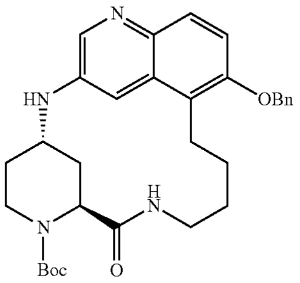

tert-Butyl (2S,4S)-4-amino-2-((4-(6-(benzyloxy)-3-bromoquinolin-5-yl)butyl)carbamoyl)piperidine-1-carboxylate (Intermediate G-1-5, 27 mg, 44 μmol) was dissolved in toluene (1.5 mL), [(2-di-tert-butylphosphino-3,6-dimethoxy-2',4',6'-triisopropyl-1,1'-biphenyl)-2-(2'-amino-1,1'-biphenyl)]palladium (II) methanesulfonate (1.9 mg, 2.2 μmol), and phosphazene base P2-Et (29 μL, 88 μmol) were added to the solution, and the resulting mixture was stirred at room temperature. The reaction mixture was purified by using automatic silica gel column chromatography (eluent, chloroform:methanol=90:10) to obtain tert-butyl ($3^2$S,$3^4$S)-$1^6$-(benzyloxy)-4-oxo-2,5-diaza-1 (3,5)-qunolina-3 (4,2)-piperidinacyclononaphane-$3^1$-carboxylate (9 mg, yield 39%).

LCMS (LC-1): RT=1.72, m/z 531 $[M+H]^+$

Method G-2

[Formula 118]

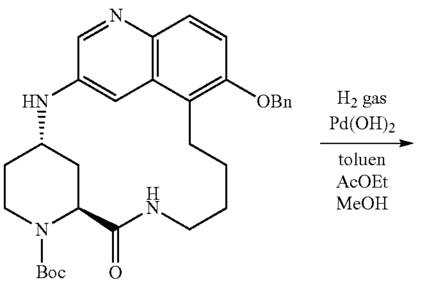

G-1-6

-continued

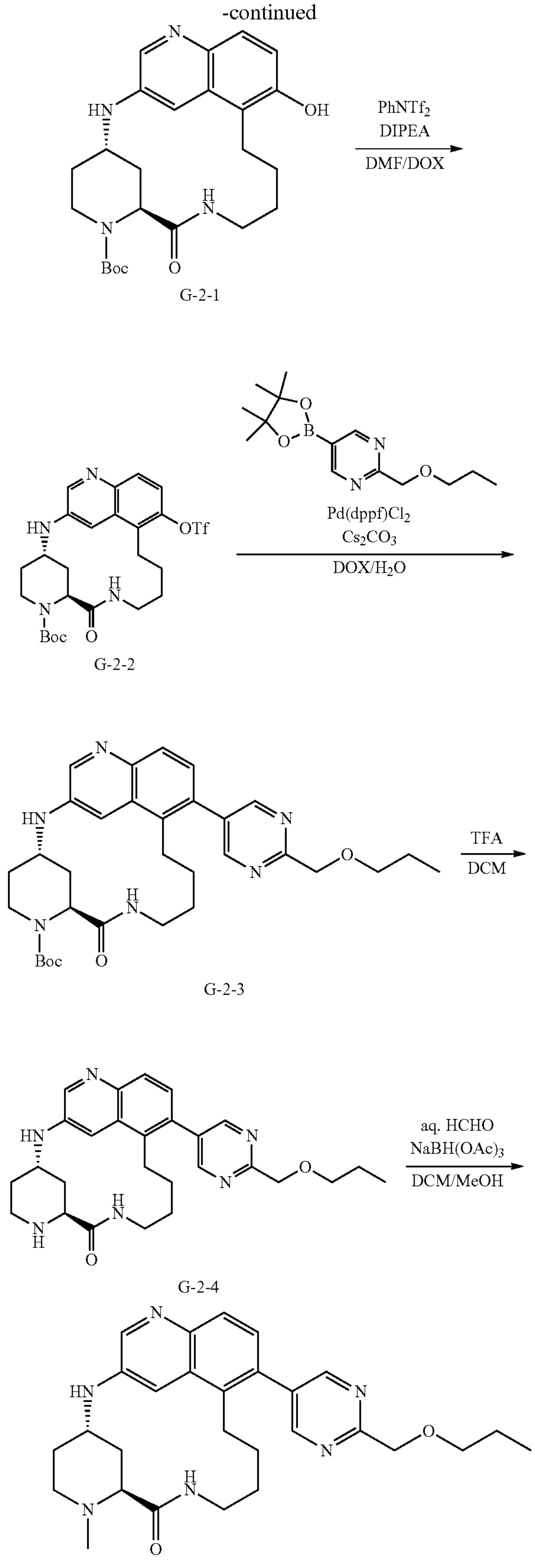

Intermediate G-2-1: tert-Butyl ($3^2$S,$3^4$S)-16-hydroxy-4-oxo-2,5-diaza-1 (3,5)-qunolina-3 (4,2)-piperidinacyclononaphane-$3^1$-carboxylate

[Formula 119]

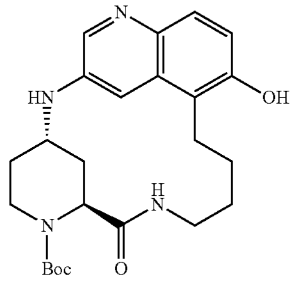

tert-Butyl ($3^2$S,$3^4$S)-$1^6$-(benzyloxy)-4-oxo-2,5-diaza-1 (3,5)-qunolina-3 (4,2)-piperidinacyclononaphane-$3^1$-carboxylate (Intermediate G-1-6, 100 mg, 0.19 mmol) was dissolved in methanol (2.7 mL), ethyl acetate (4 mL) and toluene (2.6 mL), palladium hydroxide (25 mg) was added to the solution under nitrogen atmosphere, the atmosphere was manually substituted to hydrogen gas, and the resulting mixture was vigorously stirred at room temperature for 14 hours. The insoluble matter contained in the reaction mixture was removed by filtration, and then the solvent was evaporated to obtain tert-butyl ($3^2$S,$3^4$S)-16-hydroxy-4-oxo-2,5-diaza-1 (3,5)-qunolina-3 (4,2)-piperidinacyclononaphane-$3^1$-carboxylate (70 mg, yield 84%).

LCMS (LC-1): RT=1.21, m/z 441 $[M+H]^+$

Intermediate G-2-2: tert-Butyl ($3^2$S,$3^4$S)-16-(((trifluoromethyl) sulfonyl)oxy)-4-oxo-2,5-diaza-1 (3,5)-qunolina-3 (4,2)-piperidinacyclononaphane-$3^1$-carboxylate

[Formula 120]

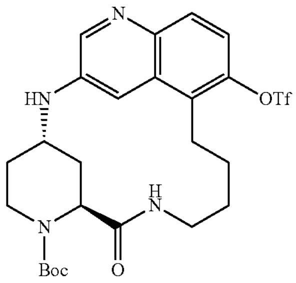

tert-Butyl ($3^2$S,$3^4$S)-16-hydroxy-4-oxo-2,5-diaza-1 (3,5)-qunolina-3 (4,2)-piperidinacyclononaphane-$3^1$-carboxylate (Intermediate G-2-1, 70 mg, 159 μmol) was dissolved in 1,4-dioxane (1.6 mL), N,N-bis(trifluoromethylsulfonyl) aniline (181 mg, 0.51 mmol), diisopropylethylamine (170 μL, 0.95 mmol), and dimethylformamide (6 drops) were added to the solution, and the resulting mixture was stirred at room temperature for 3 hours. The reaction mixture was concentrated, and the residue was purified by using automatic silica gel column chromatography (eluent, chloroform:methanol=90:10) to obtain tert-butyl ($3^2$S,$3^4$S)-16-(((trifluoromethyl) sulfonyl)oxy)-4-oxo-2,5-diaza-1 (3,5)-qunolina-3 (4,2)-piperidinacyclononaphane-$3^1$-carboxylate (88 mg, yield 97%).

LCMS (LC-1): RT=1.76, m/z 573 $[M+H]^+$

Intermediate G-2-3: tert-Butyl ($3^2$S,$3^4$S)-16-(2-(propoxymethyl)pyrimidin-5-yl)-2,5-diaza-1 (3,5)-qunolina-3 (4,2)-piperidinacyclononaphane-$3^1$-carboxylate

[Formula 121]

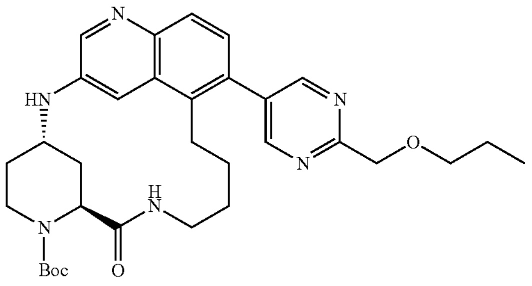

tert-Butyl ($3^2$S,$3^4$S)-16-(((trifluoromethyl) sulfonyl)oxy)-4-oxo-2,5-diaza-1 (3,5)-qunolina-3 (4,2)-piperidinacyclononaphane-$3^1$-carboxylate (Intermediate G-2-2, 44 mg, 76 μmol) was dissolved in 1,4-dioxane (300 μL), and water (30 μL), (2-(propoxymethyl)pyrimidin-5-yl)boronic acid (175 mg, 0.19 mmol), [1,1'-bis(diphenylphosphino) ferrocene] palladium (II) (32 mg, 38 μmol), and cesium carbonate (150 mg, 0.46 mmol) were added to the solution, and the resulting mixture was irradiated with microwaves at 100° C., at 3 hours. The insoluble matter contained in the reaction mixture was removed by filtration through a Celite layer, then the solvent was evaporated, and the residue was purified by using automatic silica gel column chromatography (eluent, chloroform:methanol=90:10) to obtain tert-butyl ($3^2$S,$3^4$S)-16-(2-(propoxymethyl)pyrimidin-5-yl)-2,5-diaza-1 (3,5)-qunolina-3 (4,2)-piperidinacyclononaphane-$3^1$-carboxylate (44 mg, yield 99%).

LCMS (LC-1): RT=1.46, m/z 575 $[M+H]^+$

Intermediate G-2-4: ($3^2$S,$3^4$S)-16-(2-(propoxymethyl)pyrimidin-5-yl)-2,5-diaza-1 (3,5)-qunolina-3 (4,2)-piperidinacyclononaphan-4-one

[Formula 122]

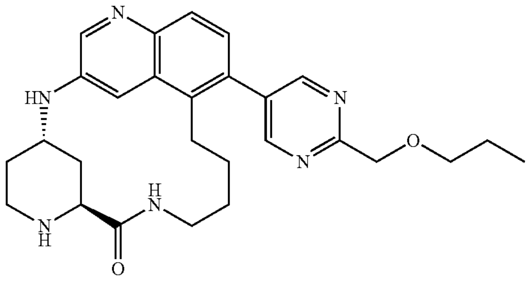

tert-Butyl ($3^2$S,$3^4$S)-16-(2-(propoxymethyl)pyrimidin-5-yl)-2,5-diaza-1 (3,5)-qunolina-3 (4,2)-piperidinacyclononaphane-$3^1$-carboxylate (Intermediate G-2-3, 22.8 mg, 39 μmol) was dissolved in dichloromethane (400 μL), trifluoroacetic acid (100 μL) was added to the solution, and the resulting mixture was stirred at room temperature for 20 minutes. The reaction mixture was treated with SCX to obtain ($3^2$S,$3^4$S)-16-(2-(propoxymethyl)pyrimidin-5-yl)-2,5-diaza-1 (3,5)-qunolina-3 (4,2)-piperidinacyclononaphan-4-one (19 mg, yield 46%).

LCMS (LC-1): RT=1.01, m/z 475 $[M+H]^+$

Example α-02-24 (End product G-2-5): ($3^2$S,$3^4$S)-31-Methyl-16-(2-(propoxymethyl)pyrimidin-5-yl)-2,5-diaza-1 (3,5)-qunolina-3 (4,2)-piperidinacyclononaphan-4-one

[Formula 123]

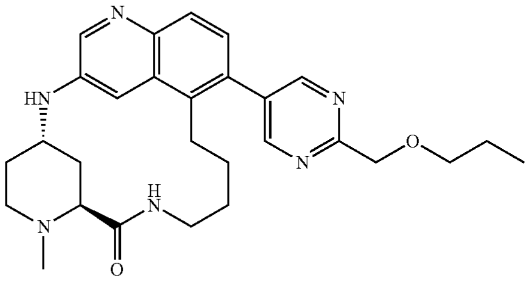

($3^2$S,$3^4$S)-16-(2-(Propoxymethyl)pyrimidin-5-yl)-2,5-diaza-1 (3,5)-qunolina-3 (4,2)-piperidinacyclononaphan-4-one (Intermediate G-2-4, 19 mg, 39 μmol) was dissolved in dichloromethane (290 μL) and methanol (290 μL), 37% aqueous formaldehyde (10 μL, 0.26 mmol), and sodium triacetoxyborohydride (27.7 mg, 130 μmol) were added to the solution, and the resulting mixture was stirred at room temperature for 35 minutes. The reaction mixture was treated with SCX, and then purified by using HPLC to obtain ($3^2$S,$3^4$S)-31-methyl-16-(2-(propoxymethyl)pyrimidin-5-yl)-2,5-diaza-1 (3,5)-qunolina-3 (4,2)-piperidinacyclononaphan-4-one (17.2 mg, yield 90%).

LCMS (LC-1): RT=1.09, m/z 489 $[M+H]^+$

1H-NMR ($CD_3OD$): δ (ppm) 8.82 (2H, s), 8.43 (1H, d, J=2.5 Hz), 7.82-7.74 (1H, m, J=8.5 Hz), 7.28-7.24 (1H, m), 7.05 (1H, d, J=2.5 Hz), 4.79 (2H, s), 3.88-3.77 (2H, m), 3.68-3.55 (4H, m), 3.12-3.02 (1H, m), 2.93-2.79 (2H, m), 2.57 (3H, s), 2.53-2.43 (1H, m), 2.07-2.01 (2H, m), 1.91-1.81 (1H, m), 1.78-1.66 (4H, m), 1.63-1.42 (2H, m), 0.99 (3H, t, J=7.5 Hz)

Method H-1

[Formula 124]

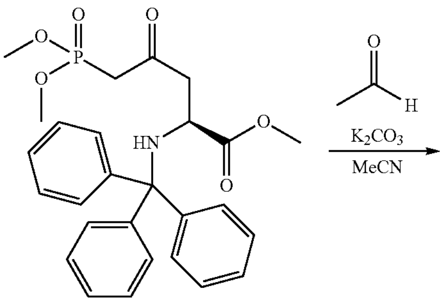

H-1-1

-continued

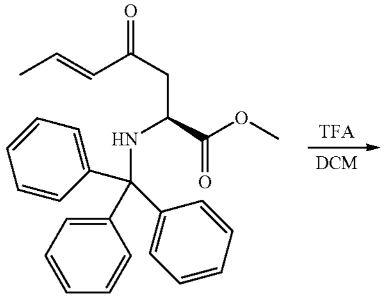

H-1-2

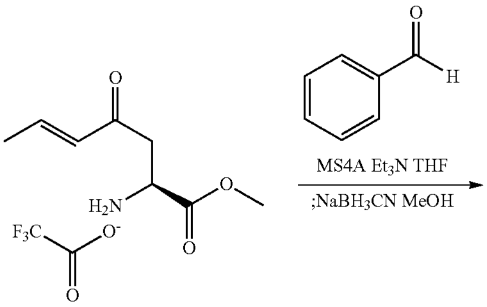

H-1-3

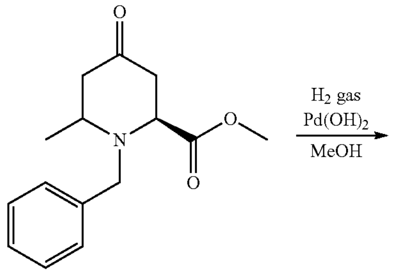

H-1-4

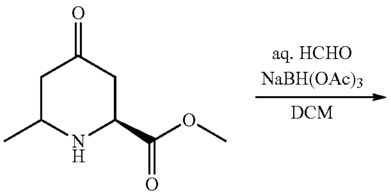

H-1-5

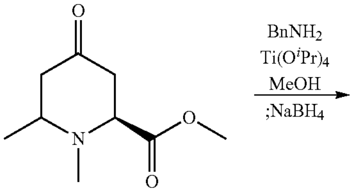

H-1-6

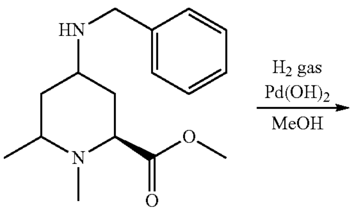

H-1-7

-continued

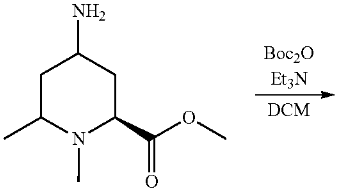

H-1-8

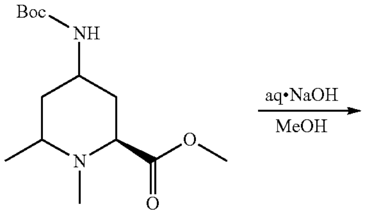

H-1-9

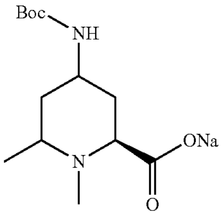

H-1-10

Intermediate H-1-2: Methyl (S,E)-4-oxo-2-(tritylamino) hept-5-enoate

[Formula 125]

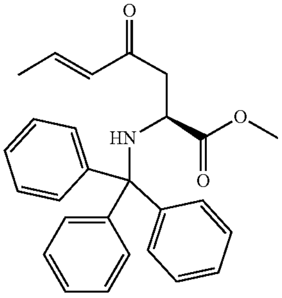

Methyl(S)-5-(dimethoxyphosphoryl)-4-oxo-2-(tritylamino) pentanoate (17 g, 35.3 mmol) prepared according to the descriptions of the literature (J. Org. Chem., 2012, 77, 10001-10009) was dissolved in acetonitrile (200 mL), potassium carbonate (5.1 g, 37 mmol), and acetaldehyde (5.92 mL, 106 mmol) were added to the solution, and the resulting mixture was stirred at 40° C. for 48 hours. The reaction mixture was cooled to room temperature, the solvent was evaporated, then ethyl acetate was added, the organic layer was washed with water and saturated brine, and dried over magnesium sulfate, the solvent was evaporated, and the residue was purified by using automatic silica gel column chromatography (eluent, hexane:ethyl acetate=75:25) to obtain methyl (S,E)-4-oxo-2-(tritylamino) hept-5-enoate (11.5 g, yield 48%).

1H-NMR ($CDCl_3$): δ (ppm) 7.55-7.41 (6H, m), 7.30-7.15 (9H, m), 6.80-6.72 (1H, m), 6.11-6.03 (1H, m), 3.79-3.63 (1H, m), 3.27 (3H, s), 2.90-2.72 (2H, m), 2.72-2.59 (1H, m), 1.89 (3H, dd, J=7.0, 2.0 Hz)

Intermediate H-1-3: Methyl (S,E)-2-amino-4-oxohept-5-enoate trifluoroacetic acid salt

[Formula 126]

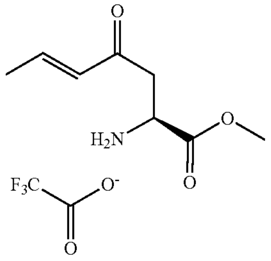

Methyl (S,E)-4-oxo-2-(tritylamino) hept-5-enoate (Intermediate H-1-2, 11.5 g, 27.8 mmol) was dissolved in dichloromethane (92 mL), trifluoroacetic acid (92 mL) was added to the solution, and the resulting mixture was stirred at room temperature for 1 hour. The reaction mixture was concentrated, the residue was dissolved in water, then the solution was washed with diethyl ether, and the solvent was evaporated to obtain methyl (S,E)-2-amino-4-oxohept-5-enoate trifluoroacetic acid salt (8.49 g, yield 99%).

1H-NMR ($DMSOd_6$): δ (ppm) 8.34 (3H, brs), 6.96 (1H, q, J=7.0 Hz), 7.00 (1H, q, J=7.0 Hz), 6.19 (1H, m), 4.37 (2H, m), 3.71 (3H, s), 3.31-3.17 (2H, m), 1.95-1.87 (3H, m)

Intermediate H-1-4: Methyl (2S)-1-benzyl-6-methyl-4-oxopiperidine-2-carboxylate

[Formula 127]

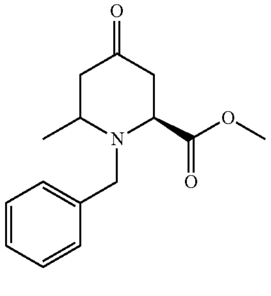

Methyl (S,E)-2-amino-4-oxohept-5-enoate trifluoroacetic acid salt (Intermediate H-1-3, 7.92 g, 27.8 mmol) was dissolved in tetrahydrofuran (100 mL), Molecular sieve 4A (8 g), triethylamine (3.87 mL, 27.8 mmol), and benzaldehyde (2.83 mL, 27.8 mmol) were added to the solution, and the resulting mixture was stirred at room temperature for 30 minutes. The insoluble matter contained in the reaction mixture was removed by filtration, then the solvent was evaporated, then the residue was dissolved in methanol (100 mL), sodium cyanoborohydride (27.8 mL, 27.8 mmol) was added to the solution, and the resulting mixture was stirred at room temperature for 14 hours. Saturated aqueous sodium hydrogencarbonate was added to the reaction mixture, the resulting mixture was extracted with dichloromethane, the organic layer was washed with saturated aqueous sodium hydrogencarbonate, and saturated brine, and then dried over magnesium sulfate, the solvent was evaporated, and the residue was purified by using automatic silica gel column chromatography (eluent, hexane:ethyl acetate=75:15) to obtain methyl (2S)-1-benzyl-6-methyl-4-oxopiperidine-2-carboxylate (2.28 g, yield 31%).

LCMS (LC-1): RT=1.54, m/z 262 $[M+H]^+$

Intermediate H-1-5: Methyl (2S)-6-methyl-4-oxopiperidine-2-carboxylate

[Formula 128]

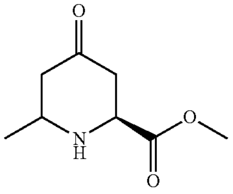

Methyl (2S)-1-benzyl-6-methyl-4-oxopiperidine-2-carboxylate (Intermediate H-1-4, 100 mg, 0.38 mmol) was dissolved in methanol (2.5 mL), palladium hydroxide (18 mg) was added to the solution under nitrogen atmosphere, the atmosphere was manually substituted to hydrogen gas, and the mixture was vigorously stirred at room temperature for 14 hours. The insoluble matter contained in the reaction mixture was removed by filtration, and then the solvent was evaporated to obtain a crude product containing methyl (2S)-6-methyl-4-oxopiperidine-2-carboxylate (64 mg, yield 97%).

1H-NMR ($DMSOd_6$): δ (ppm) 4.07-4.04 (1H, m), 3.78 (1.5H, s), 3.74 (1.5H, s), 3.27-3.23 (1H, m), 3.03-2.97 (1H, m), 2.73-2.59 (3H, m), 2.44-2.37 (3H, m), 2.17-2.07 (3H, m), 1.27 (1.5H, d, J=6.0 Hz), 1.18 (1.5H, d, J=6.0 Hz)

Intermediate H-1-6: Methyl (2S)-1,6-dimethyl-4-oxopiperidine-2-carboxylate

[Formula 129]

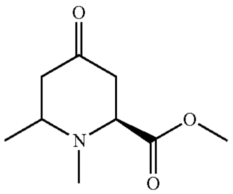

Methyl (2S)-6-methyl-4-oxopiperidine-2-carboxylate (Intermediate H-1-5, 1.54 g, 9.0 mol) was dissolved in dichloromethane (70 mL), 37% aqueous formaldehyde (7 mL, 86 mmol), and sodium triacetoxyborohydride (2.28 g, 10.8 mmol) were added to the solution, and the resulting mixture was stirred at room temperature for 1 hour. The reaction mixture was treated with SCX to obtain a crude product containing methyl (2S)-1,6-dimethyl-4-oxopiperidine-2-carboxylate (1.48 g, yield 89%).

LCMS (LC-1): RT=0.72, m/z 186 $[M+H]^+$

Intermediate H-1-7: Methyl (2S)-4-(benzylamino)-1,6-dimethylpiperidine-2-carboxylate

[Formula 130]

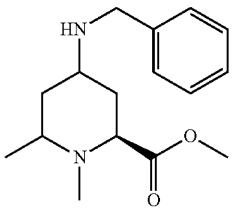

Methyl (2S)-1,6-dimethyl-4-oxopiperidine-2-carboxylate (Intermediate H-1-6, 1.48 g, 7.99 mol) was dissolved in methanol (19 mL), benzylamine (4.4 mL, 40 mmol), and titanium tetraisopropoxide (9.5 mL, 40 mmol) were added to the solution, and the resulting mixture was stirred at room temperature for 14 hours. Sodium borohydride (1.04 g, 27.6 mmol) was added to the reaction mixture under ice cooling, and the resulting mixture was stirred at the same temperature for 1.5 hours. 25% Aqueous ammonia was added to the reaction mixture, the resulting mixture was stirred for 14 hours, and then the insoluble matter was removed by filtration through a Celite layer. The solvent of the resulting organic layer was evaporated, then the residue was diluted with saturated brine, and extracted with chloroform/methanol (90:10), the organic layer was dried over magnesium sulfate, and the solvent was evaporated to dryness to obtain a crude product containing methyl (2S)-4-(benzylamino)-1,6-dimethylpiperidine-2-carboxylate (9.91 g, yield 99%).

Intermediate H-1-8: Methyl (2S)-4-amino-1,6-dimethylpiperidine-2-carboxylate

[Formula 131]

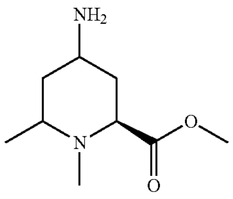

Methyl (2S)-4-(benzylamino)-1,6-dimethylpiperidine-2-carboxylate (Intermediate H-1-7, 2.21 g, 8.0 mmol) was dissolved in methanol (50 mL), palladium hydroxide (2.21 g, 15.7 mmol) was added to the solution under nitrogen atmosphere, the atmosphere was manually substituted to hydrogen gas, and the mixture was vigorously stirred at room temperature for 14 hours. The insoluble matter contained in the reaction mixture was removed by filtration, and then the solvent was evaporated to obtain a crude product containing methyl (2S)-4-amino-1,6-dimethylpiperidine-2-carboxylate (2.52 g, yield 99%).

LCMS (LC-1): RT=0.76, m/z 186 $[M+H]^+$

Intermediate H-1-9: Methyl (2S)-4-((tert-butoxycarbonyl)amino)-1,6-dimethylpiperidine-2-carboxylate

[Formula 132]

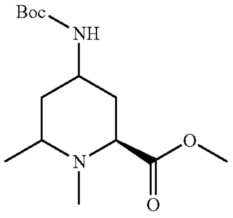

Methyl (2S)-4-amino-1,6-dimethylpiperidine-2-carboxylate (Intermediate H-1-8, 1.4 g, 7.52 mmol) was dissolved in dichloromethane (38 mL), di-tert-butyl dicarbonate (2.59 mL, 11.3 mmol), and triethylamine (2.1 mL, 15 mmol) were added to the solution, and the resulting mixture was stirred at room temperature for 3 hours. The reaction mixture was concentrated, and the residue was purified by using automatic silica gel column chromatography (eluent, chloroform:methanol: 25% aqueous ammonia =200:9:1) to obtain methyl (2S)-4-((tert-butoxycarbonyl)amino)-1,6-dimethylpiperidine-2-carboxylate (1.61 g, yield 75%).

LCMS (LC-1): RT=1.23, m/z 287 $[M+H]^+$

Intermediate H-1-10: (2S)-4-((tert-Butoxycarbonyl)amino)-1,6-dimethylpiperidine-2-carboxylic acid sodium salt

[Formula 133]

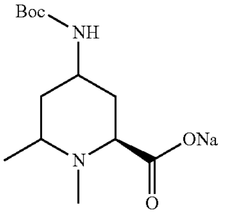

Methyl (2S)-4-((tert-butoxycarbonyl)amino)-1,6-dimethylpiperidine-2-carboxylate (Intermediate H-1-9, 1.61 g, 11.2 mmol) was dissolved in methanol (28 mL), 2 M aqueous sodium hydroxide (5.6 mL, 11.3 mmol) was added to the solution, and the resulting mixture was stirred at room temperature for 2 hours. The reaction mixture was concentrated to obtain (2S)-4-((tert-butoxycarbonyl)amino)-1,6-dimethylpiperidine-2-carboxylic acid sodium salt (1.51 g, yield 99%).

LCMS (LC-1): RT=0.70, m/z 273 $[M+H]^+$

Method H-2
[Formula 134]
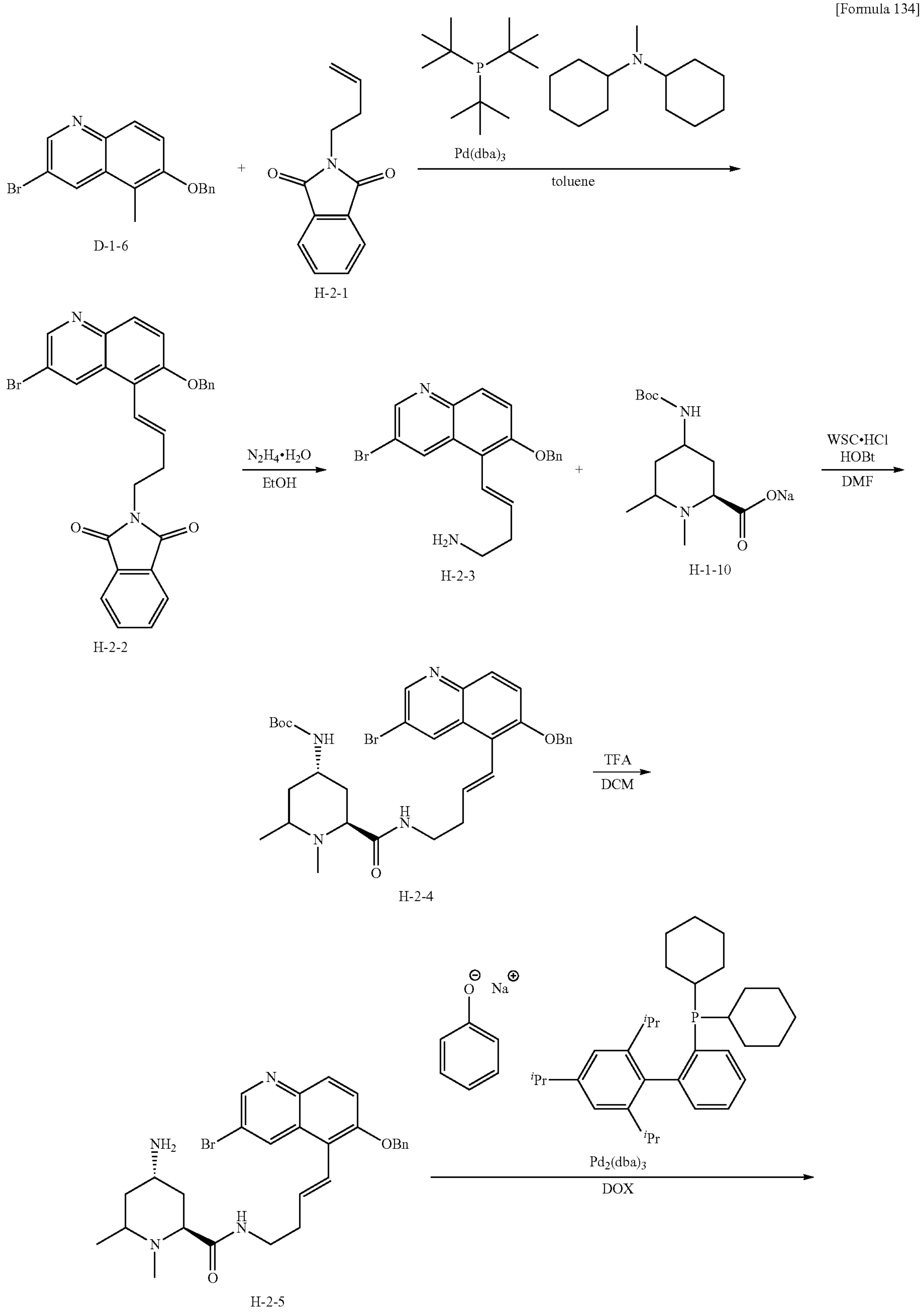

-continued

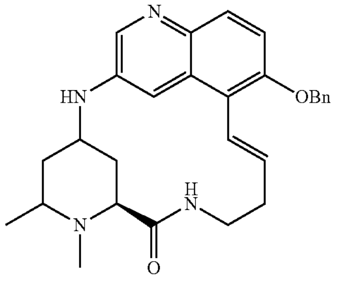

H-2-6

Intermediate H-2-2: (E)-2-(4-(6-(Benzyloxy)-3-bromoquinolin-5-yl)but-3-en-1-yl)isoindoline-1,3-dione

[Formula 135]

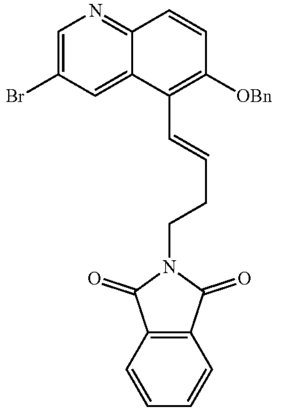

6-(Benzyloxy)-3-bromo-5-iodoquinoline (Intermediate D-1-6, 2.0 g, 4.5 mmol) was dissolved in toluene (50 mL), a 10% solution of tri-tert-butylphosphine in pentane (910 μL, 0.45 mmol), dicyclohexylmethylamine (2.6 g, 13.5 mmol), 2-(but-3-en-1-yl)isoindoline-1,3-dione (1.1 g, 5.5 mmol) prepared according to the descriptions of the literature (J. Org. Chem., 1974, 39, 1979-1980), and tris(dibenzylideneacetone) dipalladium (0) (206 mg, 0.23 mmol) were added to the solution, and the resulting mixture was stirred with heating at 120° C. for 20 hours. The reaction solution was returned to room temperature, then the solvent was evaporated, and the residue was purified by using silica gel column chromatography (eluent, hexane:ethyl acetate=86:14) to obtain (E)-2-(4-(6-(benzyloxy)-3-bromoquinolin-5-yl)but-3-en-1-yl)isoindoline-1,3-dione (1.4 g, yield 61%).

Intermediate H-2-3: (E)-4-(6-(Benzyloxy)-3-bromoquinolin-5-yl)but-3-en-1-amine

[Formula 136]

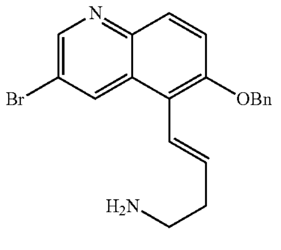

(E)-2-(4-(6-(Benzyloxy)-3-bromoquinolin-5-yl)but-3-en-1-yl)isoindoline-1,3-dione (Intermediate H-2-2, 1.29 g, 2.51 mmol) was dissolved in ethanol (25 mL), hydrazine hydrate (1.82 mL, 5.02 mmol) was added to the solution, and the resulting mixture was refluxed by heating for 4 hours. The reaction solution was cooled to room temperature, the solvent was evaporated, the residue was dissolved in water (25 mL), the solution was extracted with ethyl acetate, the organic layer was concentrated, and the residue was purified by using silica gel column chromatography (eluent, hexane: ethyl acetate=86:14) to obtain (E)-4-(6-(benzyloxy)-3-bromoquinolin-5-yl)but-3-en-1-amine (680 mg, 39%).

Intermediate H-2-4: tert-Butyl ((2S)-2-(((E)-4-(6-(benzyloxy)-3-bromoquinolin-5-yl)but-3-en-1-yl)carbamoyl)-1,6-dimethylpiperidin-4-yl)carbamate

[Formula 137]

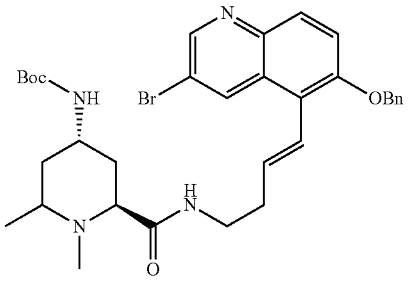

(E)-4-(6-(Benzyloxy)-3-bromoquinolin-5-yl)but-3-en-1-amine (Intermediate H-2-3, 193 mg, 0.50 mmol) was dissolved in dimethylformamide (5 mL), 1-ethyl-3-(3-dimethylaminopropyl)carbodiimide hydrochloride (193 mg, 1.01 mmol), 1-hydroxybenzotriazol (154 mg, 1.01 mmol), and (2S)-4-((tert-butoxycarbonyl)amino)-1,6-dimethylpiperidine-2-carboxylic acid sodium salt (Intermediate H-1-10, 274 mg, 1.01 mmol) were added to the solution, and the resulting mixture was stirred with heating at 50° C. for 14 hours. The reaction mixture was concentrated, and the residue was purified by using automatic silica gel column chromatography (eluent, hexane:ethyl acetate=50:50) to obtain tert-butyl ((2S)-2-(((E)-4-(6-(benzyloxy)-3-bromoquinolin-5-yl)but-3-en-1-yl)carbamoyl)-1,6-dimethylpiperidin-4-yl)carbamate (353 mg, yield 99%).

LCMS (LC-1): RT=1.95, m/z 638 $[M+H]^+$

Intermediate H-2-5: (2S)-4-Amino-N—((E)-4-(6-(benzyloxy)-3-bromoquinolin-5-yl)but-3-en-1-yl)-1,6-dimethylpiperidine-2-carboxamide

[Formula 138]

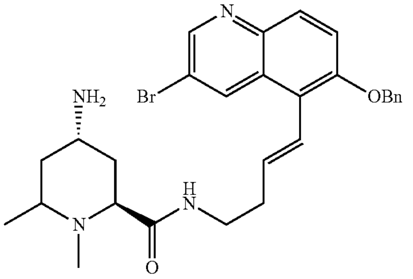

tert-Butyl ((2S)-2-(((E)-4-(6-(benzyloxy)-3-bromoquinolin-5-yl)but-3-en-1-yl) carbamoyl)-1,6-dimethylpiperidin-4-yl)carbamate (Intermediate H-2-4, 242 mg, 0.38 mmol) was dissolved in dichloromethane (3.8 mL), trifluoroacetic acid (290 μL, 3.8 mmol) was added to the solution, and the resulting mixture was stirred at room temperature for 2 hours. The reaction solution was concentrated, neutralized with 25% aqueous ammonia, and extracted with chloroform, the organic layer was dried over magnesium sulfate, and the solvent was evaporated to obtain (2S)-4-amino-N—((E)-4-(6-(benzyloxy)-3-bromoquinolin-5-yl)but-3-en-1-yl)-1,6-dimethylpiperidine-2-carboxamide (203 mg, yield 99%).

LCMS (LC-1): RT=1.42, m/z 538 $[M+H]^+$

Intermediate H-2-6: ($3^2$S,E)-16-(Benzyloxy)-31,36-dimethyl-2,5-diaza-1 (3,5)-qunolina-3 (4,2)-piperidinacyclononaphan-8-en-4-one

[Formula 139]

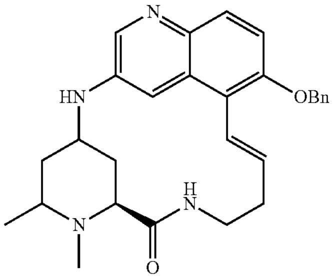

(2S)-4-Amino-N—((E)-4-(6-(benzyloxy)-3-bromoquinolin-5-yl)but-3-en-1-yl)-1,6-dimethylpiperidine-2-carboxamide (Intermediate H-2-5, 210 mg, 0.38 mmol) was dissolved in 1,4-dioxane (3.9 mL), tris(dibenzylideneacetone) dipalladium (0) (36 mg, 40 μmol), 2-dicyclohexylphosphino-2',4',6'-triisopropyl-1,1'-biphenyl (36 mg, 80 μmol), and sodium phenoxide (90 mg, 0.78 mmol) were added to the solution, and the resulting mixture was refluxed by heating for 14 hours. The reaction mixture was cooled to room temperature, then the solvent was evaporated, and the residue was purified by using automatic silica gel column chromatography (eluent, chloroform:methanol=9:1) to obtain ($3^2$S,E)-$1^6$-(benzyloxy)-31,36-dimethyl-2,5-diaza-1 (3,5)-qunolina-3 (4,2)-piperidinacyclononaphan-8-en-4-one (133 mg, yield 75%).

LCMS (LC-1): RT=1.49, m/z 457 $[M+H]^+$

Method H-3

[Formula 140]

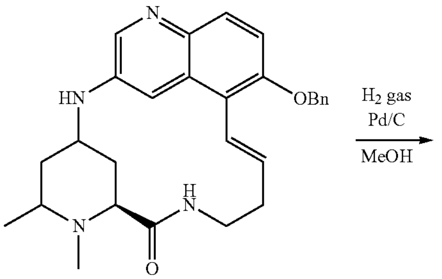

H-2-6

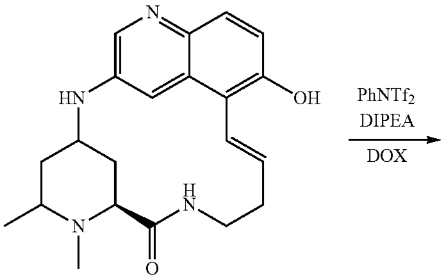

H-3-1

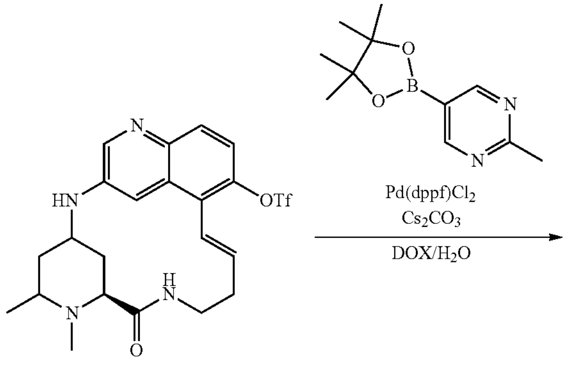

H-3-2

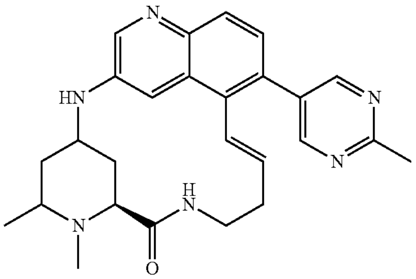

H-3-3

Intermediate H-3-1: ($3^2$S,E)-16—Hydroxy-31,36-dimethyl-2,5-diaza-1 (3,5)-qunolina-3 (4,2)-piperidinacyclononaphan-8-en-4-one

[Formula 141]

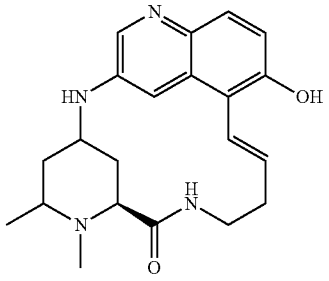

($3^2$S,E)-16-(Benzyloxy)-31,36-dimethyl-2,5-diaza-1 (3,5)-qunolina-3 (4,2)-piperidinacyclononaphan-8-en-4-one (Intermediate H-2-6, 131 mg, 0.29 mmol) was dissolved in methanol (2.8 mL), palladium carbon (24 mg) was added to the solution under nitrogen atmosphere, the atmosphere was manually substituted to hydrogen gas, and the resulting mixture was vigorously stirred at room temperature for 14 hours. The insoluble matter contained in the reaction mixture was removed by filtration, and then the solvent was evaporated to obtain a crude product containing ($3^2$S,E)-16-hydroxy-31,36-dimethyl-2,5-diaza-1 (3,5)-qunolina-3 (4,2)-piperidinacyclononaphan-8-en-4-one (105 mg, yield 99%).

LCMS (LC-1): RT=0.86, m/z 367 $[M+H]^+$

Intermediate H-3-2: ($3^2$S,E)-31,36-dimethyl-4-oxo-2,5-diaza-1 (3,5)-qunolina-3 (4,2)-piperidinacyclononaphan-8-en-16-yl trifluoromethanesulfonate

[Formula 142]

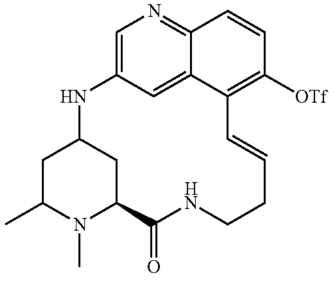

($3^2$S,E)-16—Hydroxy-31,36-dimethyl-2,5-diaza-1 (3,5)-qunolina-3 (4,2)-piperidinacyclononaphan-8-en-4-one (Intermediate H-3-1, 105 mg, 0.29 mmol) was dissolved in 1,4-dioxane (2.9 mL), N,N-bis(trifluoromethylsulfonyl) aniline) (136 mg, 0.57 mmol), and diisopropylethylamine (80 μL, 0.57 mmol) were added to the solution, and the resulting mixture was stirred at 70° C. for 14 hours. The reaction mixture was concentrated to obtain a crude product containing ($3^2$S,E)-31,36-dimethyl-4-oxo-2,5-diaza-1 (3,5)-qunolina-3 (4,2)-piperidinacyclononaphan-8-en-16-yl trifluoromethanesulfonate (143 mg, yield 99%).

LCMS (LC-1): RT=1.61, m/z 499 $[M+H]^+$

Example α-02-17 (End product H-3-3): ($3^2$S,E)-31,36-Dimethyl-16-(2-methylpyrimidin-5-yl)-2,5-diaza-1 (3,5)-qunolina-3 (4,2)-piperidinacyclononaphan-8-en-4-one

[Formula 143]

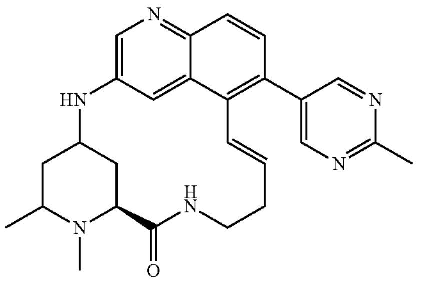

($3^2$S,E)-31,36-Dimethyl-4-oxo-2,5-diaza-1 (3,5)-qunolina-3 (4,2)-piperidinacyclononaphan-8-ene-16-yl trifluoromethanesulfonate (Intermediate H-3-2, 120 mg, 0.24 mmol) was dissolved in 1,4-dioxane (2.4 mL) and water (240 μL), 2-methylpyrimidine-5-boronic acid pinacol ester (105 mg, 0.48 mmol), [1,1'-bis(diphenylphosphino) ferrocene]palladium (II) (17 mg, 20 μmol), and cesium carbonate (156 mg, 0.48 mmol) were added to the solution, and the resulting mixture was irradiated with microwaves at 100° C. for 3 hours. The insoluble matter contained in the reaction mixture was removed by filtration through a Celite layer, then the solvent was evaporated, and the residue was purified by using HPLC to obtain ($3^2$S,E)-31,36 dimethyl-16-(2-methylpyrimidin-5-yl)-2,5-diaza-1 (3,5)-qunolina-3 (4,2)-piperidinacyclononaphan-8-en-4-one (1.1 mg, yield 1%).

LCMS (LC-1): RT=0.99, m/z 443 $[M+H]^+$

1H-NMR ($CD_3OD$): δ (ppm) 8.78-8.72 (2H, m), 8.57-8.54 (1H, m), 8.44-8.39 (1H, m), 7.88-7.83 (1H, m), 7.51-7.47 (1H, m), 7.38-7.33 (1H, m), 6.45-6.41 (1H, m), 6.40-6.36 (1H, m), 6.20-6.10 (2H, m), 3.93-3.85 (2H, m), 3.68-3.62 (2H, m), 3.52-3.44 (2H, m), 3.19-3.09 (2H, m), 2.76 (3H, s), 2.72-2.63 (2H, m), 2.54 (3H, s), 2.05-1.95 (2H, m), 1.62-1.41 (4H, m), 1.33-1.27 (2H, m), 1.17 (3H, d, J=6.5 Hz)

Method I-1

[Formula 144]

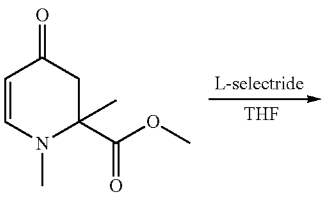

I-1-1

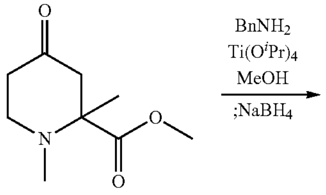

I-1-2

-continued

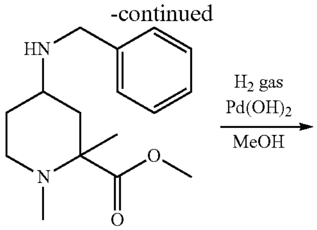

I-1-3

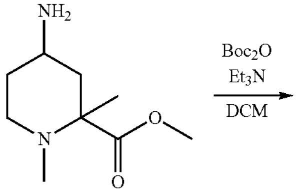

I-1-4

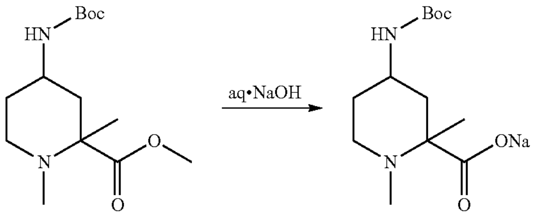

I-1-5 I-1-6

Intermediate I-1-2: Methyl 1,2-dimethyl-4-oxopiperidine-2-carboxylate

[Formula 145]

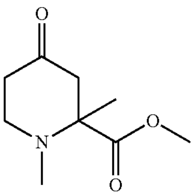

Methyl 1,2-dimethyl-4-oxo-1,2,3,4-tetrahydropyridine-2-carboxylate (1.3 g, 7.3 mmol) prepared according to the descriptions of the literature (Org. Lett., 2005, 435-437) was dissolved in tetrahydrofuran (8 mL), L-Selectride (R) (190 mL) was added to the solution at −78° C. under nitrogen atmosphere, and the resulting mixture was stirred at the same temperature for 2 hours. Methanol was added to the reaction mixture to quench the reaction, then the reaction mixture was warmed to room temperature, concentrated, and treated by using SCX cartridge to obtain a crude reaction mixture containing methyl 1,2-dimethyl-4-oxopiperidine-2-carboxylate.

LCMS (LC-1): RT=0.94, m/z 186 $[M+H]^+$

Intermediate I-1-3: Methyl 4-(benzylamino)-1,2-dimethylpiperidine-2-carboxylate

[Formula 146]

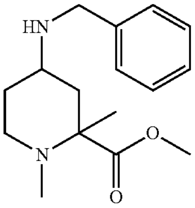

Methyl 1,2-dimethyl-4-oxopiperidine-2-carboxylate (Intermediate I-1-2, 1.0 g, 5.47 mol) was dissolved in methanol (13 mL), benzylamine (3.0 mL, 27.4 mmol), and titanium tetraisopropoxide (6.5 mL, 21.9 mmol) were added to the solution, and the resulting mixture was stirred at room temperature for 14 hours. Sodium borohydride (715 mg, 18.9 mmol) was added to the reaction mixture under ice cooling, and the resulting mixture was stirred at the same temperature for 2 hours. 25% Aqueous ammonia was added to the reaction mixture, the resulting mixture was stirred for 14 hours, and then the insoluble matter was removed by filtration through a Celite layer. The solvent of the resulting organic layer was evaporated, then the residue was diluted with saturated brine, and extracted with chloroform/methanol (90:10), the organic layer was dried over magnesium sulfate, and the solvent was evaporated to dryness to obtain a crude product containing methyl 4-(benzylamino)-1,2-dimethylpiperidine-2-carboxylate (1.51 g, yield 99%).

Intermediate I-1-4: Methyl 4-amino-1,2-dimethylpiperidine-2-carboxylate

[Formula 147]

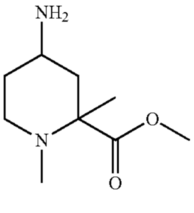

Methyl 4-(benzylamino)-1,2-dimethylpiperidine-2-carboxylate (Intermediate I-1-5, 1.51 g, 5.47 mmol) was dissolved in methanol (35 mL), palladium hydroxide (800 mg, 5.70 mmol) was added to the solution under nitrogen atmosphere, the atmosphere was manually substituted to hydrogen gas, and the resulting mixture was vigorously stirred at room temperature for 14 hours. The insoluble matter contained in the reaction mixture was removed by filtration, and then the solvent was evaporated to obtain a crude product containing methyl 4-amino-1,2-dimethylpiperidine-2-carboxylate (1.02 g, yield 99%).

Intermediate I-1-5: Methyl 4-((tert-butoxycarbonyl) amino)-1,2-dimethylpiperidine-2-carboxylate

[Formula 148]

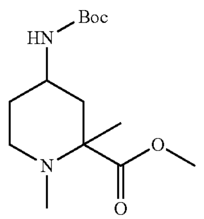

Methyl 4-amino-1,2-dimethylpiperidine-2-carboxylate (Intermediate I-1-4, 1.02 g, 5.47 mmol) was dissolved in dichloromethane (38 mL), di-tert-butyl dicarbonate (3.58 mL, 16.4 mmol), and triethylamine (7.63 mL, 54.7 mmol) were added to the solution, and the resulting mixture was stirred at room temperature for 3 hours. The reaction mixture was concentrated, and the residue was purified by using automatic silica gel column chromatography (eluent, hexane:ethyl acetate=20:80) to obtain methyl 4-((tert-butoxycarbonyl)amino)-1,2-dimethylpiperidine-2-carboxylate (205 mg, yield 13%).

LCMS (LC-1): RT=1.26, m/z 287 $[M+H]^+$

1H-NMR ($CDCl_3$): δ (ppm) 4.53-4.32 (1H, m), 3.78-3.68 (3H, m), 2.90-2.76 (1H, m), 2.64-2.45 (1H, m), 2.25-2.15 (2H, m), 1.98-1.84 (2H, m), 1.80-1.68 (1H, m), 1.43 (7H, s), 1.29 (2H, s)

Intermediate I-1-6:4-((tert-Butoxycarbonyl)amino)-1,2-dimethylpiperidine-2-carboxylic acid sodium salt

[Formula 149]

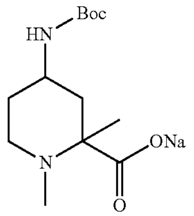

Methyl 4-((tert-butoxycarbonyl)amino)-1,2-dimethylpiperidine-2-carboxylate (Intermediate I-1-5, 687 mg, 2.40 mmol) was dissolved in 1 M aqueous sodium hydroxide (10 mL, 10 mmol), and the solution was stirred at room temperature for 2 hours. The reaction mixture was concentrated to obtain 4-((tert-butoxycarbonyl)amino)-1,2-dimethylpiperidine-2-carboxylic acid sodium salt (853 mg, yield 99%).

Method I-2

[Formula 150]

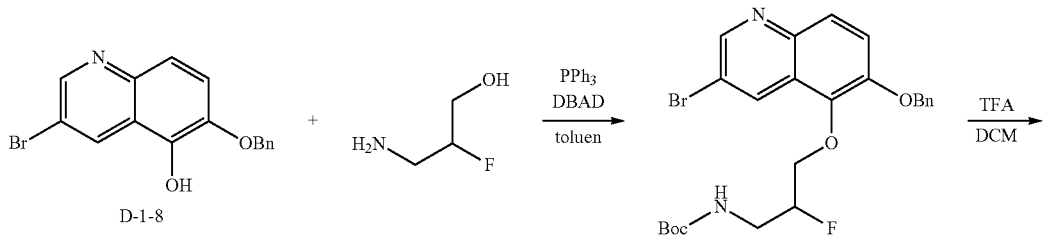

D-1-8

I-2-1

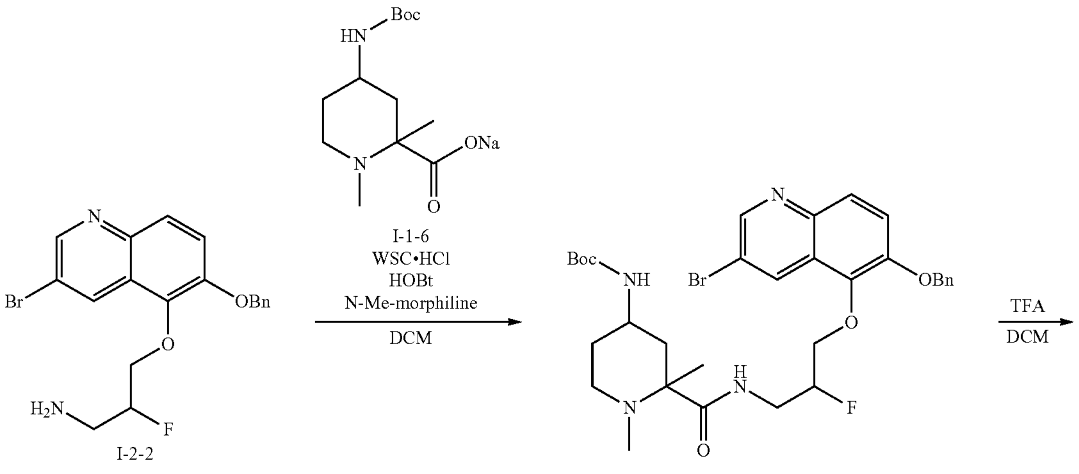

I-1-6

I-2-2

I-2-3

-continued

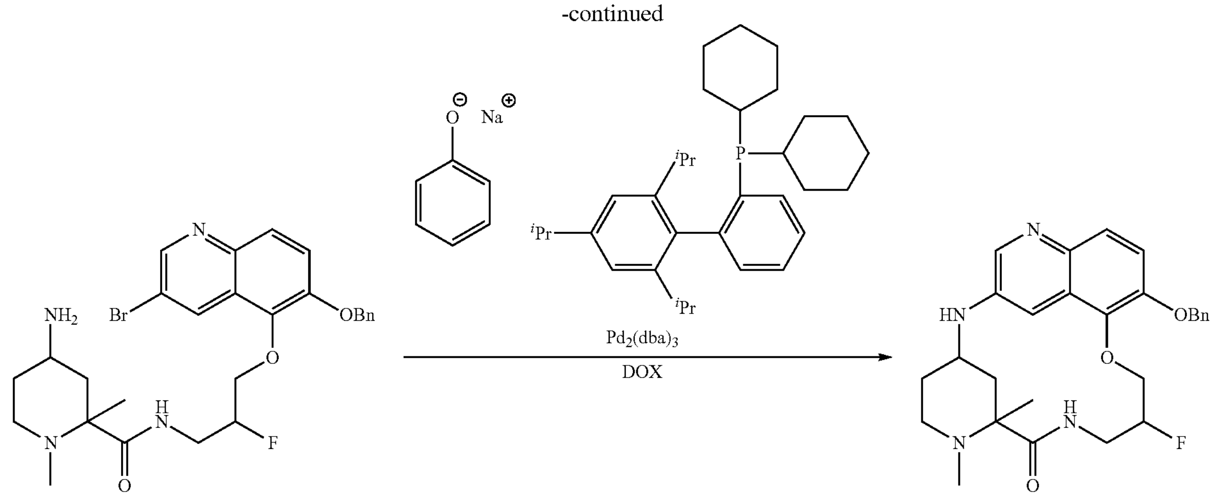

I-2-4 I-2-5

Intermediate I-2-2:3-((6-(Benzyloxy)-3-bromoquinolin-5-yl)oxy)-2-fluoropropan-1-amine

[Formula 151]

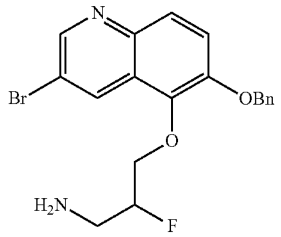

tert-Butyl(S)-(3-((6-(benzyloxy)-3-bromoquinolin-5-yl)oxy)-2-fluoropropyl)carbamate (Intermediate I-2-1, 6.59 g, 13.0 mmol) was dissolved in dichloromethane (40 mL), trifluoroacetic acid (10 mL) was added to the solution, and the resulting mixture was stirred at room temperature for 3 hours. The reaction mixture was treated with SCX to obtain (S)-3-((6-(benzyloxy)-3-bromoquinolin-5-yl)oxy)-2-fluoropropan-1-amine (2.78 g, yield 53%).

LCMS (LC-1): RT-1.38, m/z 405 $[M+H]^+$

1H-NMR ($CDCl_3$): δ (ppm) 8.84-8.76 (1H, m), 8.69-8.63 (1H, m), 7.83 (1H, d, J=9.3 Hz), 7.53 (1H, d, J=9.3 Hz), 7.49-7.32 (5H, m), 5.32-5.18 (2H, m), 4.90-4.68 (1H, m), 4.40-4.29 (2H, m), 3.08-2.97 (2H, m)

Intermediate I-2-3: tert-Butyl (2-((3-((6-(benzyloxy)-3-bromoquinolin-5-yl)oxy-2-fluoropropyl)carbamoyl)-1,2-dimethylpiperidin-4-yl)carbamate

[Formula 152]

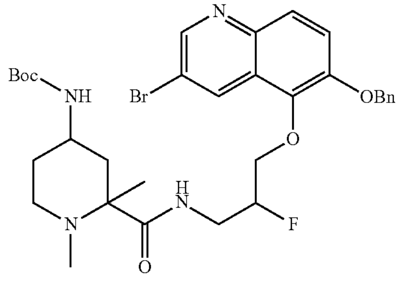

3-((6-(Benzyloxy)-3-bromoquinolin-5-yl)oxy)-2-fluoropropan-1-amine (Intermediate I-2-2, 1.02 g, 2.52 mmol) was dissolved in dichloromethane (20 mL), N-methylmorpholine (695 μL, 2.52 mmol), 1-ethyl-3-(3-dimethylaminopropyl)carbodiimide hydrochloride (1.93 g, 10.1 mmol), 1-hydroxybenzotriazol (750 mg, 5.55 mmol), and 4-((tert-butoxycarbonyl)amino)-1,2-dimethylpiperidine-2-carboxylic acid sodium salt (Intermediate I-1-6, 687 mg, 2.52 mmol) were added to the solution, and the resulting mixture was stirred at room temperature for 14 hours. Water was added to the reaction mixture, the resulting mixture was extracted with chloroform, the solvent was evaporated, and the residue was purified by using automatic silica gel column chromatography (eluent, hexane:ethyl acetate=30:70) to obtain tert-butyl (2-((3-((6-(benzyloxy)-3-bromoquinolin-5-yl)oxy-2-fluoropropyl)carbamoyl)-1,2-dimethylpiperidin-4-yl)carbamate (765 mg, yield 42%).

LCMS (LC-1): RT=2.05, m/z 659 $[M+H]^+$

1H-NMR ($CDCl_3$): δ (ppm) 8.77 (1H, d, J=2.0 Hz), 8.67-8.63 (1H, m), 7.81 (1H, d, J=9.0 Hz), 7.55-7.49 (1H, m), 7.49-7.35 (5H, m), 5.27 (2H, s), 4.98 (1H, dd, J=10.0, 7.0 Hz), 4.92-4.64 (1H, m), 4.44-4.25 (3H, m), 4.12 (1H, dd, J=7.0, 7.0 Hz), 3.83-3.67 (1H, m), 3.63-3.41 (2H, m), 2.89-2.63 (2H, m), 2.36 (3H, s), 2.34-2.22 (1H, m), 1.45-1.39 (9H, m), 1.29-1.24 (2H, m)

Intermediate I-2-4:4-Amino-N-(3-((6-(benzyloxy)-3-bromoquinolin-5-yl)oxy)-2-fluoropropyl)-1,2-dimethylpiperidine-2-carboxamide

[Formula 153]

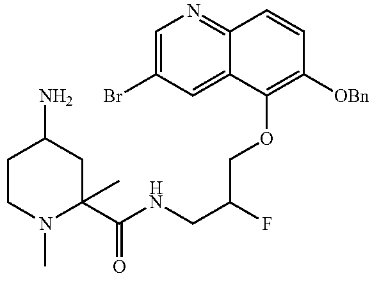

tert-Butyl (2-((3-((6-(benzyloxy)-3-bromoquinolin-5-yl) oxy-2-fluoropropyl)carbamoyl)-1,2-dimethylpiperidin-4-yl) carbamate (Intermediate I-2-3, 765 mg, 1.16 mmol) was dissolved in dichloromethane (8 mL), trifluoroacetic acid (2 mL) was added to the solution, and the resulting mixture was stirred at room temperature for 20 minutes. The reaction mixture was treated with SCX to obtain 4-amino-N-(3-((6-(benzyloxy)-3-bromoquinolin-5-yl)oxy)-2-fluoropropyl)-1, 2-dimethylpiperidine-2-carboxamide (645 mg, yield 100%).

LCMS (LC-1): RT=1.43, m/z 559 [M+H]$^+$

Intermediate I-2-5:16-(Benzyloxy)-7-fluoro-$3^1$,$3^2$-dimethyl-9-oxa-2,5-diaza-1 (3,5)-qunolina-3 (4,2)-piperidinacyclononaphan-4-one

[Formula 154]

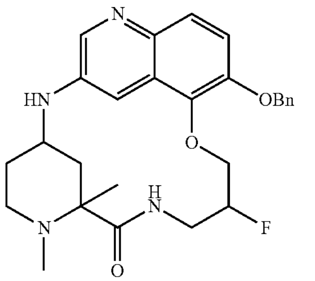

4-Amino-N-(3-((6-(benzyloxy)-3-bromoquinolin-5-yl) oxy)-2-fluoropropyl)-1,2-dimethylpiperidine-2-carboxamide (Intermediate I-2-4, 598 mg, 1.07 mmol) was dissolved in 1,4-dioxane (10 mL), tris(dibenzylideneacetone) dipalladium (0) (98 mg, 107 μmol), dicyclohexylphosphino-2',4', 6'-triisopropyl-1,1'-biphenyl (102 mg, 214 μmol), and sodium phenoxide (248 mg, 2.14 mmol) were added to the solution, and the resulting mixture was refluxed by heating for 14 hours. The reaction mixture was cooled to room temperature, then the solvent was evaporated, and the residue was purified by using automatic silica gel column chromatography (eluent, ethyl acetate: methanol=90:10) to obtain 16-(benzyloxy)-7-fluoro-$3^1$,$3^2$-dimethyl-9-oxa-2,5-diaza-1 (3,5)-qunolina-3 (4,2)-piperidinacyclononaphan-4-one (179 mg, yield 32%).

LCMS (LC-1): RT=1.39, m/z 479 [M+H]$^+$

1H-NMR ($CDCl_3$): δ (ppm) 8.32 (1H, d, J=2.5 Hz), 8.00 (1H, d, J=2.5 Hz), 7.67 (1H, d, J=9.0 Hz), 7.52-7.29 (5H, m), 7.17 (1H, d, J=9.0 Hz), 5.13-4.89 (1H, m), 4.27 (1H, dd, J=11.5, 9.0 Hz), 4.17-4.04 (2H, m), 3.97 (1H, d, J=4.4 Hz), 3.80-3.67 (1H, m), 3.54-3.26 (1H, m), 3.18 (1H, d, J=6.0 Hz), 2.92 (1H, td, J=12.0, 4.0 Hz), 2.88-2.79 (1H, m), 2.69 (2H, s), 1.96-1.83 (2H, m), 1.50 (3H, s), 1.47-1.37 (1H, m)

Method I-3

[Formula 155]

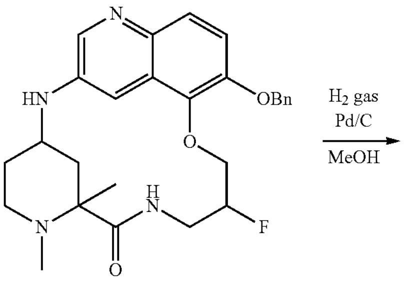

I-2-5

-continued

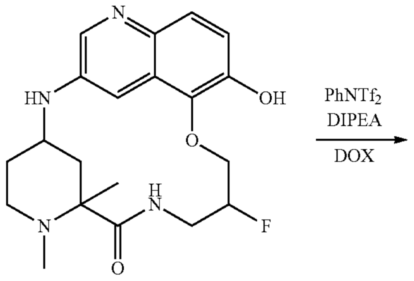

I-3-1

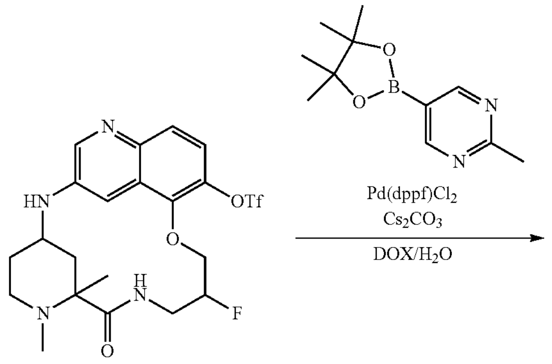

I-3-2

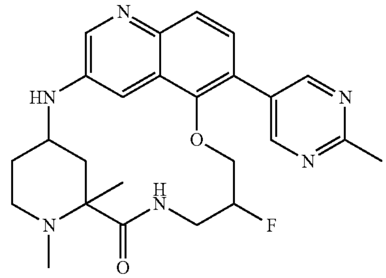

I-3-3

Intermediate I-3-1:7-Fluoro-$1^6$-hydroxy-31,$3^2$-dimethyl-9-oxa-2,5-diaza-1 (3,5)-qunolina-3 (4,2)-piperidinacyclononaphan-4-one

[Formula 156]

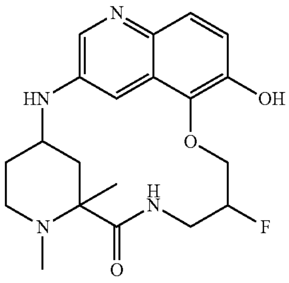

16-(Benzyloxy)-7-fluoro-$3^1$,$3^2$-dimethyl-9-oxa-2,5-diaza-1 (3,5)-qunolina-3 (4,2)-piperidinacyclononaphan-4-one (Intermediate I-2-5, 180 mg, 0.38 mmol) was dissolved in methanol (8 mL), 10% palladium carbon (90 mg) was added to the solution under nitrogen atmosphere, the atmosphere was manually substituted to hydrogen gas, and the resulting mixture was vigorously stirred at room temperature for 14 hours.

The insoluble matter contained in the reaction mixture was removed by filtration, and then the solvent was evaporated to obtain 7-fluoro-1$^6$-hydroxy-31,3$^2$-dimethyl-9-oxa-2,5-diaza-1 (3,5)-qunolina-3 (4,2)-piperidinacyclononaphan-4-one (138 mg, yield 95%).

LCMS (LC-1): RT=0.83, m/z 389 $[M+H]^+$

1H-NMR ($CD_3OD$): δ (ppm) (1H, d, J=3.0 Hz), 7.53-7.43 (1H, m), 7.33-7.20 (1H, m), 7.18-7.07 (1H, m), 7.01 (1H, d, J=9.0 Hz), 6.89-6.85 (1H, m), 5.29 (1H, tdd, J=9.0, 6.5, 3.0 Hz), 5.23-5.14 (1H, m), 5.12-4.94 (1H, m), 4.28 (1H, ddd, J=17.5, 11.0, 7.5 Hz), 4.17-3.86 (3H, m), 3.78-3.65 (1H, m), 3.51-3.39 (1H, m), 3.35 (3H, s), 3.13-3.01 (1H, m), 2.86 (1H, ddd, J=11.0, 5.0, 2.0 Hz), 2.62-2.56 (3H, m), 2.36-2.28 (1H, m), 1.99 (1H, d, J=12.0 Hz), 1.75 (1H, dq, J=12.0, 5.0 Hz), 1.46-1.41 (3H, m), 1.28-1.16 (2H, m)

Intermediate I-3-2:7-Fluoro-3$^1$,3$^2$-dimethyl-9-oxa-2, 5-diaza-1 (3,5)-qunolina-3 (4,2)-piperidinacyclononaphane-16-yl trifluoromethanesulfonate

[Formula 157]

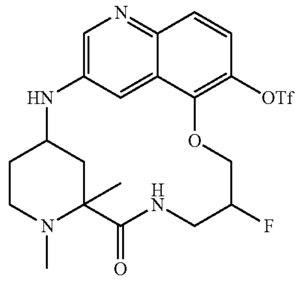

7-Fluoro-1$^6$-hydroxy-31,3$^2$-dimethyl-9-oxa-2,5-diaza-1 (3,5)-qunolina-3 (4,2)-piperidinacyclononaphan-4-one (Intermediate I-3-1, 138 mg, 0.36 mmol) was dissolved in dichloromethane (4 mL), trifluoromethanesulfonic acid anhydride (72 μL, 0.43 mmol), and pyridine (43 μL, 0.53 mmol) were added to the solution, and the resulting mixture was stirred at room temperature for 1 hour. The reaction mixture was concentrated to obtain a crude product containing (7-fluoro-3$^1$,3$^2$-dimethyl-9-oxa-2,5-diaza-1 (3,5)-qunolina-3 (4,2)-piperidinacyclononaphan-16-yl trifluoromethanesulfonate (185 mg, yield 99%).

Example a-02-23 (End product I-3-3): 7-Fluoro-3$^1$, 3$^2$-dimethyl-16-(2-methylpyrimidin-5-yl)-9-oxa-2,5-diaza-1 (3,5)-qunolina-3 (4,2)-piperidinacyclononaphan-4-one

[Formula 158]

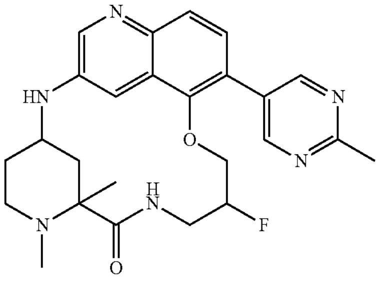

7-Fluoro-3$^1$,3$^2$-dimethyl-9-oxa-2,5-diaza-1 (3,5)-qunolina-3 (4,2)-piperidinacyclononaphane-16-yl trifluoromethanesulfonate (Intermediate I-3-2, 185 mg, 0.36 mmol) was dissolved in 1,4-dioxane (4 mL) and water (800 μL), 2-methylpyrimidine-5-boronic acid pinacol ester (147 mg, 1.07 mmol), [1,1'-bis(diphenylphosphino) ferrocene]palladium (II) (116 mg, 142 μmol), and cesium carbonate (696 mg, 2.14 mmol) were added to the solution, and the resulting mixture was stirred with heating at 80° C. for 2 hours. The insoluble matter contained in the reaction mixture was removed by filtration through a Celite layer, then the solvent was evaporated, and the residue was purified by using HPLC to obtain 7-fluoro-3$^1$,3$^2$-dimethyl-16-(2-methylpyrimidin-5-yl)-9-oxa-2,5-diaza-1 (3,5)-qunolina-3 (4,2)-piperidinacyclononaphan-4-one (43.7 mg, yield 26%) as a low polarity fraction.

LCMS (LC-1): RT=1.03, m/z 465 $[M+H]^+$

1H-NMR ($CD_3OD$): δ (ppm) 9.05 (2H, s), 8.42 (1H, d, J=2.5 Hz), 7.77 (1H, d, J=8.5 Hz), 7.50 (1H, d, J=8.5 Hz), 7.03 (1H, d, J=2.5 Hz), 5.25 (1H, d, J=6.5 Hz), 5.14 (1H, brs), 4.26-4.12 (1H, m), 4.08 (1H, dd, J=12.0, 2.0 Hz), 3.93-3.77 (2H, m), 3.69 (1H, dt, J=12.0, 3.5 Hz), 3.67-3.42 (1H, m), 2.96-2.81 (2H, m), 2.77 (3H, s), 2.57 (3H, s), 2.25 (1H, d, J=13.2 Hz), 2.02 (1H, d, J=12.0 Hz, 1H), 1.77 (1H, dq, J=12.0, 5.0 Hz), 1.40 (3H, s), 1.34-1.20 (m, 1H)

TABLE 3

| Example | Structure | Reference Methods | LCMS Data |
|---|---|---|---|
| a-02-01 | 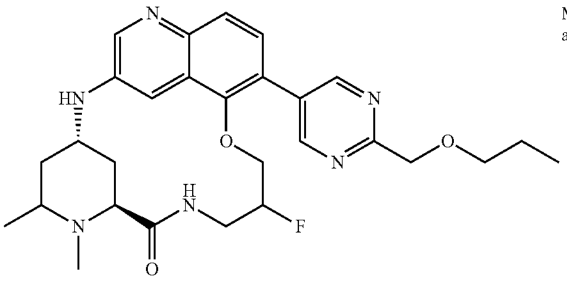 | Methods H-1, I-2, and I-3 | (LC-1): RT = 1.19, m/z 523 $[M + H]^+$ |

TABLE 3-continued
| Example | Structure | Reference Methods | LCMS Data |
|---|---|---|---|
| a-02-02 | 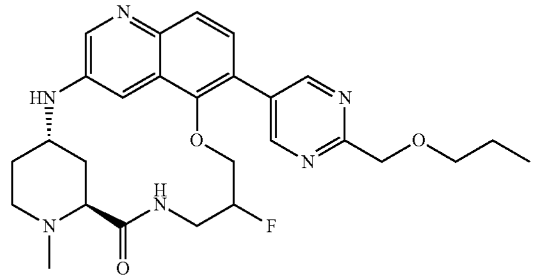 [SMILES: CCCOCc1ncc(-c2ccc3ncc4cc3c2OCC(F)CNC(=O)[C@@H]2C[C@H](CCN2C)N4)cn1] | Methods D-2, and D-3 | (LC-1): RT = 1.11, m/z 509 [M + H]+ |
| a-02-03 | 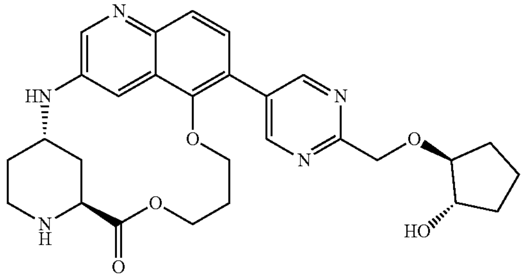 [SMILES: O=C1OCCCOc2c(-c3cnc(CO[C@H]4CCC[C@@H]4O)nc3)ccc3ncc(cc23)N[C@H]2CCN[C@H]1C2] | Methods D-3, and E-1 | (LC-1): RT = 0.97, m/z 520 [M + H]+ |
| a-02-04 | 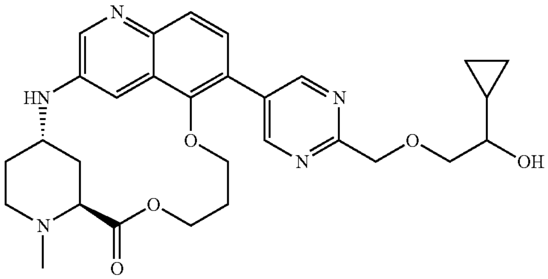 [SMILES: CN1CC[C@H]2C[C@H]1C(=O)OCCCOc1c(-c3cnc(COCC(O)C4CC4)nc3)ccc3ncc(cc13)N2] | Methods D-3, and E-1 | (LC-1): RT = 1.20, m/z 534 [M + H]+ |
| a-02-05 | 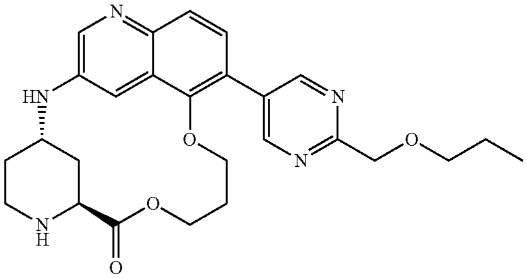 [SMILES: CCCOCc1ncc(-c2ccc3ncc4cc3c2OCCCOC(=O)[C@@H]2C[C@H](CCN2)N4)cn1] | Methods D-3, and E-1 | (LC-1): RT = 1.16, m/z 478 [M + H]+ |
| a-02-06 | 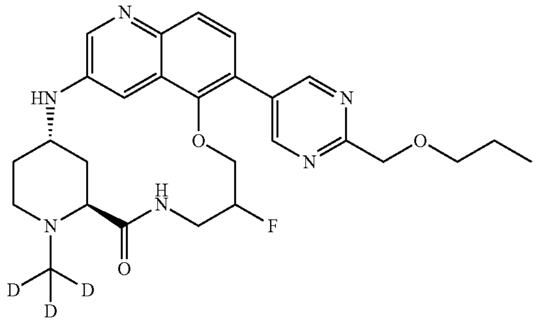 [SMILES: [2H]C([2H])([2H])N1CC[C@H]2C[C@H]1C(=O)NCC(F)COc1c(-c3cnc(COCCC)nc3)ccc3ncc(cc13)N2] | Methods D-2, and D-3 | (LC-1): RT = 1.09, m/z 512 [M + H]+ |

TABLE 3-continued
| Example | Structure | Reference Methods | LCMS Data |
|---|---|---|---|
| a-02-07 | 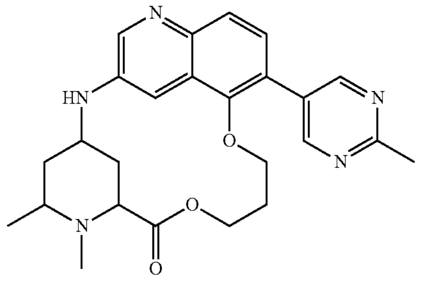 | Methods D-3, E-1, and H-1 | (LC-1): RT = 1.24, m/z 448 [M + H]+ |
| a-02-08 | 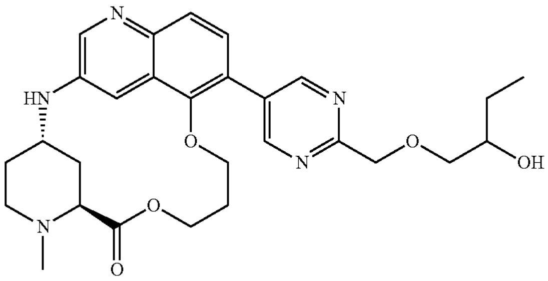 [SMILES: CCC(O)COCc1ncc(-c2ccc3ncc4cc3c2OCCCOC(=O)[C@@H]2C[C@H](CCN2C)N4)cn1] | Methods D-3, and E-1 | (LC-1): RT = 1.19, m/z 522 [M + H]+ |
| a-02-09 | 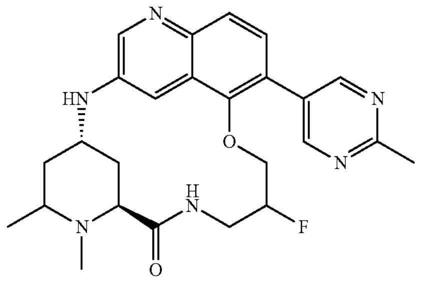 | Methods H-1, I-2, and I-3 | (LC-1): RT = 0.98, m/z 465 [M + H]+ |
| a-02-10 | 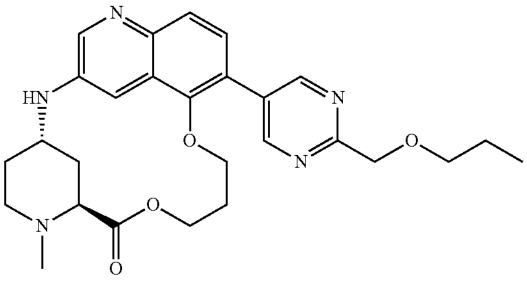 [SMILES: CCCOCc1ncc(-c2ccc3ncc4cc3c2OCCCOC(=O)[C@@H]2C[C@H](CCN2C)N4)cn1] | Methods D-3, and E-1 | (LC-1): RT = 1.40, m/z 492 [M + H]+ |
| a-02-11 | 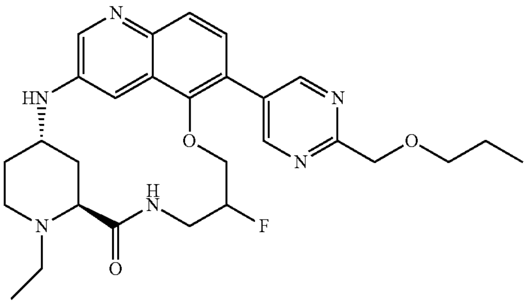 | Methods D-3, and I-2 | (LC-1): RT = 0.96, m/z 465 [M + H]+ |

TABLE 3-continued
| Example | Structure | Reference Methods | LCMS Data |
|---|---|---|---|
| a-02-12 | 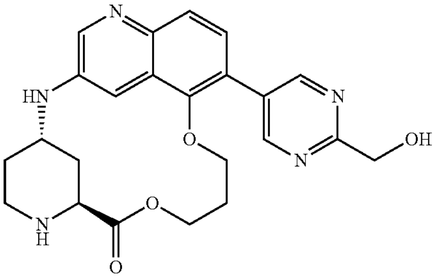 [SMILES: O=C1OCCCOc2c(-c3cnc(CO)nc3)ccc3ncc(cc23)N[C@H]2CCN[C@H]1C2] | Methods D-3, and E-1 | (LC-1): RT = 0.25, m/z 436 $[M + H]^+$ |
| a-02-13 | 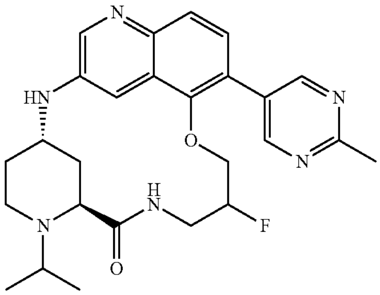 [SMILES: Cc1ncc(-c2ccc3ncc4cc3c2OCC(F)CNC(=O)[C@@H]2C[C@H](CCN2C(C)C)N4)cn1] | Methods D-3, and I-2 | (LC-1): RT = 1.00, m/z 479 $[M + H]^+$ |
| a-02-14 | 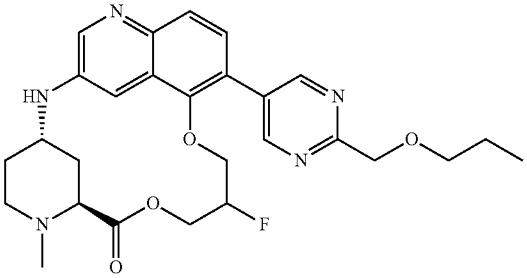 [SMILES: CCCOCc1ncc(-c2ccc3ncc4cc3c2OCC(F)COC(=O)[C@@H]2C[C@H](CCN2C)N4)cn1] | Methods D-2, and D-3 | (LC-1): RT = 1.43, m/z 510 $[M + H]^+$ |
| a-02-15 | 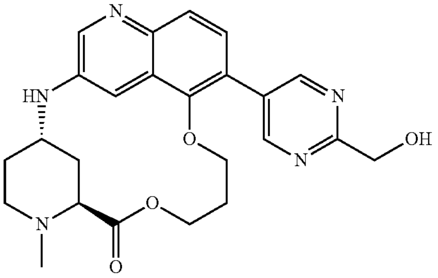 [SMILES: CN1CC[C@H]2C[C@H]1C(=O)OCCCOc1c(-c3cnc(CO)nc3)ccc3ncc(cc13)N2] | Methods D-3, and E-1 | (LC-1): RT = 0.98, m/z 450 $[M + H]^+$ |
| a-02-16 | 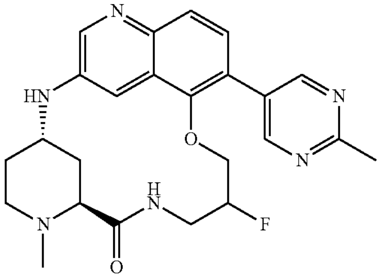 [SMILES: Cc1ncc(-c2ccc3ncc4cc3c2OCC(F)CNC(=O)[C@@H]2C[C@H](CCN2C)N4)cn1] | Methods D-2, and D-3 | (LC-1): RT = 0.91, m/z 451 $[M + H]^+$ |

TABLE 3-continued
| Example | Structure | Reference Methods | LCMS Data |
|---|---|---|---|
| a-02-17 | 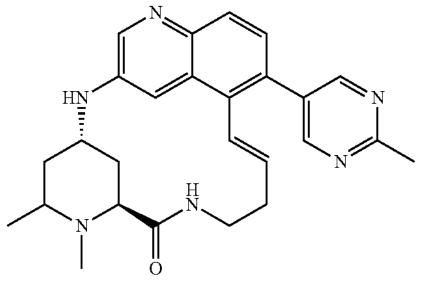 | Methods H-1, H-2, and H-3 | (LC-1): RT = 0.94, m/z 443 $[M + H]^+$ |
| a-02-18 | 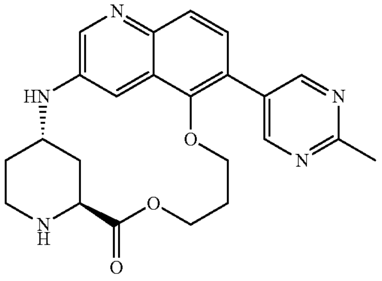 [SMILES: Cc1ncc(-c2ccc3ncc4cc3c2OCCCOC(=O)[C@@H]2C[C@H](CCN2)N4)cn1] | Methods D-3, and E-1 | (LC-1): RT = 0.97, m/z 420 $[M + H]^+$ |
| a-02-19 | 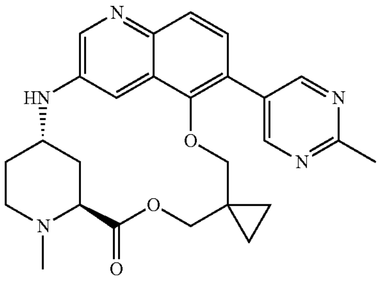 [SMILES: Cc1ncc(-c2ccc3ncc4cc3c2OCC2(CC2)COC(=O)[C@@H]2C[C@H](CCN2C)N4)cn1] | Methods D-2, and D-3 | (LC-1): RT = 1.25, m/z 460 $[M + H]^+$ |
| a-02-20 | 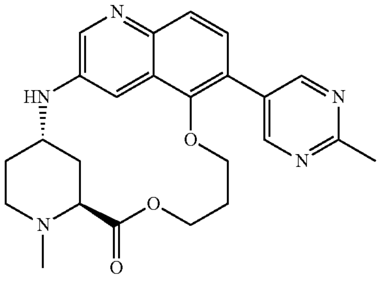 [SMILES: Cc1ncc(-c2ccc3ncc4cc3c2OCCCOC(=O)[C@@H]2C[C@H](CCN2C)N4)cn1] | Methods D-3, and E-1 | (LC-1): RT = 1.16, m/z 434 $[M + H]^+$ |
| a-02-21 | 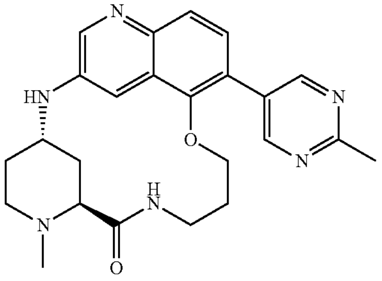 [SMILES: Cc1ncc(-c2ccc3ncc4cc3c2OCCCNC(=O)[C@@H]2C[C@H](CCN2C)N4)cn1] | Methods D-2, and D-3 | (LC-1): RT = 0.88, m/z 433 $[M + H]^+$ |

TABLE 3-continued

| Example | Structure | Reference Methods | LCMS Data |
|---|---|---|---|
| a-02-22 | 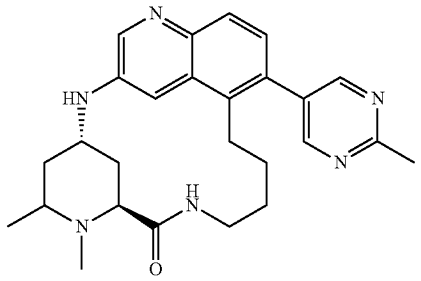 | Methods G-1, G-2, and H-1 | (LC-1): RT = 0.96, m/z 445 $[M + H]^+$ |
| a-02-23 | 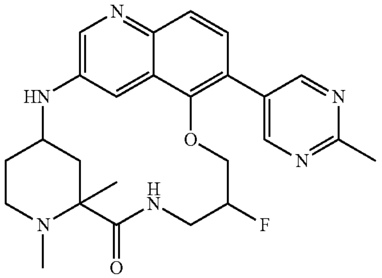 [SMILES: Cc1ncc(-c2ccc3ncc4cc3c2OCC(F)CNC(=O)C2(C)CC(CCN2C)N4)cn1] | Methods I-1, I-2, and I-3 | (LC-1): RT = 0.92, m/z 465 $[M + H]^+$ |
| a-02-24 | 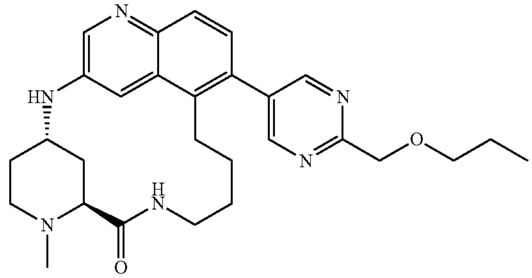 [SMILES: CCCOCc1ncc(-c2ccc3ncc4cc3c2CCCCNC(=O)[C@@H]2C[C@H](CCN2C)N4)cn1] | Methods G-1, and G-2 | (LC-1): RT = 1.12, m/z 489 $[M + H]^+$ |
| a-02-25 | 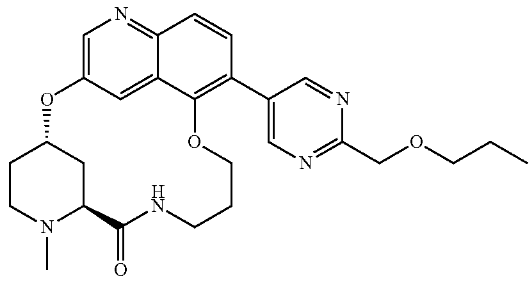 [SMILES: CCCOCc1ncc(-c2ccc3ncc4cc3c2OCCCNC(=O)[C@@H]2C[C@H](CCN2C)O4)cn1] | Methods F-1, and F-2 | (LC-1): RT = 1.06, m/z 492 $[M + H]^+$ |

Test Example 1: Measurement of Human IRAK-4 Inhibitory Activity (1) Measurement Method For the measurement of the activity of the human IRAK-4 (Invitrogen, Cat. PV3362), phosphorylation of the IRAK-4 peptide substrate (biotin-KKKKRFSFKKSFKC) by the enzyme in the presence of 10 μM ATP (Sigma-Aldrich, Cat. A7699) was measured by the TR-FRET method. The enzymatic reaction was performed in a reaction buffer containing 50 mM HEPES (pH 7.2), 1 mM DTT, 0.1 mM $Na_3VO_4$, 5 mM $MgCl_2$, 1 mM $MnCl_2$, and 0.1% bovine serum albumin. For the measurement of the IRAK-4 inhibitory activity, a test compound was added to the reaction buffer containing 1 nM IRAK-4, 0.5 μM peptide substrate, and 10 μM ATP, and the mixture was incubated at 23° C. for 30 minutes. Then, a detection solution containing an antibody labeled with europium cryptate (0.3 μg/mL, the antibody was prepared by using the IRAK-4 peptide substrate as the antigen), streptavidin-XL665 (2 μg/mL, CisBio, Cat. 610SAXLB), 50 mM HEPES (pH 7.2), 0.1% BSA, 120 mM KF, and 66.7 mM EDTA (all the concentrations of the reagents are final concentrations) was added to terminate the reaction, and then the mixture was further incubated at 23° C. for 60 minutes. Fluorescence intensity was measured at wavelengths of 665 nm and 620 nm with a microplate reader, and the enzymatic activity was calculated as the ratio of fluorescence intensities at 665 nm and 620 nm (665 nm/620 nm). The IRAK-4 suppression ratio observed with addition of 12.5 M staurosporine (LC Laboratories, Cat. S-9300) was defined to be 100%, the IRAK-4 suppression ratio observed with no addition of test compound was defined to be 0%, and $IC_{50}$ of the test compound was calculated by using the 4-parameter logistic model of the data analysis software XLfit (ID Business Solutions Ltd.).

The operations and conditions used for the measurement may be appropriately changed within such a range that those skilled in the art can understand them, and the measurement is not significantly affected.

(2) Measurement Results

As shown below, the compounds of the present invention according to a certain embodiment showed outstanding IRAK-4 inhibitory activities.

When the measurement was performed in multiplicate, the results are represented with average values.

TABLE 4

| Example | $IC_{50}$ (nM) |
|---|---|
| a-01-01 | 1.63 |
| a-01-02 | 0.89 |
| a-01-03 | 2.11 |
| a-01-04 | 4.24 |
| a-01-05 | 1.37 |
| a-01-06 | 2.53 |
| a-01-07 | 1.49 |
| a-01-08 | 1.47 |
| a-01-09 | 1.28 |
| a-01-10 | 43.44 |
| a-01-11 | 0.79 |
| a-01-12 | 1.75 |
| a-01-13 | 2.95 |
| a-01-14 | 1.73 |
| a-01-15 | 2.77 |
| a-01-16 | 1.25 |
| a-01-17 | 3.04 |
| a-01-18 | 1.84 |
| a-01-19 | 1.6 |
| a-01-20 | 1.15 |
| a-01-21 | 2.29 |
| a-01-22 | 0.89 |
| a-01-23 | 1.21 |
| a-01-24 | 2.48 |
| a-01-25 | 4.43 |
| a-01-26 | 1.41 |
| a-01-27 | 4.25 |
| a-01-28 | 4.04 |
| a-01-29 | 4.14 |
| a-01-30 | 2.8 |
| a-01-31 | 3.42 |
| a-01-32 | 1.59 |
| a-01-33 | 4.79 |
| a-01-34 | 4.19 |
| a-01-35 | 2.84 |
| a-01-36 | 8.86 |
| a-01-37 | 4.52 |
| a-01-38 | 6.73 |
| a-01-39 | 5.12 |
| a-01-40 | 14.78 |

TABLE 5

| Example | $IC_{50}$ (nM) |
|---|---|
| a-01-41 | 10.04 |
| a-01-42 | 6.61 |
| a-01-44 | 2.36 |
| a-01-45 | 3.28 |
| a-02-01 | 2.33 |
| a-02-02 | 1.09 |
| a-02-03 | 2.51 |
| a-02-04 | 5.63 |
| a-02-05 | 2.47 |
| a-02-06 | 2 |
| a-02-07 | 2.04 |
| a-02-08 | 5.73 |
| a-02-09 | 0.86 |
| a-02-10 | 2.96 |
| a-02-11 | 1.02 |
| a-02-12 | 0.93 |
| a-02-13 | 1.12 |

TABLE 5-continued

| Example | $IC_{50}$ (nM) |
|---|---|
| a-02-14 | 6.46 |
| a-02-15 | 2.23 |
| a-02-16 | 0.81 |
| a-02-17 | 1.76 |
| a-02-18 | 1.66 |
| a-02-19 | 3.9 |
| a-02-20 | 3.21 |
| a-02-21 | 2.2 |
| a-02-23 | 9.7 |
| a-02-24 | 13.18 |

Test Example 2: LPS-Stimulated TNFα Production Inhibition Test Using Human Acute Monocytic Leukemia Cell Strain THP-1

(1) Measurement Method

By the THP-1 assay, influence of a test compound on the TNFα production induced by LPS stimulation can be evaluated. The THP-1 cells (ATCC, Cat. TIB-202) were inoculated on a 96-well plate at a density of $1\times10^5$ cells/160 L/well, a test compound was added in a volume of 20 μL, and the plate was incubated at 37° C. for 1 hour in a 5% $CO_2$ incubator. Then, LPS in a volume of 20 μL (final concentration 2.5 ng/mL, Sigma, Cat. L2630) was added, and the plate was further incubated for 4 hours. After the incubation, the plate was centrifuged, and 100 μL of the supernatant was taken from each well, and used for evaluation of the amount of TNFα using HTRF (Cisbio, Cat. 62TNFαEB). In the measurement of the amount of TNFα, the supernatant was diluted twice with the medium, and then added to wells of a 384-well plate in a volume of 10 μL, then anti-TNFα-cryptate (5 μL), and anti-TNFα-XL665 (5 μL) were added, and the plate was left standing overnight. The fluorescence intensity ratio for the wavelengths of 620 and 665 nm (620 nm/665 nm) was measured with a microplate reader, and the amount of TNFα in the supernatant was calculated by using a calibration curve. The TNFα production suppression ratio observed with no addition of LPS was defined to be 100%, the TNFα production suppression ratio observed with no addition of the test compound was defined to be 0%, and $IC_{50}$ of the test compound was calculated by using the 4-parameter logistic model of the data analysis software XLfit (ID Business Solutions Ltd.).

By using the 96-well plate from which 100 μL of the supernatant was removed, cell survival ratio was measured, and influence of the off-target effect of the test compound was evaluated. CCK-8 (Dojindo, Cat. CK04-10) was added in a volume of 5 μL, the plate was incubated at 37° C. for 1 hour, and then absorbance was measured at 450 nm with a microplate reader. The cell survival ratio observed with no addition of LPS was defined to be 100%, and $IC_{50}$ of the test compound was calculated by using XLfit.

The operations and conditions used for the measurement may be appropriately changed within such a range that those skilled in the art can understand them, and the measurement is not significantly affected.

(2) Measurement Results

As shown below, the compounds of the present invention according to a certain embodiment showed outstanding TNFα production inhibitory activity.

When the measurement was performed in multiplicate, the results are represented with average values. The values were rounded to the fourth decimal place.

TABLE 6

| Example | $IC_{50}$ (μM) |
| --- | --- |
| a-01-01 | 0.028 |
| a-01-02 | 0.044 |
| a-01-03 | 0.045 |
| a-01-04 | 0.048 |
| a-01-05 | 0.048 |
| a-01-06 | 0.050 |
| a-01-07 | 0.057 |
| a-01-08 | 0.063 |
| a-01-09 | 0.064 |
| a-01-10 | 0.068 |
| a-01-11 | 0.073 |
| a-01-12 | 0.075 |
| a-01-13 | 0.076 |
| a-01-14 | 0.080 |
| a-01-15 | 0.081 |
| a-01-16 | 0.092 |
| a-01-17 | 0.099 |
| a-01-18 | 0.104 |
| a-01-19 | 0.113 |
| a-01-20 | 0.113 |
| a-01-21 | 0.117 |
| a-01-22 | 0.118 |
| a-01-23 | 0.124 |
| a-01-24 | 0.140 |
| a-01-25 | 0.141 |
| a-01-26 | 0.142 |
| a-01-27 | 0.145 |
| a-01-28 | 0.149 |
| a-01-29 | 0.150 |
| a-01-30 | 0.162 |
| a-01-31 | 0.163 |
| a-01-32 | 0.165 |
| a-01-33 | 0.170 |
| a-01-34 | 0.177 |
| a-01-35 | 0.178 |
| a-01-36 | 0.182 |
| a-01-37 | 0.189 |
| a-01-38 | 0.199 |
| a-01-39 | 0.204 |
| a-01-40 | 0.253 |

TABLE 7

| Example | $IC_{50}$ (μM) |
| --- | --- |
| a-01-41 | 0.293 |
| a-01-42 | 0.246 |
| a-01-43 | 0.237 |
| a-01-44 | 0.210 |
| a-01-45 | 0.227 |
| a-02-01 | 0.012 |
| a-02-02 | 0.013 |
| a-02-03 | 0.013 |
| a-02-04 | 0.023 |
| a-02-05 | 0.023 |
| a-02-06 | 0.024 |
| a-02-07 | 0.033 |
| a-02-08 | 0.036 |
| a-02-09 | 0.036 |
| a-02-10 | 0.043 |
| a-02-11 | 0.045 |
| a-02-12 | 0.047 |
| a-02-13 | 0.048 |
| a-02-14 | 0.058 |
| a-02-15 | 0.064 |
| a-02-16 | 0.065 |
| a-02-17 | 0.066 |
| a-02-18 | 0.081 |
| a-02-19 | 0.102 |
| a-02-20 | 0.117 |
| a-02-21 | 0.135 |
| a-02-22 | 0.324 |
| a-02-23 | 0.716 |

TABLE 7-continued

| Example | $IC_{50}$ (μM) |
| --- | --- |
| a-02-24 | 0.378 |
| a-02-25 | 0.500 |

INDUSTRIAL APPLICABILITY

The compounds of the general formula (1) and salts thereof have a superior IRAK-4 inhibitory activity, and thus they are useful as active ingredients of medicaments for prophylactic treatment and/or therapeutic treatment of diseases relating to IRAK-4 inhibition.

The invention claimed is:

1. A compound represented by the following formula (1):

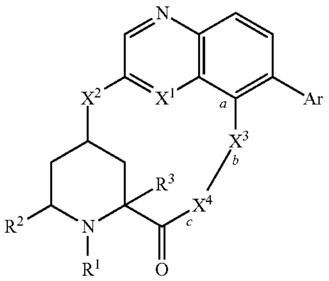

(1)

in the formula (1), $R^1$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —C(O)$R^{12}$, —S($O_2$)$R^{12}$, —C(O)N$R^{11}R^{12}$, —C(O) O$R^{12}$, or a 3- to 7-membered saturated ring group, $R^1$ may be substituted with the same or different 1 to 3 substituents selected from a group $G^1$;

the group $G^1$ is a group consisting of —F, hydroxy, cyano, halogeno-$C_{1-6}$ alkyl, $C_{1-4}$ alkoxy, phenyl, 5- to 6-membered heteroaryl, and a 3- to 7-membered saturated ring group, the phenyl and 5- to 6-membered heteroaryl included in the group $G^1$ may be substituted with the same or different 1 to 3 substituents selected from a group $G^{Ar}$;

the group $G^{Ar}$ is a group consisting of —F, —Cl, hydroxy, cyano, $C_{1-6}$ alkyl, halogeno-$C_{1-6}$ alkyl, and —$NH_2$;

$R^{11}$ is —H, $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_1$-alkyl, or a 3- to 7-membered saturated ring group;

$R^{12}$ is $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, a 3- to 7-membered saturated ring group, phenyl, or 5- or 6-membered heteroaryl, the phenyl and 5- or 6-membered heteroaryl as $R^{12}$ may be substituted with the same or different 1 to 3 substituents selected from the group $G^{Ar}$;

$R^2$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, or a 3- to 7-membered saturated ring group;

$R^3$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, or a 3- to 7-membered saturated ring group;

Ar is 6- to 10-membered aryl or 5- to 10-membered heteroaryl, Ar may be substituted with the same or different 1 to 3 substituents selected from the group $G^2$;

the group $G^2$ is a group consisting of —F, —Cl, hydroxy, cyano, $C_{1-6}$ alkyl, halogeno-$C_{1-6}$ alkyl, hydroxy-$C_{1-6}$ alkyl, $R^{Ar1}$—O—$C_{1-3}$ alkyl, $R^{Ar1}$—$NR^{13}$—$C_{1-3}$ alkyl, —$NR^{13}C(O)R^{14}$, —C(O)$NR^{13}R^{14}$, —$C(O)NH_2$, —$NR^{13}S(O_2)R^{14}$, —$S(O_2)NR^{13}R^{14}$, —$NH_2$, —$S(O_2)NH_2$, —$NR^{13}$R 14, and —NHC(O)$NHR^{15}$;

$R^{Ar1}$ is —H, $C_{1-6}$ alkyl, halogeno-$C_{1-6}$ alkyl, or a 3- to 7-membered saturated ring group, $R^{Ar1}$ may be substituted with the same or different 1 to 3 substituents selected from the group $G^3$;

the group $G^3$ is a group consisting of —F, hydroxy, $C_{1-3}$ alkyl, halogeno-$C_{1-3}$ alkyl, oxo, $C_{1-3}$ alkoxy, halogeno-$C_{1-3}$ alkoxy, and a 3- to 7-membered saturated ring group;

$R^{13}$ is —H, $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_1$-3 alkyl, or a 3- to 7-membered saturated ring group;

$R^{14}$ is $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_{1-3}$ alkyl, or a 3- to 7-membered saturated ring group;

$R^{15}$ is —H, phenyl, or 5- or 6-membered heteroaryl, $R^{15}$ may be substituted with the same or different 1 to 3 substituents selected from the group $G^4$;

the group $G^4$ is a group consisting of halogen, cyano, $C_{1-3}$ alkyl, and halogeno-$C_{1-3}$ alkyl;

$X^1$ is N or CH;

$X^2$ is NH or O;

$X^3$ is a group represented by the following formula (1-1):

(1-1)

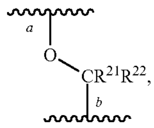

the following formula (1-2):

(1-2)

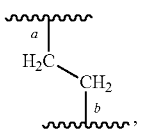

or the following formula (1-3):

(1-3)

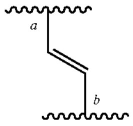

a and b represent direction of bonding:

$R^{21}$ and $R^{22}$ are independently —H, $C_{1-3}$ alkyl, or halogeno-$C_{1-3}$ alkyl;

$X^4$ is a group represented by the following formula (2-1):

(2-1)

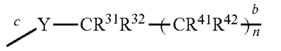

b and c represent direction of bonding;

in the formula (2-1), n is an integer of 1 to 3;

Y is $NR^{51}$ or O;

$R^{31}$ and $R^{32}$ are independently —H, $C_{1-3}$ alkyl, or halogeno-$C_{1-3}$ alkyl; or $R^{31}$ and $R^{32}$ may combine to form a 3- to 6-membered saturated ring;

$R^{41}$ and $R^{42}$ are independently —H, —F, hydroxy, $C_{1-3}$ alkyl, halogeno-$C_{1-3}$ alkyl, $C_{1-3}$ alkoxy, or halogeno-$C_{1-3}$ alkoxy; or $R^{41}$ and $R^{42}$ may combine to form a 3- to 6-membered saturated ring;

$R^{51}$ is —H, $C_{1-3}$ alkyl, or halogeno-$C_{1-3}$ alkyl; or $R^{51}$ and $R^{31}$ may combine to form a 4- to 6-membered saturated ring;

$X^4$ may be substituted with the same or different 1 to 3 substituents selected from the group $G^5$; and the group $G^5$ is a group consisting of —F, hydroxy, $C_{1-3}$ alkyl, halogeno-$C_{1-3}$ alkyl, $C_{1-3}$ alkoxy, and halogeno-$C_{1-3}$alkoxy, or a salt thereof.

2. The compound or a salt thereof according to claim 1, wherein Ar is 5- or 6-membered heteroaryl.

3. The compound or a salt thereof according to claim 1, wherein $R^1$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, or a 3- to 7-membered saturated ring group, and $R^1$ may be substituted with the same or different 1 to 3 substituents selected from the group $G^1$.

4. The compound or a salt thereof according to claim 1, wherein $X^2$ is NH.

5. The compound or a salt thereof according to claim 1, wherein:

$X^3$ is a group represented by the following formula (1-1):

(1-1)

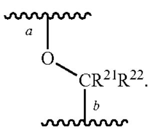

6. The compound or a salt thereof according to claim 1, wherein:

$X^3$ is a group represented by the following general formula (1-1-1):

(1-1-1)

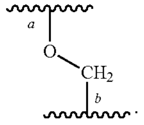

7. The compound or a salt thereof according to claim 1, wherein:

in the formula (2-1) for $X^4$, n is 1.

8. The compound or a salt thereof according to claim 1, wherein:

Ar is a group represented by the following formula (3-1):

(3-1)

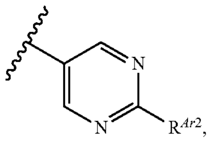

and in the formula (3-1), $R^{Ar2}$ is —H, —F, —Cl, hydroxy, cyano, $C_{1-6}$ alkyl, halogeno-$C_{1-6}$ alkyl, hydroxy-$C_{1-6}$ alkyl, $R^{Ar1}$—O—$C_{1-3}$ alkyl, or—$NR^{13}R^{14}$.

9. The compound or a salt thereof according to claim 8, wherein:

Ar is a group represented by the formula (3-1), and in the formula (3-1), $R^{Ar2}$ is —H, methyl, hydroxymethyl, or—$CH_2$—O—$R^{Ar1}$.

10. The compound or a salt thereof according to claim 1, wherein $R^3$ is —H.

11. The compound or a salt thereof according to claim 1, wherein $R^2$ is —H or methyl.

12. The compound or a salt thereof according to claim 1, wherein $R^1$ is —H or $C_{1-3}$ alkyl.

13. A compound represented by the following formula:

Formula 9

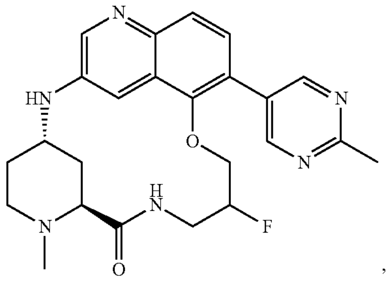

, or a salt thereof.

14. A compound represented by the following formula:

Formula 10

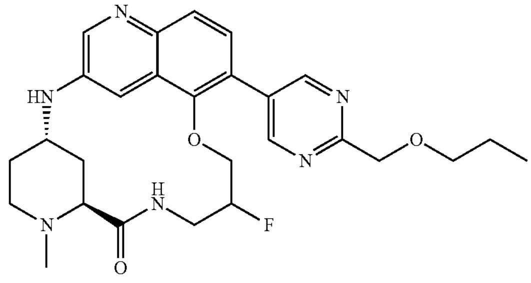

, or a salt thereof.

15. A compound represented by the following formula:

Formula 11

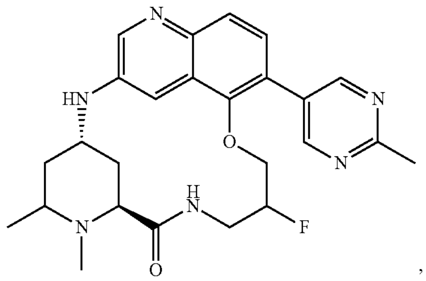

, or a salt thereof.

16. A compound represented by the following formula:

Formula 12

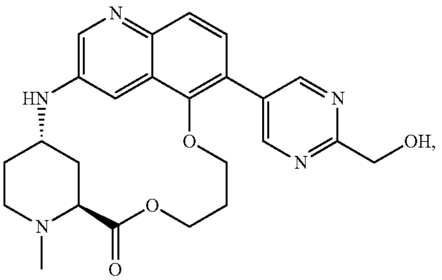

or a salt thereof.

17. A compound represented by the following formula:

Formula 13

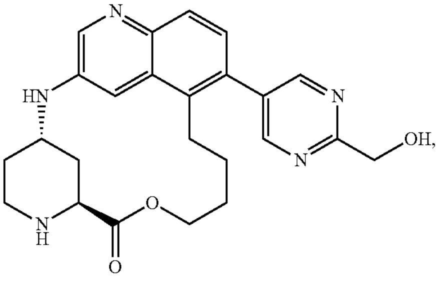

or a salt thereof.

18. A compound represented by the following formula:

Formula 14

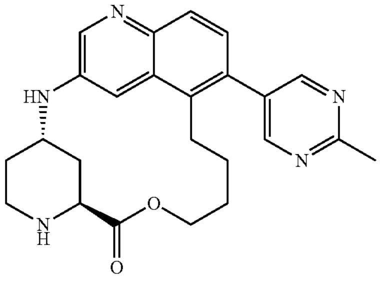

or a salt thereof.

19. A compound represented by the following formula:
Formula 15
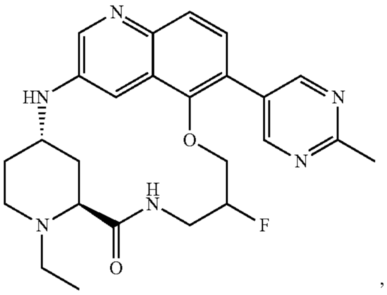
,
or a salt thereof.
* * * * *